United States Patent
Harvey et al.

(10) Patent No.: US 7,812,215 B2
(45) Date of Patent: *Oct. 12, 2010

(54) METHODS AND PROTEIN PRODUCTION USING OVOMUCOID PROMOTERS

(75) Inventors: Alex J. Harvey, Athens, GA (US); Markley C. Leavitt, Watkinsville, GA (US); Youliang Wang, Monroe, GA (US)

(73) Assignee: Synageva BioPharma Corp., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/313,064

(22) Filed: Nov. 17, 2008

(65) Prior Publication Data

US 2009/0182130 A1   Jul. 16, 2009

Related U.S. Application Data

(63) Continuation of application No. 11/649,543, filed on Jan. 4, 2007, now Pat. No. 7,507,873, which is a continuation of application No. 11/047,184, filed on Jan. 31, 2005, now Pat. No. 7,335,761, which is a continuation-in-part of application No. 10/856,218, filed on May 28, 2004, now Pat. No. 7,294,507, which is a continuation-in-part of application No. 10/496,731, filed as application No. PCT/US02/38413 on Dec. 2, 2002, now Pat. No. 7,375,258, and a continuation-in-part of application No. 09/998,716, filed on Nov. 30, 2001, now Pat. No. 6,875,588, said application No. 11/047,184 is a continuation-in-part of application No. 10/790,455, filed on Mar. 1, 2004, now abandoned.

(60) Provisional application No. 60/476,596, filed on Jun. 6, 2003, provisional application No. 60/505,562, filed on Sep. 24, 2003, provisional application No. 60/509,122, filed on Oct. 6, 2003.

(51) Int. Cl.
*C12P 21/00* (2006.01)
*A01K 67/027* (2006.01)

(52) U.S. Cl. .................. 800/4; 800/6; 800/19
(58) Field of Classification Search ............. 800/19, 800/4, 6
See application file for complete search history.

(56) References Cited

U.S. PATENT DOCUMENTS

| | | |
|---|---|---|
| 4,237,224 A | 12/1980 | Cohen et al. |
| 4,603,112 A | 7/1986 | Paoletti et al. |
| 4,722,848 A | 2/1988 | Paoletti et al. |
| 4,769,330 A | 9/1988 | Paoletti et al. |
| 5,174,993 A | 12/1992 | Paoletti et al. |
| 5,175,384 A | 12/1992 | Krimpenfort et al. |
| 5,338,683 A | 8/1994 | Paoletti et al. |
| 5,494,807 A | 2/1996 | Paoletti et al. |
| 5,505,941 A | 4/1996 | Paoletti et al. |
| 5,580,859 A | 12/1996 | Felgner et al. |
| 5,589,466 A | 12/1996 | Felgner et al. |
| 5,591,639 A | 1/1997 | Bebbington |
| 6,808,925 B2 | 10/2004 | Calos |
| 6,825,396 B2 | 11/2004 | MacArthur |
| 6,875,588 B2 * | 4/2005 | Harvey et al. ............ 435/69.51 |
| 7,294,507 B2 * | 11/2007 | Harvey et al. ............ 435/320.1 |
| 7,312,374 B2 | 12/2007 | Rapp et al. |
| 7,335,761 B2 * | 2/2008 | Harvey et al. ............. 536/24.1 |
| 7,375,258 B2 * | 5/2008 | Harvey et al. ................ 800/19 |
| 7,507,873 B2 * | 3/2009 | Harvey et al. ................ 800/19 |

FOREIGN PATENT DOCUMENTS

| | | |
|---|---|---|
| WO | WO 92/06180 | 4/1992 |
| WO | WO 92/19749 | 11/1992 |
| WO | WO 92/20316 | 11/1992 |
| WO | WO 92/22635 | 12/1992 |
| WO | WO 93/04701 | 3/1993 |
| WO | WO 93/25234 | 12/1993 |
| WO | WO 94/06920 | 3/1994 |
| WO | WO 94/11524 | 5/1994 |
| WO | WO 97/47739 | 12/1997 |
| WO | WO 99/19472 | 4/1999 |
| WO | WO 03/048364 | 6/2003 |

OTHER PUBLICATIONS

Bosselman (Science, Jan. 27, 1989, vol. 243, No. 4890, p. 533-535).*
Vick (Proc. R. Soc. Lond., 1993, vol. 251, p. 179-182).*
Love (Bio/Technology, 1994, vol. 12, p. 60-63).*
Sang (TibTech, 1994, vol. 12, p. 415-420).*
Thoroval (Transgenic Research, 1995, vol. 4, p. 369-376).*
Mohammed (1998, Immunotechnology, vol. 4, p. 115-125).*
Harvey (Nature Biotech, Apr. 2002, vol. 19, p. 396-399.*
Ivarie (Trends in Biotechnology, Jan. 2003, vol. 21, p. 14-19).*
Molecular Structure and Flanking Nucleotide Sequences of the Natural Chicken Ovomucoid Gene,Lai et al; Cell 18:829-842 (Nov. 1979).
DNA methylation: organi specific variations in the methylation pattern within and around ovalbumin and other chicken genes, Mandel et al; Nucleic Acids Research 7:2081-2103(1979).
Ovoinhibitor Introns Spefiy Functional Domains as in the Related and Linked Ovomucoid Gene*, Scott et al; Journal of Biol. Chemistry, 262:5899-5907(1987).
Deoxyribonuclease I Sensitivity of the Ovomucoid-Ovoinhibitor Gene Complex in Oviduct Nuclei and Relative Location of CR1 Repetitive Sequences, Scott et al; Biochemistry 26:6831-6840 (1987).
Isolation and characterization of the chicken ovomucoid gene, Lindenmaier et al; Nucleic Acids Research, 7:1221-1232 (1979).
The chick ovomucoid gene contains at least six intervening sequences, Catterall et al; Nature 278:323-327 (Mar. 1979).

(Continued)

*Primary Examiner*—Michael C. Wilson
(74) *Attorney, Agent, or Firm*—Kyle D. Yesland

(57) ABSTRACT

Methods of producing protein using a recombinant ovomucoid gene expression controlling region operably linked to one or more useful amino acid coding sequences.

30 Claims, 42 Drawing Sheets

OTHER PUBLICATIONS

Effect of Estrogen on Gene Expression In the Chick Oviduct. Regulation of Ovomucoid Gene, Tsai et al; Biochemistry 17:5773-5780 (1978).

Identification of potential ovomucoid mRNA precursors in chick oviduct nuclei, Nordstrom et al; Nature 278:328-331 (Mar. 1979).

mRNA Complexity and Egg White Protein mRNA Content in Mature and Hormone-Withdrawn Oviduct, Hynes et al; Cell 11:923-932 (Aug. 1977).

Multiple Initiation and Polyadenylation Sites for the Chicken Ovomucoid Transcription Unit, Gerlinger et al; J. Mol. Biol. vol. 162, p. 345-364 (1982).

Identification and fine mapping of IgG and IgE Epitopes in Ovomucoid, Mine et al; Biochem Biophys Res Comm, vol. 292 p. 1070-1074 (2002).

Heterogenous Initiation Sites for Transcription of the Chicken Ovomucoid Gene, Lai EC et al, J. of Supramolecular Structure and Cellular Biochemistry, No. 1157 p. 429 (abstract).

Chicken Ovomucoid Gene, 5' End Region, Gerlinger p. et al; Lai etal; Database Accession No. J00894 (1986).

Gallus Gallus Isolate No. 26 Ovomucoid Gene, Promoter Region and Partial cds, Wang et al, Database Accession No. AF453747.

Expression of Exogenous Protein in the Egg White of Transgenic Chicken, Harvey et al Nature Biotechnology vol. 19 p. 396-399 (2002).

* cited by examiner

| | | |
|---|---|---|
| OVINs1: | GGGAAACAATCTGCCTTGCA | SEQ ID NO: 3 |
| OVINs2: | TAGGCAGAGCAATAGGACTCTCAACCTCGT | SEQ ID NO: 1 |
| OVINs4: | AGATGAGGTGGATGGTTTAC | SEQ ID NO: 7 |
| OVINs5: | CAGCTTCTGCTAGCGTAGGT | SEQ ID NO: 8 |
| OVINs6: | ACGTGAACTCAAAGAGGCAC | SEQ ID NO: 9 |
| OVINs7: | ATCTCCTGAGCTCGGTGCTT | SEQ ID NO: 10 |
| OVINs8: | ACGAGGTTCCATGTCTTTCA | SEQ ID NO: 11 |
| OVMUa1: | AAGCCACAAAGCACGAAAGAG | SEQ ID NO: 4 |
| OVMUa2: | AAGCTTCTGCAGCACTCTGGGAGTTACTCA | SEQ ID NO: 2 |
| OVMUa3: | TAAATAGCACAGAACGCTGAGGGGAGTAAGG | SEQ ID NO: 12 |
| OVMUa4: | GAAGAGCTTGGTAGAAGACT | SEQ ID NO: 13 |
| OVMUa5: | ATGGAAATATGGGTTTCCTTC | SEQ ID NO: 14 |
| OVMUa6: | GCAGCTTATGGCTAATCGCT | SEQ ID NO: 15 |
| OVMUa7: | AGTGACCACTATCTGACCTG | SEQ ID NO: 16 |
| OVMUa8: | TAATCAGGAAGGCACACAGC | SEQ ID NO: 17 |
| OVMUP4.7.1: | AGATCTGGAGCAGCACTTGT | SEQ ID NO: 18 |
| OVMUP4.7.2: | AGCATGAAGTTCCTCACCCA | SEQ ID NO: 19 |
| OVMUP4.7.3: | ATGGAGAGGAATATTCCCTT | SEQ ID NO: 20 |
| OVMUP4.7.4: | ATTTCTCCAGGCGTGTGG | SEQ ID NO: 21 |
| OVMUP5.5.1: | ATTTCTCCAGGCGTGTGG | SEQ ID NO: 22 |
| OVMUP5.5.2: | ATGCGAGTGAAGGAGAGTTC | SEQ ID NO: 23 |
| OVMUP5.5.3: | GCAGCACGTGTAAGCTTGTA | SEQ ID NO: 24 |
| OVMUP5.5.4: | CAAGGCAAATTATCAGCAGA | SEQ ID NO: 25 |
| OVMUa9: | AAATGAAGCCGGCTGTTTTC | SEQ ID NO: 27 |
| OVINs9 | CTCTCAGCCACTCTGAACAA | SEQ ID NO: 28 |

Fig. 3

| | |
|---|---|
| TAGGCAGAGCAATAGGACTCTCAACCTCGTGAGTATGGCAGCATGTTAACTCTGCACTGG | 60 |
| OVOINHIBITOR 3' UNTRANSLATED REGION | |
| AGTCCAGCGTGGGAAACAATCTGCCTTGCACATGAGTCTTCGTGGGCCAATATTCCCCAA | |
| OVOINHIBITOR 3' UNTRANSLATED REGION | |
| CGGTTTTCCTTCAGCTTGTCTTGTCTCCTAAGCTCTCAAAACACCTTTTTGGTGAATAAA | |
| OVOINHIBITOR 3' UNTRANSLATED REGION | |
| CTCACTTGGCAACGTTTATCTGTCTTACCTTAGTGTCACGTTTCATCCCTATTCCCCTTT | |

```
CTCCTCCTCCGTGTGGTACACAGTGGTGCACACTGGTTCTTCTGTTGATGTTCTGCTCTG   300
ACAGCCAATGTGGGTAAAGTTCTTCCTGCCACGTGTCTGTGTTGTTTTCACTTCAAAAAG
GGCCCTGGGCTCCCCTTGGAGCTCTCAGGCATTTCCTTAATCATCACAGTCACGCTGGCA
GGATTAGTCCCTCCTAAACCTTAGAATGACCTGAACGTGTGCTCCCTCTTTGTAGTCAGT
GCAGGGAGACGTTTGCCTCAAGATCAGGGTCCATCTCACCCACAGGGCCATTCCCAAGAT
GAGGTGGATGGTTTACTCTCACAAAAAGTTTTCTTATGTTTGGCTAGAAAGGAGAACTCA   600
CTGCCTACCTGTGAATTCCCCTAGTCCTGGTTCTGCTGCCACTGCTGCCTGTGCAGCCTG
TCCCATGGAGGGGGCAGCAACTGCTGTCACAAAGGTGATCCCACCCTGTCTCCACTGAAA
TGACCTCAGTGCCACGTGTTGTATAGGGTATAAAGTACGGGAGGGGGATGCCCGGCTCCC
TTCAGGGTTGCAGAGCAGAAGTGTCTGTGTATAGAGTGTGTCTTAATCTATTAATGTAAC
AGAACAACTTCAGTCCTAGTGTTTTGTGGGCTGGAATTGCCCATGTGGTAGGGACAGGCC    900
TGCTAAATCACTGCAATCGCCTATGTTCTGAAGGTATTTGGGAAAGAAAGGGATTTGGGG
GATTGCCTGTGATTGGCTTTAATTGAATGGCAAATCACAGGAAAGCAGTTCTGCTCAACA
GTTGGTTGTTTCAGCCAATTCTTGCAGCCAAAGAGCCGGGTGCCCAGCGATATAATAGTT
GTCACTTGTGTCTGTATGGATGACAGGGAGGTAGGGTGACCTGAGGACCACCCTCCAGCT
TCTGCTAGCGTAGGTACAGTCACCACCTCCAGCTCCACACGAGTCCCATCGTGGTTTACC   1200
AAAGAAACACAATTATTTGGACCAGTTTGGAAAGTCACCCGCTGAATTGTGAGGCTAGAT
TAATAGAGCTGAAGAGCAAATGTTCCCAACTTGGAGATACTAGTTGGTATTAGTATCAGA
GGAACAGGGCCATAGCACCTCCATGCTATTAGATTCCGGCTGGCATGTACTTTTCAAGAT
GATTTGTAACTAACAATGGCTTATTGTGCTTGTCTTAAGTCTGTGTCCTAATGTAAATGT
TCCTTTGGTTTATATAACCTTCTTGCCATTTGCTCTTCAGGTGTTCTTGCAGAACACTGG   1500
CTGCTTTAATCTAGTTTAACTGTTGCTTGATTATTCTTAGGGATAAGATCTGAATAAACT
TTTTGTGGCTTTGGCAGACTTTAGCTTGGGCTTAGCTCCCACATTAGCTTTTGCTGCCTT
TTCTGTGAAGCTATCAAGATCCTACTCAATGACATTAGCTGGGTGCAGGTGTACCAAATC
CTGCTCTGTGGAACACATTGTCTGATGATACCGAAGGCAAACGTGAACTCAAAGAGGCAC
AGAGTTAAGAAGAAGTCTGTGCAATTCAGAGGAAAAGCCAAAGTGGCCATTAGACACACT   1800
TTCCATGCAGCATTTGCCAGTAGGTTTCATATAAAACTACAAAATGGAATAAACCACTAC
AAATGGGAAAAGCCTGATACTAGAATTTAAATATTCACCCAGGCTCAAGGGGTGTTTCAT
GGAGTAATATCACTCTATAAAGTAGGGCAGCCAATTATTCACAGACAAAGCTTTTTTTT
TTCTGTGCTGCAGTGCTGTTTTCGGCTGATCCAGGGTTACTTATTGTGGGTCTGAGAGC
TGAATGATTTCTCCTTGTGTCATGTTGGTGAAGGAGATATGGCCAGGGGAGATGAGCAT   2100
GTTCAAGAGGAAACGTTGCATTTTGGTGGCTTGGGAGAAAGGTAGAACGATATCAGGTCC
ATAGTGTCACTAAGAGATCTGAAGGATGGTTTTACAGAACAGTTGACTTGGCTGGGTGCA
GGCTTGGCTGTAAATGGATGGAAGGATGGACAGATGGGTGGACAGAGATTTCTGTGCAGG
AGATCATCTCCTGAGCTCGGTGCTTGACAGACTGCAGATCCATCCCATAACCTTCTCCAG
CATGAGAGCGCGGGGAGCTTTGGTACTGTTCAGTCTGCTGCTTGTTGCTTCCTGGGTGCA   2400
CAGTGGTGATTTTCTTACTCACACAGGGCAAAAACCTGAGCAGCTTCAAAGTGAACAGGT
TGCTCTCATAGGCCATTCAGTTGTCAAGATGAGGTTTTTGGTTTCTTGTTTTGTAAGGTG
GGAAGAAGCACTGAAGGATCAGTTGCGAGGGCAGGGGTTTAGCACTGTTCAGAGAAGTCT
TATTTTAACTCCTCTCATGAACAAAAAGAGATGCAGGTGCAGATTCTGGCAAGCATGCAG
TGAAGGAGAAAGCCCTGAATTTCTGATATATGTGCAATGTTGGGCACCTAACATTCCCCG   2700
CTGAAGCACAGCAGCTCCAGCTCCATGCAGTACTCACAGCTGGTGCAGCCCTCGGCTCCA
GGGTCTGAGCAGTGCTGGGACTCACGAGGTTCCATGTCTTTCACACTGATAATGGTCCAA
```

| | |
|---|---|
| TTTCTGGAATGGGTGCCCATCCTTGGAGGTCCCCAAGGCCAGGCTGGCTGCGTCTCCGAG | |
| CR1 | |
| CAGCCCGATCTGGTGGTGAGTAGCCAGCCCATGGCAGGAGTTAGAGCCTGATGGTCTTTA | |
| CR1 | |

FIG. 4A

```
AGGTCCCTTCCAACCTAAGCCATCCTACGATTCTAGGAATCATGACTTGTGAGTGTGTAT  3000
                        CR1
TGCAGAGGCAATATTTTAAAGTTATAAATGTTTTCTCCCCTTCCTTGTTTGTCAAAGTTA
     CR1
TCTTGATCGCCTTATCAATGCTTTTGGAGTCTCCAGTCATTTTTCTTACAMCAAAAAGAG
GAGGAAGAATGAAGAGAATCATTTAATTTCTTGATTGAATAGTAGGATTCAGAAAGCTGT
ACGTAATGCCGTCTCTTTGTATCGAGCTGTAAGGTTTCTCATCATTTATCAGCGTGGTAC
ATATCAGCACTTTTCCATCTGATGTGGAAAAAAAAATCCTTATCATCTACAGTCTCTGTA  3300
CCTAAACATCGCTCAGACTCTTTACCAAAAAAGCTATAGGTTTTAAAACTACATCTGCTG
ATAATTTGCCTTGTTTTAGCTCTTCTTCCATATGCTGCGTTTGTGAGAGGTGCGTGGATG
GGCCTAAACTCTCAGCTGCTGAGCTTGATGGGTGCTTAAGAATGAAGCACTCACTGCTGA
AACTGTTTTCATTTCACAGGAATGTTTTAGTGGCATTGTTTTTATAACTACATATTCCTC
AGATAAATGAAATCCAGAAATAATTATGCAAACTCACTGCATCCGTTGCACAGGTCTTTA  3600
TCTGCTAGCAAAGGAAATAATTTGGGGATGGCAAAAACATTCCTTCAGACATCTATATTT
AAAGGAATATAATCCTGGTACCCACCCACTTCATCCCTCATTATGTTCACACTCAGAGAT
ACTCATTCTCTTGTTGTTATCATTTGATAGCGTTTTCTTTGGTTCTTTGCCACGCTCTGG
GCTATGGCTGCACGCTCTGCACTGATCAGCAAGTAGATGCGAGGGAAGCAGCAGTGAGAG
GGGCTGCCCTCAGCTGGCACCCAGCCGCTCAGCCTAGGAGGGGACCTTGCCTTTCCACCA  3900
GCTGAGGTGCAGCCCTACAAGCTTACACGTGCTGCGAGCAGGTGAGCAAAGGGAGTCTTC
ATGGTGTGTTTCTTGCTGCCCGGAAGCAAAACTTTACTTTCATTCATTCCCCTTGAAGAA
TGAGGAATGTTTGGAAACGGACTGCTTTACGTTCAATTTCTCTCTTCCCTTTAAGGCTCA
GCCAGGGGCCATTGCTGAGGACGGCATCGGGGCCCCCTGGACCAAATCTGTGGCACAGAT
GGTTTCACTTACATCAGTGGATGTGGGATCTGCGCCTGTAATGTGTCCTTCTGAAGGAAG  4200
GAACGTGCCTTCCAAGTGCCAGCCCCACAGCCCCCAGCCCCTCCCTGTGCTGCTCCAATT
CATCTCCTCTTCCTCCTTCTCCCTTTGCTGTTTGTGCTCGGGTAGAAATCATGAAGATTT
AGAAGAGAAAACAAAATAACTGGAGTGGAAACCCAGGTGATGCAGTTCATTCAGCTGTCA
TAGGTTTGTCGTTGCTATAGGTCTGTATCAGAGATGCTARCACCACTTTGCTGTCGGTGC
TTAACTCGGGTGAACTCTCCTTCACTCGCATCATTTGCGGGCCTTATTTACATCCCCAGC  4500
ATCCATCACCCTCTGGGAAAATGGGCGCACTGGATCTCTAATGGAAGACTTTCCCTCTTT
CAGAGCCTGTGGGATGTGCAGTGACAAGAAACGTGGAGGGGCTGAGCAGCAGCACTGCCC
CCAGGGAGCAGGAGCGGATGCCATCGGTGGCAGCATCCCAAATGATGTCAGCGGATGCTG
AGCAGGCAGCGGACGAACGGACAGAAGCGATGCGTACACCTTCTGTTGACATGGTATTTG
GCAGCGATTTAACACTCGCTTCCTAGTCCTGCTATTCTCCACAGGCTGCATTCAAATGAA  4800
CGAAGGGAAGGGAGGCAAAAAGATGCAAAATCCGAGACAAGCAGCAGAAATATTTCTTCG
CTACGGAAGCGTGCGCAAACAACCTTCTCCAACAGCACCAGAAGAGCACAGCGTAACCTT
TTTCAAGACCAGAAAAGGAAATTCACAAAGCCTCTGTGGATACCAGCGCGTTCAGCTCTC
CTGATAGCAGATTTCTTGTCAGGTTGCGAATGGGGTATGGTGCCAGGAGGTGCAGGGACC
ATATGATCATATACAGCACAGCAGTCATTGTGCATGTATTAATATATATTGAGTAGCAGT  5100
GTTACTTTGCCAAAGCAATAGTTCAGAGATGAGTCCTGCTGCATACCTCTATCTTAAAAC
TAACTTATAAATAGTAAAACCTTCTCAGTTCAGCCACGTGCTCCTCTCTGTCAGCACCAA
TGGTGCTTCGCCTGCACCCAGCTGCAAGGAATCAGCCCGTGATCTCATTAACACTCAGCT
CTGCAGGATAAATTAGATTGTTCCACTCTCTTTTGTTGTTAATTACGACGGAACAATTGT
TCAGTGCTGATGGTCCTAATTGTCAGCTACAGAAAACGTCTCCATGCAGTTCCTTCTGCG  5400
CCAGCAAACTGTCCAGGCTATAGCACCGTGATGCATGCTACCTCTCACTCCATCCTTCTT
CTCTTTCCCACCAGGGAGAGCTGTGTGTTTTCACTCTCAGCCACTCTGAACAATACCAAA
CTGCTACGCACTGCCTCCCTCGGAAAGAGAATCCCCTTGTTGCTTTTTTATTTACAGGAT
CCTTCTTAAAAAGCAGACCATCATTCACTGCAAACCCAGAGCTTCATGCCTCTCCTTCCA
CAACCGAAAACAGCCGGCTTCATTTGTCTTTTTAAATGCTGTTTTCCAGGTGAATTTTG  5700
GCCAGCGTGTTGGCTGAGATCCAGGAGCACGTGTCAGCTTTCTGCTCTCATTGCTCCTGT
TCTGCATTGCCTCTTTCTGGGGTTTCCAAGAGGGGGGGAGACTTTGCGCGGGGATGAGAT
AATGCCCCTTTTCTTAGGGTGGCTGCTGGGCAGCAGAGTGGCTCTGGGTCACTGTGGCAC
CAATGGGAGGCACCAGTGGGGGTGTGTTTTGTGCAGGGGGGAAGCATTCACAGAATGGGG
CTGATCCTGAAGCTTGCAGTCCAAGGCTTTGTCTGTGTACCCAGTGAAATCCTTCCTCTG  6000
TTACATAAAGCCCAGATAGGACTCAGAAAATGTAGTCATTCCAGCCCCCCTCTTCCTCAGA
TCTGGAGCAGCACTTGTTTGCAGCCAGTCCTCCCCAAAATGCACAGACCTCGCCGAGTGG
AGGGAGATGTAAACAGCGAAGGTTAATTACCTCCTTGTCAAAAACACTTTGTGGTCCATA
```

FIG. 4B

```
GATGTTTCTGTCAATCTTACAAAACAGAACCGAGAGGCAGCGAGCACTGAAGAGCGTGTT
CCCATGCTGAGTTAATGAGACTTGGCAGCTCGCTGTGCAGAGATGATCCCTGTGCTTCAT  6300
GGGAGGCTGTAACCTGTCTCCCCATCGCCTTCACACCGCAGTGCTGTCCTGGACACCTCA
CCCTCCATAAGCTGTAGGATGCAGCTGCCCAGGGATCAAGAGACTTTTCCTAAGGCTCTT
AGGACTCATCTTTGCCGCTCAGTAGCGTGCAGCAATTACTCATCCCAACTATACTGAATG
GGTTTCTGCCAGCTCTGCTTGTTTGTCAATAAGCATTTCTTCATTTTGCCTCTAAGTTTC
TCTCAGCAGCACCGCTCTGGGTGACCTGAGTGGCCACCTGGAACCCGAGGGGCACAGCCA  6600
CCACCTCCCTGTTGCTGCTGCTCCAGGGACTCATGTGCTGCTGGATGGGGGGAAGCATGA
AGTTCCTCACCCAGACACCTGGGTTGCAATGGCTGCAGCGTGCTCTTCTTGGTATGCAGA
TTGTTCCAGCCATTACTTGTAGAAATGTGCTGTGGAAGCCCTTTGTATCTCTTTCTGTG
GCCCTTCAGCAAAAGCTGTGGGAAAGCTCTGAGGCTGCTTCTTGGGTCGTGGAGGAATT
GTATGTTCCTTCTTTAACAAAAATTATCCTTAGGAGAGAGCACTGTGCAAGCATTGTGCA  6900
CATAAAACAATTCAGGTTGAAAGGGCTCTCTGGAGGTTTCCAGCCTGACTACTGCTCGAA
GCAAGGCCAGGTTCAAAGATGGCTCAGGATGCTGTGTGCCTTCCTGATTATCTGTGCCAC
CAATGGAGGAGATTCACAGCCACTCTGCTTCCCGTGCCACTCATGGAGAGGAATATTCCC
TTATATTCAGATAGAATGTTATCCTTTAGCTCAGCCTTCCCTATAACCCCATGAGGGAGC
TGCAGATCCCCATACTCTCCCCTTCTCTGGGGTGAAGGCCGTGTCCCCCAGCCCCCCTTC  7200
CCACCCTGTGCCCTAAGCAGCCCGCTGGCCTCTGCTGGATGTGTGCCTATATGTCAATGC
CTGTCCTTGCAGTCCAGCCTGGGACATTTAATTCATCACCAGGGTAATGTGGAACTGTGT
CATCTTCCCCTGCAGGGTACAAAGTTCTGCACGGGGTCCTTTCGGTTCAGGAAAACCTTC
ACTGGTGCTACCTGAATCAAGCTCTATTTAATAAGTTCATAAGCACATGGATGTGTTTTC
CTAGAGATACGTTTTAATGGTATCAGTGATTTTTATTTGCTTTGTTGCTTACTTCAAACA  7500
GTGCCTTTGGGCAGGAGGTGAGGGACGGGTCTGCCGTTGGCTCTGCAGTGATTTCTCCAG
GCGTGTGGCTCAGGTCAGATAGTGGTCACTCTGTGGCCAGAAGAAGGACAAAGATGGAAA
TTGCAGATTGAGTCACGTTAAGCAGGCATCTTGGAGTGATTTGAGGCAGTTTCATGAAAG
AGCTACGACCACTTATTGTTGTTTTCCCCTTTTACAACAGAAGTTTTCATCAAAATAACG
TGGCAAAGCCCAGGAATGTTTGGGAAAAGTGTAGTTAAATGTTTTGTAATTCATTTGTCG  7800
GAGTGCTACCAGCTAAGAAAAAGTCCTACCTTTGGTATGGTAGTCCTGCAGAGAATACA
ACATCAATATTAGTTTGGAAAAAAACACCACCACCACCAGAAACTGTAATGGAAAATGTA
AACCAAGAAATTCCTTGGGTAAGAGAGAAAGGATGTCGTATACTGGCCAAGTCCTGCCCA
GCTGTCAGCCTGCTGACCCTCTGCAGTTCAGGACCATGAAACGTGGCACTGTAAGACGTG
TCCCCTGCCTTTGCTTGCCCACAGATCTCTGCCCTTGTGCTGACTCCTGCACACAAGAGC  8100
ATTTCCCTGTAGCCAAACAGCGATTAGCCATAAGCTGCACCTGACTTTGAGGATTAAGAG
TTTGCAATTAAGTGGATTGCAGCAGGAGATCAGTGGCAGGGTTGCAGATGAAATCCTTTT
CTAGGGGTAGCTAAGGGCTGAGCAACCTGTCCTACAGCACAAGCCAAACCAGCCAAGGGT
TTTCCTGTGCTGTTCACAGAGGCAGGGCCAGCTGGAGCTGGAGGAGGTTGTGCTGGGACC
CTTCTCCCTGTGCTGAGAATGGAGTGATTTCTGGGTGCTGTTCCTGTGGCTTGCACTGAG  8400
CAGCTCAAGGGAGATCGGTGCTCCTCATGCAGTGCCAAAACTCGTGTTTGATGCAGAAAG
ATGGATGTGCACCTCCCTCCTGCTAATGCAGCCGTGAGCTTATGAAGGCAATGAGCCCTC
AGTGCAGCAGGAGCTGTAGTGCACTCCTGTAGGTGCTAGGGAAAATCTCTGGTTCCCAGG
GATGCATTCATAAGGGCAATATATCTTGAGGCTGCGCCAAATCTTTCTGAAATATTCATG
CGTGTTCCCTTAATTTATAGAAACAAACACAGCAGAATAATTATTCCAATGCCTCCCCTC  8700
GAAGGAAACCCATATTTCCATGTAGAAATGTAACCTATATACACACAGCCATGCTGCATC
CTTCAGAACGTGCCAGTGCTCATCTCCCATGGCAAAATACTACAGGTATTCTCACTATGT
TGGACCTGTGAAAGGAACCATGGTAAGAAACTTCGGTTAAAGGTATGGCTGCAAAACTAC
TCATACCAAAACAGCAGAGCTCCAGACCTCCTCTTAGGAAAGAGCCACTTGGAGAGGGAT
GGTGTGAAGGCTGGAGGTGAGAGACAGAGCCTGTCCCAGTTTTCCTGTCTCTATTTTCTG  9000
AAACGTTTGCAGGAGGAAAGGACAACTGTACTTTCAGGCATAGCTGGTGCCCTCACGTAA
ATAAGTTCCCCGAACTTCTGTGTCATTTGTTCTTAAGATGCTTTGGCAGAACACTTTGAG
TCAATTCGCTTAACTGTGACTAGGTCTGTAAATAAGTGCTCCCTGCTGATAAGGTTCAAG
TGACATTTTAGTGGTATTTGACAGCATTTACCTTGCTTTCAAGTCTTCTACCAAGCTCT
TCTATACTTAAGCAGTGAAACCGCCAAGAAACCCTTCCTTTTATCAAGCTAGTGCTAAAT  9300
ACCATTAACTTCATAGGTTAGATACGGTGCTGCCAGCTTCACCTGGCAGTGGTTGGTCAG
TTCTGCTGGTGACAAAGCCTCCCTGGCCTGTGCTTTTACCTAGAGGTGAATATCCAAGAA
TGCAGAACTGCATGGAAAGCAGAGCTGCAGGCACGATGGTGCTGAGCCTTAGCTGCTTCC
TGCTGGGAGATGTGGATGCAGAGACGAATGAAGGACCTGTCCCTTACTCCCCTCAGCATT
```

FIG. 4C

CTGTGCTATTTAGGGTTCTACCAGAGTCCTTAAGAGGTTTTTTTTTTTTTGGTCCAAAA 9600
GTCTGTTTGTTTGGTTTTGACCACTGAGAGCATGTGACACTTGTCTCAAGCTATTAACCA
AGTGTCCAGCCAAAATCAATTGCCTGGGAGACGCAGACCATTACCTGGAGGTCAGGACCT
CAATAAATATTACCAGCCTCATTGTGCCGCTGACAGATTCAGCTGGCTGCTCCGTGTTCC
AGTCCAACAGTTCGGACGCCACGTTTGTATATATTTGCAGGCAGCCTCGGGGGGACC<u>ATC</u>
<u>TCAGGAGCAGAGCACCGGCAGCCGCCTGCAGAGCCGGGCAGTACCTCACC</u>ATGGCCATGG 9900
   OVOMUCOID 5' UNTRANSLATED REGION
<u>CAGGTGTCTTCGTGCTGTTCTCTTTCGTGCTTTGTGGCTTCCTCCCAGGTGAGTAACTCC</u>
      OVOMUCOID CODING REGION
<u>CAGAGTGCTGCAGAAGCTT</u>                           9979

FIG. 4D

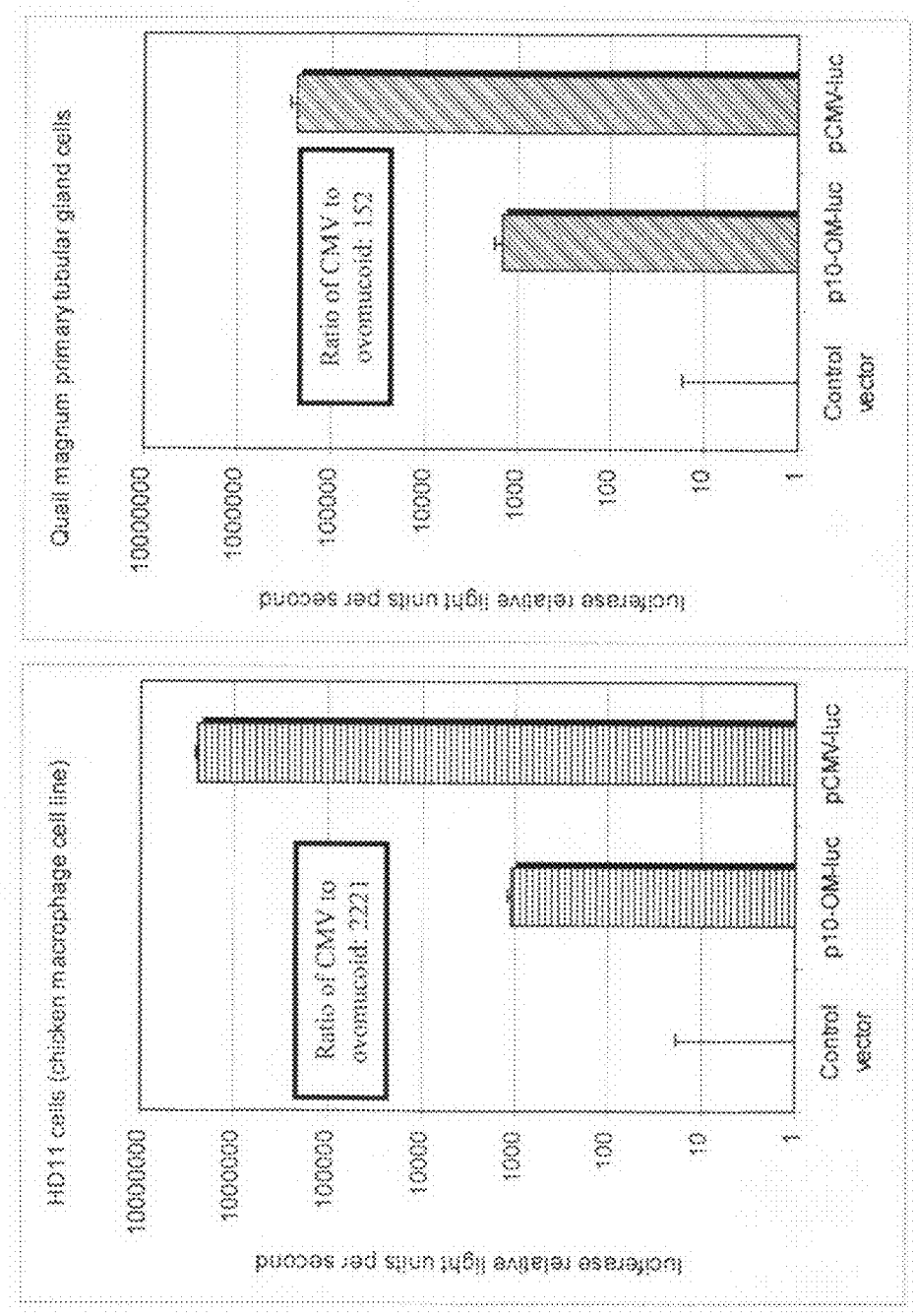

```
AAGCTTTGTGCTTTCTGCCTGAATAAAAGAAACCTGAACTCTGTTCACCCAGTCCCTGTC    60
AGGCAATTACTGACAGAGCACCTATGGTCTGTGTTTGGCCAGAACATAGGCTAAGGAAGA
TACCTCCTGTTTATAAAGCACGCCTTTGGCATCTGGCAAGTAATTAGTGATGGCGCATGA
GAGCTCTGACTAGGGCAGGGTGTGGGACAGGCTGGCTCTAATTGTGCCCTGTTTATCTTG
TTGATGCACACGGCTGGTTTCTTTCACCCACAGCTGTCTCTCTAGACAACATACCTTTAT   300
GGAGAGGAACGTGTCTTTTCCAATCTTGGGTTTTCATTCAGAATTGGAGTGAACTGGTCT
CCATCAGATAGCATTGGCTGCGGTGATTTATTCTTTTACACTTCCTAGTTAAGCAGGATA
ACTCTCTGGCTCTGCTGTGTCTAGGCAATTTAAATGATTTATAAAGCATAGCTGTTTTAA
GGAAATCTTTTTTTAAACATTTGACTTGCCAATGTGTGGTCCTAAAGGCAGAAGGACTGT
TCCAGAGTGTCAGGCAGAGACCTACCCTGGATTTCGTTGTTCAGCTACCCATTCAGTGTG   600
GCTTTTGGCAAGGAATTCTCTGGACCTGACTTCCCTACCTGCAGAGCTGGGATAAGCTAT
CAAACCATCTCCTCCACACACTGTGAGGGTGGGAAAAAAACCCAAACCCTTAAAAGTGCT
GTATAAAGGCGCCTTAAGGCTCAGTATAGCATGTGTGCTGCTGATGCCCCAGACCTGTTT
GCGGGTCCTGAAGGTCATAGGAGAACTGCTCAGAAGAGACAGAAATGCTTAAGAAGGTTT
TACTACAAAAGTCTTGTGATGTTAACACATAATATCACATTGTGCAGAAGGTACAAATGC   900
CCCCTCCTATCCCTGCACACCTGGAAGCTCAAGGTATGGAAGGGTTTGTTGTCTGCAGCC
TCTTCGCTGCCCTCTGCTTTTTAAGATCCTGGGTAGTGTGCTCAGTGTGTGCCCTCAGCA
GTTTGGGAAACGGACATCTTCATGCAAAATTAAGCAAGGAAGTGTTGCTTTTATACTCAG
AGTAGAATCTAAGTTCTTCAGGCAGGCTCTTGTGTGCCGCCTCTATTAGAAATAAAACTC
CCCCGGATCAGAAGATGAATGTGCTCAGCTAAGAACACAGATTTATTTGCTTTACAATGC   1200
GTGCTATGGTTTAAGAAAAACACATCAGGCAAACAATTTATGGTTTGCCACTGAGTTGTG
CCTGAAGGAAACACAACTGTTAGAGATGTAATTGATTGGGCGGTGACGCTGTGTGGATTC
ATGGGAGATGCATCTTGGTCAGCATGTCTGTGTGAAACCACATTTCTGGTGCTGCTGCAG
GACGAGTGCCGGGAGTTCCGGGATCTGTTCAAGAATGGGAAGCTTTCCTGCACGAGGGAG
AATGATCCCGTCCGGGATTCCTCGGGGAAGCAGCACAGCAATAAGTGCATCATGTGTGCG   1500
GAGAAGTTGTGAGTAGAGGAAGCCAATGTTTGTTATCGAGAGTGGCAATGGGGCCGGGGT
GGGCTCCTACAGCAATGTTCTCCTCACTTTCTCATCCTTCTCTTTCAGCAAAAGGGAGAA
TGAGCAGAAGGCGACCTCAACCAGAGGGAAACAAAAGGTGAGGTTAAAGTATTGGGTTCA
TATACAAGTCTATAGGATTCTTACCCAATATTACCACACTTGATTTCTTTGTCACTCTGG
GGATCCATGTGGCTTTTCCTGCTTGTATCTCGTTGATGCTCTTTCATGCCCTGAGAGAAT   1800
AGTTTGTCTGAACGCTGCAGTCTATCCCACTGACCGCAGTGACATGGGAGCAAACCCCAT
CGCAATAAGAAGCTGAGCAGAACTGCCCTGACATCTGGCACAAGGGCAAGAAGGCACTGC
TGCTGAGAGCGCTAATGAGGTTGAAAAGAAATCTGGGTGAGAAGCTTTAAATGTGAGCT
CTGAGATGCTCAAAAGTTCATTATGTCGTGGGAGGAGAGTTCAGCCCTGTGCTGTCCCTG
GGGTGGCTCGGTTTCAGCTTTCCCTGATTGGAAACCTCACTCTCATGATGCAGCTGCTGT   2100
GCCCTTGTGCACCGATACTTCTCTGGTGAGAGCAATTCAGCAAGGGGAAGGAAAAAGAAG
CACTAAGTAAATCTTGCCATTTCTGTCTTGCGAGGAACTGGTACGGTCCCCTTAAGCCTC
ATTCTTGGGATAATCCTGTTTCAGTGCTTTTCCTAATGACAGTGGCACAAAAAAAATGG
AAGCGTTAATGAAACTTGCTGATGGCAAAGCTGGGAGGGAGGATCAGCAGATCACTCAGG
ACTAATTGGATAGCACTGAGGCCTGGAGTAATAGAAACAAGATAAAATGTAATAACAGAG   2400
AGTGCAAGATCACACAGGCAGTGATTAACGAGAATTCCTGCTCATCAATTAGAAATGACA
AAGGATAAGAAAGCTCTGCATTTATTAGTGGGTCACGGATGCGGCAGGCCTGAGAAGGAG
GCAAATGCACATCTCAGCAAGGTCTGTGCAGCAGAGGTCGGCTGGCAGCAAATCTCCAG
AAATACTGCTTTGAAGAGAGAGGGTTTGAGAGACGCTGTTAGGGAGAAGCAGCTCTGCCA
CAGCAGGTCTGGGGTTCACCTGGGGTTTGGCTCATTGCCTCCCTGTGTCCCTCCTCCACG   2700
CTGCCAGTGCTGCACTGGGAAGGTGTGGGTAAGAAGCAATGGCTAAGGGATCTGGTTATA
CACCTCCTGTATCTGCTATTTGGGATTGGCTACTGCAGGGCCTCAGGTCCCTGACTTAAA
AGTGGGGACTTCGAAGCATGTTTGCATTGTGCTGTCGTGCCTTAGATGTTGCTGCTGGGT
CCTCAAAGTCCTGTTGGTTGTGGGTGGGGGGACTTCTTGCTTCCTATGTGAAGTTTTC
TGAGCTGCAACTTCAGCAACAGCTGTAAGAGTGCATTAAGGGCAGTGGGAGAAGTGGGAG   3000
GGACCCCATTACCTCATCGGGTATCGCTGGCATGCTTTGGATAGCCCCACGTGGAGCGTG
ACAATTAGAGCACGGCAGAGAGCTCCCAACACGTGCCATGCAGGCAGAGGCACCCGCCGC
TCTTCTGACTCACTCTGTTTGTAGCCATGAGGCTGTGCCACGTGCCCTCTTCTCTCTCTC
ACACCTGGGCTCTCCTGGGGCGCGTTTGGGAAGCCTCTGGAGGATCGGAGGGATGTGGCA
```

FIG. 14A

```
GGGTGCCCTGACTGCTGCTCCTTCCGCAGGATGACTGCAGTGAGTACCGCTCCCAGTTTG   3300
AGGCTGGCGGACGCCTGTCCTGCACGCGGGAGAACGACCCCGTCAGGGATTCCTCTGGCA
AGCAGCACACCAACAAGTGCCTCATGTGTGCCGAGAAGCTGTGAGTACAGTTCCTGGCAA
CAGCAAAGAGGGAAACCTCACATTGCGAAACTGCAGCTTCTGCCTGTGTGGCTGCGCCTG
GGGGAGTCCCGAGTCCCAGCGGCCCCCAGGAGCTGCTCCTGCTGTAGGGCTGTGGCTAC
TGCCCCTCTTCCCACCTCCCCCCTAACCCCTCAGGGAGCAGAGGAGAAGCAGGGTTGATA   3600
GAGAGCAGCCCTTTCCTTGGGGCAGCTCCCAAGGAAAGTTTCCCACGCGTGTACTTTGCC
TTCCAGATGCTCTCTACTCCCATAGAGCATATGCAGAAGCAGCCCTGATATGAAAGCA
GCCACCTGGAGCCGGGATGTAGCATACAGTGGGAATGGTGAGGAGAAGGGAGAAGGCTTA
GGGGTGGGAATTAGGTGCAGGGCCACCAGGGATGGGGAGGCTGGTGCCTAATGACATGAT
GCTGGCTTGCAGGGCAGCCCCAGGTCCTGGCAGCGTTCGCACTGCCATAGTGCTCCTTTC   3900
TTTCTCCTCTCCCTTTTTCCAGCAAAAAGAAGCTCAAAGAGGAGGTCAGTCTGGTGGA
ACTGCCCAGCGCAACAAGCAGTCCACTGCAGAGTGTGCAAACCAGGTGAGACTGAGCTCA
GAGCCTCACCAGGCTTGGGAAAAGGGGTTGGTGGATCTGGGGACCCCGATGGTCAAGGGC
TGCCTGTGGTCCTGGTGTTTGGGGTGCAGGAGCCTGCTGGTGATGGCAGAGAGGCAGGTT
GCATTGCAAGCCCTGCTAGTTCATGGGATGGGTTTGTGTATGAGCGTGCATAGTGGGCAG   4200
TTCTGGACTCCTCTATGGGGCACGCATCAGAGCTATTCTTCAGAAAGAGCCCCATGGTT
CCTAGGGTCCAGGGGGATGAGAGGGAAGGACAGGAGCTGCTTTAATCTCACTGCTTTACT
GCTTGGTTGTCAAACACGATCCTGCCCCTTTTCCAGAAGAGCTGCAGTGGCTCAGGGTTA
CAGCGGGGTGTAAATGAGAGACGGCCGTTCTCCACAAACAGAGGGTGAGTACAGCAGCAC
TGGGATCCCAGCCTGGCCCCACAAGTCCTGGGGTCTTGACACTGAGAAGAAACACATAAA   4500
ATAGGGCATATACAACCCTTTCTCCTTTCCAAAGACATTCTTGCTTCCCTGCACACGAA
GCACTGGTGACTGCTACACTCAAAATCCCTCCCCAGCCTTGCCCCCTGAATCCTGCCTCC
TGGCAGGCACACACTTGTCCTGCTGCCTGGTCCAGCGCATCCTCATCTGCTGACCTGAGG
CAGTGCTGTGTGTGCACCATGTGCTGTCTGGGCACTGAGCGACTCCTCTGGGTTTTTAGG
GCTGCCAGGCTCTGGCAGGGTGCAGATGCTGTGTTATCTAAGCCTTGAGGAACTCTCTTA   4800
GTCTTCCTGTTTTTGTTGGTGAGGCCCATTCATCTGCCCCAGTCAGCACTGCCAGCAGA
CAAACAGTGCACAGCTCTCCATGGCAGCAATGGCTGTAGCATATGTAGGGGCCAGGTTTC
TGGGATCATCTCTGTGACGGACATCTCTTGCTGACCGCCCATAAGGACTCAAAAGTCCCG
TTGCAGGGAGTGCCTCCATCCCATGGCAAGCCAAGTGCCCTGTTGAAAAAACAAGGTGCA
GAATAATGGCAATGGACCTTAGTGCAGTTTAATTCCACCCTGGGGTGATGATGTGGCTGA   5100
GTGGGTCTGCATACCCTTGGCTGTGCCATGAGCTCTGTGCTTTCTCTCCCTGCCAGCCCA
CAAGGAGACTTGGCTCAGGACTGCAGCCCGGCACCTGGCCGCCAGGGACAGAGCGGAGGC
ACCAACACCTACCAGCCGGTATGCCCAGCTCATGGGTCAGGCACAGCCTTTCCCAGCA
GCTGCCCCAGTTTCCATTGTCAACCTAAAGCCTCACAATGGGACCTGTATCCTTGGAGGG
GTTTAAATGGGTGGTAGAGTCCGTACCCTGATGCTGTCCCCTGGCCTCAAAGAGGAGTGA   5400
GGCTGCACACGTCCAAACGGGAGTCACTGAAGCCAGTGCTGCTGCTGGTGTTGGCTCACT
GTAGAAGTATGTCAGGTATGAGAGAGCATCCTCCAGGAGGTGATGGTGGTGTCCCTTCCT
GCATGCTGAGATGTTGGGTTGAAGACTGTGGCCAGAGCAGGGTGCTGGGGCTGAGCGGGG
GATAAGGACAAGGCTGATAAGAGGAGGGGAGAGGGAGTAGTGGGGAGGACACGGTGAGC
AATAGATAACGACTGTTTGTGGAATCATGTGGGAGGGAGAAGAGGGTGTATGCTCTCTCC   5700
ATCTCCACAAAAAGAAAATTTGTTATTTTCAACCAAGCTAAAGCAGAAATTATGAAACTA
ATAGGAGAAATAAGTTACTATAAAAGGATGACTAACCTGTGGATCTTGCTGTCACGGG
GTGTTGCCAAGAGCTACAGTGATTAAAAAAAATGACTTGCCACTTATAGTCCATACAGCA
ATTTAGGTAACATTTTGGAAGGGATAGGAAATGCCTTTCTGTGGGCTGGAGGGACCTGA
GTGCAGACTGCCTTAACTCTCTCTGAAGTCTCTGTCACTGACTGCCCTTAGAAAAATGAT   6000
ATTAGAATAGAAAAACCAGGGAGGCGGTTCAGGTATGGCAGTTTTAATGCATTCCAGAGG
AAGCATTAGGCATAATAATGCCAGTCTGCTTCAGGGCTTAGTGGTATTTCCTGGTAGCTC
CGGTGAAGGAGTGGATGCTGATCAGCCTGACTGACGAGGGTGATTCAGAGAGCAGATCT
GTGTCTCTCCTCGCTGCAGGGCCACCCGTGGGCTCTGTCCCAGGGAGATGCTGTCCTGAA
GGAGAGGTGGCAGTCACTGTGAGGACTGTGGGGACTGTTGGTGTGGCGGCGGTTGCACA   6300
CGCGTGGGTCACACCGTGGGCAGTGGTGTCTGGTGTGTGGGAAGGCATCTGGCAGGGAAC
TGCAAAGGTCAGCGCTGTCTGTCTTTGTGTCATCGTTAATTACCCAGGTGAGGGAGGAAG
CAGCACATTAATGAAATTAGCAAGTGATGTTTAAACAGAGGGTGTTACTGCAGCAACCTG
```

FIG. 14B

```
TGCCACTGAACCCCCTGCATTGCCCAGCTGGGAAACCTTTCTTCTCCATGGTGCTTTCAA
CCCCATAGTGCTGCTGACCCCAGCAAAGCAATGAGCCATTGCTTAGTGCTGAATGGGGTT    6600
TTTTTCTCCAAGTGGGACAGGAGGTGAGATGTCCTTCCTGCAGCTCTTCTCCAATTGCA
CCATTTGCAGTCATTGCAACATTTTTTATAGGACCTGGAGAAGGGGATGGGAACAGAGAA
TTCACTCCTTTTGTCTCTGCATCTTTTTTTTTGGCCTTTGGTGCAGAGGTGGGCAGTG
AGGCTGAGGAAGAGAGGGGGCTGTAGGATCTCTGACCTCTGCTGTCTGAAACTTGCCATG
ATTCTGCAGGCACCTGTGCCAGAATGCTCATGGGCTGATAATCTAATCATGAGGAGTCTT    6900
GTTCCTCCTGCTCCGAGCTCTTTCTAGCTGTGCCACGTCTGCTTTGTAGGAAATTCGATG
CCTAGATGCTCCTGCTGTTATGCTGGAGAATAAAACGAGAGGGCACGCTTAATTAGTCAG
AGCTTTTCATACATGTTTGCATCTCTTCATTCCGTGGGTGTCAAGTTGTGCTGTGTGTCG
GGCTGCCCTTGGGCAGCTGGACTCAATTGTCAAGGTTTTCCCTTTGTTTCTGCCAAGTGG
CTTGCAGAAGCAACAGGTGTGAAAGCTCTGATAAAGGACAAAGGACAGGTAGCAGAAGTT    7200
TATTGTATTCTCGTGGATTTGCAGGGAGAAGTAAAAGTGCCCTGGACTGAGATGTCAGGG
TGGATCAGATGAGTGTATCCATGCCTGGCAATGGGGTCAGGGCAGCTTTGTCCCCACATC
GTGGCTGGTTGGCCCAATAGGAGGCGTTACCTCTTTGCTGAAGGTGTGATGGAGCTCAGG
GCAACGCCTGGTTTGTGAGTGCTTTGAGCGGTGCGCAGGAGGGTCTTGCAAGAGAACCAG
CACCAAATGTGATTTCTTTCTCTTCAGCTGGACTGTGATCGAATTCTGCACGGGGTAA    7500
AGGGTGGAAGGATTTTCTGCAGCGAATCCTCACAACCCGTCTGTGGCACTGATGGGAAAA
CATACAGAAATGAATGTGACTTGTGTTCAGCTGCCATGTGAGTAGGCGGAGAGATTTCAG
TAATACAGGGCCATCCACCATTCCCGAGTGTCTTTTGCAGCACAGTGTTTGTTTTGATAT
ACCATGACTCACTATCAAGTGTGTCCTTGGTGCCTCGCTGTTAAGCAAACATAGATCAAA
TGTCTGAGATTAATATGATGACAGCTAATTAAGATACACAACTTTCCAGAGTCCCTTATT    7800
CCCTTTCTGCTCAATCATAGGATTGTTTGGGGAGTAATAAATGCCATCAAATTGGAAGTA
GCATCAAAGGTTTAAGGAGCCCACAGAGGACCACCGTGACGATGTCAGGGAGCTGTGGCA
CTGGAAGTGAATAAGCAATGTCTTGTTCTCCCTTTGCAGGAGAGCATCAGTTTACATCAC
GGTAAACTACCGAGGTGAATGCCGAAAGACTGTCCCTGAAATGGTAAGTGCCTCCCTGCT
GTGGCATCCCATTTCTTGTTCTGGGTGTGTGCTGGAGACCCAGCCTGGATCCCGTATCTG    8100
TGGTGGGATCATCAGAGCCCTGTTAGCAGGGTGCTTGTGGTTCACATGCGTAAATACACT
TCAGGCTTGGATTTAAGGCATTTTGAGGCATAATCTCCACGTTTTTCCAGGCTGTGTGG
TAGGGAGTGACATGTCTGGGAAAACATGTGGCTTTCCTCCTGGGATTTTGGTGAGGCCA
AGAAAAGATTGCAATCGCACAAACCATAAGGGCCTAATTTCCCAAATGATATCCAGGCAG
TTGGTTGGGAAGGAAATATATTCCCTAAGTGGTATCCTTTTGGGAAAGGTCTTGAATCTT    8400
GTGTGATTGCCTTGTAGTAGATGAGTCAAAGATTTGTTAGTGGTGCTTTGTCTTCCCGCT
CGTGGCAGCTCAGCGGCATTCAGAGCTTTGGTTTGGAGCCAGGGTGTCCCAGTTTGTGTG
TCTTGAGTGTATGGGACTGACCTTAGTGTTGGCATGGACTGTTGGAAAGCTGAGTATTCA
TTTCCCCAGGGAAACACCGACATCTATCCCCATTCCAAACTTGGAATGAATCAAAATATC
AAATCAGCCAAATGGAGAAGTTGTGCAAGTTTTTTTTGCAATGAGAGAGATGGCTTCTGA    8700
ATATGAATTTGCTGACAGTTTGTAGGTAAAACAGTATTGCCCGTTGAAAAGCTTTAGAGC
AAAATTACCATCATAGGGCTTTTACTCTCCTCTGCTTATTGACAGGATGCCCACCCATCC
CCACAACATTAGAAATGAGGCATCCCCATTCCTCTTCCTCTCTTCTGTGAAGTACCAGAG
TGCTCTCAACGCTGTTTAAAGCTGAAGAAAAATGCAGAGAAAGAGTTTTGCTTGTGATC
GTGCTGGAGGTCTTTGTGTCTCGCCCTTTGGTGCGATGGAGCCATTGCTGGTTTGTGTAT    9000
GCTGGGAGTGGAGGCACTATGCATACCTGCTGGTGGCTGTGCTAATGATGCTGGAGACAG
ACAAGGTTGGGTGTACCACGGCAACTGAAAACCAGAGAGGACTCCCTCAGAGTTGTGCCT
GGCTGGGATTCCTCACCATTTTGTGTTTTACCAAGACGTTTTACCAGCTCTCCAGTCTTT
GCAGTTAGAGGAATATGCCATACACTAAAAGTCAGACAATTTGTAGCTATTCCAAGGAGA
GCTGGAAGCAATTAAAGGGAAAGTGATAAGGTTTTCCACTGGGGAAAATCCCCACAAA     9300
AAACACCCCTCCAAACAAAGACTTATTATTTCGTTCTTTATGTATATTGTGTCACCTGAA
GAATCAGATTGGAAATTTATGGAAGCCCATTTCCTTAGCAAACCCCTTGTGTCCATCAAA
GACTTCCCTTTTTTTTCTCAGTTGGAAGCTTATGAACAATGTACTGACCAGTGTTATTTT
ATGCCTCTGAAATTCATGCTAACATTCAGCTTAATGCATCCTTCTGAAGGCCCAGGCACT
CGCTGTGTGAAGGAGATCACAGTGCCTTTGGCGTCAGAAATGATTTCAGGCTGTTGCAAT    9600
ACGCAGCACGAAGATGCAAAGGCCCAAAGACTTGAGCCTTGGAAAAAGATAGGAGATTGC
```

FIG. 14C

```
TGCCCGAAAATGTAGTTTGTCCTTGAGTTGTGTTTTGAAATTAGCCACGGTAATGCTGTG
TTGCCTGCCAAAATGTGTGTCCAAGCTCAGAGCCTGCAGCCATTCCTGCTAGCAAAGCCC
CTCCTGGATTTCCAGCAGTTTGTGGCAGTCCTTCCCTAGCAGTGGCTGGATTGCCATCAG
GGAGGGATGGCTGTAGGAAGGGACAGGAGAAATGTGGTTGGAGAGAGATCTGACATTAAA    9900
GGGTGCATCCGGACAGCCTGCACTGATGTGGTGGAAAACCTTCCTGCAGAGAGAGCCCTG
GGGCTGGCTGGCAGCTGGGCCCCTGCTGCCTGTGTGAGCTCTGTGCCACAACCAGCCTCC
TCTGATCCTGTTCTGCTTTACTGCAGATGAATGTAGCTGAGTCTAGGGTTTAGATTTCTA
TGTTTATTTTTAACAAGGCAGCTGGCCTCTGCGTCCTCCATGCTGTGACATACAGCTGTA
TTAATGGTGGGTCTTTCCAGAATGTTTCACTTTCAATGCTGTATTTTTTTTATTTTGCA    10200
GTTTCTCTTTTGTTCAGATGCTTTTCACACATCTCCCATGTGACAGATACCAGTCTGT
CCATGTTAGTTGACAGGTCAGGCAAAAAAAAAAAGGGATATCCAGTTTCTCCTTTTAA
TCTGTTTTCTAAAGAACAAAGAACTCCCAGCTTTCTAATGGGCAAGGCCATTTTCTTACA
GTGCTCTTTTTGTCATACCTTTCTTAAGAATGTAGTAGAAGGGAAAAGAAACAAACAAAA
AACCCAGGACCTTTTCCAGCTTGATATTGGTTTTGGAAAGCACACAGATCCAGGCTGAAA    10500
TCTGTTTGTTTTCTGAGTCTGGCAGTGACCCATCCACTGCCCCATCCCACCTGGTTCCTG
TGGCCACTGAGCTGCCCAAAGGGGCTGTCATGTAGCCCCTAATGCTCTGCCAGCGTAACA
GCAGTGGATGTACTTGTGGATCCACTTATATTTGCTCTTTCTTTCCAGAAATAATGGAG
TTCAGACTGCCAGCAAATACCAGGGATCAGCTGTGACCAAAGGTACAGTGGTGCGGTGAT
TTGCTCCCTCTTGGACAACTTGTCCGCATTTCACAAGGGTTTGGGTGTCAGACCTTGCCT    10800
GGGCAGGCTGCTGGGTATGTCTGGGGCAAAGGGCTCTGCAACACACCCTTCCCTATTGCC
ACAGCACAAGAATGAGGCGTGTGTCTTTTGCAGAAGTAGCAAGGTGATGGGAAGCCCCTG
CCAAGGGGGCTGAGCCCTTTGGGGTGTGCAAACTTCATGAGGACCTCCTCATCTCTCAGG
GGTGGGCCTTGCCCGTTCCTTTTCCCTCAGATATCCCTGCAGAGGGGGAAGGATGCTGGC
AGAGCAGAGTACTGCAGTCCCTCCTCACAAGGAGGTGGAGGTGGCCCAAAGCAACCTGGC    11100
TTTGAGCTTTCCTTGTGGTTCTTCTGTGTCCCTTGCCTTTTGGAGCCATAGTAATAAACC
CGTCTGCCCCCTGTTTCTCTAGGACAAGTAAAGGAAGATCTGATGTCAGGCACCAGGGAA
GCTGCTGAGTTCCCCAGTGCTGTTGGATCCACCTTCATCTCCTTCTGCAGCCAACGGGCC
TGTCCTTGCTCAGGTGGAGGGTGAAGGGCTGTGGGACCCAGTGGTGGCTTCCCACGTTG
GCCCCACGCATGTTGTTGTAGTCGCTGCTCGGCTCGGGCTCTGCCGCCTCGCTGTGTCTT    11400
AGCATGTTTCTACAATAAAGATAACTCCACAGCGTCCTGTCGCTTTTCTTCACTGAGCCT
CACGGGAGGGACGTGTGAGTCCCCGCTCCGGCTGCTCGCCACGCGTCCCTTGAGCTCTAA
AGCACCAAACCCAAGCGGAGATGTCAGACGCAGAGAAGAAGAACGTGGTCTGGGTTCTGT
TAGCAGGGACCAGCAGTTGGGTTCTCTGACTCGCTGTGTAGGGCTTTGGGTGTATCTCTT
TGTCTCCCTTCAGCCCTTTTCTCTTGCCTGTAAAAACGGACATTAAAGGATGCTTACCTA    11700
CCTCAGAGGGTTGTTTGGAGATTTTAATTGGTTTACGTTAGAGAGCCCACGGGTGGAATT
CTGTTCCTATGTGCCAATGCTGGTGTGCAGGAGGTTTAACTGTTGCAGTCATGGCCTCTT
CCAGCCAACACCCGATGGGCCGTATGTATTTCCTGTTCTTTCGTTTATGGCTGTTACTTA
AAGCAAATATGTTCTTATTTGTATAAACTTTATTGCAGGACATTTCCAGAAGACCTTGAG
TGAACGTACAGTGTTTGAGTCCACTTTAGCTGTGACCTGATCTGCAAATACACTCTGCTG    12000
TAGATAAGGCTGGAGTAACTTTCAGATTTTGGCAGGGTTTCGCTCAATGCCAATTAATTT
GGCTCCCTCCACAGATATTGATTTTTTTTTTCTTTTCAATTAAGTTATCGAGATCTTTT
TTTCTTAATGCAGCTAATGAAAATCGATTTTACTCTCATAAAGTACTTCCGCATGTGTC
ACATTGATCTGTCTATGGCTTGATTATCGGCAGGCTTTGACATGAGGTTAATATTTTGTG
TGCTGGTTTTTTTTCACCGTGTGCAAACACTGTGGTTTAGAAATATGTTACCGCTGCTTA    12300
TTTCTACGTGGAAAATCCCACGGCGTGGTTATGCATGGCAGAAGTCACCAGTTTGATCCA
ATTAGCTGTTTCTAGGGATGCAAGATTCCTCTGCCTTTGAGCGGGTGAATCCTCGGGTG
TTATTTATACATTCTGAGAAGGATGAACAGAAGACGGTAAAAACGTTTGCTAATGATGTC
TGCTGGCTGATTCCGGCTAAAATCGTGTGCAGGGACCTCGACGTGATTTTATAAAGGCA
GCTCACAATTTGAGGCTTAAAGTAAGTTCTTGCAAATGAAAATGGGCGCACTTGAGCGCG    12600
CTATTATAACTTGTAGTGATTTCAAGCACTTAGATTTTGAAATAATCGCCCATAAAAACC
TGCATTAATTGTGCTCCAAAACCAATGAGCTGATGAGGAGGTGCCCTGGTAGCCTCTTT
TGCTGGATTTGAGCACCTTCTGAATTTCTCCTGCCACCAGCAGAAATTAGCCACAGAAAT
```

FIG. 14D

```
CATAGCTGCTATAAGGGTTTATTAATCAGATTACGAAACTGCTAAGAAGGCACACAACAG
TGACTTGCTGAAGCTGCCTGTGCTGCTGTTAGCGAGCCTCCCGTAGGTAGCAATGCTAAC   12900
TCCTTCCTTTTAGCAGTTTACCCACTGCTTCCTTCCATCACTCCTTCCTTTTGTAGGGCC
TACTTTTGCAGTTTGATCCAGTGGCTTGCAGGCAATATCTGTCCCCAGCGGTGCTCTATG
CAGCTGACCTCCAGGTAGGGCTCCATGTGAGCGATGCAATGTGTTATTTCCATGGGGTTC
CTAAGAAGGAGGAAGCAAAAAGCTCAGGAGGTGCTCCAAATATATTATCCTGTCCTCTGT
TTTGCTCTTTGTGGTGCCCTTTAACACTGTAAAGAGACCATAGGAGTCCTCTATGAACCT   13200
GGAAAGGTACCAGCACTATGGGAGGTCTTCAGTTTGCTGTAAATTATGCTTTATTAGAGG
TATTTCTTCTGCCAAGACCCACTGACCCCATGCGGCTCACAGTGTTTTCTAAGGCTTTGC
AGGACTGGTGTTACGAATTGGCACCCTCCAGGCCTCTCACAAATCTCCTGCTTCTCACAG
CGTTTCTTCAAGTTCTCCCAAGCACAGCTGAGTTTTGAGCTCAACTGCTCCCTGCAGGGG
CCTTGAGCCTCCTGCCTTTTTGCATAAAAGGTGTCAGGTACTTATGCAATCCTTAGAGGC   13500
ATGCAAATGCTGCTCTGGTTATATACTGAGGACTGTTGATTCTGGCAGAACCCTTTGCAG
ACCTTGTACTCCCTTGCTATTTCCCAATCCCTGCAGCCTAGCAGCTCTGCCTAACAACTG
CCATAGCCAACACAGCAGCAGGCTGTGCATGGTGCAAGGTGATGTGGAAAGGGATGATTG
TATGAAAGCGTGATGCTGTGGTACTGCCTCTGCAGGAGACTCGCACTATTTGTGTAAGAG
GACCTTATTTGTCTGCTGCAGAGCTGTTTCAAGGCTGTCCATACACCCCTGTGATGCTGA   13800
GCCCCTCCAAGCAATGCACTGGGAAAAGGAGGCTGGGGGGAGACCTTATTGCTCTCCTCC
AATATTTGAAAGGTGCTTACAGCGAGAGCAGGGTTGGTCTCTTCTCACTGGTGACAGGAT
GAGGGGAAATGGCCTCAAGTTGCACCAGGGTATGTTTAGATTGGATATCAGGAAACACTT
ATTTACTAAAAGGTTGTTAAGCACTGGAATCAGCTCCCCAGGGAGGTGGTTGAGTCACCA
TCCCTGGATGTGTTTAAAAACTGTTTGGATATGGTGCTCAGGGACATGATTTAGCGGAGG   14100
GTTGTTAGTTAGGGTAGTGTGGTTAGGTTGTGGTTCACTCGATGGTCTTTAAGGTCTTTT
CCAACCTGAGCAATTCTATGATATGGATCCCTGGGGCTTTCAGTCTTATCTCCCTGGATT
ATCACAGGTTCAGCTCTATGGCCCATTTGATTTATACCGGGGTCTGATGAACAGGTTTTT
CTCTTGGCTCTTCAGGGATCCTATTTAGCACTTTTTGGTACATTCCCCTGCCCTACAAGT
CTCCCTGATACACAGAGCTCTTATCCAAGACTTGGGACCTTCCCTACTCCAGCCCTCTGC   14400
AGGAGGTTTCTTGCTAACCAGTCCTCCAACCAGGACTGCAGTACACGACAAAGAGCTGGA
AGAGGTCTGCAATACTTCCCCAGCATGAAGGTATGAGCACTCCTTTTGAGTAGGTTACTG
AAAGTAGTAAGATGTCAATACAACCAACTGCAAGATACAAAACCGCATGAAAATTCAGTT
TACTTTGATGCTGAAGGGCTGAAAAGAAATGCTGTGGTGTTAGCACAGATGCACTGCTGG
CAAAGTGAAAATGAGCAAAGAGGATGAGATGGATGGACAGCTGATGGAAAAACTCTTCCT   14700
AATTGCTCCACAGAGCAGCTTGCTCGCCTGCAGGGCTGCAGCATGGAGCTGCTTGTGCAT
AATGCAGACACCCCAAGACCAGTGCTGTTTGTCTTAGCCAAGACACAGTTGCAGCTGCAG
CAATTTTTTCTAGATGTCAGTTCCTTCCCTATGTTGCTGACAGGTGTTTGCTGTTCTGTC
CCTTTAATCTGTATCCTACAGCAAACATTCCTTGAATTTAATAACTTAGCTGGAAGACAA
TTGCTGTGATCTTGATAGAACATGCTGAGCCAATCTATTTTAACTGCAGATTTAGTTTGC   15000
AAATACTGTCTCCTTGCCGATAAGATTCAGGTGTCATCTTTGTGGACATTGGCAGGAATT
TTCTTGACCGTGACAGGTTTTACAGAGTCTGGCAATTAAGCTGTCAAGACACATTTTCCT
CTGCCAGGAAGCATTAATTGATGATAGTCTTGGCTGCAATAGGCACAGAGAGATGGATAT
TGTAATCAGAATGAATAGAGGTCCTTGTAGTTGAGAGCTACGTTGGTCCAAAGTTTTGTA
GTCGTTGACGTTTGGTGATACTGAGATAAGGAACAAGGCACGAGATATTAGAGCTAAATA   15300
TCAGGCACAGCATGAGAATAAAGACCTCTCTAGCTGGAACTGTTGGTATCTGGGGAGATT
TTAACTTTCTGGATGCATACTGCAAAGTACTAATATTAGTAGAGCTACTGGATGCGAGAG
CAAATAGTTTTCCATTAAGTAATCCCAAAAATCATGTTGTTGTTGGTTTGCTTTTCAAGT
GCGAGGGGTGTTGGAGATGTATTTCCCTCAGAAAATAAACCTGATATGATTCAACCTGAG
CTCTCTCTGTTTAAATCACACTGAAAATAGATCTGCAAATGGGGATTTTGATTACCGAGT   15600
ACAGAATATGAAAGATTAAAACTTGGGAAAGTTAGGGTTCTGATTGAGAAACTTTTGTT
TTTGTGGCCGACCCTTGCAGCTTACAAAAATCTGCCTAAATAAAGGAGAAAACCACATTT
AGAACCCATCCAAGCTATGCTACTTCAGTACTGGGCAAAACTTCAGGAGACGTTTGAAGA
AAACTGAAGACGTGAAGTATAAAGGAATGATTGATGTGCACAGTAAACTTTCTTGGAAGG
TAATCACGCATGGGCTAATATCAATCTTTACAAAGTTGGCTGACTTCCTAGATAAAGGAA   15900
```

FIG. 14E

```
GTACAGTAGATCTAGTCTACCCAGGCAGCAAAAATGTTTGACCTGTTGCCCTGTGGGGTG
GTGTCACCTGGGCTTGGGGAGGGGGTCAGGATGAGGTTACAGGGGATGTGGAAGCATAC
TGTGGAGGAGCAGGTGGGGCACCCACAGGAGTTAGCAGTGAGCAGACAGAAAGGTGGATC
TGAGGACCGAACTTCGTATTTTTGTTCCTTGCATTAATACACAAAAAGCAGACACACACA
CAGAGCAGATTGCTGCTGGTTTTTGTTTTCTTTTTTAAACAGCAGAAGAGCAGGATTTTT     16200
CCCACAGAGAATGGGGTGACCTTCTAGGCTGTGATTGCCTGGGCTCAAGCTGAGATGAAA
CGCAGTGATGAGGAGCACAAAACCGTGCTCTGAGGTTAAATAATGAGGGCTTCGGCTATC
AGTTCAGAGCTCAGTAAAAACTGCAGAGGAGGAGGAAGACCTAATTGCATGTAGCCAGCC
ACAGGGCAAATGAGAGCTGCAGCGTGCTGGGGCAGATCCGGGAGCAGAGGGGCCGTGGCA
CGCTCCCTGTTCACTGGCTCCCCTGGAGCCACACAAAAGGCCCCTTCCTGGCAATTGTGC     16500
CCACATCAATCATTAGCTAGAAACCCAGAGCTGGGTAAATACGTTTTGGCTTCCCGTCTT
GATGACAGATTGGGTGTTACATCACAAGGTGGGACCACTTGATATGACAACACGCTATAT
ATTCCCGCTGCTACCTCTGCCCTTCCTCCCCCACTCTGAGAGCAAGCGGGCTGTGTGTGC
ACCGAGGTGCTCTGCCATGAGGACTGCCAGGCAGTTTGTACAGGTGGCTCTGGCCCTCTG
CTGCTTTGCAGGTGAGTGTTTCCTGCTATACCCCGTAGGTGACTATAGCTAGACCAGAGA     16800
CTAGGCTATCTGTGAGAGTATCTGGGTATTGTAATGTGTTAGAGAGCCTTGTTCCATGAA
GGAATGCTCTTTCTGACAGTGTAGCAAAACACCAGACTGCAAGATCCAGGTTTCAGCAAA
CCTCATACAGACGACTGTTTTCGTCGTGGTTTATAGGAGCAAATTGCTGAGGGAGCAGTG
CTAGTGCAGGGCAGGAGCTTGCACGTGCAAGCACTGAGTATAACGGCAAAGCAAAGCTAT
GTGAAATGGCTCCTGTGTCCATGTAAGCAATACAAACACTGCATCTTGTATCATCTATAA     17100
ATTTTCTGTGCTGTTCCTGGCAGCTGAGAAGTTTGTTGTGGGAAGAACAGTGCTAGTGGT
CAACAGCCACCTGAAACGTGCATGTCTGAGCTCCTGCAAGTCAAATACAGAGTCTTGCAG
AAGAGTTTAAACTCAGTGCAGGCTTGAAAATACCTACATTTCTTCCCTGGGGCATCTTAG
GAACTGGCTAACACATGTGGCCTCCTACTGAAAGTGCAGTGAAACTTCATTTAATAACCT
CTGATTCATTTATGGACGTACATCACTGGCATAATGTAAAATTGCATTTTCCTAAACCC     17400
AATAAGCCAATCAACAACGGTATCTAAATGTAACTGTTTCATCGAAAGATTTGCATATGT
CATCTCTGCATATTAATAATATGTATTTATTTTCTGTCTCTACTTTTCTTTTAGATATTG
CCTTTGGAATTGAGGTGAGTTACAGATTTTTTTCCCATTTATTCTTTTCTATTCCAGGC
TTCTGGTCAAATAAGAGCAGTATATAATTACCTGATGAGCAAGTGGATTAATCTAATGAA
AGCCTGGTTGCTCAAATAATACTTGCCAGTGCATGATTGAATGATATTGCCAAGTCACGA     17700
AAAAGTAAAACACACCCGTTTATACTATTTTCCATTCATGCAATAAAATGAAGAAAGGA
AGAATTGTACGATCCTATTATGTTAACTTTTGGATATAACTGCGTTAGTCCAAGTCAAGG
GGTGGTAGTTACCTCCTCGAGAGGAAAGCTGTCTTAAGATGATAAGCTCCAAAGCATCAA
AGACAGTGATTCTGGTATCTTTTTCTATACAGTAAGACACACACTACAGTGTTCCTGCCT
ATACCCATATCAAAGCGAGGAAAGCAGCAGGGTCTGTGCAGTGCATTTGTCTGCAGGTTC     18000
TTCCCACGCAGTTATGAGATTCCTGCAAATCACCAGAGACTGCAGCGTGATTGGAAACGA
TCAGATTTTGAGTTGAGCGGCTGTGGAGCATGGCCAGGCTCCCAATTACCAGCTGCCTTC
GTTAGGCGCTGTCTCACCCACAGCTCTCCTTCCTCCATGTCATGCTTCCCCCAGTCCCCC
GCAGGAAAGCGTGATCAGAAGAAGATTCCCACCTCCTGACTGCCTGAGCAGATTCCAAAT
GATACCTCAGGTGTTTGTCCCGGCTGGAGCTGTGGGTGGCAGGAGGTTTCCATACTGTCT     18300
TTTGTTGTGGAAACTGACCCCAGGGCTGATGTTGTGCTGCTTCCATAGGTTAATTGCAGC
CTGTATGCCAGCGGCATCGGCAAGGATGGGACGAGTTGGGTAGCCTGCCCGAGGAACTTG
AAGCCTGTCTGTGGCACAGATGGCTCCACATACAGCAATGAGTGCGGGATCTGCCTCTAC
AACAGGTGAGCTTÀTGTGGAAGCCCAGGGGAGCTGCAGGGCAGGAGACTCGAGGTGAGGG
CGGCAGCTCTGTCCCCAAAATATGGTCTGTGTGGAGGAGTATGTGAGTTAGTACCAGGAT     18600
GCTGACCTCCAGCCTGGGGGTGGTGGCTGCTCTCTGCCATCTCTGACACAGATCTGCGTT
CTTCCAGGGAGCACGGGGCAAACGTGGAGAAGGAATATGATGGAGAGTGCAGGCCAAAGC
ACGTTACGGTAAGTCCAACAGTAAGATGAAGTCTTGCTCTGTTGGTGCCCATAAAGACTT
ATTTTTATTTCATAGAATCATTGAACAGCTTAGGTTGGAAGGGACCTTAAAGATCATTGG
GCTCTAACCCCCCTGGCCTGGCCGGGCTGCCTTCAACCAAATCAGTTTGCCCAGTCAAAT     18900
GGGCCTTGGGCACCTCCAGGGATGGGGCACCTGCTCTGCTCAGCCTGTTACTTATTTACT
TGTTTTTTTCCCATTCCTGCTATCCTTACAGATTGATTGCTCTCCGTACCTCCAAGTTGT
AAGAGATGGTAACACCATGGTAGCCTGCCCAAGGATTCTGAAACCAGTCTGTGGCTCAGA
TAGCTTCACTTATGACAACGAATGTGGGATTTGCGCCTACAACGCGTAAGTCTTTTCTGT
```

FIG. 14F

```
GGAGCATCCTTCTGGGTAATTAGAGATGGCTAAGTCCCTTGGAAACGCTTACATAAAACA  19200
CTTTCTAAGCCTTTCTTAGGGTAGATGTTTCTGTGGGACTCTTTGAAGCTGGCTACTTGT
GATTCTCCAGCCAGCTGCAGATTTCTTCCCCATCCTCTGTCTGTGCTCATGAAGGGAATC
ACAAAAAAGACAGAGGACAACCCACAGCAGAGGCATGAATAGATCAAAGTGTTGCTCAGT
GCTGTGTGATATGGAAATACCATGCATTTTCTGCTCACAAGTGGTTGCTACCACCTGTGG
GCTGCATCCAGACCACTCAGCAGTTCCTTACGTGAAGGGTGGGACCTTGCTTTCTTGCCC  19500
CAGTATCTAAGGCTTTTCACGAGGCTCTCTAACTAAAACAGCTCTTTCTTTCAGAGAACA
TCACACCAACATTTCCAAACTGCACGATGGAGAATGCAAGCTGGAGATCGGCTCGGTAAG
TGTAACAGAAATAAAAATCCATCTCCTAGGGCTGTTAACGGAGAGAATCCCATTGATTTT
CCTAAGAAAATGTATGACCGGGCTGATCGGGGTCCCGGTCCACGCTCTGCTTCCTGCCT
GGTGAGGGTGGCTTCTGAAACAAAGCGGTAAAGGAAGAGGCCCCAGATTTTCCTTGCATT  19800
GTGCTGTGCAGATTGGCAGGTTTCTCTCTGGAGGCGACAAGCATTTCCACCCTTTGTAAC
AAGCATTCAAAATTCTAGTGCTGGTAGCTTGGTTAGATATAGTGAGATTCATAAGAGCAC
CAAGCATACATATTTATAGGGTATAGCTTATTGTATATTTATACTGGGGTAAGAGTCCAG
TGCCTCAGGAAGAAAAGCTTATATATTTCAGCACAAAAATTCTGGGATGCAGGGAGTCCG
TTCTCCAACAGACGGATTCCTCCTTTATCACTTCAACTCCCGTGCTTAACTGCAGGGAAT  20100
CTGAATTATTAAGCAATCACAGCACTGGGGAAGGAAGGAGAAAAACCAACACAAACCAAA
ACAATGTTAATCAGATTTCCAGCTGTTGGAAAATATTTCCCACTTAATTCAAGGCTGTTG
TGTCGATGAGAAGAGGGCTGAAAAGGCTGTTTTCAGTTCCTCTGCCTGAAGGTTTCATTC
TCTAAGAGAGGTCCCTTTTCTTGTCTCCTAGAGAATGAGGGTAGTGTTCTGAAAGCCTAT
TTCTGATAGACAGTTTAGTTAAGTGTAGCAGGGCTTTGTCCTGTCACAAAAACTAGGAAG  20400
CCGGGAATACAGGATGAAAAGGTGTTACATTGACTTCTCCCGTGTAGCACAGGCTCCGGG
AGGGCTTATTCTCCTTATTTTGGCAGGTTGACTGCAGTAAGTACCCATCCACAGTCTCTA
AGGATGGCAGGACTTTGGTAGCCTGCCCAAGGATCCTGAGCCCGGTTTGCGGCACCGATG
GTTTCACCTATGACAACGAATGCGGGATCTGCGCCCACAATGCGTAAGTGCTGCTCATCT
CCCACTCCTCCAAAGTAGCCAGCAATGCTTTGCCGTGCTGGGAGCCTTCCTTCTACGTTG  20700
CTGCTTATGCCTGTTTCTTCAAGCCTCTTAGAAACTGCATTTTTTTGTTGTTGTTCTTA
CTGAGTTTTCTTCTGATGCCTTCTTTGTGATCACGAGGGGAAATCTGCAAGACTCAGAAC
ACAGCTCCTTGGATTAGTCTGTGGGCTGGGCAGTGACTGAGCAGAGAAAGGAATAGTTCA
GAATCTTGCTTTAAATAACACGAGAAGACGTGATGAGCTTGTTAACGAGCAGAGTAATGT
AGCTATATCAATACAATCGTGCAGAGAGGCTGAAGCCCTACTTTGTTAGGTACCTGCTTT  21000
AGGCTACGTCTGGTTCATTCTGCATGCAAGTGTTTAAACCAAGAGTTAAAGCATCTCCTT
ACTCACTTTGTCTCCCTCTTTCAGAGAGCAGAGGACCCATGTCAGCAAGAAGCATGATGG
AAAATGCAGGCAGGAGATTCCTGAAGTGAGTATACAACGTAAGGTGTATTTCTCCCCTTG
CCTCTGCCCACTGAGCTATTTGCTGAGGCCACGTCTACTCTGAAAGTGAGCTGGCTTGAA
GCCTGGCTCTCTGCACGTGTCCTTTGGGATGTGCCAACGTGTATCCAACACACAAACAGT  21300
GTGGAAGTTGGGCAGGGGGAACTTAGGTCTTTTAAGGATGATCACTAAATGCATTGCCAG
CAAAGTCCTTTTGTGCCAGTGAAGTCCTATTATGTTTGCCTTCTTTTGTTTCATTCTATA
GTGCAGAGAGAAAAGGAGATGATATATCTTTGTTGGTTTTTTTTTGTTTGTTTGTTTTG
CTTTTCTGCCATATCTAGCAAACTGTTTCAGTAGGTTGTGACCCCTTTGGATCACAAGTG
AAGCTCAGTGGCATTTGGGATTGACTGAGCTGTCTGCCCTGGTGATTTGGCATCTCACAG  21600
ATTACACAGCGCCATGTAGCTCCTCCTGGGCATGAGAGAGTTTCTGCAGAGCTGACTCAG
GCTGGCTTTGAGAGAACTGAAGTGTAGCACCAGCGTTGTTTCAGCATCCCAGCGTAAAAG
ACATGGATTGCAGCAGGAGGCAATGCTAGGGTTTGTCTTTGAGAGCAAGGGCTTTTTCAG
GGCTGACGCTCCTACTTTTGCAGATTGACTGTGATCAATACCCAACAAGAAAAACCACT
GGTGGCAAACTCCTGGTGCGCTGCCCAAGGATTCTGCTCCCAGTCTGTGGCACAGACGGA  21900
TTTACTTATGACAACGAGTGTGGCATTTGTGCCCATAATGCGTAAGTACTGCAAACAGGA
CTTCCTTTTGTAGCGACTAGCCACGTTAGTACTGCAGATGGCTTCCCCTCCACCCTTCAT
CTTCTTCTTTCTTTCTTTTTTTGATAGCAGTATGTCTATATGTCTCCTGTTCTTCCTT
CAACCTCCTGAAGCTCTGTCGCCTCGGTTTCCTTTCCTGATGTGCTCCTCAGGGAGCTGT
GGGAGAGCCAGCTAACAGCTGAGTGTCCTATGAGGGCTGTGGCATTTGTGCAGAGGAAAA  22200
AGAGAATGGGTCTGCTACAAGTAGACCTGAGAAGCCTGTAACTTCTTAGGATCATGATCC
```

FIG. 14G

```
CTAATGGCAGCCTTTCCCTTTCAGACAACATGGGACTGAGGTTAAGAAGAGCCACGATGG
AAGATGCAAGGAGCGGAGCACCCCGGTAAGTGGGGATGGATGTCAGATGAGCGCCAGCTC
CTGTACGTGCCTTGTGGCTGCAGAGGTTGCTAACCAGGGTCTGTCCATTCAGGCAGCAGA
GAAGGGGAATGGGCCAGGATTTAGGTAACAAAATGTCCCAATACTGCAGGTCTCTGGAGG  22500
GAAACATCAGAGGCAGCCCAGAACAGCACAGCCTGTTTTAGCACAGTAGGAGAGGAAGAG
CAGAAGCTGTGTTAGATGCCTGTGTAGTCATTCAGTGCTAGGATTTCCATTGCAGCAGAC
AGGTTAAAAAATCTCTGTACCGTGGTCAGCCAAGAAAGGCTGCTTGCAGGAATGCACGC
AGAAATAGCTCTATAAACATGCACGGTAACAATATGTGCTGATAATATCTCAGCACATTT
ATTCTGCTTATGCAGAGCAGCTCTAAAACACTGAAAATAACTTTGTGCATCTCAAGGGAT  22800
TGCTGTATCTTTTCTGTAGTAAAGACACACTGTTATGGTGCTGTCTTTGCTATAATTTGC
TCTTGGACTGTGTGGGGAAATATGGGTAATAAGAGCTACTACACAGGGGAAGGTATGCAA
AACGATTGTGAAGTGTCAGAAGCTTAGCCAGTGTAGACTGACTTCCAGTGCCATCAGTAG
ATACTTGCTTATTTATCCTCAAATATTGGAACTGTTTTTAAGTACTGTGAGGATTTCTGC
AGCAGCAGCTGATGAGCTGATGGAACAGTTTCTTCTTGCCGTTTTGAAAACGTGGAAACA  23100
AAATCTAAGGCTTAGCTAAGTCAGGCATGACCTAATGTCAAACTGGACATAACATCAAAC
TCCTTATATCAAATTCCTTTGAATAATGCTTGTTTTGAAACTTGGACATACGCTGCATAA
GGAAGATGATCTTTCTGGTCTGCTATTCCTTTGCGTTCCCTTTGTTAGTGAGCAATATCA
AACCCAACCACAATTAGTTCATTTATAATGGGAGACTAAACTGAAATCAACCCTGATTTT
TCCTATGGCTCGAGGCAGTCTGTCCCCCAGCTCCCAGCACCTGACTCAGCATCCTTACTG  23400
TTTTCTCCCCAGCTTGACTGCACCCAATACCTGAGCAATACCCAAAACGGTGAAGCCATT
ACCGCCTGCCCCTTCATCCTGCAGGAGGTCTGTGGCACTGACGGCGTCACCTACAGCAAC
GACTGTTCTCTGTGTGCCCACAACATGTAAGCCCTGCAGGTCACCCACTCGTGTGTCACC
GCAGCTGCTTGTTGAGCTTTGTCAACTCTGTTTTCTCTCTCTTCCAGTGAATTGGGAACC
AGCGTTGCCAAAAAGCACGATGGGAGGTGCAGAGAGGAGGTTCCTGAGGTAAGCGATAAA  23700
GAAAACAAGAGCTTGAGGTGGTGCTTATTGCCTAACAAGTACAACGCTGGCTGGTTTTGG
TGATGCTGGGTCATGCCCTCCTGCTGCCATCCTTCCTGCAGGTAAACATCAACCCTGGCA
GCAGGGATGCTGTGCATTTTCTGCATGTAGTCAGGGAAAGAAAGAGAAGAGGACGGGTGA
GGAATGAGTTATGATGCAGGTAGCATAAATGATTTAAGGCGTTACGAAGAAATCTCTTTC
CCACAGCAGTCTATCATACCTGCCGTGGGAGTGTAGCTGTCTGTTCTGGCAATATGGGAA  24000
AGGGACACAGAGCACCCGCAGGTACCTGGTGCCTTCTGGATACCTGTGCTGTGCAAAAGG
ATGTTGTGCAAAGATCAGAAAACTACCTGCATTTTGAATGCTTTTACCTAATGTACCAGA
GGATTCAAACACCTCTCTCTTCCTATTGTAAATGCGATATAATGTAATGTATACCAACAA
TGAATCTTGTAAAAATACCAGATAAACTATATTTGGCCAGCTCTAAACTATTTACGCTCA
CTGGGGAATAGAAAAACAAAGCCATCTCATTATCTTGTGTTTGAAAGAGTCAACGTCGTG  24300
AGTCAGATATTTCATTTCTATGCAAACAGACTATGAAATGTCATTGCTTTGTTTCCTGCG
TATGCTCTGTGCTCAGACCAAGTCAGATGCATAAATCAGTGAGGAAGAGCTCACACTGGA
GAAACTGGGATAGCTGAAACTCAAGGCCAGTTCTTCAAATGGCATAAATCATTTTGAACT
GCTGTTGGTCCTTCTGTCCGATTGCAACACACAGAACCAGCCCCTCGCAACAAAAGGCAT
GTCAGCACATCTCCTCAGTTCTTGTGGGCCGTGACACACTCCTTGGCCACACTGAGCTTC  24600
TCTTGCAGGAATTGCATAAATCACGCCAGTTTGATTTGCAGATTATTTATGAGCTGCGTT
TTGCAGCGTCCCAGCAAGTGGTTCAGCAAGCTCTAAGGGCATCGTGATAAATGCAGGGCT
GAATGAGTGATACGCGCCTTCAAGCTTTGATTCAGTCTTCTCCAGTATAAGGCTGTGACA
GAAATTGATAGTTTTCAATGAAGAATGAGTCAATGCATAACCATAATCCATCCTGTGGC
AGATCTTGAAAGGCAGAGGCGTAAGGAAGGGGTTGTGTCTGAGCACCCTTACACAGAGC  24900
ATTTGCTGCCTTTGTTTCCTAGCTTGACTGCAGCAAGTACAAAACCTCCACGCTGAAGGA
TGGCAGACAGGTGGTGGCCTGCACCATGATCTACGATCCCGTCTGTGCTACCAATGGTGT
CACCTATGCCAGCGAATGCACGCTGTGCGCTCACAACCTGTAAGTACTCATTCATCTCCA
GGGGGACCCACCGTGGCTGTGACTGGACACATCTTTGAGTGCTGAATAACATGCAAGGGC
TCTGTCTAAAATCTCGTGCTGCATGGGTCCTGTCTGCCTATCCCCGTTTCCTGGTTGCC   25200
ATGGTTGGTGTTTGAGATGGGCATTTAGCAAGGCCCACTGCCCCAGTGACCCAGAAAAA
GGGTTCACTGCCTGGGAAAGCATTATTCCAAAAGACACATCCCTAGTCCTTAAGGGCATG
TTCTTGCTAATGCTTCTCAGGCAATGCTTAGCTAATTTATCTGAAATTGTCCTGTGTACC
```

FIG. 14H

```
ACATGGGAACGAGGTTGTGCTCTTGTACTACGGTTGTAAATGGGAAGGGTTTCTGCTAAT
ATCCATCTCTCCTTCCTCCAGGGAGCAGCGGACCAATCTTGGCAAGAGAAAGAATGGAAG  25500
ATGTGAAGAGGATATAACAAAGGTGAGTGTGAAAGGATGGGCACAAAGAGTTACAGTCGT
AGGGGACCGTCCTCTGCTCCACATCAAAAACTGGGGGAGCGGTGTGCAGCCCTGGCGAGG
TCGCTTGGGAATGTCATACTGGTTATAGAATAGCTGCCATCCATCCCATGGGAATGGACA
TGGCAGTGAACAGGAACAGTGTGAGGTCACATCCCTCACCAGGAGGAACTGAGCTGATTA
CTGCCGTAATTTTCCAGTTTCACTCTTTGTGCTGGGGAATACTGTTTGCTCCCAGGCAG  25800
AGACTCACATCTTCCTTGTGTGTGCAGGAACATTGCCGTGAGTTCCAGAAAGTCTCTCCC
ATCTGCACCATGGAATACGTACCCCACTGTGGCTCTGATGGCGTAACATACAGCAACAGA
TGTTTCTTCTGCAACGCATATGTGTAAGTATAGGAGTGAAACCCTTCCTGTAACTGCTAC
AAACGCAGAGTTGATTTTATAAGGAGTTCTTTACTAACACTTTATGGGTGTGTGCTAGAC
ATTTCGGATGCACCGTGACGTGCAAGGAGGTGCTTTTTGCTTTTTAAGAAAAAATGCAA  26100
AGCACCCACATCTGCCCATGTGTATGTGGCTTCCTGTTTTATTTAGTTTCAAAGACATTT
TGCTAATTTTCACCAGCATAGTTTGTCCCACAAGCTCATCAGGGTATGGGGAAAGTACTT
CACCAAACTACCTGGAGCGTTTCAAGTGTGTGAAACCTGTCATCTTTCCTTTAATTTTCA
TAATGAAAGGAAGTGGTTGGCCTTCTGAGACTGTTCTTTATCTTCTGCCAACATTATCAA
CATTTGGGCTGGTAAGGAGAGGAACAAGGCTGCAGCACAAATTCTATTGTGTTAATCCT  26400
TTCTTCTCTTTTCATTAGGCAGAGCAATAGGACTCTCAACCTCGTGAGTATGGCAGCGTG
TTAACTCTGCACTGGAGTCCATCGTGGGAAACAATCTGCCTTGCACATGAGTCTTCGTGG
GCCAATATTCCCCAACGGTTTTCCTTCAGCTTGTCTTGTCTCCCAAGCTCTCAAAACACC
TTTTGGTGAATAAACTCACTTGGCAACGTTTATCTGTCTTACCTTAGTGTCACGTTTCA
TCCCTATTCCCCTTTCTCCTCCTCCGTGTGGTACACAGTGGTGCACACTGGTTCTTCTGT  26700
TGATGTTCTGCTCTGACAGCCAATGTGGGTAAAGTTCTTCCTGCCATGTGTCTGTGTTGT
TTTCACTTCAAAAAGGGCCCTGGGCTCCCCTTGGAGCTCTCAGGCATTTCCTTAATCATC
ACAGTCACGCTGGCAGGATTAGTCTCTCCTAAACCTTAGAATGACCTGAACGTGTGCTCC
CTCTTTGTAGTCAGTGCAGGGAGACGTTTGCCTCAAGATCAGGGTCCATCTCACCCACAG
GGCAATTCCCAAGATGAGGTGGATGGTTTACTCTCACAAAAAGTTTTCTTACGTTTTGCT  27000
AGAAAGGAGAGCTCACTGCCTACCTGTGAATTCCCCTAGTCCTGGTTCTGCTGCCACCGC
TGCCTGTGCAGCCTGTCCCATGGAGGGGCAGCAACTGCTGTCACAAAGGTGATCCCACC
CTGTCTCCACTGAAATGACCTCAGTGCCACGTGTTGTATAGGATATAAAGTACGGGAGGG
GAATGCCCGGCTCCCTTCAGGGTTGCAGGGCAGAAGTGTCTGTGTATAGAGTGTGTGTCT
TAATCTATTAATGCAACAGAACAACTTCAGTCCTGGTGTTTTGTGGGCTGGAATTGCCCA  27300
TGTGGTAGGGACAGGCCTGCTAAATCACTGCAATCGCCTATGTTCTGAAGGTATTTGGGA
AAGAAAGGGATTTGGGGGATTGCCTGTGATTGGCTTTAATTGAATGGCAAATCACAGGAA
AGCAGTTCTGCTCAACAGTTGGTTGTTTCAGCCAATTCTTGCAGCCAAAGAGCCGGGTGC
CCAGCGATATAATAGTTGTCACTTGTGTCTGTATGGATGACAGGGAGGTAGGGTGACCTG
AGGACCACCCTCCAGCTTCTGCCAGCGTAGGTACAGTCACCACCTCCAGCTCCACACGAG  27600
TCCCATCGTGGTTTACCAAAGAAACACAATTATTTGGACCAGTTTGGAAAGTCACCCGGT
GTATTGTGAGGCTAGATTAATAGGCTGAAGGCAAATGTTCCCAACTTGGAGATACTGTTG
GTATTGTATCAGGGAACAGGGCCATAGCACCTCCATGCTATTAGATTCCGGCTGGCATGT
ACTTTTCAAGATGATTTGTAACTAACAATGGCTTATTGTGCTTGTCTTAAGTCTGTGTCC
TAATGTAAATGTTCCTTTGGTTTATATAACCTTCTTGCCGTTTGCTCTTCAGGTGTTCTT  27900
GCAGAACACTGGCTGCTTTAATCTAGTTTAACTGTTGCTTGATTATTCTTAGGGATAAGA
TCTGAATAAACTTTTTGTGGCTTTGGCAGACTTTAGCTTGGGCTTAGCTCCCACATTAGC
TTTTGCAGCCTTTTCTGTGAAGCTATCAAGATCCTACTCAGTGACATTAGCTGGGTGCAG
GTGTACCAAATCCTGCTCTGTGGAACACATTGTCTGATGATACCGAAGGCAAACGTGAAC
TCAAAGAGGCACAGAGTTAAGAAGAAGTCTGTGCAATTCAGAGGAAAAGCCAAAGTGGCC  28200
ATTAGACACACTTTCCATGCAGTATTTGCCAGTAGGTTTCATATAAAACTACAAAATGGA
ATAAACCACTACAAATGGGAAAAACCTGATACTGGAATTTAAATATTCACCCAGGCTCAA
GGGGTGTTTCATGGAGTAACATCACTCTATAAAAGTAGGGCAGCCAATTATTCACAGACA
AAGCTTTTTTTTTTTCTGTGCTGCAGTGCTGTTTTTCGGCTGATCCAGGGTTACTTATT
GTGGGTCTGAGAGCTGAATGATTTCTCCTTGTGTCATGTTGGTGAAGGAGATATGGCCAG  28500
```

FIG. 14I

```
GGGGAGATGAGCATGTTCGAGAGGAAACGTTGCATTTTGGTGGCTTGGGAGAAAGGTAGA
ACGATATCAGGTCTACAGTGTCACTAAGGGATCTGAAGGATGGTTTTACAGAACAGTTGA
CTTGGCTGGGTGCAGGCTTGGCTGTAAATGGATGGAAGGATGGACAGATGGGTGGACAGA
GATTTCTGTGCAGGAGATCATCTCCTGAGCTCGGTGCTTGACAGACTGCAGATCCATCCC
ATAACCTTCTCCAGCATGAGAGCGCGGGGAGCTTTGGTACTGTTCAGTCTGCTGCTTGTT  28800
GCTTCCTGGGTGCACAGTGGTGATTTTCTTACTCACACAGGGCAAAAACCTGAGCAGCTT
CAAAGTGAACAGGTTGCTCTCATAGGCCATTCAGTTGTCAAGATGAGGTTTTTGGTTTCT
TGTTTTGTAAGGTGGGAAGAAGCACTGAAGGATCGGTTGCGAGGGCAGGGGTTTAGCACT
GTTCAGAGAAGTCTTATTTTAACTCCTCTCATGAACAAAAAGAGATGCAGGTGCAGATTC
TGGCAAGGATGCAGTGAAGGAGAAAGCCCTGAATTTCTGATATATGTGCAATGTTGGGCA  29100
CCTAACATTCCCTGCTGAAGCACAGCAGCTCCAGCTCCATGCAGTACTCACAGCTGGTGC
AGCCCTCGGCTCCAGGGTCTGAGCAGTGCTGGGACTCATGAGGTTCCATGTCTTTCACAC
TGATAATGGTCCAATTTCTGGAATGGGTGCCCATCCTTGGAGGTCCCCAAGGCCAGGCTG
GCTGCGTCTCCGAGCAGCCCGATCTGGTGGTGAGTAGCCAGCCCATGGCAGGAGTTAGAG
CCTGATGGTCTTTAAGGTCCCTTCCAACCTAAGCCATCCTACGATTCTAGGAATCATGAC  29400
TTGTGAGTGTGTATTGCAGAGGCAATATTTTAAAGTTATAAATGTTTTCTCCCCTTCCTT
GTTTGTCAAAGTTATCTTGATCGCCTTATCAATGCTTTTGGAGTCTCCAGTCATTTTTCT
TACAACAAAAAGAGGAGGAAGAATGAAGAGAATCATTTAATTTCTTGATTGAATAGTAGG
ATTCAGAAAGCTGTACGTAATGCCGTCTCTTTGTATCGAGCTGTAAGGTTTCTCATCATT
TATCAGCGTGGTACATATCAGCACTTTTCCATCTGATGTGGAAAAAAAAATCCTTATCAT  29700
CTACAGTCTCTGTACCTAAACATCGCTCAGACTCTTTACCAAAAAGCTATAGGTTTTAA
AACTACATCTGCTGATAATTTGCCTTGTTTAGCTCTTCTTCCATATGCTGCGTTTGTGA
GAGGTGCGTGGATGGGCCTAAACTCTCAGTTGCTGAGCTTGATGGGTGCTTAAGAATGAA
GCACTCACTGCTGAAACTGTTTTCATTTCACAGGAATGTTTAGTGGCATTGTTTTATA
ACTACATATTCCTCAGATAAATGAAATCCAGAATAATTATGCAAACTCACTGCATCCGT  30000
TGCACAGGTCTTTATCTGCTAGCAAAGGAAATAATTTGGGGATGGCAAAAACATTCCTTC
AGACATCTATATTTAAAGGAATATAATCCTGGTACCCACCCACTTCATCCCTCATTATGT
TCACACTCAGAGATACTCATTCTCTTGTTGTTATCATTTGATAGCGTTTTCTTTGGTTCT
TTGCCACGCTCTGGGCTATGGCTGCACGCTCTGCACTGATCAGCAAGTAGATGCGAGGGA
AGCAGCAGTGAGAGGGGCTGCCCTCAGCTGGCACCCAGCCGCTCAGCCTAGGAGGGGACC  30300
TTGCCTTTCCACCAGCTGAGGTGCAGCCCTACAAGCTTACACGTGCTGCGAGCAGGTGAG
CAAAGGGAGTCCTCATGGTGTGTTTCTTGCTGCCCGGAAGCAAAACTTTACTTTCATTCA
TTCCCCTTGAAGAATGAGGAATGTTTGGAAACGGACTGCTTTACGTTCAATTTCTCTCTT
CCCTTTAAGGCTCAGCCAGGGGCCATTGCTGAGGACGGCATCGGGGCCCCCTGGACCAAA
TCTGTGGCACAGATGGTTTCACTTACATCAGTGGATGTGGGATCTGCGCCTGTAATGTGT  30600
CCTTCTGAAGGAAGGAACGTGCCTTCCAAGTGCCAGCCCCACAGCCCCCAGCCCCTCCCT
GTGCTGCTCCAATTCATCTCCTCTTCCTCCTTCTCCCTTTGCTGTTTGTGCTCGGGTAGA
AATCATGAAGATTTAGAAGAGAAAACAAAATAACTGGAGTGGAAACCCAGGTGATGCAGT
TCATTCAGCTGTCATAGGTTTGTCATTGCTATAGGTCTGTATCAGAGATGCTAACACCAC
TTTGCTGTCGGTGCTTAACTCGGGTGAACTCTCCTTCACTCGCATCATTTGCGGGCCTTA  30900
TTTACATCCCCAGCATCCATCACCCTCTGGGAAAATGGGCACACTGGATCTCTAATGGAA
GACTTTCCCTCTTTCAGAGCCTGTGGGATGTGCAGTGACAAGAAACGTGGAGGGGCTGAG
CAGCAGCACTGCCCCCAGGGAGCAGGAGCGGATGCCATCGGTGGCAGCATCCCAAATGAT
GTCAGCGGATGCTGAGCAGGCAGCGGACGAACAGACAGAAGCGATGCGTACACCTTCTGT
TGACATGGCATTTGGCAGCGATTTAACACTCGCTTCCTAGTCCTGCTATTCTCCACAGGC  31200
TGCATTCAAATGAACGAAGGGAAGGGAGGCAAAAGATGCAAAATCCGAGACAAGCAGCA
GAAATATTTCTTCGCTACGGAAGCGTGCGCAAACAACCTTCTCCAACAGCACCAGAAGAG
CACAGCGTAACCTTTTTCAAGACCAGAAAAGGAAATTCACAAAGCCTCTGTGGATACCAG
CGCGTTCAGCTCTCCTGATAGCAGATTTCTTGTCAGGTTGCAAATGGGGTATGGTGCCAG
GAGGTGCAGGGACCATATGATCATATACAGCACAGCAGTCATTGTGCATGTATTAATATA  31500
TATTGAGTAGCAGTGTTACTTTGCCAAAGCAATAGTTCAGAGATGAGTCCTGCTGCATAC
CTCTATCTTAAAACTAACTTATAAATAGTAAAACCTTCTCAGTTCAGCCACGTGCTCCTC
```

FIG. 14J

```
TCTGTCAGCACCAATGGTGCTTCGCCTGCACCCAGCTGCAAGGAATCAGCCCGTGATCTC
ATTAACACTCAGCTCTGCAGGATAAATTAGATTGTTCCACTCTCTTTTGTTGTTAATTAC
GACGGAACAATTGTTCAGTGCTGATGGTCCTAATTGTCAGCTACAGAAAACGTCTCCATG        31800
CAGTTCCTTCTGCTCCAGCAAACTGTCCAGGCTATAGCACCGTGATGCATGCTACCTCTC
ACTCCATCCTTCTTCTCTTTCCCACCAGGGAGAGCTGTGTGTTTTCACTCTCAGCCGCTC
TGAACAATACCAAACTGCTACGCACTGCCTCCCTCGGAAAGAGAATCCCCTTGTTGCTTT
TTTATTTACAGGATCCTTCTTAAAAAGCAGACCATCATTCACTGCAAACCCAGAGCTTCC
TGCCTCTCCTTCCACAACCGAAAACAGCCGGCTTCATTTGTCTTTTTTAAATGCTGTTTT        32100
CCAGGTGAATTTTGGCCAGCGTGTTGGCTGAGATCCAGGAGCACGTGTCAGCTTTCTGCT
CTCATTGCTCCTGTTCTGCATTGCCTCTTTCTGGGGCTTCCAAGAGGGGGGGAGACTTTG
CACGGGGATGAGATAATGCCCCTTTTCTTAGGGTGGCTGCTGGGCAGCAGAGTGGCTCTG
GGTCACTGTGGCACCAATGGGAGGCACCAGTGGGGGTGTGTTTTGTGCAGGGAGGAAGCA
TTCACAGAATGGGGCTGATCCTGAAGCTTGCAGTCCAAGGCTTTGTCTGTGTACCCAGTG        32400
AAATCCTTCCTCTGTTACATAAAGCCCAGATAGGACTCAGAAATGTAGTCATTCCAGCCC
CCCTCTTCCTCAGATCTGGAGCAGCACTTGTTTGCAGCCAGTCCTCCCCAAAATGCACAG
ACCTCGCCGAGTGGAGGGAGATGTAAACAGCGAAGGTTAATTACCTCCTTGTCAAAAACA
CTTTGTGGTCCATAGATGTTTCTGTCAATCTTACAAAACAGAACCGAGGGCAGCGAGCAC
TGAAGGCGTGTTCCCATGCTGAGTTAATGAGACTTGGCAGCTCGCTGTGCAGAGATGATC        32700
CCTGTGCTTCATGGGAGGCTGTAACCTGTCTCCCCATCGCCTTCACACCGCAGTGCTGTC
CTGGACACCTCACCCTCCATAAGCTGTAGGATGCAGCTGCCCAGGGATCAAGAGACTTTT
CCTAAGGCTCTTAGGACTCATCTTTGCCGCTCAGTAGCGTGCAGCAATTACTCATCCCAA
CTATACTGAATGGGTTTCTGCCAGCTCTGCTTGTTTGTCAATAAGCATTTTTTCATTTTG
CCTCTAAGTTTCTCTCAGCAGCACCGCTTTGGGTGACTTCAGTGGCCGCCTGGAACCCGA        33000
GGGCACAGCCACCACCTCCCTGTTGCTGCTGCTCCGGGGACTCACGTGCTGCTGGATGG
GGGGAAGCATGAAGTTCCTCACCCAGACACCTGGGTTGCAATGGTTGCAGTGTGCTCTTC
TTGGTATGCAGATTGTTTCTAGCCATTACTTGTAGAAATGTGCTGTGGAAGCCCTTTGTA
TCTCTTTCTGTGGCCCTTCAGCAAAAGCTGTGGGAAAGCTCTGAGGCTGCTTTCTTGGGT
CGTGGAGGAATTGTATGTTCCTTCTTTAACAAAAATTATCCTTAGGAGAGAGCACTGTGC        33300
AAGCATTGTGCACATAAAACAATTCAGGTTGAAAGGGCTCTCTGGAGGTTTCCAGCCTGA
CTACTGCTCGAAGCAAGGCCAGGTTCAAAGATGGCTCAGGATGCTGTGTGCCTTCCTGAT
TATCTGTGCCACCAATGGAGGAGATTCACAGCCACTCTGCTTCCCGTGCCACTCATGGAG
AGGAATATTCCCTTATATTCAGATAGAATGTCATCCTTTAGCTCAGCCTTCCCTATAACC
CCATGAGGGAGCTGCAGATCCCCATACTCTCCTCTTCTCTGGGGTGAAGGCCGTGTCCTC        33600
CAGCCCCCCTTCCCACCCTGTGCCCTGAGCAGCCCGCTGGCCTCTGCTGGATGTGTGCCC
ATATGTCAATGCCTGTCCTTGCAGTCCAGCCTGGAACATTTAATTCATCACCAGGGTAAT
GTGGAACTGTGTCATCTTCCCCTGCAGGGTACAAAGTTCTGCACGGGGTCCTTTCGGTTC
AGGAAAACCTTCGCTGGTGCTACCTGAATCAAGCTCTATTTAATAAGTTCATAAGCACAT
GGATGTGTTTTCCTAGAGATACGTTTTAATGGTATCAGTGATTTTTATTTGCTTTGTTGC        33900
TTACTTCAAACAGTGCCTTTGGGCAGGAGGTGAGGGACGGGTCTGCCGTTGGCTCTGCAG
TGATTTCTCCAGGCGTGTGGCTCAGGTCAGATAGTGGTCACTCTGTGGCCAGAAGAAGGA
CAAAGATGGAAATTGCAGATTGAGTCATGTTAAGCAGGCATCTTGGAGTGATTTGAGGCA
GTTTCATGAAAGAGCTACGACCACTTATTGTTGTTTCCCCTTTTACAACAGAAGTTTTC
ATCAAAATAACGTGGCAAAGCCCAGGAATGTTTGGGAAAGTGTAGTTAAATGTTTTGTA        34200
ATTCATTTGTCGGAGTGTTACCAGCTAAGAAAAAGTCCTACCTTTGGTATGGTAGTCCT
GCAGAGAATACGACATCAATATTAGTTTGGAAAAAAACACCACCACCACCAGAAACTGTA
ATGGAAAATGTAAACCAAGAAATTCCTTGGGTAAGAGAGAAAGGATGTCGTATACTGGCC
AAGTCCTGCCCAGCTGTCAGCCTGCTGACCCTCTGCAGCTCAGGACCATGAAACGTGGCA
CTGTAAGACGTGTCCCTGCCTTTGCTTGCTCAgatctctgccctcgtgctgactcctg        34500
cacacaagagcatttccctgtagccaaacagcgattagccataagctgcacctgactttg
aggattaagagtttgcaattaagtggattgcagcaggagatcagtggcagggttgcagat
gaaatcctttctaggggtagctaagggctgagcaacctgtcctacagcacaagccaaacc
agccaagggttttcctgtgctgttcacagaggcagggccagctggagctggaggaggttg
```

FIG. 14K

```
tgctgggactcttctccctgtgctgagaatggagtgatttctgggtgctgttcctgtggc   34800
ttgcactgagcagctcaagggagatcggtgctcctcatgcagtgccaaaactcgtgtttg
atgcagaaagatggatgtgcacctccctcctgctaatgcagccgtgagcttatgaaggca
atgagccctcagtgcagcaggagctgtagtgcactcctgtaggtgctagggaaaatctct
ggttcccagggatgcattcataaggacaatatatcttgaggctgtgccaaatctttctga
aatattcatgcatgttcccttaatttatagaaacaaacacagcagaataattattccaat   35100
gcctcccctcgaaggaaacccatatttccatgtagaaatgtaacctatatacacacagcc
atgctgcatccttcagaacatgccagtgctcatctccatggcaaaatactacaggtatt
ctcactatgttggacctgtgaaggaaccatggtaagaaactcaggttaaaggtatggct
gcaaaactactcataccaaaacagcagagctccagacctcctcttaggaaagagccactt
ggagagggatggtgtgaaggctggaggtgagagacagagcctgtcccagttttcctgtct   35400
ctattttctgaaatgtctgcaggaggaaaggacaactgtactttcaggcatagctggtgc
cctcacgtaaataagttccccgaacttctgtgtcatttgttcttaagatgctttggcaga
acactttgagtcaattcgcttaactgtgactaggtctgtaaataagtgctccctgctgat
aaggttcaagtgacattttagtggtatttgacagcatttaccttgctttcaagtcttct
accaagctcttctatacttaagcagtgaaaccgccaagaaacccttccttttatcaagct   35700
agtgctaaataccattaacttcataggttagatacggtgctgccagcttcacctggcagt
ggttggtcagttctgctggtgacaaagcctccctggcctgtgcttttacctagaggtgaa
tatccaagaatgcagaactgcatggaaagcagagctgcaggcacgatggtgctgagcctt
agctgcttcctgctgggagatgtggatgcagagacgaatgaaggacctgtcccttactcc
cctcagcgttctgtgctatttaggggttctaccagagtccttaagaggttttttttttttt   36000
ttggtccaaaagtctgtttgtttggttttgaccactgagagcatgtgacacttgtctcaa
gctattaaccaagtgtccagccaaaatcaattgcctgggagacgcagaccattacctgga
ggtcaggacctcaataaatattaccagcctcattgtccgctgacagattcagctggctg
ctctgtgttccagtccaacagttcggacgccacgtttgtatatatttgcaggcagcctcg
gggggaccATCTCAGGAGCAGAGCACCGGCAGCCGCCTGCAGAGCCGGGCAGTACCTCAC   36300
CATGGCCATGGCAGGCGTCTTCGTGCTGTTCTCTTTCGTGCTTTGTGGCTTCCTCCCAGG
TGAGTAACTCCCAGAGTGCTGCAGAAGCTTTGTGCCTGCCAGTCCTGGCTCTCCTTAGCA
GAACATGGTGGTGACCATCAGAGAGAGACTCCCCTACAAAGTGCCTGCAAAGGCTGCCTC
AGTACATCAGTATTAAACGGATTACTGTTGTGCTGGGTGTCTGTTGGGTTCTGTGCTCCC
AACACATTTCTTACGCTCTCAGCTCTGTTACACTGCTTGCATTTGCTGCACAGTTGCATA   36600
GAATGGATAAATGCTTGAAACAAGGCCATAACGAGGTGGTCAGACCTCCAGGAACTAGTT
AGGGAAATATTGTCATGGCCCAAGCAAGCTCTGTGCAGGAACCTGGCAGCTTTCCTGCAA
TGCTTTTGCTGCTAATGGAGAAACAAGAGATGCAAACAAGCCAGGATCTGATGTTCTCCT
TCTGTATTTACATCTCATGAAATTACAAAGTCAAAGACAAGCGTGGTTTATTTCTTACAC
TCAGCTTCTTTAAAATGTATATCCCTGACAACAGATGCTGTGTATGTTTGCTTATCCTGT   36900
ATGTGACTATTTGCATTTGCATTTATCTCTATTGACTCAGGTTTCTTTTCAGATATGTGA
TAGATGTTTTCTAGGGACAAAACGGATGTGTAATAGATAAGGAAGGAAAAGATATTCAT
TTTTCAATTAATAAATCTACCTATCTCTTAACTTTTTTTTTTTTTAAGAACAGAGCTAT
TCAAGAACTCGTTTCATCAGCCAGCAATAAGAAGCTAAATTATGTTTATCAGCATTAAAC
AAAAATCATATATAGTTTGCTTAGTTCAAGAATCGAATCGGTGGAAATCACTCAGTTTGG   37200
TTCTCTGTGCTGGAGTTTTGCACACACATTTCAGCTAGCTGTGGTCTCACTGATCAGACT
GCCTTTGTTTCCCATTTTTGTCCCCTTTTTTCCCCAGATGCTGCCTTTGGGGCTGAGGT
GAGTAAGAGAGTTCTTCTTGTCCACTTTTCTCTTTTCTCTTTTCTCTCTCTCTCTTTTTT
TCCCCCGTCTTAATTAGTATCACTATAATCAGATCCCAGAGTGTAAAATGTTAAATTAT
GCAGTTCTGAGCTCTACATCTATGCTGCATGTAAGTAATGTAGCAGTGATATAAAACTGT   37500
TAGATGAATTAATTTCTGACCAACTCTGAACTGGTCTAAGCTTTAAGTTGATCATATGTT
CTACTAAATAATACAGTGGTTTGGGTTGGAAGGGTCCTTTAAGATCATCTACTTCCAACC
CCTCTGCTATAGGCAGGGACAACTCCCACTAGACAAGATTGCTCAAAGCTCCATCCATAT
GATCAGCTGTAGACTGATGGCTGTAGACTATAGCATTAAAAACTACCCCAAAGCAGCCTA
CTGAAAGAAGAAAGTACTGTGAGGTGCTACAGCTTCCAAATCCCATGTTGTTAGACCTGT   37800
TCTTTTGAATAAACGTGTTTGTACGTTGAGAATGAATGAGTAACAATGGCAGAACACTGG
```

FIG. 14L

```
AGGGGCCAACTCTCAGGCTTTGCAAAATGGTGCCTGGGGGGCATGATAGATCCCTGCTGG
TTTATCACATGGGGAGCTGCATGGCTATAACCCCATTGCCCAGTTCTCTCCCACTGCATG
GAGAGAAGGCTGGATCTGGTCGCTGCCCTGCTGAAAATGGCAGATGTAACTACAAAATGT
CACTTTGTCCTGTTACTGTGTGTTTCTTTGTCAGGTGGACTGCAGTAGGTTTCCCAACGC   38100
TACAGACAAGGAAGGCAAAGATGTATTGGTTTGCAACAAGGACCTCCGCCCCATCTGTGG
TACCGATGGAGTCACTTACACCAACGATTGCTTGCTGTGTGCCTACAGCATGTGTGTACT
GCAGAGAGAGCTCATACTGCAAGCAAGCAGCTGTGCTTAGGGCTCCTGACAGCACCCCTT
TCCAACAAACAGTGATCTGTCACATGTCACTTATGTCAACTCTTTCAGGGAAAGCTTGAG
TATCACTGCGTGACACTCGGTTGCCTAGACATCACTTTGGTTACTGTGTCTTTTTTGTTG   38400
ATGTAATTTATTCAGGTTTTTCTCCTCCATCTCGGGGATGAGGCAGATGACAGCCCCTAG
GGCATATTTCATCCCAGCAAAAAAGGAGCAAAAGGATGGAGAGGTGCTCCAGTCTGAATG
GTCCAAAACAGTCCTAAAGATTTCAGAGTCTTTAGATCCCTGCCAGCCACTCAGTATGGC
ACTACCCTCTCCAATACAAATATATATATATACAAAGATGACTTAGCCAGACTCAGCCTC
ATTGCATTAGGTACATATTCCCAATAACGAGAAGCTGAGCTTCCTAATACCTGTTTTCCC   38700
TCTTCAGAGAATTTGGAACCAATATCAGCAAAGAGCACGATGGAGAATGCAAGGAAACTG
TTCCTGTAAGTGAAACCAAGTTCATCCTTTGTGCAGCCAAAACTGCTTATTGACTTGCCC
AATAAATAATGTAAATGCTGACTAAGAGGCCATGTGAGATGTCAGAATCTTGTATTGATC
ATCTTCAGGTGAAGTTTCATCACAATAACACAAAAAAGACTTTATTTCCTGCTGAGGTG
GCATTTTAGGAGACCCAACGCACGCGCTCCGCTGGTCTACGTGGTCCCTGTAAGCCCTCA   39000
CCAGCGCTTTGCTGTGTGCTCCTTCCACAGATGAACTGCAGTAGTTATGCCAACACGACA
AGCGAGGACGGAAAAGTGATGGTCCTCTGCAACAGGGCCTTCAACCCCGTCTGTGGTACT
GATGGAGTCACCTACGACAATGAGTGTCTGCTGTGTGCCCACAAAGTGTAAGTACCGAGC
TGTGCTCCCTTGGCAGGAATGGGTCCTGCGCTCCTGGCAGCCACTCTTTGAGCACTGGGA
TTTCCAATGAGGCTTTTTCTGTATGGCTCTTGGACTCCGTCCCTCCTCTCCCTGATAACC   39300
TCATGCTGTTTTCCTTTGTGATTAGAAAGAGAACTGTGGCTTTGATCTTGAGAGAGAAGC
AGAGAGCTGGGTGGGGACTTAAGAGAAGCACTCTGTTCTGTGTTAACTAAGTTAAAAGGG
TCTGTGTGGCACACACTGCCTTGCAGAGGACAGCAGTGAACCTCTGCTGCACCTATATTG
TAAAACAACCTAGCTCCTAGGCCATGACAGCCTGTCACCTCTCCTCCTTTGCATCATGCA
ATACTGCAACACTGTGGCACATAGTACCACCTCCCATAAGGACTGATATGTTGAACCAGT   39600
GTGTCAGAGACCAGTAGCATCTCTGTCTTCAGGATCATCAGGTAGCATTCTATATACAGG
GTGTTGCCCAGGACTCCGAGTCCCATGAAGTATGGCAGGGGTTTTGGAACTGGATGACCT
TCGAGGTCACTTCCAACCCAAGCCATTCTATTATTCTGTGAAAGCCAGGGAGGTGGGGGT
GCTTGCAGGGCTGGTATCTTGAGCAGTGTGGGCACAAACTAGGCTGGGCATCTGCAGCCC
ATCAGCACTGCGGGGATGTGGAGTTCAGCACAGCAGGATGCAGGCACAGCTCCCTAACAT   39900
GGATTTTTTTCCTTTCAGAGAGCAGGGGGCCAGCGTTGACAAGAGGCATGATGGTGGATG
TAGGAAGGAACTTGCTGCTGTGAGTGTGAGTAGCACAATGAAGGAGCAGGTTCTGGTCCC
ACTGATGTCAAGGGAAACATGGCCAGCATCTTTAGTAGCCTCAGGAGCATCAGTTGTGCT
TCAGCACAGAGAAGATTTTACTTTCTACACACGTAATACACATTATCCACAGTAATGTCA
GGAAGGGAAGAGGATGACTGCACAGGCAGGGATCAGTAAAAGACCATAAGCAGAAATAAC   40200
CCATGAGGGCAGAACTGAGAATAAGAACTGAGACTAGATCCAGGGGTCAGACCAATGGG
CCATCAAACCCATGATGGTTTGATGCAGAGTCCACTCTTTCAGCATTCATAAGAATTGAG
TAGGGGGGAGTAAGGGTGGGGTGAGTACGTACGGATCTTCCCAAACACCCTTCCAACCTA
CAGCTATGCACCTCAGCCAGGTGTGATTTCTGTGTAGTTCACAAGCCTCAGTGGATTTCT
CTCCCATGGGATTCTCCAGCCTCTTTCTGGACCTGTATACACGGTAGTTGGGTTGGTTTT   40500
TTTTTTCTGTCTCTCTTTTTTCCCCCACTACAATGTCCCTCAGCAAACATAGTCCTCA
TCTCTCAAACAAACAAATCTCATTCTCTAAGTACCCAGATAAGAGCTGATTTTGCTTTA
AGCCTGTGGGGAGATGCTGGACTATTATAAAGGTATCAGTGCTGCCTCTTCTCCAGACA
CCAATGTTTTTTCCATTTAATTTCCTGAACAGGTCAGGAACACGGTGCAACATGATTGTA
AGCACAGCACGTTCATGGAGCGAGCTGCTGCTGCAGCTCAGAAATGCAGCAGTCAGATTG   40800
TGATATGCATCTCTTACACAGGAAATTATGCTCTATTTTATATTATTAAATCTAGCATA
CGAGAAAGGACATCCAGTTTATATCAGATCGTGCAAGGAAGTTAATTATTTTAGTTTGA
TCATTATCATCGGCACTGCAGCTGTAGCTAGGGAGGGGTTGAAGCTCTTCAGCTATCGAC
```

FIG. 14M

```
TCCTTCATATCCTCCACGTTACAATTGTGTTTTTGCAGGTTGACTGCAGCGAGTACCCTA
AGCCTGACTGCACGGCAGAAGACAGACCTCTCTGTGGCTCCGACAACAAAACATATGGCA  41100
ACAAGTGCAACTTCTGCAATGCAGTCGTGTACGTACAGCCCTGATTGCATTCACGTTGTC
GGCTGCCTCCTACAGGCACCAGCTTGCACAGTTCCTGCTTTCGTTGCTGATTGCTGACCA
GGATCTGGGGGCAGAAAAGAACACCGGGCATCACGCCAGCCATTCATTTGATTTTTCACC
AGAGCTTGTCTGGTTTGTTAGGATGGATGTTTTGAACGCCATTAACCTTAAGGGAAGTTT
TCCTTGCTGCGAAGAAAATCAGATTTGGTGTTTCATTATAGTTTTCAGAAGGGGTTAAAC  41400
GATTTCACTCATCTCCTAATAATCAGGTAGCTGAGGAGATGCTGAGTCTGCCAGTTCTTG
GGCTCTGGGCAGGATCCCATCTCCTGCCTTCTCTAGGACAGAGCTCAGCAGGCAGGGCTC
TGTGGCTCTGTGTCTAACCCACTTCTTCCTCTCCTCGCTTTCAGGGAAAGCAACGGGACT
CTCACTTTAAGCCATTTTGGAAAATGCTGAATATCAGAGCTGAGAGAATTCACCACAGGA
TCCCCACTGGCGAATCCCAGCGAGAGGTCTCACCTCGGTTCATCTCGCACTCTGGGGAGC  41700
TCAGCTCACTCCCGATTTTCTTTCTCAATAAACTAAATCAGCAACACTCCTTTGTCTTGT
TTAATGCTCTGCCTCATGCAATGTTTTCTTCTGATTTGTTGGACGGTGATACCAGACTCA
ATATGTTCCATGCTCGTGGCTCTGGGGTATAACAAGAACAACATCTTGCTCCCATCCCTG
TCATAAAAGGCAGAAAATTAAATACAGATGCATAAACCTCGGCTGTGTGACTTTGCGCAT
AAATGACAGTCAGCCTCCATTAGTGTTCAGACCCTTTTAGACAGCTGAAATACTGCTACG  42000
AACTGCTGATGCTGGCTGAGCTCCCCATGGTACGTGTGGTGCACTTTCCCTGCGCAGCAT
TAGCAGTGAAAGCAGCTCAGGGTGCGGTGGTGGCCAAACCCAGGGCCGATCCCACGGCCT
CCTGTACCTGGTCATACCCACGGGCACAGCTGCTAGTGAGGTGCGTGCTTTTCAGACACG
TCATATAAGTGTGCCCTGCCTACATGTCTGGGTCCTCCAAATGACGTTGCAAGGTTTATC
TCATCTTGGAATTGTCCCTTACTGACCACCAAGTGTTTTGAGATGAATGCCCTCCTAGGT  42300
CTGGTTCTGCTCTTGCCTGCTGGTCTTTTCTCATAGTAGTCCTTGCCAGCCCAAGTATCT
GAGCAGTGTTTTGCAATCCAAGGACAAAGTACCCCTCTGCCTTTGAGAGTGTGACCTCTG
TCATTGGCACATTGTCCGTGAAATATATTTTGCTTTTGTCCTTTGTTGGTGTATTGAACT
GATGTTTTCTTGATCCACATGAGAGAAACTTTAATAAAAATTATAAAAAATAATGCCTCC
CTTAAGCATTTCTTTTCCCTGATGGAATGAGGCCATTCAAAAGAAGGATGCTTTGGCGGT  42600
AAAACAGAGGATTTATGTTGAGATGGGCAGATGAATCAAGCAGTGATTTCCAGTTTGGAT
TGAACTTTTCTGGGATCCAGGCTGTGGGCCTCATGTCATTCTGTCATCATCAGGCTATCA
GTCTGCTGCTGCAAATCCTCCCCACAACGCTAATGGCTTTTAGGGAAAATCGCAATTGTT
AGTTCTTTGCTAATGCCCATAAAACTTCTTCCATCACTTGTCCAGCTCCAGGACTCCCTT
CAGCCCCAGGTTTCCTCTTGCTCTCTCTCCCAGTTCAGTTTTTCTGGATTTGCTATGAT  42900
TTGATGATGCATTATTGACAGGACAAGGGGAAATGGTTTCAAACCAGAGGAGAGGAGATT
TAGACTGGACATAAGCAAGACATTTTTTACAATGGTGGTGAGGCACTGACAGAGGTTGCC
CAGAGAGGTGGTGGTGCCCCATCCATGGAGACAGCCAAGGTCAGGAGGGGCTCTGAGCAC
TGATGGAGCTGTGGGTGCCCCTGTTCATTGCAGGGGGTTGGACCAGATGGCCTTTAAAGA
TCCCTTCCAACTCAAATGCTTCAATGATTCTGTGATTCTATTGGGTTGAAGCATGCCAAC  43200
TAAGACTTTCCACTCTGGAAAACATTCAATTCAGTTCAACAACATTTTCCAGCAACAGTG
AGAAAGCACTGCATATAGGTAAGCACTGATAACATGCACATGGAGGAAATCCTGCAGCAT
TCTCTCTTCAGGTTTGTACAGTTGCCCTTTTGCCCACAGGAATTTTCCATGGTCCTTCAG
CAGGCACCTGTCACACACTTCACTGGAAATAATGAAGCCGAGGCGTACTTCACATATTT
AAACCTGCAATTGCTGTTGATAAAGAAGCATTCTTTGTGGCTCACTTGTGTAAGTGCCAT  43500
CAAGATTTACAACCCTGACACCAGAGCTGGAACGCTGGTTATTTCAAAGTAGGGGTGGC
TAAACCAAACGTGAATGCACACAGCCACGCACACACAGATCAGGTGGCCATCCAAGGGCA
GAAGGGCCGCATTCCATGAGCACGATGCACTTCTGCCCTTTGCTGCTGCCCAGGTGAGTG
GCTGTGCTCCTGCTCCGTGCTTCGTCGAGTGCTGGCTGTAAAAACACAACAAACATCCTC
AGACTGGAAAGAGCTGTGTTCTACAAGGACTTATTTACTCCAGAGGGATGGTGTTGAAA  43800
AGACTTGACATCAAAGACTATCACTTATGGGGTAATATTTTAGCAACAGAACTGAGTGGG
TAAGAACAACTGTGGGAACAGCTCCGCGCTCGGTGCTAGTTTATGCATAATGAAAGCAGT
GACACGTACGTGGTACCACGACATCCACCATTGAACCTCCGAAACGCTGCAGAATCACAA
ATTCTTTTACTGAATGGAAGCGAGCGTTTCCCGCAGTCATCCTGAACTGAGATGCAATTG
GAGGGGCTGAGCGGCTGCAGCAGCGTTAGGGGAGTTTCACCTCGCTGAGCCCTCCCGTTA  44100
```

FIG. 14N

```
TTTCAGTGCTGTTGTGGAGCTGCACGCAGGAGCTGCCGCCAGTCCGTGCCAGCTCTGCGG
CCCTGCTTCCCCGGCACCTTGCTTATCTCTGAGCACCTGTCCTTGCTCATCCTGTGAATC
ACGGAGAATTGCTTTCTCTTCCTCCCTTTCATTTCGCGCGTCCTTCTCCACCCGGGCTGT
AACCCTCCTGAGAAAAAACGTAGTACGGAATCGATGTTGTAAACACTCAGCGTGGCACAA
CGTTTTGCCTGAAATCCCTTTTGTCTGAGAGTCACACACTGAATTGCAAGTTGTTTATTC  44400
AGGACATGCACTCACGGATTTTAACACTAACGAAGGAGATGAATTGCATTTGTGTCACAC
TTCCTATTCCCTTCTTTACTCCAGACCCCACTGCACTGAAGGTAAGGGACAGATCTTTCA
GGTTTTTTTTTTTTTCTCCATCATTTCTTTCCTCAAAGCAGTTTCCGTATAAATCATT
ACTAATCGCATTGTGATCGAGCGTTTGAAAGCCCTGAGTCATCCCACAGCCTGAGCAATA
TTTGCTACAGATATTACCGAGTGAAATGGCCATTTTCATCTGATGGTTTCAAAAAAAAA  44700
AAAAGATAATAATAATAATAATAATAATAAATAAATAGCGCAGCATTCAGTTGGTGTCCA
AGTTATTGTCACGGTTACTGCAGCAGCACTGAGGATGTTTACATGGGATTTACATCACTG
GAGGCTGAAAGGGCACTGCAGGCGTGTACCGCGCTATTCGCTGCCCATCCTTAAGCTCT
TCTTTGACATCTGCTGATGGTCGGTGCTGGGGGAAGCCCGGGGCTGTGGGGGTCTCCTGG
CATCTGCCCTGCTGATAGCTGTGCTGCTGAGGGTATTTCTGTGAGCACAAGGCTGCATCG  45000
ATCCACAGGGCGACTGCAGTGCCTGCGCCGTACCCGCAATTTCTGCTCTCGGGAGCGCA
TCCCACACTGCGGGTCTGATGGCGTAACATATGCCAGCGAGTGTTTATTCCGCAATGCAT
TTCTGGGTGTATGAAAATAAATCTCTTCGCTCACTGAGTGGTGAACTTCAACTGTCTTAT
CAACCTCAGGGACTGCCTGGAGATGGAAGGTGGTTGTGTTTGGCGCTCTCCTCTTCTCTT
GCTAGCAAGGGCAGCACTTTTTTTTTTAAACTGGGAGGATTTACCAGGGACTCCTTTCTT  45300
TCAGGTAAAAAGAAGTCACATTTAGCAGAGATCTTCATCTCCACGTTGGGTAATTTGCTG
AAGAGCTCGCTTCCAGCAAATACAGTCTATTTCCTACAGCCTATTTGTTCTTCTTTTAAA
TTAAGTCTTTATCGTGCCTTTGAATGTTAGTAATAAGAGGAAGTAGCTGGAATAGCTTTC
CGAATGTTCTGTTTTGGTTAAGTTCCTCTGTGATGTATCCTTAAGCAGAGGGAGGGATGC
ACAGCAGAAGCGCAGAGGTTCAATCTCTGAGGCCCTGAGCTCTTTCTCTCCAGAACTCAT  45600
TGAGTTCTCACCTTGCTGTGCCCTGCGCAGCGCTCACATCACAGCCCACCGGGCTCCAGC
TCAGACAGGAGGACCCTCTCTGGCTGTGTTCCTTACAGGGGATGCTGCCCAAAGCCTCGT
CCTGAACTTTGAGTGCTCCTGATAAAGCCTGAAGCTATGCTCAATAAAAAAAAAAAACCT
TCAGCATTTTGGTCTTGCTTTCATACTACGTATCATGCTGTTGTTTTTTTTCTTAAGAT
GCTGTGTGATTGCATCACTGCAACAGTCCTGGGGTGTGGGTCTTAATGGGAAAATTACAG  45900
GGAGAAAGAACGGGTTGTCTGATTTATGAAGAAATCAACCCCTCCAAAAGGCCATGAGCT
TCTGCTTTCTTCCAGATTTCCAAAAGAAAGCCACTGCTGGGGATGAGATCCAGTGCAGTG
TTCAGGGCATCCTGTGCAGACATTGACTCCTTAGGAGCTGAAAATAAAGTAGTGGTGGGT
ACCCGTAGGTGTGGGAAGCCTTTCTGCAGCCACCTGGTCTGCCTCCCAAAGCAGAGGATG
GGATGTTTTCCCCTCCGGGCAGCACCAACAGAGGGTGGCAGCAGGGTGAGGAAGATGAT  46200
TGGCCCCTCTGCTCTGCTCTTGTGGGACCACATGCAGTATTGCATCCAGGCCTGGGGCC
CCAGCATGAGAAAGACGTGGAACTGTTGGAGTGGGTCCATAGGAGGCCATGAAGACAATC
ACAGGGCTGGAGCACCTCTCTTATGAAGAAAGGCTGAGGGAGCTGGGCTTGTTCAGCATC
AAGAAGGGAAAGCTGAGAGGACACCTCATTGGAGTCTTCCAGTACTTGAAGGGAGCTTGC
AAGCAGGAAGGGGAACAAACTTCTACATGGTCTGACAGAGATAGAACAAGGGGAGTGGC  46500
TTTAAGCTAAAAGAGGGAAGATTTGGGTGAGATGTTGGAAGAAATACTTTACTCAGAGG
TTGGTGTGACACTGGCACTGCTGCCCAGAGCTGTGGGTGCCCCATCCCTGTACATGAGCT
GAAGGCCAGATTGGATGGGCTCTGTGCAGCCTGATCTGGTGGGGGGCAGCCAGCCCATG
GCAGGGGTTGGGGTAGATGGGTTGTATGGCCCTTTTCAACCCAAACCATTCAATGATTCT
ATGATTCTCAGATAAGCCTGCCTGCCCACATCTGAGCTCACGGTGCTCGCTGGGGGTGGG  46800
GTATGGTACACTAAATGATGCTCAGAGGACTGCACGCAGGACCTGCCGCAGACGTTTATC
ACCTCACCCACCACTTAGCTGCTGCTTGTAGTTAATTACGTCAGCTGTCACTTGTAGAGA
ATCCTTTGAGATCCTTGGGCCTCCGGAAATCTTGGCTGATGAAGGAAGGGCTCAGAGTC
ATAGCGTTAATTTATTATTCATTAACACCAAAGTGTCGGCTGTACGGGCAGTGGGCTCAC
AGTCAAATAGTTAATGATCTTAAGTGACAATGTGTCACTTTGCAGACAGCAGAGAGAACA  47100
GCTCTCCTAAGGGAGACAGCATCTTTCCAATTCTGCAGCCATTCAGTGCCAAGCTCCTCT
TTGGGACGAAAGTGAAGATGAGGAAGGCAATGAGGATGAGGAGGGGCCTCAAGGAACCTG
```

FIG. 14O

```
GCTGGCTTGGAGACAAGTGATGATCCCAGCTGCTCTCAGGGTCCCAGCGGTCTTCAAAGG
GCATCTTGCAGGGGCTGTGTCCTCTGAACAGCAAAACCCAGGTCATAGAGGGGAAAGTGT
GAGCAGAGATGGGACAAATCTCCCATCCTGCCACGGAGCTGCACTGCTAAGGGGGTGATG    47400
GGGAGCAGCATGGGACCCCAGCGTTCCCCCCATCCCTGCACCAGGCCCAGCTCTGCGGGA
TGGCGAGGAGGACAAGGCTCTGTCACAAGCATCGCTGGCAATTATTATTTTGTTGTTGCT
GCTCAATAAAATCCTGACACAGTACAACACAATATCCTCTCATCATTACTAATCTAACTC
TCCCTCCAGGAAATTTCAGGCAGGAAACGTTGTCTGCCTGCCGAGGTGCTTTATGGCACT
GTTCTTTAGTGGTACCTCAGCACTTCGTGTCATTATCTGGTGTCAGTGAATTTAGGAAAT    47700
GCCATTCAATTACCCCGCAAACTGATTAACGCATTGCGTGCAGTTATTTTGTTCTGCTCT
ATTTTATATCAGTTCCTCTGTTTTATGTATTTCTCTACTTGTTGCTGGCCAGAACACACC
TCGGGCCAGTCTAGACCTTGCTGTTGATGCAGCTTTTCCCCAGGGCTTCATCAGCACAAA
TGGTTTGTCAACGTGGGGAAAAATAAAATTATGCTTTAAAATAAAACCACCTGGAGATGC
TGTTCTGGGGTCTGGCTGTGTCACAGCTATTGCAGCGATGGAGCTGAGGGATTGGGATGT    48000
GCTGGGCCGGATCCTCAGCGCTTTGCTATAAGCCAAATAATTCCAGACACCCTTCTTCCC
TCAGATATCATCTGTGCTTAAGCAGCAGGAGATATGCAGGCAGCGATCAGATAGCTGAGC
TGCAAGGAGAAATATCACAAGAGCGCGGCTTAGAGCAGGGCTTTGCTCGCTCTAAATTG
AATTCCCATCCTCATAGGAGATCCAGTCCTGCCCCCGTGTGCATCGCTCCGGTAACAGCA
ATGTGTTTTGCTCCATCTTGCAGAGGGTCCAGAAGCTGGGGAAAGGAAATGTGTCGTGCG    48300
TTCGTCCCTGCAGCAGCTCGGCCCATAAAATTAATGAAAATCTTTTTAGGTCATGGTAG
ATTACAGATTTCTTTGAGATAGAGAATCTCAAGAGCAGAGGAGAAGATTCTCAGAAAATA
GCAGTGATATGAGATGGCATAACGCTGAGTTGGAAACTGGGGAGGATTTCCAGGGTTACT
GGAAATTTACTTAAGCACGAGAGAATGCATCGTGTGACTGCCAGTGCTTCCCCACTCACA
TGGCTATAACCTTCTTGCATACAATTACCATCTTGGAACTTGAAATAGCTGAAAGAGTTT    48600
TATTTGATCTTTTCAATGGATCTTACATCTGCAGAAAAAAAAAAAAAGGCTAGAAATAA
TCCTGCACTCAAACTCACTTTACTGAACCACCATCATGAAACTCCAGCAACACACAGGGA
TTTGGGCAGGCGTGTTCATCTTCCTCTTCCCATTTGCAACATGTGTATGGCATTTCCTGA
AGCTCACTCCTCCAAATGCATTGAGACAGTTGTTTTTCATTCTTCCTAATGCCTGCATCC
ACCCATCTGCTGATCGGCAATTATTTCTATCCCATTCCCTTCTGTTTCTTATTAATCAAG    48900
CTCTTTATGCAATCCCACGTAACACTTTGCCCAGCTGCCCTGCCCTAACCACTACCAATT
ATCTCATCCTGTTTTATAGACCCTGTAGCAAGACTCTGGCCTTGCTCCTCTTCCTCTCCC
TGATAGAGCTTTTGGTGCAGGGCTGGCTGGCTCCTCAGGTGTTCAGAGGATCAGAGGTCT
CCCAGAAGGATCTTGTTAATCAAGGACAGGTGCTGGCTATATGGGAGGATGGCACCGTAT
CCTAAAGCTCTACAAGAAGGAGACGGAGCTCAGCCTGGGAGGACAGAGAGAAGCAGCAGC    49200
ACAGGTTTCAGGATCCAGGGATGGCAGACCTGGGTGTGGGCTCATAGGATTGAAGAAGGG
ATAGGCTGTGCTCCTGTAGCCTCACTGCAGAAGCAGCACTGCTATCTCCCCAGCGAAGCT
GTGTGTGCCCCATCCCTGGAGGTGCTCAGGACCAGGTGGGATGGGGCCCTGGGCAGTCTG
AGCCGGAGGGAGCAGCCGGCCCACAGCAGGGGTTGGAATGGGGTGGGTTTTAAGTTCCCC
TCCAACCAAAGCCATTTCTTGATCTCTGTTGGTGGCTGGTGCAAGTTCTGAGGAAACCTC    49500
ATTTTCAGCTCAGGCGTTCTTGTCCCTGGGGAAAAATCAATATTAATGCTTCAGTGATTA
CTGCTCGCCTTCCAAATGTGCTTCTGATCAGTTCAAGAAATCTGACAGTCACGTCGCTCA
GGATGCTAAGAATACAACAGAAACAGCTTTGAAAGGAACCCTTCAACTCTTGATATTTGT
GAATGAGCTCCAAAGAACATTACTCATTTATTTTTCAGGAAATGATTTCATTGACATGA
ACAGGCCAAAGCCTACAAGCTCTGTTTTGTGACTGCAGCTCCTTACACTTTCAGCTGCAT    49800
TTTCATGATTTATGTGCCCATGATGAGACTTGAACACCTCCAGGATAATGGGAAAGCA
GTTCTGATTTCCCATTTAAAACGTAGGCTGCCTTTAAGCCATGTGTGTGGCTCAGGCTCC
TTCTGAAGCACAAAGGTGTTCCACCCCTCGCTCCTTTTCATTACAACTTTCAATCAAAA
ATGTGTTTTATGAGATATTTGTTTTGCCATGTATCTGTGACGGAGTTGAACCCCTTAGTG
AAACCTCTGTTCTTCACTTAGCTGAGAGGTATTTCTTAGGGAATGTGATGCCCTAAATTT    50100
ATTGTGGTGTAATAGAAGGGGGGATGTGTGGACTCACCTTCTGTTTGTTGTGGCTGCAGT
GGTTTTATGCACTACCTGAGTATTAAGCAAGCCCTTTTCATCTGCACGGAACACCTCCTG
CTTGCCAGTGGGATGAAACAACAACAACAAAGATTTAAGGTTTGCTATTCTCAATGTTTC
TTAATCGGGTTCACATTGATTGCCAACAGATGAATAATTCCTCCTTCTCCATGGATGTAC
```

FIG. 14P

```
CTCTTAAACTTGTGAAGTCTTAGGTAACGCTTTTCTGCTGTGATGACTGTTTCAGTCCCC 50400
TCAGTGAGAAATCAGGCGCACCAGTAAGACACAAAGGAGACCGTGGAGATGTTCATTGTG
CCCTCAGCATCTCCAAAAGGCACTGCTGCCTGCCGAGCCCCAGACTTCGCTCCTGTAAAA
GCAAAGCATGTCCAATTCTGCTGTGCCATAAGAGTCCTGTGGAGCCCAGACACGGCGTAG
CGTGTGTAACATAGCGTGCACGAGCTCAAACGCTTTCAACAAATCAGCTTTTTTGCTTTG
CCAACTTCCATATGTAATTTCACAACATCTAGTATTGAGACAGTGCTGTTGTTTGGGCAG 50700
CATAAATCACTCATTGTACAGCAGGGCGCCTCTCTTAACAAGTTGGGTGTAGTTCATGTT
TTTGTCTAATTCCTCTGCGCATCTCTCTAACAAACAACTATTCTTTAGGGCTCGACTCAA
TAATCAATACATTTTTTTCAGTTTACAGAGCAAATAATTACTTGACCTGATGACTTCACA
AGGTTAGGGAGATGGGTGTATAAAGTCTGCAGTGTGAAGGCAGAGCAACATCTCTGCAGA
CCTTGAGAGCAACAGGTCTGCAAGTAACAGGCTGCACAGCCACCTCTGCCATGGAGGCAA 51000
TGAGAGCTGCTGCCCTCCTTGGATTGGTGCTTCTCAGCTCCTTTCCTGGTAAGTTGTTTT
TGTTACATTCTCTGCTTATATCTCTACTCCTACTGAACTAAATGTGGTTCAGGATGCCTT
TAGAATCCTAAAAGAGAGCTCAGCCTGCCGGAGAAGTGATGGTTTGGTAAAACATGAGCT
CTCTTCTAATGATCTTTATCCTTGTGCAAATATTTACGTAACTCTAGCAGGATGCCTCTG
TCTGACATAAACTCATTATCCTCAGTAAGTCTCATAGCACTCGAGAGAGAAAATGTATAC 51300
CCTATTTCTTCCTTAGTGAGTCAAAGTTTATATTTTCACCCAAAATGGCTATTTTTTTA
ATCATAGGATATAGCTTGCTTATAGGAACTGGATAAAATATTTAGGAAACAAGTAATTCT
CAGTGATAAAAAAGAAGTATGTGATGACTCTGTAGGGAAATTGATAATTCCAGAGGAATT
GTAACCAAGGACGCCGTAACATTCTGTATTTTATAACCTCTGTTTTTTCCAGATATTGTT
TCTGGTCATCAACGGGTGAGTAGCAGATCTGCATCATTTAGTTGTGGTTTCTATGAATAG 51600
ATGAATAATTCATACTCACACCATATCCTACGGGAGCCTAGAGGGAGAAAAAAAAAAAG
AAAAGAAAATAACAAGGGAAGGAGAAAAAGGGCCCCCAGGAATTATGTGACATTTTTCCC
CCAGCAAATAAGAAAACATCTTTGTCAGAGAAAGATAACGTACCACGTTGGTGATAAGAG
TTGGCAATTAATAATGCAGAGTGGGAGCCGGCGTGGCACAGCGTGCCAGCAGAAAATCTG
CACAGCTTTTCCCTAACTGCCTCCATATCTCCCCTGCCTGATTCCCTGAGGACCCATCAG 51900
TCAGTCGTGTGTCTGCCATGCCAAAAGCCTCAGTAGTGACACTGTGCTCAGGCATACTGT
AAGGAACGCTGTAATTTGCTCCCACTTCTTCACCGTGGAGGAGTGACAGAGAATAAAATG
ACCGCCTGCAGCACGGCTATGCGTGGAAAACACAAGCAGACCCTTCCGTGCCCTGCAGAG
CTGTCCCACTTGTGCTCTTCCCAGGCCTCCTGCGGTGAGTACCGGCTGTTAGGCAGCAGG
AACCTCGCCTGTTCCAGGATCTTCCAGCCCGTCTGTGGCACCAATAACATCACCTACCCC 52200
AATGAGTGCTCGCTCTGCAGAGAAATCCTGTGAGTAGCGATCGCCCGATTACCCATCGTG
ATGGCTCAGGTGGCAGACAGAAGCCTTTTGAATTGTGACTAATCACGGGTGGATTCGATT
TTTTTTCCCCCTGTTTCTGTCTTCCCAGAGTGCAGGCTGTGTTTCTTCCTTGTCAAAACT
CCTGAGTCTAATTAATTAGTGGGGCTGGGCGTGGAGAGGCTTGATGAGTGAGGTGACTGC
ATGGCACCACCAGGTTAACCCTTCCCCTCCTTCTCTCCTAGCCGGAGTGGGACGGTTGAC 52500
AAGAAGCACGATGGGAGGTGTGTGAAGGTATGGTTCCAGCTCAGCCACTGTGTGGAGCGA
TGGCAGAATCCCTTCCCAGCACTGATTGTACATTTAGAATGGACAGCTCCAAACCCATTG
GAAATGTAACAGAAAGGAAGAATTTCAGGTCTTTTATATATATATATATATATATATATA
TGTATGTATTAATTTCATTTTGAACAGTGCAAATCTGTTTCAACGGTGAGTTTTGAGATG
TTATCTTGTGTAGCACAGCTGACTTAAAAACAGAATCCTCTCATTTCAATAATCCTTTGG 52800
TGTTGTTGAAATAGTTCCCTTTAGACTTAGACAGAAGTCTGTTGAAATTAAGAAGTTCCC
CAAGGAAGTCTGGATTTTGACTAAATCATAATTTTGTAACAGGGAAAAGAAAAAAAAAA
AGGATTCCATCAGAACATCTACCCTGAGGTTTGTTTATCAATACACGGAGCTGCCACGAA
GTGGAGAAGTGTCTCTATTTTAGATTAGAGAGATAATGTAAAGAAACACTCCGGCTGTG
CAATTGAACATAATGCTACAATTTTCACTTCAGTACACTCAGAGTAATGGCAGGAACACC 53100
GAGGTGAGCATCAGCTCCATTTTCAAGTGGAGCAGACATTTCACAGCAGCAGTTGCTGCC
ATGTAGGGCATGTTAGGCACAGATCCTATGTGGTGGCATTTGGGGTGGAAAGCCCTAAGA
TGACACCAACAAAACCCATTCTGTGAACCCATTTCCTCCAGGATTCTGCTGGGCTCATGT
CCTCAAAGGCAGGACTTCACCTGCCTGTGCTCCCTTGCCCGCACTGTGCTGGGTTGGAAG
CTCACATCTCCATACAGCCCCACTCACCGTGAGTCTGGGGTGGGAGACACCTCTCACAC 53400
CATGCACCATTACACAGGGCTGACGGAAGTGTTGTTCTGTGGCTGTTTCAGGTTGATTGC
```

FIG. 14Q

ACTGGCTACATGAGAACAACTGATGGGCTTGGAACAGCCTGCATCCAGCAGTACAGCCCG
CTCTATGCCACCAACGGGCTCGTCTACAGCAACAAGTGCACCTTCTGCTCGGCAGTGGCG
TGAGTGGTGGGTCACACCCTGGGTGCTGGGGTCTGGGTGGTGGTGTTTGCAGCATATTGA
GGCTTCTGGAGTGGCTGTGCTGTGCTCATTCATTCTCAACTTGCTTTCTTCCCCAAGGAA 53700
TGGAGAGGACATAGATCTGCTCGCTGTTGGAAAAGAGCCCGAGGTAAAGCTCGAAAGTCT
GCGCTATGAACTGTTGTTATAATATATTATACAGCACAAATTCAGTGAGTCAGAACTACG
CAATAGCAATGTCTTCACTGTGCTGGTGTATTTGTCCTGGAAAAAGGGTTTGAGGAAAAT
GACTCAAGTATGCCAGGGTCAGAGGACGATGAACAAAACTCCTGGCTCCTGTGTCAGTAT
CACCTGCACAGCCCCTGACAGGGGTTGATGCTCAGAGCATTGTTCAGATGGTGGCTGTGC 54000
CAGAGGTGCTCACCGCTCCTGGTGAGCGTGGGGCTCATGCAGCACCAGCTGTCATTACTT
GGGTGGGTGGACTTCATAGTGTGCTGTTGGAGACACACTGCTTCCTGGCAGCCCCTCTCT
GCTGGCTGCTGAACCAGAGCAGAGCAGGTAGCGGGCCGCCAGCCGGGGAGCACTGCTTTG
GCTGTGTCGCTGCTTCTGAGGGTATTTAGTAGATTTTTCCCTCTGACTTCTCCTTTTGTG
CTCTGCTGGGCAAGAGCATTAGAATTTGCAGAGTTGCTAGAACAACAGGAGCCTGCATCT 54300
GAAAAAATGTTTTTTTTGCTTTGCCATGACATAAATGTAAAGCGCCCATGTAGGAAAATA
CACCAAACAAAGGCTTCTCAATACGTTCTTGCTCCATTACCTACAGATTGACTGCAGTGA
ATTCAAGAGCACTGATGCCTACTGCACTGAAGAGTACATGCCCCTTTGCGGCTCTGACGG
CGTAACGTATGGGAACAAATGCCACTTCTGCATTGCAGTTTTGTAAGTACAGTGCTCCCC
ATGCAGCCATGAAACCACTGCTGTGCCGGAGTATGAAGGCAGAAGCTGCCAGGAAGCCTT 54600
TGTGCTCCCGTTATCCCCTTGGTAAATCCGTCCCCATCCCCAACCTGATCCCAGCTCTAC
CTCTGCTGTGCCTTCCCCAAGCACTGCAGATCTTGAACACAGGTGAGTCTTCTCCCTCCC
TCACCATTAAATTCAGATTCTCATTTGCGGGCTCATAGCGCTCCTGATCCATCCCTGCGA
GAGTAATTTGAGTGGTAACTGTAGAAGGAGTATCCAAAATTACAGGGTTTGTCCCAGATC
TCTCTAACATGACAAAACGTGTAACCTGGGGAATCAGGAGACGGGTGAAGGTGCAACTGG 54900
GACAGCATGGAGCATTGGCTTGCCCATGCAAAGTCAGCAGTGGCACCATCAGGGCTATAA
AACCACCTTCCATGTCAGTGATTTTGGCCTCCTCCTTTCTCTGCAGGAAGAGTCATGGAT
CTCTGTCTCTGCAGCACCGTGGAGAATGCTGAATGCTGGATCGTAACCTTTACCCTCATC
CATCTTTCACTTCCAAAGCCTGCAATTCCAACACGCTCTTCCCCGCTCCCTGCTGTACAT
TGCTTTCTGCCTTGACCCGCCAGTAAATCACAGACAGCAACTCTCTTCGCCATGGGCTGG 55200
TGTGTTATTTATTTATTTATTTATTGTTGTTATTATTTTTCCAGGGCAGAGGTAA
AAGTCTTCAGGCTTTCAGGCACTTATCTGTCAGGCAGGAGAAGTTTTGAAATAAACCACA
ATAAAGGCCAAAGTGCAACACCCATCACACAAAAGCCATAAGCCCTCACGAAAGTGCGTC
ACCCCATTCCAAACCATCAGAAGAGGAAATGTTGCTATAAAACACATGCTGCTCTCCCCA
GTTCTGTGTCTTACAGCACATAAATGGATTTGCTTTAAGAGTCAGGATGTGGCTTTGTAG 55500
AAGCACGGAGCCCTGGAGGAAGCAGTCCTTTTGGGAGCCTTGGTATGGAGGAAAGATGGC
TTTGATACACCTGAGCAAGGGGCAAGTCTGGCGGCACGTTACAAGGAGGCTTATGGCAAA
GGGAGGAGACTATCTCACAGGGAAGAAAATTAGGAACTGTTGCTTCCTTGAAGGGTGTGT
CCCTTGAGAGTGTGGTGATCAGCAGAAAATTGCAGCCAGCTGGGCAAGGCTGTAATGAGC
CTAATGAGGACCAGAGGAGAAACCAGATTGGGCTCAGGCTTCTTGGAAAAGAGATCTGAA 55800
AAGCTGCACTGGGAGCGTTTGAGGCAGAGGAAAGAGAAAGGACTCTTCAGGAAAAGGTTT
GGGAGTCTTCATGCCTAGAAAAGAAAGGACAGAAGGAGTGCTTGGTAGCTCCAAGGTCGT
TTCTGTCTGCAGTGAAAGGTGATGTGTGGATGATGCGTGTGAGCGTTCACAGTGATGTGC
CATCTCTTTGGGCGAGTCAAGGAATGAGTATGCAAACAACAGGTGAAAAGTCCCAAGTGC
CTCCACTCATGCCACCTTCCCCTTCCTTTCTCCACCTCCCATCCTCTCATTACGTAGGAA 56100
GACATTCAGCTGTTCAGGCTGATATTGAGGACAAAATCTGTGACTTCCAAGCTTTTCTCT
GGCTTTATTTCCTGAAATAGGCTGTATCTTGACCTAGAAATCTTATGGGTGCTTCCTGCC
AGAAGATGGGAAGCTGTCCTTTAATAGCGTGTCAGGGCAGTGCTCCGTCCTAGGAAGACA
GATGGAACTTTGAAATGTTTATTCTATTAGCACAGGCAGTATAAAGCACAGTGTGCCTCT
GTGCCTGCTGGTGAGAAAAGGCAAGCTGCAGAGCCGTGAGGGTGCTCCCTGCTAATCTGC 56400
CTAGAAGGGAAAAGAGTAGACAAGAAATAGCATATGCTACTACTGAATGTGAGCAGAAGA
CCTTTAGTGAAGGACACAGCTCAGCTGTAATGTCCTGTTGGCCAGGAGGTTTGTTGAGTT
ATCGCAGAGCGGTAGAGTTCTGGTCAGAGCAGGAAGGTGCCTTCAACAGCAAGATCCCAT

FIG. 14R

```
GGTAGGCCTCTTCTGCAGTGTGCTGGCACAAGCCTGGTACCTGCTCAGGAGCAAAAAAAG
GCTTTGGAAAAGCTCAAAGAAGGGCTGATGTCTTACAGGGAAAGGGAGGGCAAAAGGCAA  56700
GTGCAGAGCATATGGCTGTACAGACAAAAACCCTTCAGAAAATGGAAAAGGTTTTTATCA
AGTAAGCCCAGAAGTTGGCCCAGTGCAGGTAAACACTTGGCTAGGTAACAGTGAGGCTCT
GCCCAGCCATACCCATTCCTCTGTAAGGCAAATCCCAGGTGCCTTTGTCTTGTCTGGTCC
TGTTCTGTTCCTATTTTTCTGAGAAATCAGACAGAACTTCCCCACCTACAGCATCAAGCA
GCTACTTTATAGGTGAAGAAGTGCAAAGAGAAGCAATAAGGATAATCACCACTTGGCTAA  57000
TTTAGTCTCTTCCTCTCAGCCCACAAAGGACTGGTCCCTGTGGTACATTTTCTAAGGCTT
TTCCCAGTCAGCTGTGCTGTAGCAAATGAAATGTTTGGCTAGATAAAGAGCTGAGGTATT
AGTGCTGGGCGGCGAGCAGTGTCTGGAGCAAGAAAAGGCAAACGAGGGATTCTGCGAGT
GGCAGAACTAAGCCTGATTTTGAATGGCGTTGTGGCTGGCGGACTTGTAAATTATATGAG
AGGCTGTGCTGTGAGCTCACCCTAATAGACATCTGAGAACTCACCTGTCAATCGCGGTTC  57300
CTCTGCTGTGTGGGTTTTATGGTGTCTAGTGAGCTGCAAGCTCTAATGCTTTCCCAGGTG
CAGGGCAGTTGTGGCATTGCTCTCCTACAGAAACTCTCACTTGCTGGCTGAGGATGTTTA
GGAAGTCCTTGGTTGCTAGAAAAAATATATTGAAGTGCTTTTTTTGTTTGTTTGTTTTCC
ATTCTTGTGTGAAATTTTGTTGGAATCACAGAATCATAGAGGTTGAAAGAGAAACTCTGG
AAATTATCAAGTTCAACCCCTTGCTAAAGCAGGCTTCATACAGTAGGTTGCAGTTACAAC  57600
ATTTGCTGGGGAAATGAATATGAAGATCTGTCTATAAAGAGTGTTCCCATAGCACTTGTT
TCTTTAGGAAAGCATGCTGAAATTCTAAAGGCTGTGCCTATCTGAAGAGATACTTTGCAA
GTGGTGCAACTAAATGCTGCTCTTGGTGGAGAGATGGCTGGAGATGGATCGATGGTTGGG
TGATCTTCGTGGTCTTTTCCAACTTTAATGATTCTATGATTCTATACTCTTTACACAGAA
TCAGCTGGGAATAGAGTGAGAGTCTCCTGATTCCCCACCAAATTCCTTTGATTGATGCTT  57900
GGTGTGGAAGCAGAGCTCTGGGACACGTTGGTGAGTGTGAAAACTGGAAAACATTGACAG
CTATAGTTTAAATAGTTCAGGGAGGAGAGGCAGCCATCCTATGTGGGACTCTGCACACGG
CTATGAGAGCATCAGTGCGCTTCTCCACCCCAACCCAACAAATTTAGAGCCATCCTCCAA
AATAGCCAGGGAACAACGCATAATTGGTTTCACAGACAACACATTCTCATGCTGTGATTT
ATTTCGTAATGTCTGGTGAGTGTCATCACGCCGTGCTCAAAGCCTGGAGCTGGCATTCAG  58200
CGAGGACCCAGAGAATGAAAATTACCAGCTTCCCCGATGAATCACCACTTTGAAAATTCA
CCCTTGTGAGAATCCTGTGACTATTCAGAAAAAAAAAAAAAAAAGAAGAAGAAGAAGAAG
AAGATATTACAGGCCCAAGTCTATCAGTCATGTAATTAGCCCTTTCTAGGTTTGATGTGG
ACAGGGCGGCATTCCTAAAGCACCATAAACACGGCCGGGACCAATAATGGCTCTAGAATC
GAAGCGGAGAAGTTCTCACAATTAAGGTGAGGAATGAGGCCAGCAGCGGATAGGTACATA  58500
AATACACGGAGGCAGGGCCGTGAGCACGCTGTGGGCTTGTGGCTGAGACAACACCTCCCA
AACCGGTCGCTTGCCGGGGACTAAAAGAGCAGCATGAAGGCAACAGGCACCTCGGTGCTC
CTCAGCCTGCTGCTGCTGCTGTCGTTCTTCTCGGGTAAGTTATATTTCTGTAGCCTAGAA
AGAAACTTTATGACGAGAGCAACTTCAGAGAGCCTTGATCAACGGATGACAGGCTTGAAG
AGAAAGCTGAGCAAGTAGAAAATATCTGCGGGACTCGCTTGCTTGTGTCACATCTTTCCA  58800
TTCCTCGTGTGCCTCCGCAGTGAATAACACTGTGGAGGTGTCACTGGGAGACAGAATGAG
CAAATTGTAAGCAGCTCGTTCAGCAGAGGCACCAAAGCAGAGCGTAATTATGAGTTTTGG
TGGAAATGTTTGCTGGAGAGCTTTGCTGAACCAGTTAGAGAAGAAACTCATACCTCAGGG
TCATCAGCTCCTGTTCTGATGCTAAGCACTTGGGGGTTGGTGTTCTCCTCAGAGATGTGG
CAGCGTAATTAGATGAAAGTTTCAGCTTCCAAATACGTTGCAGAGGAGGGCTCGAAAATT  59100
AAATTCAGATGTCCTCGAGGAACCCGAACAAAGAGGGCAAATTGAAAGGGTCCAGCGTTT
ATTTATCTTGAGGTTTACACGTCTCTCTGTTGGTCTGGGGAGGCTGGCTGATGGTTTGGG
GGTGTGTAGGGCACACCGGGGTGCTCAAATGCTCGCGTGCGGCCGATGCGAATGTGGAAG
CGTTGCGGTGGCCATTACTGAAGACTGCAGACCAAGGATTATTTATACTTGTTTTTCTGT
GAATAATTTGAATAAAGAATTCGCTTGAGAAAATCGCAGGCTGTGCATGGAGAGAAGAGG  59400
TGAATTACTTTGTACACATCATTAATTATGAAATATTCATCTGTCTTTAATTGAGTCTTA
ATTGGGGCTGGGTTCCGTCAGAGTGCTAAAGCTTCTTTCCAAGGCCAGGCAGAATAGCAG
CAAACTCTGTGATCTCAAATAAGATAAACAGATGCCAAGAGACGTTCTCACAAAGTCTTG
TGTAGCTGCATGTAATATTTATAAAAATTATCTAATGAGCTGTTTTGTAAATAATATGCA
GATAGCCCTAACGGCGGCTTCCCTGTCCAGCCTAGCTGAGGATGTGACAGATACAGCAGT  59700
```

FIG. 14S

```
GGCAAGGATCAAACACTGAAAGGCATCGCAGCAGGCAGAAGCTGGGTGGGGTGATGGATG
GTCCCGCTGAGCGTGATGCTGCAATGCTCCCAGCCTGCACCCTAACCAAAGGGATGCCCC
ATTGCAATGCGCCCCAGCCCCTGCAGCGCTGTGTGCAGCCCACTCCCTGTCCCCGACACC
ACAGGATCCATCCCGTGGCTGTGACCTGGCCCCATGCAAAGTTTGCAGGCAGGAAATAGC
AAAGAGGATGGACTGATTGTCTCCAGGCCCAGAGCCTGTGCCTGCAGCAGGTATTTTGC   60000
TCTGCTGCTGTCTGGCACTGCCTGTTCTGCCCCAGATCACGCCAGGCTATCCCTTTGTAT
CTCATCCGGATGAGGCTGTTCTGGGAGCCTCGGCTGTGCTGTACTGCAGACGGCTCTGAT
GCTGACTGCGGGTCTCCTCCATCTCCCTGTGTGCTTTTGTTACCGTACTGGCCAGTTT
TGTAATTCAGAGGTGCAAGAGCCTAAAAGCCATAAGACTCAATGAAGCTTTAAAATCTCT
GCTGAGAGAGGCTCAGCTCTTACATAGCTCCCCGCTTCCCCGGCGGTGGCTGCCTGCCAG   60300
GGAGATGGGTTTATGTGTCTGTGGTGCAGTTAGCAGCTGAATGACTGATTACATGGTATT
TTAGTAACATTTTTCAAATAGCAAATACTGAAAAGCAATTCCGATAATGTATTTCCTAC
CCCTCCTCCACCACACAGAACGGCAGAGGAGGGAAAACCTGGTGTGTGCTGTGCTGCAGT
TTGCAAAGGGATTTGTGACTTCGGTTCAGTCCTCTCAGAAATAATGCTAATGTGGATAA
AATCTTTTTTTTGTTGCAATTCTAGGTGTAGCAGCTCAAGACATTGAAGAGGTTAGTGC   60600
AGCTCTTTCTGCTTTCTGAATCTGCATTTTCTCCTGGCTCTGGAAGAATGCTTTTCTAAC
AGATCTTGGTGCATTGGTGCATGCTGAACTGCTTTGGGTTTTGCTGGGATCAGGTGGGTC
CTGCCAAGGTGCCCCAATGCTTCGGAGTGCTCACACAGTACAGGGGTGTTAGCTATGGCC
ACAGTAGCAAACAAGTTGGGGATGATTTAGCTGGTTTAGCACATGCTCCCCATGGTCTGA
TCCAGCACAGGGCTGTCTGCAGTATCGCTTCTGTCTGCTTTGCTCCTCCACGAAACAAAT   60900
GTGATATCAGGAGTGATATACTCCTTTAAACCATATCCATAACTGGGGCTTGTCCAAAAG
CCTGTTCACTTCATAGAATCATTAAGGTTGGAAAGACCACTATGGTCATCGAGTGCAACC
ACTCCATGCCCAGATCCCTGTGTATGGCAGCCCCAGGCCACGTGGTGGTGTGAGCTGCAT
GGTACCGGGCACTGATATGGGGCTGCATCAGTGCTGATGCTCTCCTGTTGAACCCACTCA
TGTTCTTGGAACACCAGAGCTGCTCCCTGGTGGTGACAGCTTCCCTCCTCTGCCACAGGG   61200
CAGAAATTCCCCCATTTCAGCCAGTTCTGACAGGCCTTTGTTTTCAAGTAAGCAGGCCG
TGCCTCGTTGCTGCTTTTGGCCTCTGGGTGGAAGAAGATCACATTAGAGATCTTCTTTC
CTGTTTGGAAAGCGAAACCCGACGGTTTATTGCTGTTATTATTTTTGATTTCTTTTGCAG
ATCTGCAAAGAGTTCTTAAACAGGAGCGTGTTCTGCACCAGGGAGTCCAACCCTCACTGC
GGCACGGATGGCGTGACGTACGGCAACAAGTGTGCCTTCTGCAAGGCCGTGCTGTAAGTG   61500
GGGGCGGTGGGATACGGACCCACACAGGGATGGTCCACTTCCAACCCCGCGCTGCTGCTC
CCCTCACACAGAGCAATCCCTGGCCATAGAATCATAGAACTAGAGAATGGTTAAGGTTGG
AAAAGACCAATAAGTGCATCTAGTTCAAATGGCAGCTCCTCACCGCCACGCTTGGGAATA
TTTCAGCTTAATGTTGATTCATTTCTAGGCTTAGTGTGATGCTCATAGCCGTACAGAGAT
GGCACAGAGCCTGGGAGGCCATTGTACCTGCCTGTACCTTCTGCGTGGGCTAAATTGATG   61800
CACATTTTCCTCTGTGTGCCACAGGCTGAAGCTCTCCCTGTCCACACCTCTGGATGCTGA
AGTGTGTGGAGGAACGCAGGCTTATGCATGCCAAATTATTAGAGGAAAGTCATAGACTCG
TAGAATCATAGATTCGTTTGAGTCGAATGGGACCTTTGAAGGTCATCTGGTCCAGCATCC
CTGCAACGAGCAGGGAAAGTGCTGAAATGAAAGTCTGAATGGACTTAGTGGAAAAGTACA
CAAAATCTCAGAGGAAGGGCTGCAGTTTCTCCTCTCCTGTCTCCTCTAAAGGAGCTGTAA   62100
TAGGAGCCAACACCTCTGGACTGAAGGCCTGCAAAAATTGATTTATCCTTATCAATCCTG
CACTCTGGAGGCTGCCTTATCCTAAGGGAAATTAGAGAAGAGGGAAAGATGGCTTGATGC
TCCCTGTGAGGCACCAGAGTGAGGCAAATGATCGTGCTCGGAGGGACAAGCTCCCTGTCC
CAGCCGCTGTGTCTGTGCTGGATGCCATACACTGCTTTGTTTCCATACCGCTCCTTTTAC
AGGAGGAGTGGAGGGAAGATACGATTGAAGCACATGGGAAGTGCTGAGCCTGAGCACCA   62400
AGCACTGATCTTCGTCGGTCACAGGTGCAGGAGCCTGGGCACGGCAGCAGCTGTCCTCAT
CTCTGCCATATCTGCTCAATAAAGTAAAGCTCAGCACACCTCCTTGACTGGATTCCTTTT
TCCATAACACCCGGATAAGCCTTCCATGCAGCCGTGCTAGCAGCTAAAATGTTTGCCGCA
CTGTGCTGTTACATCTTAGAATCACAGAATCAGGCACCATGCTGCCTGAGCAGGAGCAAT
GATTCCCACAGCTCTTCCATGCCATGCCATGCCATGCCATGCCATGCCATGCCATGCCAT   62700
GCCATGCCATGCCATGCCATGCCATGCCATGCCATGCCATGCCATCCCATCCCATCCCAT
CCCATCCCACTGACAAATGGACACATGGCCACCCAGCTTGACTGTCCCATGGGTGGGTGA
```

FIG. 14T

```
CAGCATGCAACGTTGCCTCTCAGCAGCCTCCCCATATGTGTCCCTCTCGCTGAGGTGTGA
GCATGAAGGTGGCAGAGAGCTATGAGTGGTGTGGCTGTGGATGCCTCATCTGCTTGGGAA
GCCAGAAGCAAACAGGCTGAGGCTGAGGAGTGTTGCTGCATGTAAGCCTGCACCGGGAAG   63000
GTGGCAGGGGAAGCTGGCTTTAGGCAGAAACACAAAGGCTTTGCTTTCCTTGTGTGTCCT
AAGAGAGGACTTTGCCTCAAAGACTGTCAACTCGCCAGCATCAGGTTGCAGTTGCACACA
AACTTGATTTCTTTCTTTAGTTTTCACACTGCTGCTCTCTCTCCTTGATGCTGGCTGG
AAAATCCTTCTTTGCGCCAGCGAGGGAAATAAAGCCTATAGTCTCTCCCATTCGCTGT
ACAAAATATACACAGGGAAATGCTTGTGGCATCCCCTCGTTAAAACGTTGGCAGCACATC   63300
AATGGGACTCTACTCACTTAATGTTGAACACTTAAGTTTCAAAGGGAGCTTTAGATTTTA
TCGTGAGGTCAGCCAACTCATTTTGCAAACACCTCTATGCTGAGCATCTCAGCTCCTGGA
TGGTGTTTGGACAGAGCTGAGTGTTTGCCTGTGGTGCCACGCTGCAGGCTTTGAAGTGAA
TTGGGACATTATATTTTGTAGCCAAGGAGAGTTGCAGTTTGCTTTGTTCCAATTCAGATG
TTTCTTTAGTAAACACAACAGCTAGACCTCCAGAACATGGATAAGCTTGAGGGGAGGAAA   63600
AAGCACCTCCTGCACGAGGACAGCTGATCACAAAGGACCCCAGTGGGCAGTGGGAGAACC
TTCATCATCCTCTACCGCCTGGATCAGGATGAGCCCTGCATACCCTTTCCAACTGGAG
TTACCCTGTGAGCCAACTTGTGGCTCTGGAGTAGTGCTGTATCTCAATACAGTTTCTCAG
ATGGGAAGAGGCATTTCAATGAGAGGGGGGATATGGGACATTTCTATGCCTGAGATGGCT
CTCGGAGACTCCAAAAGCCTCACGGCGTATCCCCATGCCTAATCCTTTTAATCTGGAGG   63900
CTGAAATAACAAGGACAGATCACAAGAGAACAGAAGCGGCGAGACTTCTCTGCTTTATAA
TCAGCCTGCATTTTGCTCTTTCAGTGCAAACAGCAAATAGAACCGCCTCTGTACCCCTCC
AGACCCAACCACCATCCCCAGCAACACTGTGGCAGGCTGGAGAAGGGTGGCTCTGCCCCT
CCTTGCCTCAACTGGTTGTGTCAGCACGACCATAACCAGAGCTCTCCTTGGCCCCAGCTG
GGCTTATCCATGTAAACCTCTCAGTGCCCCAGGAGCTGGCTGGTGGTCCTGTCCATTTCA   64200
CTTTCCTCCAGCAGGTGTTCCCTTTAACAAGCATCCAAGTGCCTGGAGCAGGAGCAGGCA
CTGCAGAAGATGAGCTCAGGCAAGGACATGGCATGTGGGGATCCATGCTGTTGTGCAATG
CAGATGACGTTAGATACGTGCAAAGCAGATCTCAGCAATCACCCAACGACTCATAACTGC
AATCATGGAACGCAATTGCATCTGGAAGTATAAAAGCACAGTGATACCAGGAAGCTCTTG
TTAATGGCACAGCCATTTTGGAGCAATTTGCCCAGGTGGGGAGAGCCCTCACAGCGCCTT   64500
CAGTCACAGGGAGTGGTGTGAGTGCCCCCATGGCTGCTCCCAGCCCCCAGCCCTGGGTGA
TGGGGGTCACTTGGCTGTAACCCTCTGAACACAGGGACAGTGAGACAGCCCTCTGGCCTG
GCTGAGCTCTTGGCTACGTCCAGCTGCAGTCCTGGGCACATACTGAACCAGAAAGCAAGC
ATTCAGCTGGTATTTTCCTTTAATTCCTTCCTCCACATTTTAAGTTGTGGGATTTTTT
TTTTTTTTTTTGACAGCTTTGAGAGATGAGTGAGTCACGAAGCACTCGAGATCTCTATT   64800
AGATAACAGAGCATCTCTGCAGCTCTTCCTGGGGAGGGAGTTCCTTGGACCAAGGGCCAA
GGCTGGGTGAGAATTGTCCCAGCATCACAGTGGCTGCTCCATCACCTGACACAGCCCCTC
TGCAGTGAAACAAGGGAAGCATTACATCTTTGCACGGCTGCTTTCACTGAACAAAAAGCG
CTGCTTCACAGCTGAGCACCATGATGAAGGGGAAGGAGCATCTCCATGATGAAGGGGAAG
GAGCATCTCCACATCTCCATCACGAGCTCTGCTCTGCTGGTGATGCGGCTGACACCATGG   65100
TGTGCCCTGACTCCTGGCCCATTTAACTGCTGTGCACCAGTGCCTCCTCCCAGCATAGC
CCTGTGTCCCTGCCACAACTCATTGCAATCCTTTGTCCTACTTCTTCCCTTGACATTCAC
AGCTCTTGATAAGGCTTTTTGAGCCACTCCTGGCTGATGTGGGCTGGTGGTTCCTGCTGC
AGGGTTCCCACCACCCAGCTGGGCAGCATTCGGTTGTTGTTCCAGTTCCCAGGGGATTGG
GACAGATTGGAAGGGTCTTTGGGACTGTGGAAGAGTATCTCCTGAAGTCAGGGCAGACTG   65400
CTCAGCGCTTTGTCCCATCCAGACTTGAAAACATCCAAGGGTGGAGAACACACAGACTCC
CTGGGCTGCCAGTCCCAGAGTTTGACTGTCATCACGTTGAAGACTTTTTGCCTTGTCTCC
ATTTGCAACCTCTTTCCTTTCAGCTGCCCATCTCTCAGCCATGCACCACTGGGGAGCCC
AGCTCTGTCTGGTCAGGAACAGAGCCCTTACAGAGCCACAGCATCCTCCTGAAGTGTCCA
TCTCACCACTCAGCCTCAGCAAGTGCTCCAGCCCTCAACTCCCATTTTCCATTATCTTTC   65700
TATCACTGGATATGGGAGGGAAGGCAGAGCTGTGGGCCAAGAGAAACGATTGCTCAGGA
GGCAGTTGGGAGAACTTTATTGCAAAGCACTGAAGAGATATAAAGTGACATTTGCAGGAA
AAAGTAGAAGGGTATCTGTGTGTGTTGGTTCCTTTAAGGATTAGAGAGCAGCTGAGCTTT
GGGATGAGAGGGCTCCCAGATGCTGTGAATCAGCTAACAGATCCCTCCACCCCGTCATTG
```

FIG. 14U

```
GTGGTGAAGTTAAATAGGGGCCCAGGGGAAACATCAGGGTTGTTTTTCTTTTTACGGACT   66000
CCAGAGCAAGGAGAAGGTGAGGGGGTTGTGCTTTGGAATGGGAGTGAAAGAGTTTGTTGG
TGTTTTCCTCTCCCCAGAATAAGTAGTGTGGTGTAGGAGCGTCTCATAGGAGTAGCTGCG
TTAATTGTGGCTGGTGTTAGCATCCTATAATGTTGCTCCAGAAATGCTGGAGCAGGCTTA
TAATGATGTGTATGTATTACCATAATACATGAAGGGAGAATGGGGGGGGGGGGGTAGAT
TTAAGATGTATGCCCTTAGAAAGGCGGGTGTCACTTAAAGAAGTACTTGCTTTATAGCTC   66300
CAGTGATAGAATTCATTGAGATACTCTGAACCTATGGGGCATGAAGTGACCAGATCTTCA
GTTTGGTCAGCTCTGGGGGTTTCTGGGGGGAGCGGGGATAGAGCCTCAATCCAGGTCTGA
AAGACAAGGCTGAGATGTGCTGGGCCTGGGGTGCTGCCCTGAGCAACGTGGGGCTGGCCC
TAGAGAGCAGCATTAGTGCCTGCAGCAGGGCTGGCCCTTGTGCCCAGTGTGTGGGGTAAG
GTGGGGAACGTAGGTGCTGCATAATGTGGTGCTTCTGATCTAAAACTGCTCTGTTAATTG   66600
GGAGTGACCAGAGATGGCCCTATGGCTTTCTTCCCAAAGAGCTCTGTGTCCTTCTCTGCA
GGGTAATCTGTGATAAAAACATCGCCTATGCTCTGCCCTGCAGATGCAGGGGTTTTGTC
ATCCTCCTTCTCGAGACATACTCTAATCCTTACGCAAGCAGGGAGCTCCAAGCTTTTGGT
GATAACCTCTCAAGGAGGAGCTGGAAGGGCAGCTCTGCCGAGCAGTGACTGCGCTGCACG
GGGCGCATCCTGCAGGAGGCGGTGGTGTAAGCGGGACTCCGCTCGTTCCCGGCTATGGGG   66900
CTCCCCCTGCTGACCGCCGGGCGGTGGCCAGGAGACCTCGGGGCCGCTGCTGCCCCTCGG
TGGTGCTTTTCGGGACAGCTTTCAGGATGGGGCAGCCCAGCTGCTCTCGCGGGGAATTAA
GCGGCTCGGTGCAGGGCGGCACGGCGCTGAGCTGCCCCAGCAAAGCGCCGCTCGTCCCGC
GGCACCTTCGGTAGATGCTCTCTGCTTGGCAGCTCCTTGGTCGTTCTCTTGGCCGGTGGC
CACCCCAGCATCGCTCGGGGCTCGGTGCCATCCCCCCAGGGCCTGCGGAGGTGCCGGTG   67200
CCCGTCCCGGGGTGGCGGACGGGCGGTGCAGTACCGATGCTGGGCGCTGGGTGCTGCCG
CAGACCGAGCGGCGCTGCGCGGCTCCGGGGCGCTCCTGGAGTGCGAGCTGAGCAACCTGG
TAGAAAAATAAGTGTTGTCCCGTGATAAACGTCATCGTGCTGAGCTCTCAGACTCTGCCA
GAGGCCTGAATGAAGCTGCGTCAGGGGAGAATCAGGTTGGGCTAAGGAAAGGTCCTGCC
CCAGAGGGCGGTGGGTATAGAAGGGGTGCCCAGGGCAGTGGGTGCAGTGCTGGGCTCCCA   67500
GAGCTGGAGGAGCGTCTGGACAGTGCTCAGGTTTGGATGTTGGGTGGTTTTCTGAAGGGA
CGGATTCTGGGCTCGTTTATCCTGAGGGTCCCTTCCAACTTGGGTTGTTCTATTCAATGA
ATATTGTTTATGTTCATTCTATTCTATGATCTTGTTCAGGCTCTCACTGCTGCCTCCAAG
GGTTCAGCTCCCCAGAGCTGGCAGGGCTTCAGCCACTTGCTTACAGTGCTCATTTCATG
CCTGGCCCATGGCTTCTGCCTGAGCCTTGTGGGAGATCAGCTGCTGCCAGAAACCCAGCC   67800
CTCAGCACTCCACTTGCCCAGCTTGCTGCCTTAGTAGTCTAACTTGGCAGTGGTCTGACA
TGACTTGAGGTTGTTTTTTATTTCCAAGGTGCCACTGACTTTTTTCCTTCCATAGTTTCT
GGAAGCATTTCCTTCCTACTTGACTGAGTCGTGCTCTGTGGATCTGTAATTATCCACCTT
GGCTATGTGTCCTTTACGGGATTTTATATGTTAACCTCCCAAGATCATTTTGCTGCTCTC
ATCTTAGTGGCTGCTGTGAGCTCCACCAGCACCACACTGGATGAGCTGCAGGCTGAGGCC   68100
GGGCACCTCTCCTGACTCTGCTCTTCTCTGACCCCAGAGCTGTGCAGTTGGGATCCTAAC
ACCATGCAGATGCTCCAGGACCTGCACCGAGCCCCAGCACTGGCACTCATCTCTTCTTTC
CACCCCTCTGAGAGCAACAAGTGGCTCTGCAATGGCAATGTAAGTGAAACCGGGCGGGTA
TCTTAGAGCACCTGG
```

FIG. 14V

SEQUENCE LISTING

```
<160> NUMBER OF SEQ ID NOS: 46

<210> SEQ ID NO 1
<211> LENGTH: 30
<212> TYPE: DNA
<213> ORGANISM: Artificial Sequence
<220> FEATURE:
<223> OTHER INFORMATION: Primer OVINs2

<400> SEQUENCE: 1
taggcagagc aataggactc tcaacctcgt                                     30

<210> SEQ ID NO 2
<211> LENGTH: 30
<212> TYPE: DNA
<213> ORGANISM: Artificial Sequence
<220> FEATURE:
<223> OTHER INFORMATION: Primer OVMa2

<400> SEQUENCE: 2
aagcttctgc agcactctgg gagttactca                                     30

<210> SEQ ID NO 3
<211> LENGTH: 20
<212> TYPE: DNA
<213> ORGANISM: Artificial Sequence
<220> FEATURE:
<223> OTHER INFORMATION: Primer OVINs1

<400> SEQUENCE: 3
gggaaacaat ctgccttgca                                                20

<210> SEQ ID NO 4
<211> LENGTH: 21
<212> TYPE: DNA
<213> ORGANISM: Artificial Sequence
<220> FEATURE:
<223> OTHER INFORMATION: Primer OVMUa1

<400> SEQUENCE: 4
aagccacaaa gcacgaaaga g                                              21

<210> SEQ ID NO 5
<211> LENGTH: 20
<212> TYPE: DNA
<213> ORGANISM: Artificial Sequence
<220> FEATURE:
```

```
<223> OTHER INFORMATION: Primer T3

<400> SEQUENCE: 5
taatacgact cactataggg                                               20

<210> SEQ ID NO 6
<211> LENGTH: 20
<212> TYPE: DNA
<213> ORGANISM: Artificial Sequence
<220> FEATURE:
<223> OTHER INFORMATION: Primer T7

<400> SEQUENCE: 6
attaaccctc actaaaggga                                               20

<210> SEQ ID NO 7
<211> LENGTH: 20
<212> TYPE: DNA
<213> ORGANISM: Artificial Sequence
<220> FEATURE:
<223> OTHER INFORMATION: Primer OVINs4

<400> SEQUENCE: 7
agatgaggtg gatggtttac                                               20

<210> SEQ ID NO 8
<211> LENGTH: 20
<212> TYPE: DNA
<213> ORGANISM: Artificial Sequence
<220> FEATURE:
<223> OTHER INFORMATION: Primer OVINs5

<400> SEQUENCE: 8
cagcttctgc tagcgtaggt                                               20

<210> SEQ ID NO 9
<211> LENGTH: 20
<212> TYPE: DNA
<213> ORGANISM: Artificial Sequence
<220> FEATURE:
<223> OTHER INFORMATION: Primer OVINs6

<400> SEQUENCE: 9
acgtgaactc aaagaggcac                                               20

<210> SEQ ID NO 10
<211> LENGTH: 20
<212> TYPE: DNA
<213> ORGANISM: Artificial Sequence
<220> FEATURE:
<223> OTHER INFORMATION: Primer OVINs7

<400> SEQUENCE: 10
atctcctgag ctcggtgctt                                               20

<210> SEQ ID NO 11
<211> LENGTH: 20
<212> TYPE: DNA
<213> ORGANISM: Artificial Sequence
<220> FEATURE:
<223> OTHER INFORMATION: Primer OVINs8

<400> SEQUENCE: 11
acgaggttcc atgtctttca                                               20
```

```
<210> SEQ ID NO 12
<211> LENGTH: 31
<212> TYPE: DNA
<213> ORGANISM: Artificial Sequence
<220> FEATURE:
<223> OTHER INFORMATION: Primer OVMUa3

<400> SEQUENCE: 12
taaatagcac agaacgctga ggggagtaag g                           31

<210> SEQ ID NO 13
<211> LENGTH: 20
<212> TYPE: DNA
<213> ORGANISM: Artificial Sequence
<220> FEATURE:
<223> OTHER INFORMATION: Primer OVMUa4

<400> SEQUENCE: 13
gaagagcttg gtagaagact                                        20

<210> SEQ ID NO 14
<211> LENGTH: 21
<212> TYPE: DNA
<213> ORGANISM: Artificial Sequence
<220> FEATURE:
<223> OTHER INFORMATION: Primer OVMUa5

<400> SEQUENCE: 14
atggaaatat gggtttcctt c                                      21

<210> SEQ ID NO 15
<211> LENGTH: 20
<212> TYPE: DNA
<213> ORGANISM: Artificial Sequence
<220> FEATURE:
<223> OTHER INFORMATION: Primer OVMUa6

<400> SEQUENCE: 15
gcagcttatg gctaatcgct                                        20

<210> SEQ ID NO 16
<211> LENGTH: 20
<212> TYPE: DNA
<213> ORGANISM: Artificial Sequence
<220> FEATURE:
<223> OTHER INFORMATION: Primer OVMUa7

<400> SEQUENCE: 16
agtgaccact atctgacctg                                        20

<210> SEQ ID NO 17
<211> LENGTH: 20
<212> TYPE: DNA
<213> ORGANISM: Artificial Sequence
<220> FEATURE:
<223> OTHER INFORMATION: Primer OVMUa8

<400> SEQUENCE: 17
taatcaggaa ggcacacagc                                        20

<210> SEQ ID NO 18
<211> LENGTH: 20
<212> TYPE: DNA
<213> ORGANISM: Artificial Sequence
<220> FEATURE:
<223> OTHER INFORMATION: Primer OVMUP4. 7. 1
```

```
<400> SEQUENCE: 18
agatctggag cagcacttgt                                             20

<210> SEQ ID NO 19
<211> LENGTH: 20
<212> TYPE: DNA
<213> ORGANISM: Artificial Sequence
<220> FEATURE:
<223> OTHER INFORMATION: Primer OVMUP4. 7. 2

<400> SEQUENCE: 19
agcatgaagt tcctcaccca                                             20

<210> SEQ ID NO 20
<211> LENGTH: 20
<212> TYPE: DNA
<213> ORGANISM: Artificial Sequence
<220> FEATURE:
<223> OTHER INFORMATION: Primer OVMUP4. 7. 3

<400> SEQUENCE: 20
atggagagga atattccctt                                             20

<210> SEQ ID NO 21
<211> LENGTH: 18
<212> TYPE: DNA
<213> ORGANISM: Artificial Sequence
<220> FEATURE:
<223> OTHER INFORMATION: Primer OVMUP4. 7. 4

<400> SEQUENCE: 21
atttctccag gcgtgtgg                                               18

<210> SEQ ID NO 22
<211> LENGTH: 18
<212> TYPE: DNA
<213> ORGANISM: Artificial Sequence
<220> FEATURE:
<223> OTHER INFORMATION: Primer OVMUP5. 5. 1

<400> SEQUENCE: 22
atttctccag gcgtgtgg                                               18

<210> SEQ ID NO 23
<211> LENGTH: 20
<212> TYPE: DNA
<213> ORGANISM: Artificial Sequence
<220> FEATURE:
<223> OTHER INFORMATION: Primer VMUP5. 5. 2

<400> SEQUENCE: 23
atgcgagtga aggagagttc                                             20

<210> SEQ ID NO 24
<211> LENGTH: 20
<212> TYPE: DNA
<213> ORGANISM: Artificial Sequence
<220> FEATURE:
<223> OTHER INFORMATION: Primer OVMUP5. 5. 3

<400> SEQUENCE: 24
gcagcacgtg taagcttgta                                             20

<210> SEQ ID NO 25
<211> LENGTH: 20
```

```
<212> TYPE: DNA
<213> ORGANISM: Artificial Sequence
<220> FEATURE:
<223> OTHER INFORMATION: Primer OVMUP5.5.4

<400> SEQUENCE: 25
caaggcaaat tatcagcaga                                                     20

<210> SEQ ID NO 26
<211> LENGTH: 9980
<212> TYPE: DNA
<213> ORGANISM: Gallus gallus
<220> FEATURE:
<221> NAME/KEY: 3'UTR
<222> LOCATION: (1)..(255)
<223> OTHER INFORMATION: 3' untranslated region of ovoinhibitor
<220> FEATURE:
<221> NAME/KEY: misc_feature
<222> LOCATION: (2761)..(3024)
<223> OTHER INFORMATION: CR1-like element
<220> FEATURE:
<221> NAME/KEY: 5'UTR
<222> LOCATION: (9403)..(9920)
<223> OTHER INFORMATION: 5' untranslated region of ovomucoid

<400> SEQUENCE: 26
taggcagagc aataggactc tcaacctcgt gagtatggca gcatgttaac tctgcactgg         60
agtccagcgt gggaaacaat ctgccttgca catgagtctt cgtgggccaa tattccccaa        120
cggttttcct tcagcttgtc ttgtctccta agctctcaaa acaccttttt ggtgaataaa        180
ctcacttggc aacgtttatc tgtcttacct tagtgtcacg tttcatccct attccccttt        240
ctcctcctcc gtgtggtaca cagtggtgca cactggttct tctgttgatg ttctgctctg        300
acagccaatg tgggtaaagt tcttcctgcc acgtgtctgt gttgttttca cttcaaaaag        360
ggccctgggc tcccttggga gctctcaggc atttccttaa tcatcacagt cacgctggca        420
ggattagtcc ctcctaaacc ttagaatgac ctgaacgtgt gctccctctt tgtagtcagt        480
gcagggagac gtttgcctca agatcagggt ccatctcacc cacagggcca ttcccaagat        540
gaggtggatg gtttactctc acaaaaagtt ttcttatgtt tggctagaaa ggagaactca        600
ctgcctacct gtgaattccc ctagtcctgg ttctgctgcc actgctgcct gtgcagcctg        660
tcccatggag ggggcagcaa ctgctgtcac aaaggtgatc ccaccctgtc tccactgaaa        720
tgacctcagt gccacgtgtt gtatagggta taaagtacgg gaggggatgc ccggctccc         780 ttcagggttg cagagcagaa gtgtctgtgt atagagtgtg tcttaatcta ttaatgtaac        840
agaacaactt cagtcctagt gttttgtggg ctggaattgc ccatgtggta gggacaggcc        900
tgctaaatca ctgcaatcgc ctatgttctg aaggtatttg ggaaagaaag ggatttgggg        960
gattgcctgt gattggcttt aattgaatgg caaatcacag gaaagcagtt ctgctcaaca       1020
gttggttgtt tcagccaatt cttgcagcca agagccgggt gcccagcgat ataatagtt        1080 gtcacttgtg tctgtatgga tgacagggag gtagggtgac ctgaggacca ccctccagct       1140
tctgctagcg taggtacagt caccacctcc agctccacac gagtcccatc gtggtttacc       1200
aaagaaacac aattatttgg accagtttgg aaagtcaccc gctgaattgt gaggctagat       1260
taatagagct gaagagcaaa tgttcccaac ttggagatac tagttggtat tagtatcaga       1320
ggaacagggc catagcacct ccatgctatt agattccggc tggcatgtac ttttcaagat       1380
gatttgtaac taacaatggc ttattgtgct tgtcttaagt ctgtgtccta atgtaaatgt       1440
tcctttggtt tatataacct tcttgccatt tgctcttcag gtgttcttgc agaacactgg       1500
```

```
ctgctttaat ctagtttaac tgttgcttga ttattcttag ggataagatc tgaataaact    1560
ttttgtggct ttggcagact ttagcttggg cttagctccc acattagctt ttgctgcctt    1620
ttctgtgaag ctatcaagat cctactcaat gacattagct gggtgcaggt gtaccaaatc    1680
ctgctctgtg aacacattg tctgatgata ccgaaggcaa acgtgaactc aaagaggcac     1740
agagttaaga agaagtctgt gcaattcaga ggaaaagcca aagtggccat tagacacact    1800
ttccatgcag catttgccag taggtttcat ataaaactac aaaatggaat aaaccactac    1860
aaatgggaaa agcctgatac tagaatttaa atattcaccc aggctcaagg ggtgtttcat    1920
ggagtaatat cactctataa aagtagggca gccaattatt cacagacaaa gcttttttt    1980 ttctgtgctg cagtgctgtt tttcggctga tccagggtta cttattgtgg gtctgagagc    2040
tgaatgattt ctccttgtgt catgttggtg aaggagatat ggccagggggg agatgagcat   2100 gttcaagagg aaacgttgca ttttggtggc ttgggagaaa ggtagaacga tatcaggtcc    2160
atagtgtcac taagagatct gaaggatggt tttacagaac agttgacttg gctgggtgca    2220
ggcttggctg taaatggatg gaaggatgga cagatgggtg gacagagatt tctgtgcagg    2280
agatcatctc ctgagctcgg tgcttgacag actgcagatc catcccataa ccttctccag    2340
catgagagcg cggggagctt tggtactgtt cagtctgctg cttgttgctt cctgggtgca    2400
cagtggtgat tttcttactc acacagggca aaaacctgag cagcttcaaa gtgaacaggt    2460
tgctctcata ggccattcag ttgtcaagat gaggttttttg gtttcttgtt ttgtaaggtg   2520
ggaagaagca ctgaaggatc agttgcgagg gcagggttt agcactgttc agagaagtct     2580
tattttaact cctctcatga acaaaaagag atgcaggtgc agattctggc aagcatgcag    2640
tgaaggagaa agccctgaat ttctgatata tgtgcaatgt tgggcaccta acattccccg    2700
ctgaagcaca gcagctccag ctccatgcag tactcacagc tggtgcagcc ctcggctcca    2760
gggtctgagc agtgctggga ctcacgaggt tccatgtctt tcacactgat aatggtccaa    2820
tttctggaat gggtgcccat ccttggaggt ccccaaggcc aggctggctg cgtctccgag    2880
cagcccgatc tggtggtgag tagccagccc atggcaggag ttagagcctg atggtcttta    2940
aggtcccttc caacctaagc catcctacga ttctaggaat catgacttgt gagtgtgtat    3000
tgcagaggca atattttaaa gttataaatg ttttctcccc ttccttgttt gtcaaagtta    3060
tcttgatcgc cttatcaatg cttttggagt ctccagtcat ttttcttaca mcaaaaagag    3120
gaggaagaat gaagagaatc atttaatttc ttgattgaat agtaggattc agaaagctgt    3180
acgtaatgcc gtctctttgt atcgagctgt aaggtttctc atcatttatc agcgtggtac    3240
atatcagcac ttttccatct gatgtggaaa aaaaaatcct tatcatctac agtctctgta    3300
cctaaacatc gctcagactc tttaccaaaa aagctatagg ttttaaaact acatctgctg    3360
ataatttgcc ttgttttagc tcttcttcca tatgctgcgt ttgtgagagg tgcgtggatg    3420
ggcctaaact ctcagctgct gagcttgatg ggtgcttaag aatgaagcac tcactgctga    3480
aactgttttc atttcacagg aatgttttag tggcattgtt tttataacta catattcctc    3540
agataaatga aatccagaaa taattatgca aactcactgc atccgttgca caggtcttta    3600
tctgctagca aaggaaataa tttggggatg gcaaaaacat tccttcagac atctatattt    3660
aaaggaatat aatcctggta cccacccact tcatccctca ttatgttcac actcagagat    3720
actcattctc ttgttgttat catttgatag cgttttcttt ggttctttgc cacgctctgg    3780
gctatggctg cacgctctgc actgatcagc aagtagatgc gagggaagca gcagtgagag    3840
gggctgccct cagctggcac ccagccgctc agcctaggag gggaccttgc ctttccacca    3900
```

```
gctgaggtgc agccctacaa gcttacacgt gctgcgagca ggtgagcaaa gggagtcttc   3960
atggtgtgtt tcttgctgcc cggaagcaaa actttacttt cattcattcc ccttgaagaa   4020
tgaggaatgt ttggaaacgg actgctttac gttcaatttc tctcttccct ttaaggctca   4080
gccaggggcc attgctgagg acggcatcgg ggcccctgg accaaatctg tggcacagat    4140
ggtttcactt acatcagtgg atgtgggatc tgcgcctgta atgtgtcctt ctgaaggaag   4200
gaacgtgcct tccaagtgcc agccccacag cccccagccc ctccctgtgc tgctccaatt   4260
catctcctct tcctccttct ccctttgctg tttgtgctcg ggtagaaatc atgaagattt   4320
agaagagaaa acaaaataac tggagtggaa acccaggtga tgcagttcat tcagctgtca   4380
taggtttgtc gttgctatag gtctgtatca gagatgctar caccactttg ctgtcggtgc   4440
ttaactcggg tgaactctcc ttcactcgca tcatttgcgg gccttattta catccccagc   4500
atccatcacc ctctgggaaa atgggcgcac tggatctcta atggaagact ttccctcttt   4560
cagagcctgt gggatgtgca gtgacaagaa acgtggaggg gctgagcagc agcactgccc   4620
ccagggagca ggagcggatg ccatcggtgg cagcatccca aatgatgtca gcggatgctg   4680
agcaggcagc ggacgaacgg acagaagcga tgcgtacacc ttctgttgac atggtatttg   4740
gcagcgattt aacactcgct tcctagtcct gctattctcc acaggctgca ttcaaatgaa   4800
cgaagggaag ggaggcaaaa agatgcaaaa tccgagacaa gcagcagaaa tatttcttcg   4860
ctacggaagc gtgcgcaaac aaccttctcc aacagcacca gaagagcaca gcgtaacctt   4920
tttcaagacc agaaaaggaa attcacaaag cctctgtgga taccagcgcg ttcagctctc   4980
ctgatagcag atttcttgtc aggttgcgaa tggggtatgg tgccaggagg tgcagggacc   5040
atatgatcat atacagcaca gcagtcattg tgcatgtatt aatatatatt gagtagcagt   5100
gttactttgc caaagcaata gttcagagat gagtcctgct gcatacctct atcttaaaac   5160
taacttataa atagtaaaac cttctcagtt cagccacgtg ctcctctctg tcagcaccaa   5220
tggtgcttcg cctgcaccca gctgcaagga atcagcccgt gatctcatta acactcagct   5280
ctgcaggata aattagattg ttccactctc ttttgttgtt aattacgacg gaacaattgt   5340
tcagtgctga tggtcctaat tgtcagctac agaaaacgtc tccatgcagt tccttctgcg   5400
ccagcaaact gtccaggcta tagcaccgtg atgcatgcta cctctcactc catccttctt   5460
ctctttccca ccagggagag ctgtgtgttt tcactctcag ccactctgaa caataccaaa   5520
ctgctacgca ctgcctccct cggaaagaga atcccttgt tgcttttta tttacaggat    5580 ccttcttaaa aagcagacca tcattcactg caaacccaga gcttcatgcc tctccttcca   5640
caaccgaaaa cagccggctt catttgtctt ttttaaatgc tgtttccag gtgaattttg    5700 gccagcgtgt tggctgagat ccaggagcac gtgtcagctt tctgctctca ttgctcctgt   5760
tctgcattgc ctctttctgg ggtttccaag aggggggag actttgcgcg gggatgagat   5820
aatgcccctt ttcttagggt ggctgctggg cagcagagtg gctctgggtc actgtggcac   5880
caatgggagg caccagtggg ggtgtgtttt gtgcaggggg gaagcattca cagaatgggg   5940
ctgatcctga agcttgcagt ccaaggcttt gtctgtgtac ccagtgaaat ccttcctctg   6000
ttacataaag cccagatagg actcagaaat gtagtcattc cagccccct cttcctcaga    6060 tctggagcag cacttgtttg cagccagtcc tccccaaaat gcacagacct cgccgagtgg   6120
agggagatgt aaacagcgaa ggttaattac ctccttgtca aaacacttt gtggtccata    6180 gatgtttctg tcaatcttac aaaacagaac cgagaggcag cgagcactga agagcgtgtt   6240
```

```
cccatgctga gttaatgaga cttggcagct cgctgtgcag agatgatccc tgtgcttcat   6300
gggaggctgt aacctgtctc cccatcgcct tcacaccgca gtgctgtcct ggacacctca   6360
ccctccataa gctgtaggat gcagctgccc agggatcaag agactttcc taaggctctt    6420
aggactcatc tttgccgctc agtagcgtgc agcaattact catcccaact atactgaatg   6480
ggttctgcc agctctgctt gtttgtcaat aagcatttct tcattttgcc tctaagtttc    6540
tctcagcagc accgctctgg gtgacctgag tggccacctg gaacccgagg ggcacagcca   6600
ccacctccct gttgctgctg ctccagggac tcatgtgctg ctggatgggg gaagcatga    6660
agttcctcac ccagacacct gggttgcaat ggctgcagcg tgctcttctt ggtatgcaga   6720
ttgtttccag ccattacttg tagaaatgtg ctgtggaagc cctttgtatc tctttctgtg   6780
gcccttcagc aaaagctgtg ggaaagctct gaggctgctt tcttgggtcg tggaggaatt   6840
gtatgttcct tctttaacaa aaattatcct taggagagag cactgtgcaa gcattgtgca   6900
cataaaacaa ttcaggttga aagggctctc tggaggtttc cagcctgact actgctcgaa   6960
gcaaggccag gttcaaagat ggctcaggat gctgtgtgcc ttcctgatta tctgtgccac   7020
caatggagga gattcacagc cactctgctt cccgtgccac tcatggagag gaatattccc   7080
ttatattcag atagaatgtt atcctttagc tcagccttcc ctataacccc atgagggagc   7140
tgcagatccc catactctcc ccttctctgg ggtgaaggcc gtgtcccca gccccccttc    7200
ccaccctgtg ccctaagcag cccgctggcc tctgctggat gtgtgcctat atgtcaatgc   7260
ctgtccttgc agtccagcct gggacattta attcatcacc agggtaatgt ggaactgtgt   7320
catcttcccc tgcagggtac aaagttctgc acggggtcct ttcggttcag gaaaaccttc   7380
actggtgcta cctgaatcaa gctctattta ataagttcat aagcacatgg atgtgttttc   7440
ctagagatac gttttaatgg tatcagtgat ttttatttgc tttgttgctt acttcaaaca   7500
gtgcctttgg gcaggaggtg agggacgggc tgccgttgg ctctgcagtg atttctccag    7560
gcgtgtggct caggtcagat agtggtcact ctgtggccag aagaaggaca aagatggaaa   7620
ttgcagattg agtcacgtta agcaggcatc ttggagtgat ttgaggcagt ttcatgaaag   7680
agctacgacc acttattgtt gttttcccct tttacaacag aagttttcat caaaataacg   7740
tggcaaagcc caggaatgtt tgggaaaagt gtagttaaat gttttgtaat tcatttgtcg   7800
gagtgctacc agctaagaaa aaagtcctac ctttggtatg gtagtcctgc agagaataca   7860
acatcaatat tagtttggaa aaaaacacca ccaccaccag aaactgtaat ggaaaatgta   7920
aaccaagaaa ttccttgggt aagagagaaa ggatgtcgta tactggccaa gtcctgccca   7980
gctgtcagcc tgctgaccct ctgcagttca ggaccatgaa acgtggcact gtaagacgtg   8040
tccccctgcct ttgcttgccc acagatctct gcccttgtgc tgactcctgc acacaagagc  8100
atttccctgt agccaaacag cgattagcca taagctgcac ctgactttga ggattaagag   8160
tttgcaatta agtggattgc agcaggagat cagtggcagg gttgcagatg aaatcctttt   8220
ctaggggtag ctaagggctg agcaacctgt cctacagcac aagccaaacc agccaagggt   8280
tttcctgtgc tgttcacaga ggcagggcca gctggagctg gaggaggttg tgctgggacc   8340
cttctccctg tgctgagaat ggagtgattt ctgggtgctg ttcctgtggc ttgcactgag   8400
cagctcaagg gagatcggtg ctcctcatgc agtgccaaaa ctcgtgtttg atgcagaaag   8460
atggatgtgc acctccctcc tgctaatgca gccgtgagct tatgaaggca atgagccctc   8520
agtgcagcag gagctgtagt gcactcctgt aggtgctagg gaaaatctct ggttcccagg   8580
gatgcattca taagggcaat atatcttgag gctgcgccaa atctttctga aatattcatg   8640
```

-continued

```
cgtgttccct taatttatag aaacaaacac agcagaataa ttattccaat gcctcccctc    8700
gaaggaaacc catatttcca tgtagaaatg taacctatat acacacagcc atgctgcatc    8760
cttcagaacg tgccagtgct catctcccat ggcaaaatac tacaggtatt ctcactatgt    8820
tggacctgtg aaaggaacca tggtaagaaa cttcggttaa aggtatggct gcaaaactac    8880
tcataccaaa acagcagagc tccagacctc ctcttaggaa agagccactt ggagagggat    8940
ggtgtgaagg ctggaggtga gagacagagc ctgtcccagt tttcctgtct ctattttctg    9000
aaacgtttgc aggaggaaag gacaactgta cttcaggca tagctggtgc cctcacgtaa     9060
ataagttccc cgaacttctg tgtcatttgt tcttaagatg ctttggcaga acactttgag    9120
tcaattcgct taactgtgac taggtctgta aataagtgct ccctgctgat aaggttcaag    9180
tgacattttt agtggtattt gacagcattt accttgcttt caagtcttct accaagctct    9240
tctatactta agcagtgaaa ccgccaagaa acccttcctt ttatcaagct agtgctaaat    9300
accattaact tcataggtta gatacggtgc tgccagcttc acctggcagt ggttggtcag    9360
ttctgctggt gacaaagcct ccctggcctg tgcttttacc tagaggtgaa tatccaagaa    9420
tgcagaactg catggaaagc agagctgcag gcacgatggt gctgagcctt agctgcttcc    9480
tgctgggaga tgtggatgca gagacgaatg aaggacctgt cccttactcc cctcagcatt    9540
ctgtgctatt tagggttcta ccagagtcct taagaggttt ttttttttt tggtccaaaa     9600 gtctgtttgt ttggttttga ccactgagag catgtgacac ttgtctcaag ctattaacca    9660
agtgtccagc caaaatcaat tgcctgggag acgcagacca ttacctggag gtcaggacct    9720
caataaatat taccagcctc attgtgccgc tgacagattc agctggctgc tccgtgttcc    9780
agtccaacag ttcggacgcc acgtttgtat atatttgcag gcagcctcgg ggggaccatc    9840
tcaggagcag agcaccggca gccgcctgca gagccgggca gtactctcac catggccatg    9900
gcaggtgtct tcgtgctgtt ctctttcgtg ctttgtggct tcctcccagg tgagtaactc    9960
ccagagtgct gcagaagctt                                               9980
```

```
<210> SEQ ID NO 27
<211> LENGTH: 20
<212> TYPE: DNA
<213> ORGANISM: Artificial Sequence
<220> FEATURE:
<223> OTHER INFORMATION: Primer OVMUa9

<400> SEQUENCE: 27
aaatgaagcc ggctgttttc                                               20

<210> SEQ ID NO 28
<211> LENGTH: 20
<212> TYPE: DNA
<213> ORGANISM: Artificial Sequence
<220> FEATURE:
<223> OTHER INFORMATION: Primer OVINs9

<400> SEQUENCE: 28
ctctcagcca ctctgaacaa                                               20

<210> SEQ ID NO 29
<211> LENGTH: 40
<212> TYPE: DNA
<213> ORGANISM: Artificial Sequence
<220> FEATURE:
<223> OTHER INFORMATION: Primer
```

```
<400> SEQUENCE: 29
gcgcggccgc ccgggacatg tccatggtga gagtactgcc                            40

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30
ggcccgggat tcgcttaact gtgactagg                                        29

<210> SEQ ID NO 31
<211> LENGTH: 802
<212> TYPE: DNA
<213> ORGANISM: Artificial Sequence
<220> FEATURE:
<223> OTHER INFORMATION: primer

<400> SEQUENCE: 31
gcgcggccgc ccgggacatg tccatggtga gagtactgcc cggctctgca ggcggctgcc      60
ggtgctctgc tcctgagatg gtccccccga ggctgcctgc aaatatatac aaacgtggcg     120
tccgaactgt tggactggaa cacggagcag ccagctgaat ctgtcagcgg cacaatgagg     180
ctggtaatat ttattgaggt cctgacctcc aggtaatggt ctgcgtctcc caggcaattg     240
attttggctg dacacttggt taatagcttg agacaagtgt cacatgctct cagtggtcaa     300
aaccaaacaa acagactttt ggaccaaaaa aaaaaaaac ctcttaagga ctctggtaga     360
accctaaata gcacagaatg ctgaggggag taagggacag gtccttcatt cgtctctgca     420
tccacatctc ccagcaggaa gcagctaagg ctcagcacca tcgtgcctgc agctctgctt     480
tccatgcagt tctgcattct tggatattca cctctaggta aaagcacagg ccagggaggc     540
tttgtcacca gcagaactga ccaaccactg ccaggtgaag ctggcagcac cgtatctaac     600
ctatgaagtt aatggtattt agcactagct tgataaaagg aagggtttct tggcggtttc     660
actgcttaag tatagaagag cttggtagaa gacttgaaag caaggtaaat gctgtcaaat     720
accactaaaa atgtcacttg aaccttatca gcagggagca cttatttaca gacctagtca     780
cagttaagcg aattcccggg cc                                              802

<210> SEQ ID NO 32
<211> LENGTH: 17
<212> TYPE: DNA
<213> ORGANISM: Artificial Sequence
<220> FEATURE:
<223> OTHER INFORMATION: Primer

<400> SEQUENCE: 32
ctccacatgg ccatggc                                                    17

<210> SEQ ID NO 33
<211> LENGTH: 17
<212> TYPE: DNA
<213> ORGANISM: Artificial Sequence
<220> FEATURE:
<223> OTHER INFORMATION: Primer

<400> SEQUENCE: 33
gagtggtacc ggtaccg                                                    17
```

<210> SEQ ID NO 34
<211> LENGTH: 17
<212> TYPE: DNA
<213> ORGANISM: Artificial Sequence
<220> FEATURE:
<223> OTHER INFORMATION: Primer

<400> SEQUENCE: 34
ctcaccatgg acatgga                                                  17

<210> SEQ ID NO 35
<211> LENGTH: 17
<212> TYPE: DNA
<213> ORGANISM: Artificial Sequence
<220> FEATURE:
<223> OTHER INFORMATION: Primer

<400> SEQUENCE: 35
gagtggtacc ggtaccg                                                  17

<210> SEQ ID NO 36
<211> LENGTH: 75815
<212> TYPE: DNA
<213> ORGANISM: chicken

<400> SEQUENCE: 36
aagctttgtg ctttctgcct gaataaaaga aacctgaact ctgttcaccc agtccctgtc    60
aggcaattac tgacagagca cctatggtct gtgtttggcc agaacatagg ctaaggaaga   120
tacctcctgt ttataaagca cgcctttggc atctggcaag taattagtga tggcgcatga   180
gagctctgac tagggcaggg tgtgggacag gctggctcta attgtgccct gtttatcttg   240
ttgatgcaca cggctggttt cttcacccca cagctgtctc tctagacaac ataccttat   300 ggagaggaac gtgtcttttc caatcttggg ttttcattca gaattggagt gaactggtct   360
ccatcagata gcattggctg cggtgattta ttcttttaca cttcctagtt aagcaggata   420
actctctggc tctgctgtgt ctaggcaatt taaatgattt ataaagcata gctgttttaa   480
ggaaatcttt ttttaaacat ttgacttgcc aatgtgtggt cctaaaggca gaggactgt   540 tccagagtgt caggcagaga cctaccctgg atttcgttgt tcagctaccc attcagtgtg   600
gcttttggca aggaattctc tggacctgac ttccctacct gcagagctgg ataagctat    660 caaaccatct cctccacaca ctgtgagggt gggaaaaaaa cccaaaccct aaaagtgct   720 gtataaaggc gccttaaggc tcagtatagc atgtgtgctg ctgatgcccc agacctgttt   780
gcgggtcctg aaggtcatag agaactgctc cagaagagac agaaatgctt aagaaggttt   840
tactacaaaa gtcttgtgat gttaacacat aatatcacat tgtgcagaag gtacaaatgc   900
cccctcctat ccctgcacac ctggaagctc aaggtatgga agggtttgtt gtctgcagcc   960
tcttcgctgc cctctgcttt ttaagatcct gggtagtgtg ctcagtgtgt gccctcagca  1020
gtttgggaaa cggacatctt catgcaaaat taagcaagga agtgttgctt ttatactcag  1080
agtagaatct aagttcttca ggcaggctct tgtgtgccgc ctctattaga aataaaactc  1140
ccccggatca gaagatgaat gtgctcagct aagaacacag atttatttgc tttacaatgc  1200
gtgctatggt ttaagaaaaa cacatcaggc aaacaattta tggtttgcca ctgagttgtg  1260
cctgaaggaa acacaactgt tagagatgta attgattggg cggtgacgct gtgtggattc  1320
atgggagatg catcttggtc agcatgtctg tgtgaaacca catttctggt gctgctgcag  1380
gacgagtgcc gggagttccg ggatctgttc aagaatggga agctttcctg cacgagggag  1440

```
aatgatcccg tccgggattc ctcggggaag cagcacagca ataagtgcat catgtgtgcg    1500
gagaagttgt gagtagagga agccaatgtt tgttatcgag agtggcaatg gggccggggt    1560
gggctcctac agcaatgttc tcctcacttt ctcatccttc tctttcagca aaagggagaa    1620
tgagcagaag gcgacctcaa ccagagggaa acaaaaggtg aggttaaagt attgggttca    1680
tatacaagtc tataggattc ttacccaata ttaccacact tgatttcttt gtcactctgg    1740
ggatccatgt ggcttttcct gcttgtatct cgttgatgct ctttcatgcc ctgagagaat    1800
agtttgtctg aacgctgcag tctatcccac tgaccgcagt gacatgggag caaaccccat    1860
cgcaataaga agctgagcag aactgccctg acatctggca caagggcaag aaggcactgc    1920
tgctgagagc gctaatgagg ttgaaaagaa atctgggtg agaagcttta aatgtgagct     1980
ctgagatgct caaaagttca ttatgtcgtg ggaggagagt tcagccctgt gctgtccctg    2040
gggtggctcg gtttcagctt ccctgattg gaaacctcac tctcatgatg cagctgctgt     2100
gcccttgtgc accgatactt ctctggtgag agcaattcag caaggggaag gaaaaagaag    2160
cactaagtaa atcttgccat ttctgtcttg cgaggaactg gtacggtccc cttaagcctc    2220
attcttgggg ataatcctgt ttcagtgctt ttcctaatga cagtggcaca aaaaaaatgg    2280
aagcgttaat gaaacttgct gatggcaaag ctgggaggga ggatcagcag atcactcagg    2340
actaattgga tagcactgag gcctggagta atagaaacaa gataaaatgt aataacagag    2400
agtgcaagat cacacaggca gtgattaacg agaattcctg ctcatcaatt agaaatgaca    2460
aaggataaga aagctctgca tttattagtg ggtcacggat gcggcaggcc tgagaaggag    2520
gcaaatgcac atctcagcaa ggtctgtgca gcagaggtcg ggctggcagc aaatctccag    2580
aaatactgct ttgaagagag agggtttgag agacgctgtt agggagaagc agctctgcca    2640
cagcaggtct ggggttcacc tggggttttgg ctcattgcct ccctgtgtcc ctcctccacg    2700
ctgccagtgc tgcactggga aggtgtgggt aagaagcaat ggctaaggga tctggttata    2760
cacctcctgt atctgctatt tgggattggc tactgcaggg cctcaggtcc ctgacttaaa    2820
agtggggact tcgaagcatg tttgcattgt gctgtcgtgc cttagatgtt gctgctgggt    2880
cctcaaagtc ctgttggttg tggggtgggg gggacttctt gcttcctatg tgaagttttc    2940
tgagctgcaa cttcagcaac agctgtaaga gtgcattaag ggcagtggga gaagtgggag    3000
ggaccccatt acctcatcgg gtatcgctgg catgctttgg atagccccac gtggagcgtg    3060
acaattagag cacggcagag agctcccaac acgtgccatg caggcagagg cacccgccgc    3120
tcttctgact cactctgttt gtagccatga ggctgtgcca cgtgccctct tctctctctc    3180
acacctgggc tctcctgggg cgcgtttggg aagcctctgg aggatcggag ggatgtggca    3240
gggtgccctg actgctgctc cttccgcagg atgactgcag tgagtaccgc tcccagtttg    3300
aggctggcgg acgcctgtcc tgcacgcggg agaacgaccc cgtcagggat tcctctggca    3360
agcagcacac caacaagtgc ctcatgtgtg ccgagaagct gtgagtacag ttcctggcaa    3420
cagcaaagag ggaaacctca cattgcgaaa ctgcagcttc tgcctgtgtg gctgcgcctg    3480
ggggagtccc gagtcccagc ggccccccag gagctgctcc tgctgtaggg ctgtggctac    3540
tgcccctctt cccacctccc ccctaacccc tcagggagca gaggagaagc agggttgata    3600
gagagcagcc ctttccttgg ggcagctccc aaggaaagtt tcccacgcgt gtactttgcc    3660
ttccagatgc tctctctact cccatagagc atatgcagaa gcagccctga tatgaaagca    3720
gccacctgga gccgggatgt agcatacagt gggaatggtg aggagaaggg agaaggctta    3780
ggggtgggaa ttaggtgcag ggccaccagg gatggggagg ctggtgccta atgacatgat    3840
```

```
gctggcttgc agggcagccc caggtcctgg cagcgttcgc actgccatag tgctcctttc    3900
tttctcctct ccctttttc  cagcaaaaaa gaagctcaaa gaggaggtca gtctggtgga    3960
actgcccagc gcaacaagca gtccactgca gagtgtgcaa accaggtgag actgagctca    4020
gagcctcacc aggcttggga aaaggggttg gtggatctgg gaccccgat  ggtcaagggc    4080 tgcctgtggt cctggtgttt ggggtgcagg agcctgctgg tgatggcaga gaggcaggtt    4140
gcattgcaag ccctgctagt tcatgggatg ggtttgtgta tgagcgtgca tagtgggcag    4200
ttctggactc ctctatgggg cacgcatcag agctatttct tcagaaagag ccccatggtt    4260
cctagggtcc aggggatga  gagggaagga caggagctgc tttaatctca ctgctttact    4320
gcttggttgt caaacacgat cctgcccctt ttccagaaga gctgcagtgg ctcagggtta    4380
cagcggggtg taaatgagag acggccgttc tccacaaaca gagggtgagt acagcagcac    4440
tgggatccca gcctggcccc acaagtcctg gggtcttgac actgagaaga aacacataaa    4500
atagggcata tacaaccctt tctcctttcc aaagacattc ttgcttcccc tgcacacgaa    4560
gcactggtga ctgctacact caaaatccct ccccagcctt gcccctgaa  tcctgcctcc    4620 tggcaggcac acacttgtcc tgctgcctgg tccagcgcat cctcatctgc tgacctgagg    4680
cagtgctgtg tgtgcaccat gtgctgtctg ggcactgagc gactcctctg gttttagg     4740 gctgccaggc tctggcaggg tgcagatgct gtgttatcta agccttgagg aactctctta    4800
gtcttcctgt ttttgttggt gaggcccatt catctgcccc cagtcagcac tgccagcaga    4860
caaacagtgc acagctctcc atggcagcaa tgctgtagc  atatgtaggg gccaggtttc    4920
tgggatcatc tctgtgacgg acatctcttg ctgaccgccc ataaggactc aaaagtcccg    4980 ttgcaggag  tgcctccatc ccatggcaag ccaagtgccc tgttgaaaaa acaaggtgca    5040
gaataatggc aatggacctt agtgcagttt aattccaccc tggggtgatg atgtggctga    5100
gtgggtctgc ataccettgg ctgtgccatg agctctgtgc tttctctccc tgccagccca    5160
caaggagact tggctcagga ctgcagcccg gcacctggcc gccagggaca gagcggaggc    5220
accaacacct accagccggt atgcccagct catgtgggtc aggcacagcc tttcccagca    5280
gctgccccag tttccattgt caacctaaag cctcacaatg ggacctgtat ccttggaggg    5340
gtttaaatgg gtggtagagt ccgtaccctg atgctgtccc ctggcctcaa agaggagtga    5400
ggctgcacac gtccaaacgg gagtcactga agccagtgct gctgctggtg ttggctcact    5460
gtagaagtat gtcaggtatg agagagcatc ctccaggagg tgatggtggt gtcccttcct    5520
gcatgctgag atgttgggtt gaagactgtg gccagagcag ggtgctgggg ctgagcgggg    5580
gataaggaca aggctgataa gaggagggga gaggagtag  tgggggagga cacggtgagc    5640
aatagataac gactgtttgt ggaatcatgt gggagggaga agagggtgta tgctctctcc    5700
atctccacaa aaagaaaatt tgttattttc aaccaagcta aagcagaaat tatgaaacta    5760
ataggagaaa ataagttact ataaaaagga tgactaacct gtggatcttg ctgtcacggg    5820
gtgttgccaa gagctacagt gattaaaaaa aatgacttgc cacttatagt ccatacagca    5880
atttaggtaa cattttggaa gggataggaa atgcctttct gtgggctgg  agggacctga    5940 gtgcagactg ccttaactct ctctgaagtc tctgtcactg actgcccttta gaaaatgat    6000 attagaatag aaaaaccagg gaggcggttc aggtatggca gttttaatgc attccagagg    6060
aagcattagg cataataatg ccagtctgct tcagggctta gtggtatttc ctggtagctc    6120
cggtgaagga gtggatgctg atcagcctga ctgacgaggg gtgattcaga gagcagatct    6180
```

```
gtgtctctcc tcgctgcagg gccacccgtg ggctctgtcc cagggagatg ctgtcctgaa    6240
ggagaggtgg cagtcactgt gaggactgtg ggggactgtt ggtgtggcgg cggttgcaca    6300
cgcgtgggtc acaccgtggg cagtggtgtc tggtgtgtgg gaaggcatct ggcagggaac    6360
tgcaaaggtc agcgctgtct gtctttgtgt catcgttaat tacccaggtg agggaggaag    6420
cagcacatta atgaaattag caagtgatgt ttaaacagag ggtgttactg cagcaacctg    6480
tgccactgaa cccctgcat tgcccagctg ggaaaccttt cttctccatg gtgctttcaa    6540
ccccatagtg ctgctgaccc cagcaaagca atgagccatt gcttagtgct gaatggggtt    6600
ttttttctcc aagtgggaca ggaggtgaga tgtccttcct gcagctcttc tccaattgca    6660
ccatttgcag tcattgcaac attttttata ggacctggag aaggggatgg gaacagagaa    6720
ttcactcctt ttgtctctgc atctttttt ttttggcctt tggtgcagag gtgggcagtg    6780
aggctgagga agagagggggg ctgtaggatc tctgacctct gctgtctgaa acttgccatg    6840
attctgcagg cacctgtgcc agaatgctca tgggctgata atctaatcat gaggagtctt    6900
gttcctcctg ctccgagctc tttctagctg tgccacgtct gctttgtagg aaattcgatg    6960
cctagatgct cctgctgtta tgctggagaa taaaacgaga gggcacgctt aattagtcag    7020
agcttttcat acatgtttgc atctcttcat tccgtgggtg tcaagttgtg ctgtgtgtcg    7080
ggctgccctt gggcagctgg actcaattgt caaggttttc cctttgtttc tgccaagtgg    7140
cttgcagaag caacaggtgt gaaagctctg ataaaggaca aaggacaggt agcagaagtt    7200
tattgtattc tcgtggattt gcagggagaa gtaaaagtgc cctggactga gatgtcaggg    7260
tggatcagat gagtgtatcc atgcctggca atggggtcag ggcagctttg tccccacatc    7320
gtggctggtt ggcccaatag gaggcgttac ctctttgctg aaggtgtgat ggagctcagg    7380
gcaacgcctg gtttgtgagt gctttgagcg gtgcgcagga gggtcttgca agagaaccag    7440
caccaaatgt gatttctttc tctcttcagc tggactgtga tcgaattctg cacggggtaa    7500
agggtggaag gattttctgc agcgaatcct cacaacccgt ctgtggcact gatgggaaaa    7560
catacagaaa tgaatgtgac ttgtgttcag ctgccatgtg agtaggcgga gagatttcag    7620
taatacaggg ccatccacca ttcccgagtg tcttttgcag cacagtgttt gttttgatat    7680
accatgactc actatcaagt gtgtccttgg tgcctcgctg ttaagcaaac atagatcaaa    7740
tgtctgagat taatatgatg acagctaatt aagatacaca actttccaga gtcccttatt    7800 cccttctgc tcaatcatag gattgtttgg ggagtaataa atgccatcaa attggaagta    7860
gcatcaaagg tttaaggagc ccacagagga ccaccgtgac gatgtcaggg agctgtggca    7920
ctggaagtga ataagcaatg tcttgttctc cctttgcagg agagcatcag tttacatcac    7980
ggtaaactac cgaggtgaat gccgaaagac tgtccctgaa atggtaagtg cctccctgct    8040
gtggcatccc attctcttgtt ctgggtgtgt gctggagacc cagcctggat cccgtatctg    8100
tggtgggatc atcagagccc tgttagcagg gtgcttgtgg ttcacatgcg taaatacact    8160
tcaggcttgg atttaaggca ttttgaggca taatctccac gttttttcca ggctgtgtgg    8220
taggggagtg acatgtctgg gaaaacatgt ggctttcctc ctgggatttt ggtgaggcca    8280
agaaaagatt gcaatcgcac aaaccataag ggcctaattt cccaaatgat atccaggcag    8340
ttggttggga aggaaatata ttccctaagt ggtatccttt tgggaaaggt cttgaatctt    8400
gtgtgattgc cttgtagtag atgagtcaaa gatttgttag tggtgctttg tcttcccgct    8460
cgtggcagct cagcggcatt cagagctttg gtttggagcc agggtgtccc agtttgtgtg    8520
tcttgagtgt atgggactga ccttagtgtt ggcatggact gttggaaagc tgagtattca    8580
```

```
tttccccagg gaaacaccga catctatccc cattccaaac ttggaatgaa tcaaaatatc   8640
aaatcagcca aatggagaag ttgtgcaagt ttttttgca atgagagaga tggcttctga    8700
atatgaattt gctgacagtt tgtaggtaaa acagtattgc ccgttgaaaa gctttagagc   8760
aaaattacca tcatagggct tttactctcc tctgcttatt gacaggatgc ccacccatcc   8820
ccacaacatt agaaatgagg catccccatt cctcttcctc tcttctgtga agtaccagag   8880
tgctctcaac gctgtttaaa gctgaagaaa aaatgcagag aaagagttttt gcttgtgatc  8940
gtgctggagg tctttgtgtc tcgccctttg gtgcgatgga gccattgctg gtttgtgtat   9000
gctgggagtg gaggcactat gcatacctgc tggtggctgt gctaatgatg ctggagacag   9060
acaaggttgg gtgtaccacg gcaactgaaa accagagagg actccctcag agttgtgcct   9120
ggctgggatt cctcaccatt ttgtgtttta ccaagacgtt ttaccagctc tccagtcttt   9180
gcagttagag gaatatgcca tacactaaaa gtcagacaat ttgtagctat tccaaggaga   9240
gctggaagca attaaaggga aagtgataag gttttttccac tggggaaaat cccccacaaa  9300
aaacacccct ccaaacaaag acttattatt tcgttcttta tgtatattgt gtcacctgaa   9360
gaatcagatt ggaaatttat ggaagcccat ttccttagca aaccccttgt gtccatcaaa   9420
gacttcccctt tttttctca gttggaagct tatgaacaat gtactgacca gtgttatttt    9480
atgcctctga aattcatgct aacattcagc ttaatgcatc cttctgaagg cccaggcact   9540
cgctgtgtga aggagatcac agtgcctttg gcgtcagaaa tgatttcagg ctgttgcaat   9600
acgcagcacg aagatgcaaa ggcccaaaga cttgagcctt ggaaaaagat aggagattgc   9660
tgcccgaaaa tgtagtttgt ccttgagttg tgttttgaaa ttagccacgg taatgctgtg   9720
ttgcctgcca aaatgtgtgt ccaagctcag agcctgcagc cattcctgct agcaaagccc   9780
ctcctggatt ccagcagtt tgtggcagtc cttccctagc agtggctgga ttgccatcag    9840
ggagggatgg ctgtaggaag ggacaggaga aatgtggttg gagagagatc tgacattaaa   9900
gggtgcatcc ggacagcctg cactgatgtg gtggaaaacc ttcctgcaga gagagccctg   9960
gggctggctg gcagctgggc ccctgctgcc tgtgtgagct ctgtgccaca accagcctcc  10020
tctgatcctg ttctgcttta ctgcagatga atgtagctga gtctagggtt tagatttcta  10080
tgtttatttt taacaaggca gctggcctct gcgtcctcca tgctgtgaca tacagctgta  10140
ttaatggtgg gtctttccag aatgtttcac tttcaatgct gtattttttt ttattttgca  10200
gtttctcttt ttgttcagat gcttttttcac acatctccca tgtgacagat accagtctgt  10260
ccatgttagt tgacaggtca ggcaaaaaaa aaaagggat atccagtttc tccttttta   10320
tctgttttct aaagaacaaa gaactcccag cttttctaatg gcaaggcca ttttcttaca   10380
gtgctctttt tgtcatacct ttcttaagaa tgtagtagaa gggaaaagaa acaaacaaa   10440
aacccaggac cttttccagc ttgatattgg ttttggaaag cacacagatc caggctgaaa  10500
tctgtttgtt ttctgagtct ggcagtgacc catccactgc cccatcccac ctggttcctg   10560
tggccactga gctgcccaaa ggggctgtca tgtagcccct aatgctctgc cagcgtaaca  10620
gcagtggatg tacttgtgga tccacttata ttttgctctt tctttccaga aataatggag  10680
ttcagactgc cagcaaatac cagggatcag ctgtgaccaa aggtacagtg gtgcggtgat  10740
ttgctccctc ttggacaact tgtccgcatt tcacaagggt ttgggtgtca gaccttgcct  10800
gggcaggctg ctgggtatgt ctggggcaaa gggctctgca acacacccctt ccctattgcc  10860
acagcacaag aatgaggcgt gtgtcttttg cagaagtagc aaggtgatgg gaagcccctg  10920
```

```
ccaaggggc tgagcccttt ggggtgtgca aacttcatga ggacctcctc atctctcagg    10980
ggtgggcctt gcccgttcct tttccctcag atatccctgc agaggggaa ggatgctggc    11040
agagcagagt actgcagtcc ctcctcacaa ggaggtggag gtgcccaaa gcaacctggc    11100
tttgagcttt ccttgtggtt cttctgtgtc ccttgccttt tggagccata gtaataaacc    11160
cgtctgcccc ctgtttctct aggacaagta aggaagatc tgatgtcagg caccagggaa    11220
gctgctgagt tccccagtgc tgttggatcc accttcatct ccttctgcag ccaacgggcc    11280
tgtccttgct caggtggagg gtgaagggct gtgggaccc agtggtggct tcccacgttg    11340
gccccacgca tgttgttgta gtcgctgctc ggctcgggct ctgccgcctc gctgtgtctt    11400
agcatgtttc tacaataaag ataactccac agcgtcctgt cgcttttctt cactgagcct    11460
cacgggaggg acgtgtgagt ccccgctccg gctgctcgcc acgcgtccct tgagctctaa    11520
agcaccaaac ccaagcggag atgtcagacg cagagaagaa gaacgtggtc tgggttctgt    11580
tagcagggac cagcagttgg gttctctgac tcgctgtgta gggctttggg tgtatctctt    11640
tgtctcccctt cagcccttt ctcttgcctg taaaaacgga cattaaagga tgcttaccta    11700
cctcagaggg ttgtttggag attttaattg gtttacgtta gagagcccac gggtggaatt    11760
ctgttcctat gtgccaatgc tggtgtgcag gaggtttaac tgttgcagtc atggcctctt    11820
ccagccaaca cccgatgggc cgtatgtatt tcctgttctt tcgtttatgg ctgttactta    11880
aagcaaatat gttcttattt gtataaactt tattgcagga catttccaga agaccttgag    11940
tgaacgtaca gtgtttgagt ccactttagc tgtgacctga tctgcaaata cactctgctg    12000
tagataaggc tggagtaact ttcagatttt ggcagggttt cgctcaatgc caattaattt    12060
ggctccctcc acagatattg atttttttt ttcttttcaa ttaagttatc gagatctttt    12120
tttcttaatg cagctaatga aaatcgattt ttactctcat aaagtacttc cgcatgtgtc    12180
acattgatct gtctatggct tgattatcgg caggctttga catgaggtta atattttgtg    12240
tgctggtttt ttttcaccgt gtgcaaacac tgtggtttag aaatatgtta ccgctgctta    12300
tttctacgtg gaaaatccca cggcgtggtt atgcatggca gaagtcacca gtttgatcca    12360
atttagctgt ttctagggat gcaagattcc tctgcctttg agcgggtgaa tcctcgggtg    12420
ttatttatac attctgagaa ggatgaacag aagacggtaa aaacgtttgc taatgatgtc    12480
tgctggctga ttccggctaa aatcgtgtgc agggacctcg acgtgatttt tataaaggca    12540
gctcacaatt tgaggcttaa agtaagttct tgcaaatgaa aatgggcgca cttgagcgcg    12600
ctattataac ttgtagtgat ttcaagcact tagattttga ataatcgcc cataaaaacc    12660
tgcattaatt gtgctccaaa accaatgagc tgatgaggag ggtgccctgg tagcctcttt    12720
tgctggattt gagcaccttc tgaatttctc ctgccaccag cagaaattag ccacagaaat    12780
catagctgct ataagggttt attaatcaga ttacgaaact gctaagaagg cacacaacag    12840
tgacttgctg aagctgcctg tgctgctgtt agcgagcctc ccgtaggtag caatgctaac    12900
tccttccttt tagcagttta cccactgctt ccttccatca ctccttcctt ttgtagggcc    12960
tacttttgca gtttgatcca gtggcttgca ggcaatatct gtcccagcg gtgctctatg    13020
cagctgacct ccaggtaggg ctccatgtga gcgatgcaat tgttatttc catggggttc    13080
ctaagaagga ggaagcaaaa agctcaggag gtgctccaaa tatattatcc tgtcctctgt    13140
tttgctcttt gtggtgccct ttaacactgt aaagagacca taggagtcct ctatgaacct    13200
ggaaaggtac cagcactatg ggaggtcttc agtttgctgt aaattatgct ttattagagg    13260
tatttcttct gccaagaccc actgaccca tgcggctcac agtgttttct aaggctttgc    13320
```

```
aggactggtg ttacgaattg gcaccctcca ggcctctcac aaatctcctg cttctcacag    13380
cgtttcttca agttctccca agcacagctg agttttgagc tcaactgctc cctgcagggg    13440
ccttgagcct cctgccttt tgcataaaag gtgtcaggta cttatgcaat ccttagaggc    13500
atgcaaatgc tgctctggtt atatactgag gactgttgat tctggcagaa ccctttgcag    13560
accttgtact cccttgctat ttcccaatcc ctgcagccta gcagctctgc ctaacaactg    13620
ccatagccaa cacagcagca ggctgtgcat ggtgcaaggt gatgtggaaa gggatgattg    13680
tatgaaagcg tgatgctgtg gtactgcctc tgcaggagac tcgcactatt tgtgtaagag    13740
gaccttattt gtctgctgca gagctgtttc aaggctgtcc atacacccct gtgatgctga    13800 gccctccaa gcaatgcact gggaaaagga ggctgggggg agaccttatt gctctcctcc    13860
aatatttgaa aggtgcttac agcgagagca gggttggtct cttctcactg gtgacaggat    13920 gagggaaat ggcctcaagt tgcaccaggg tatgtttaga ttggatatca ggaaacactt    13980
atttactaaa aggttgttaa gcactggaat cagctcccca gggaggtggt tgagtcacca    14040
tccctggatg tgtttaaaaa ctgtttggat atggtgctca gggacatgat ttagcggagg    14100
gttgttagtt agggtagtgt ggttaggttg tggttcactc gatggtcttt aaggtctttt    14160
ccaacctgag caattctatg atatggatcc ctggggcttt cagtcttatc tccctggatt    14220
atcacaggtt cagctctatg gcccatttga tttataccgg ggtctgatga acaggttttt    14280
ctcttggctc ttcagggatc ctatttagca ctttttggta cattcccctg ccctacaagt    14340
ctccctgata cacagagctc ttatccaaga cttgggacct tccctactcc agccctctgc    14400
aggaggtttc ttgctaacca gtcctccaac caggactgca gtacacgaca aagagctgga    14460
agaggtctgc aatacttccc cagcatgaag gtatgagcac tccttttgag taggttactg    14520
aaagtagtaa gatgtcaata caaccaactg caagatacaa aaccgcatga aaattcagtt    14580
tactttgatg ctgaagggct gaaaagaaat gctgtggtgt tagcacagat gcactgctgg    14640
caaagtgaaa atgagcaaag aggatgagat ggatggacag ctgatggaaa aactcttcct    14700
aattgctcca cagagcagct tgctcgcctg caggctgca gcatggagct gcttgtgcat    14760
aatgcagaca ccccaagacc agtgctgttt gtcttagcca agacacagtt gcagctgcag    14820 caatttttc tagatgtcag ttccttccct atgttgctga caggtgtttg ctgttctgtc    14880
cctttaatct gtatcctaca gcaaacattc cttgaattta ataacttagc tggaagacaa    14940
ttgctgtgat cttgatagaa catgctgagc caatctattt taactgcaga tttagtttgc    15000
aaatactgtc tccttgccga taagattcag gtgtcatctt tgtggacatt ggcaggaatt    15060
ttcttgaccg tgacaggttt tacagagtct ggcaattaag ctgtcaagac acattttcct    15120
ctgccaggaa gcattaattg atgatagtct tggctgcaat aggcacagag agatggatat    15180
tgtaatcaga atgaatagag gtccttgtag ttgagagcta cgttggtcca agttttgta    15240 gtcgttgacg tttggtgata ctgagataag gaacaaggca cgagatatta gagctaaata    15300
tcaggcacag catgagaata aagacctctc tagctggaac tgttggtatc tggggagatt    15360
ttaactttct ggatgcatac tgcaaagtac taatattagt agagctactg gatgcgagag    15420
caaatagttt tccattaagt aatcccaaaa atcatgttgt tgttggtttg cttttcaagt    15480 gcgagggggtg ttggagatgt atttccctca gaaaataaac ctgatatgat tcaacctgag    15540
ctctctctgt ttaaatcaca ctgaaaatag atctgcaaat ggggattttg attaccgagt    15600
acagaatatg aaagattaaa acttgggaaa gttagggttc tgattgagaa aacttttgtt    15660
```

```
tttgtggccg accccttgcag cttacaaaaa tctgcctaaa taaaggagaa aaccacatttt   15720 agaacccatc caagctatgc tacttcagta ctgggcaaaa cttcaggaga cgtttgaaga   15780
aaactgaaga cgtgaagtat aaaggaatga ttgatgtgca cagtaaactt tcttggaagg   15840
taatcacgca tgggctaata tcaatctttta caaagttggc tgacttccta gataaaggaa   15900
gtacagtaga tctagtctac ccaggcagca aaaatgtttg acctgttgcc ctgtggggtg   15960
gtgtcacctg ggcttgggga gggggtcag gatgaggtta caggggatgt ggaagcatac   16020
tgtggaggag caggtggggc acccacagga gttagcagtg agcagacaga aaggtggatc   16080
tgaggaccga acttcgtatt tttgttcctt gcattaatac acaaaaagca gacacacaca   16140
cagagcagat tgctgctggt ttttgttttc tttttttaaac agcagaagag caggatttttt   16200 cccacagaga atggggtgac cttctaggct gtgattgcct gggctcaagc tgagatgaaa   16260
cgcagtgatg aggagcacaa aaccgtgctc tgaggttaaa taatgagggc ttcggctatc   16320
agttcagagc tcagtaaaaa ctgcagagga ggaggaagac ctaattgcat gtagccagcc   16380
acagggcaaa tgagagctgc agcgtgctgg ggcagatccg ggagcagagg ggccgtggca   16440
cgctccctgt tcactggctc ccctggagcc acacaaaagg ccccttcctg gcaattgtgc   16500
ccacatcaat cattagctag aaacccagag ctgggtaaat acgttttggc ttcccgtctt   16560
gatgacagat tgggtgttac atcacaaggt gggaccactt gatatgacaa cacgctatat   16620
attcccgctg ctacctctgc ccttcctccc ccactctgag agcaagcggg ctgtgtgtgc   16680
accgaggtgc tctgccatga ggactgccag gcagtttgta caggtggctc tggccctctg   16740
ctgctttgca ggtgagtgtt tcctgctata ccccgtaggt gactatagct agaccagaga   16800
ctaggctatc tgtgagagta tctgggtatt gtaatgtgtt agagagcctt gttccatgaa   16860
ggaatgctct ttctgacagt gtagcaaaac accagactgc aagatccagg tttcagcaaa   16920
cctcatacag acgactgttt tcgtcgtggt ttataggagc aaattgctga gggagcagtg   16980
ctagtgcagg gcaggagctt gcacgtgcaa gcactgagta taacggcaaa gcaaagctat   17040
gtgaaatggc tcctgtgtcc atgtaagcaa tacaaacact gcatcttgta tcatctataa   17100
attttctgtg ctgttcctgg cagctgagaa gtttgttgtg ggaagaacag tgctagtggt   17160
caacagccac ctgaaacgtg catgtctgag ctcctgcaag tcaaatacag agtcttgcag   17220
aagagtttaa actcagtgca ggcttgaaaa tacctacatt tcttccctgg ggcatcttag   17280
gaactggcta acacatgtgg cctcctactg aaagtgcagt gaaacttcat ttaataacct   17340
ctgattcatt ttatggacgt acatcactgg cataatgtaa aattgcattt tcctaaaccc   17400
aataagccaa tcaacaacgg tatctaaatg taactgtttc atcgaaagat ttgcatatgt   17460
catctctgca tattaataat atgtatttat tttctgtctc tacttttctt ttagatattg   17520
cctttggaat tgaggtgagt tacagatttt ttttcccatt tattctttttc tattccaggc   17580 ttctggtcaa ataagagcag tatataatta cctgatgagc aagtggatta atctaatgaa   17640
agcctggttg ctcaaataat acttgccagt gcatgattga atgatattgc caagtcacga   17700
aaaagtaaaa cacaccccgt ttatactatt ttccattcat gcaataaaat gaagaaagga   17760
agaattgtac gatcctatta tgttaacttt tggatataac tgcgttagtc caagtcaagg   17820
ggtggtagtt acctcctcga gaggaaagct gtcttaagat gataagctcc aaagcatcaa   17880
agacagtgat tctggtatct ttttctatac agtaagacac acactacagt gttcctgcct   17940
atacccatat caaagcgagg aaagcagcag ggtctgtgca gtgcatttgt ctgcaggttc   18000
ttcccacgca gttatgagat tcctgcaaat caccagagac tgcagcgtga ttggaaacga   18060
```

```
tcagattttg agttgagcgg ctgtggagca tggccaggct cccaattacc agctgccttc   18120
gttaggcgct gtctcaccca cagctctcct tcctccatgt catgcttccc ccagtccccc   18180
gcaggaaagc gtgatcagaa gaagattccc acctcctgac tgcctgagca gattccaaat   18240
gatacctcag gtgtttgtcc cggctggagc tgtgggtggc aggaggtttc catactgtct   18300
tttgttgtgg aaactgaccc cagggctgat gttgtgctgc ttccataggt taattgcagc   18360
ctgtatgcca gcggcatcgg caaggatggg acagttggg tagcctgccc gaggaacttg    18420
aagcctgtct gtggcacaga tggctccaca tacagcaatg agtgcgggat ctgcctctac   18480
aacaggtgag cttatgtgga agcccagggg agctgcaggg caggagactc gaggtgaggg   18540
cggcagctct gtccccaaaa tatggtctgt gtggaggagt atgtgagtta gtaccaggat   18600
gctgacctcc agcctggggg tggtggctgc tctctgccat ctctgacaca gatctgcgtt   18660
cttccaggga gcacgggca  aacgtggaga aggaatatga tggagagtgc aggccaaagc   18720
acgttacggt aagtccaaca gtaagatgaa gtcttgctct gttggtgccc ataaagactt   18780
attttatttt catagaatca ttgaacagct taggttggaa gggaccttaa agatcattgg   18840
gctctaaccc ccctggcctg gccgggctgc cttcaaccaa atcagtttgc ccagtcaaat   18900
gggccttggg cacctccagg gatggggcac ctgctctgct cagcctgtta cttatttact   18960 tgttttttc  ccattcctgc tatccttaca gattgattgc tctccgtacc tccaagttgt   19020
aagagatggt aacaccatgg tagcctgccc aaggattctg aaaccagtct gtggctcaga   19080
tagcttcact tatgacaacg aatgtgggat ttgcgcctac aacgcgtaag tcttttctgt   19140
ggagcatcct tctgggtaat tagagatggc taagtcccTt ggaaacgctt acataaaaca   19200
ctttctaagc ctttcttagg gtagatgttt ctgtgggact cttTgaagct ggctacttgt   19260
gattctccag ccagctgcag atttcttccc catcctctgt ctgtgctcat gaagggaatc   19320 acaaaaaga  cagaggacaa cccacagcag aggcatgaat agatcaaagt gttgctcagt   19380
gctgtgtgat atggaaatac catgcatttt ctgctcacaa gtggttgcta ccacctgtgg   19440
gctgcatcca gaccactcag cagttcctta cgtgaagggt gggaccttgc tttcttgccc   19500
cagtatctaa ggcttttcac gaggctctct aactaaaaca gctctttctt tcagagaaca   19560
tcacaccaac atttccaaac tgcacgatgg agaatgcaag ctggagatcg gctcggtaag   19620
tgtaacagaa ataaaaatcc atctcctagg gctgttaacg gagagaatcc cattgatttt   19680
cctaagaaaa tgtatgaccg ggctgatcgg gggtcccggt ccacgctctg cttcctgcct   19740
ggtgagggtg gcttctgaaa caaagcggta aggaagagg  ccccagattt tccttgcatt   19800
gtgctgtgca gattggcagg tttctctctg gaggcgacaa gcatttccac cctttgtaac   19860
aagcattcaa aattctagtg ctggtagctt ggttagatat agtgagattc ataagagcac   19920
caagcataca tatttatagg gtatagctta ttgtatattt atactggggt aagagtccag   19980
tgcctcagga agaaaagctt atatatttca gcacaaaaat tctgggatgc agggagtccg   20040
ttctccaaca gacggattcc tcctttatca cttcaactcc cgtgcttaac tgcagggaat   20100
ctgaattatt aagcaatcac agcactgggg aaggaaggag aaaaaccaac acaaaccaaa   20160
acaatgttaa tcagatttcc agctgttgga aaatatttcc cacttaattc aaggctgttg   20220
tgtcgatgag aagagggctg aaaaggctgt tttcagttcc tctgcctgaa ggtttcattc   20280
tctaagagag gtcccttttc ttgtctccta gagaatgagg gtagtgttct gaaagcctat   20340
ttctgataga cagtttagtt aagtgtagca gggctttgtc ctgtcacaaa aactaggaag   20400
```

```
ccgggaatac aggatgaaaa ggtgttacat tgacttctcc cgtgtagcac aggctccggg   20460
agggcttatt ctccttattt tggcaggttg actgcagtaa gtacccatcc acagtctcta   20520
aggatggcag gactttggta gcctgcccaa ggatcctgag cccggtttgc ggcaccgatg   20580
gtttcaccta tgacaacgaa tgcgggatct gcgcccacaa tgcgtaagtg ctgctcatct   20640
cccactcctc caaagtagcc agcaatgctt tgccgtgctg ggagccttcc ttctacgttg   20700
ctgcttatgc ctgtttcttc aagcctctta gaaactgcat tttttttgtt gttgttctta   20760
ctgagttttc ttctgatgcc ttctttgtga tcacgagggg aaatctgcaa gactcagaac   20820
acagctcctt ggattagtct gtgggctggg cagtgactga gcagagaaag gaatagttca   20880
gaatcttgct ttaaataaca cgagaagacg tgatgagctt gttaacgagc agagtaatgt   20940
agctatatca atacaatcgt gcagagaggc tgaagcccta ctttgttagg tacctgcttt   21000
aggctacgtc tggttcattc tgcatgcaag tgtttaaacc aagagttaaa gcatctcctt   21060
actcactttg tctccctctt tcagagagca gaggacccat gtcagcaaga agcatgatgg   21120
aaaatgcagg caggagattc ctgaagtgag tatacaacgt aaggtgtatt tctccccttg   21180
cctctgccca ctgagctatt tgctgaggcc acgtctactc tgaaagtgag ctggcttgaa   21240
gcctggctct ctgcacgtgt cctttgggat gtgccaacgt gtatccaaca cacaaacagt   21300
gtggaagttg ggcaggggga acttaggtct tttaaggatg atcactaaat gcattgccag   21360
caaagtcctt ttgtgccagt gaagtcctat tatgtttgcc ttcttttgtt tcattctata   21420
gtgcagagag aaaaggagat gatatatctt tgttggtttt ttttttgttt gtttgttttg   21480
cttttctgcc atatctagca aactgtttca gtaggttgtg accccttttgg atcacaagtg   21540
aagctcagtg gcatttggga ttgactgagc tgtctgccct ggtgatttgg catctcacag   21600
attacacagc gccatgtagc tcctcctggg catgagagag tttctgcaga gctgactcag   21660
gctggctttg agagaactga agtgtagcac cagcgttgtt tcagcatccc agcgtaaaag   21720
acatggattg cagcaggagg caatgctagg gtttgtcttt gagagcaagg gcttttttcag   21780
ggctgacgct cctacttttt gcagattgac tgtgatcaat acccaacaag aaaaaccact   21840
ggtggcaaac tcctggtgcg ctgcccaagg attctgctcc cagtctgtgg cacagacgga   21900
tttacttatg acaacgagtg tggcatttgt gcccataatg cgtaagtact gcaaacagga   21960
cttccttttg tagcgactag ccacgttagt actgcagatg gcttcccctc cacccttcat   22020
cttcttcttt ctttcttttt ttttgatagc agtatgtcta tatgtctcct gttcttcctt   22080
caacctcctg aagctctgtc gcctcggttt ccttteстga tgtgctcctc agggagctgt   22140
gggagagcca gctaacagct gagtgtccta tgagggctgt ggcatttgtg cagaggaaaa   22200
agagaatggg tctgctacaa gtagacctga gaagcctgta acttcttagg atcatgatcc   22260
ctaatggcag ccttteccctt tcagacaaca tgggactgag gttaagaaga gccacgatgg   22320
aagatgcaag gagcggagca ccccggtaag tgggatggaa tgtcagatga cgccagctc   22380
ctgtacgtgc cttgtggctg cagaggttgc taaccagggt ctgtccattc aggcagcaga   22440
gaaggggaat gggccaggat ttaggtaaca aaatgtccca atactgcagg tctctggagg   22500
gaaacatcag aggcagccca gaacagcaca gcctgtttta gcacagtagg agaggaagag   22560
cagaagctgt gttagatgcc tgtgtagtca ttcagtgcta ggatttccat tgcagcagac   22620
aggttaaaaa atctctgtac cgtggtcagc caagaaaagg ctgcttgcag gaatgcacgc   22680
agaaatagct ctataaacat gcacggtaac aatatgtgct gataatatct cagcacattt   22740
attctgctta tgcagagcag ctctaaaaca ctgaaaataa ctttgtgcat ctcaagggat   22800
```

```
tgctgtatct tttctgtagt aaagacacac tgttatggtg ctgtctttgc tataatttgc   22860
tcttggactg tgtggggaaa tatgggtaat aagagctact acacagggga aggtatgcaa   22920
aacgattgtg aagtgtcaga agcttagcca gtgtagactg acttccagtg ccatcagtag   22980
atacttgctt atttatcctc aaatattgga actgttttta agtactgtga ggatttctgc   23040
agcagcagct gatgagctga tggaacagtt tcttcttgcc gttttgaaaa cgtggaaaca   23100
aaatctaagg cttagctaag tcaggcatga cctaatgtca aactggacat aacatcaaac   23160
tccttatatc aaattccttt gaataatgct tgttttgaaa cttggacata cgctgcataa   23220
ggaagatgat ctttctggtc tgctattcct ttgcgttccc tttgttagtg agcaatatca   23280
aacccaacca caattagttc atttataatg ggagactaaa ctgaaatcaa ccctgatttt   23340
tcctatggct cgaggcagtc tgtcccccag ctcccagcac ctgactcagc atccttactg   23400 tttctcccc agcttgactg cacccaatac ctgagcaata cccaaaacgg tgaagccatt   23460
accgcctgcc ccttcatcct gcaggaggtc tgtggcactg acggcgtcac ctacagcaac   23520
gactgttctc tgtgtgccca caacatgtaa gccctgcagg tcaccactc gtgtgtcacc   23580 gcagctgctt gttgagcttt gtcaactctg ttttctctct cttccagtga attgggaacc   23640
agcgttgcca aaaagcacga tgggaggtgc agagaggagg ttcctgaggt aagcgataaa   23700
gaaaacaaga gcttgaggtg gtgcttattg cctaacaagt acaacgctgg ctggttttgg   23760
tgatgctggg tcatgccctc ctgctgccat ccttcctgca ggtaaacatc aaccctggca   23820
gcagggatgc tgtgcatttt ctgcatgtag tcagggaaaa aaagaagaa ggacgggtga   23880 ggaatgagtt atgatgcagg tagcataaat gatttaaggc gttacgaaga aatctctttc   23940
ccacagcagt ctatcatacc tgccgtggga gtgtagctgt ctgttctggc aatatgggaa   24000
agggacacag agcacccgca ggtacctggt gccttctgga tacctgtgct gtgcaaaagg   24060
atgttgtgca aagatcagaa aactacctgc attttgaatg cttttaccta atgtaccaga   24120
ggattcaaac acctctctct tcctattgta aatgcgatat aatgtaatgt ataccaacaa   24180
tgaatcttgt aaaaatacca gataaactat atttggccag ctctaaacta tttacgctca   24240
ctggggaata gaaaacaaa gccatctcat tatcttgtgt ttgaaagagt caacgtcgtg   24300
agtcagatat ttcatttcta tgcaaacaga ctatgaaatg tcattgcttt gtttcctgcg   24360
tatgctctgt gctcagacca agtcagatgc ataaatcagt gaggaagagc tcacactgga   24420
gaaactggga tagctgaaac tcaaggccag ttcttcaaat ggcataaatc attttgaact   24480
gctgttggtc cttctgtccg attgcaacac acagaaccag cccctcgcaa caaaaggcat   24540
gtcagcacat ctcctcagtt cttgtgggcc gtgacacact ccttggccac actgagcttc   24600
tcttgcagga attgcataaa tcacgccagt ttgatttgca gattatttat gagctgcgtt   24660
ttgcagcgtc ccagcaagtg gttcagcaag ctctaagggc atcgtgataa atgcagggct   24720
gaatgagtga tacgcgcctt caagctttga ttcagtcttc tccagtataa ggctgtgaca   24780
gaaaattgat agtttcaat gaagaatgag tcaatgcata accataatcc atcctgtggc   24840
agatcttgaa aggcagaggc gtaaggaagg gggttgtgtc tgagcaccct tacacagagc   24900
atttgctgcc tttgtttcct agcttgactg cagcaagtac aaaacctcca cgctgaagga   24960
tggcagacag gtggtggcct gcaccatgat ctacgatccc gtctgtgcta ccaatggtgt   25020
cacctatgcc agcgaatgca cgctgtgcgc tcacaacctg taagtactca ttcatctcca   25080
gggggaccca ccgtggctgt gactggacac atctttgagt gctgaataac atgcaagggc   25140
```

```
tctgtctaaa atctcgtgct gcatgggtcc tgtctgccta tccccgtttc cctggttgcc   25200
atggttggtg tttgagatgg gcatttagca aggcccactg cccccagtga cccagaaaaa   25260
gggttcactg cctgggaaag cattattcca aaagacacat ccctagtcct taagggcatg   25320
ttcttgctaa tgcttctcag gcaatgctta gctaatttat ctgaaattgt cctgtgtacc   25380
acatgggaac gaggttgtgc tcttgtacta cggttgtaaa tgggaagggt ttctgctaat   25440
atccatctct ccttcctcca gggagcagcg gaccaatctt ggcaagagaa agaatggaag   25500
atgtgaagag gatataacaa aggtgagtgt gaaaggatgg gcacaaagag ttacagtcgt   25560
aggggaccgt cctctgctcc acatcaaaaa ctgggggagc ggtgtgcagc cctggcgagg   25620
tcgcttggga atgtcatact ggttatagaa tagctgccat ccatcccatg ggaatggaca   25680
tggcagtgaa caggaacagt gtgaggtcac atccctcacc aggaggaact gagctgatta   25740
ctgccgtaat tttccagttt cactctttgt gctgggggaa tactgtttgc tcccaggcag   25800
agactcacat cttccttgtg tgtgcaggaa cattgccgtg agttccagaa agtctctccc   25860
atctgcacca tggaatacgt accccactgt ggctctgatg gcgtaacata cagcaacaga   25920
tgtttcttct gcaacgcata tgtgtaagta taggagtgaa accttcctg taactgctac    25980 aaacgcagag ttgattttat aaggagttct ttactaacac tttatgggtg tgtgctagac   26040
atttcggatg caccgtgacg tgcaaggagg tgcttttttg cttttttaaga aaaaatgcaa   26100 agcacccaca tctgcccatg tgtatgtggc ttcctgtttt atttagtttc aaagacattt   26160
tgctaatttt caccagcata gtttgtccca caagctcatc agggtatggg gaaagtactt   26220
caccaaacta cctggagcgt ttcaagtgtg tgaaacctgt catctttcct ttaattttca   26280
taatgaaagg aagtggttgg ccttctgaga ctgttcttta tcttctgcca acattatcaa   26340
catttgggct ggtaaggaga ggaacaaggc tgcagcacaa attctattgt gtttaatcct   26400
ttcttctctt ttcattaggc agagcaatag gactctcaac ctcgtgagta tggcagcgtg   26460
ttaactctgc actggagtcc atcgtgggaa acaatctgcc ttgcacatga gtcttcgtgg   26520
gccaatattc cccaacggtt ttccttcagc ttgtcttgtc tcccaagctc tcaaaacacc   26580
tttttggtga ataaactcac ttggcaacgt ttatctgtct taccttagtg tcacgtttca   26640
tccctattcc cctttctcct cctccgtgtg gtacacagtg gtgcacactg gttcttctgt   26700
tgatgttctg ctctgacagc caatgtgggt aaagttcttc ctgccatgtg tctgtgttgt   26760
tttcacttca aaaagggccc tgggctcccc ttggagctct caggcatttc cttaatcatc   26820
acagtcacgc tggcaggatt agtctctcct aaaccttaga atgacctgaa cgtgtgctcc   26880
ctctttgtag tcagtgcagg gagacgtttg cctcaagatc agggtccatc tcacccacag   26940
ggcaattccc aagatgaggt ggatggttta ctctcacaaa aagttttctt acgttttgct   27000
agaaaggaga gctcactgcc tacctgtgaa ttcccctagt cctggttctg ctgccaccgc   27060
tgcctgtgca gcctgtccca tggagggggc agcaactgct gtcacaaagg tgatcccacc   27120
ctgtctccac tgaaatgacc tcagtgccac gtgttgtata ggatataaag tacgggaggg   27180
gaatgcccgg ctcccttcag ggttgcaggg cagaagtgtc tgtgtataga gtgtgtgtct   27240
taatctatta atgcaacaga acaacttcag tcctggtgtt ttgtgggctg gaattgccca   27300
tgtggtaggg acaggcctgc taaatcactg caatcgccta tgttctgaag gtatttggga   27360
aagaaaggga tttgggggat tgcctgtgat tggctttaat tgaatggcaa atcacaggaa   27420
agcagttctg ctcaacagtt ggttgtttca gccaattctt gcagccaaag agccgggtgc   27480
ccagcgatat aatagttgtc acttgtgtct gtatggatga cagggaggta gggtgacctg   27540
```

```
aggaccaccc tccagcttct gccagcgtag gtacagtcac cacctccagc tccacacgag    27600
tcccatcgtg gtttaccaaa gaaacacaat tatttggacc agtttggaaa gtcacccggt    27660
gtattgtgag gctagattaa taggctgaag gcaaatgttc ccaacttgga gatactgttg    27720
gtattgtatc agggaacagg gccatagcac ctccatgcta ttagattccg gctggcatgt    27780
acttttcaag atgatttgta actaacaatg gcttattgtg cttgtcttaa gtctgtgtcc    27840
taatgtaaat gttcctttgg tttatataac cttcttgccg tttgctcttc aggtgttctt    27900
gcagaacact ggctgcttta atctagttta actgttgctt gattattctt agggataaga    27960
tctgaataaa cttttgtgg ctttggcaga ctttagcttg ggcttagctc ccacattagc    28020
ttttgcagcc ttttctgtga agctatcaag atcctactca gtgacattag ctgggtgcag    28080
gtgtaccaaa tcctgctctg tggaacacat tgtctgatga taccgaaggc aaacgtgaac    28140
tcaaagaggc acagagttaa gaagaagtct gtgcaattca gaggaaaagc caaagtggcc    28200
attagacaca ctttccatgc agtatttgcc agtaggtttc atataaaact acaaaatgga    28260
ataaaccact acaaatggga aaaacctgat actggaattt aaatattcac ccaggctcaa    28320
ggggtgtttc atggagtaac atcactctat aaaagtaggg cagccaatta ttcacagaca    28380 aagcttttt tttttctgt gctgcagtgc tgttttcgg ctgatccagg gttacttatt    28440
gtgggtctga gagctgaatg atttctcctt gtgtcatgtt ggtgaaggag atatggccag    28500
ggggagatga gcatgttcga gaggaaacgt tgcattttgg tggcttggga gaaaggtaga    28560
acgatatcag gtctacagtg tcactaaggg atctgaagga tggttttaca gaacagttga    28620
cttggctggg tgcaggcttg gctgtaaatg gatggaagga tggacagatg ggtggacaga    28680
gatttctgtg caggagatca tctcctgagc tcggtgcttg acagactgca gatccatccc    28740
ataaccttct ccagcatgag agcgcgggga gctttggtac tgttcagtct gctgcttgtt    28800
gcttcctggg tgcacagtgg tgattttctt actcacacag ggcaaaaacc tgagcagctt    28860
caaagtgaac aggttgctct cataggccat tcagttgtca agatgaggtt tttggtttct    28920
tgttttgtaa ggtgggaaga agcactgaag gatcggttgc gagggcaggg gtttagcact    28980
gttcagagaa gtcttatttt aactcctctc atgaacaaaa agagatgcag gtgcagattc    29040
tggcaaggat gcagtgaagg agaaagcccc tgaatttctga tatatgtgca atgttgggca    29100
cctaacattc cctgctgaag cacagcagct ccagctccat gcagtactca cagctggtgc    29160
agccctcggc tccagggtct gagcagtgct gggactcatg aggttccatg tctttcacac    29220
tgataatggt ccaatttctg gaatgggtgc ccatccttgg aggtccccaa ggccaggctg    29280
gctgcgtctc cgagcagccc gatctggtgg tgagtagcca gcccatggca ggagttagag    29340
cctgatggtc tttaaggtcc cttccaacct aagccatcct acgattctag gaatcatgac    29400
ttgtgagtgt gtattgcaga ggcaatattt taaagttata aatgtttct ccccttcctt    29460 gtttgtcaaa gttatcttga tcgccttatc aatgcttttg gagtctccag tcattttct    29520 tacaacaaaa agaggaggaa gaatgaagag aatcatttaa tttcttgatt gaatagtagg    29580
attcagaaag ctgtacgtaa tgccgtctct ttgtatcgag ctgtaaggtt tctcatcatt    29640
tatcagcgtg gtacatatca gcacttttcc atctgatgtg gaaaaaaaa tccttatcat    29700 ctacagtctc tgtacctaaa catcgctcag actctttacc aaaaaagcta taggttttaa    29760
aactacatct gctgataatt tgccttgttt tagctcttct tccatatgct gcgtttgtga    29820
gaggtgcgtg gatgggccta aactctcagt tgctgagctt gatgggtgct taagaatgaa    29880
```

-continued

```
gcactcactg ctgaaactgt tttcatttca caggaatgtt ttagtggcat tgtttttata   29940
actacatatt cctcagataa atgaaatcca gaaataatta tgcaaactca ctgcatccgt   30000
tgcacaggtc tttatctgct agcaaaggaa ataatttggg gatggcaaaa acattccttc   30060
agacatctat atttaaagga atataatcct ggtacccacc cacttcatcc ctcattatgt   30120
tcacactcag agatactcat tctcttgttg ttatcatttg atagcgtttt ctttggttct   30180
ttgccacgct ctgggctatg gctgcacgct ctgcactgat cagcaagtag atgcgaggga   30240
agcagcagtg agagggctg ccctcagctg gcacccagcc gctcagccta ggagggacc    30300
ttgcctttcc accagctgag gtgcagccct acaagcttac acgtgctgcg agcaggtgag   30360
caaagggagt cctcatggtg tgtttcttgc tgcccggaag caaaacttta ctttcattca   30420
ttccccttga agaatgagga atgttgaa acggactgct ttacgttcaa tttctctctt    30480
cccctttaagg ctcagccagg ggccattgct gaggacggca tcgggcccc ctggaccaaa   30540
tctgtggcac agatggtttc acttacatca gtggatgtgg gatctgcgcc tgtaatgtgt   30600
ccttctgaag gaaggaacgt gccttccaag tgccagcccc acagccccca gcccctccct   30660
gtgctgctcc aattcatctc ctcttcctcc ttctcccttt gctgtttgtg ctcgggtaga   30720
aatcatgaag atttagaaga gaaaacaaaa taactggagt ggaaacccag gtgatgcagt   30780
tcattcagct gtcataggtt tgtcattgct ataggtctgt atcagagatg ctaacaccac   30840
tttgctgtcg gtgcttaact cgggtgaact ctccttcact cgcatcattt gcgggcctta   30900
tttacatccc cagcatccat caccctctgg gaaaatgggc acactggatc tctaatggaa   30960
gactttccct ctttcagagc ctgtgggatg tgcagtgaca agaaacgtgg aggggctgag   31020
cagcagcact gccccccaggg agcaggagcg gatgccatcg gtggcagcat cccaaatgat   31080
gtcagcggat gctgagcagg cagcggacga acagacagaa gcgatgcgta caccttctgt   31140
tgacatggca tttggcagcg atttaacact cgcttcctag tcctgctatt ctccacaggc   31200
tgcattcaaa tgaacgaagg gaagggaggc aaaaagatgc aaaatccgag acaagcagca   31260
gaaatatttc ttcgctacgg aagcgtgcgc aaacaacctt ctccaacagc accgaagag    31320
cacagcgtaa cctttttcaa gaccagaaaa ggaaattcac aaagcctctg tggataccag   31380
cgcgttcagc tctcctgata gcagatttct tgtcaggttg caaatggggt atggtgccag   31440
gaggtgcagg gaccatatga tcatatacag cacagcagtc attgtgcatg tattaatata   31500
tattgagtag cagtgttact ttgccaaagc aatagttcag agatgagtcc tgctgcatac   31560
ctctatctta aaactaactt ataaatagta aaaccttctc agttcagcca cgtgctcctc   31620
tctgtcagca ccaatggtgc ttcgcctgca cccagctgca aggaatcagc ccgtgatctc   31680
attaacactc agctctgcag gataaattag attgttccac tctcttttgt tgttaattac   31740
gacggaacaa ttgttcagtg ctgatggtcc taattgtcag ctacagaaaa cgtctccatg   31800
cagttccttc tgctccagca aactgtccag gctatagcac cgtgatgcat gctacctctc   31860
actccatcct tcttctcttt cccaccaggg agagctgtgt gttttcactc tcagccgctc   31920
tgaacaaatac caaactgcta cgcactgcct ccctcggaaa gagaatcccc ttgttgcttt   31980
tttatttaca ggatccttct taaaaagcag accatcattc actgcaaacc cagagcttcc   32040
tgcctctcct tccacaaccg aaaacagccg gcttcatttg tctttttaa atgctgtttt   32100
ccaggtgaat tttggccagc gtgttggctg agatccagga gcacgtgtca gctttctgct   32160
ctcattgctc ctgttctgca ttgcctcttt ctggggcttc caagagggg ggagactttg    32220
cacggggatg agataatgcc ccttttctta gggtggctgc tgggcagcag agtggctctg   32280
```

```
ggtcactgtg gcaccaatgg gaggcaccag tgggggtgtg ttttgtgcag ggaggaagca    32340
ttcacagaat ggggctgatc ctgaagcttg cagtccaagg ctttgtctgt gtacccagtg    32400
aaatccttcc tctgttacat aaagcccaga taggactcag aaatgtagtc attccagccc    32460
ccctcttcct cagatctgga gcagcacttg tttgcagcca gtcctcccca aaatgcacag    32520
acctcgccga gtgagggag atgtaaacag cgaaggttaa ttacctcctt gtcaaaaaca    32580
ctttgtggtc catagatgtt tctgtcaatc ttacaaaaca gaaccgaggg cagcgagcac    32640
tgaaggcgtt ttcccatgct gagttaatga gacttggcag ctcgctgtgc agagatgatc    32700
cctgtgcttc atgggaggct gtaacctgtc tccccatcgc cttcacaccg cagtgctgtc    32760
ctggacacct caccctccat aagctgtagg atgcagctgc ccagggatca agagactttt    32820
cctaaggctc ttaggactca tctttgccgc tcagtagcgt gcagcaatta ctcatcccaa    32880
ctatactgaa tgggtttctg ccagctctgc ttgtttgtca ataagcattt tttcattttg    32940
cctctaagtt tctctcagca gcaccgcttt gggtgacttc agtggccgcc tggaacccga    33000
ggggcacagc caccacctcc ctgttgctgc tgctccgggg actcacgtgc tgctggatgg    33060
ggggaagcat gaagttcctc acccagacac ctgggttgca atggttgcag tgtgctcttc    33120
ttggtatgca gattgtttct agccattact tgtagaaatg tgctgtggaa gcccttgta    33180
tctctttctg tggcccttca gcaaaagctg tgggaaagct ctgaggctgc tttcttgggt    33240
cgtggaggaa ttgtatgttc cttctttaac aaaaattatc cttaggagag agcactgtgc    33300
aagcattgtg cacataaaac aattcaggtt gaaagggctc tctggaggtt ccagcctga    33360
ctactgctcg aagcaaggcc aggttcaaag atggctcagg atgctgtgtg ccttcctgat    33420
tatctgtgcc accaatggag gagattcaca gccactctgc ttcccgtgcc actcatggag    33480
aggaatattc ccttatattc agatagaatg tcatccttta gctcagcctt ccctataacc    33540
ccatgaggga gctgcagatc cccatactct cctcttctct ggggtgaagg ccgtgtcctc    33600
cagccccct tcccaccctg tgccctgagc agcccgctgg cctctgctgg atgtgtgccc    33660
atatgtcaat gcctgtcctt gcagtccagc ctggaacatt taattcatca ccagggtaat    33720
gtggaactgt gtcatcttcc cctgcagggt acaaagttct gcacggggtc ctttcggttc    33780
aggaaaacct tcgctggtgc tacctgaatc aagctctatt taataagttc ataagcacat    33840
ggatgtgttt tcctagagat acgttttaat ggtatcagtg attttattt gctttgttgc    33900
ttacttcaaa cagtgccttt gggcaggagg tgagggacgg gtctgccgtt ggctctgcag    33960
tgatttctcc aggcgtgtgg ctcaggtcag atagtggtca ctctgtggcc agaagaagga    34020
caaagatgga aattgcagat tgagtcatgt taagcaggca tcttggagtg atttgaggca    34080
gtttcatgaa agagctacga ccacttattg ttgttttccc cttttacaac agaagttttc    34140
atcaaaataa cgtggcaaag cccaggaatg tttgggaaaa gtgtagttaa atgttttgta    34200
attcatttgt cggagtgtta ccagctaaga aaaagtcct acctttggta tggtagtcct    34260
gcagagaata cgacatcaat attagtttgg aaaaaaacac caccaccacc agaaactgta    34320
atggaaaatg taaaccaaga aattccttgg gtaagagaga aaggatgtcg tatactggcc    34380
aagtcctgcc cagctgtcag cctgctgacc ctctgcagct caggaccatg aaacgtggca    34440
ctgtaagacg tgtccctgcc tttgcttgct cacagatctc tgccctcgtg ctgactcctg    34500
cacacaagag catttccctg tagccaaaca gcgattagcc ataagctgca cctgactttg    34560
aggattaaga gtttgcaatt aagtggattg cagcaggaga tcagtggcag ggttgcagat    34620
```

```
gaaatccttt ctaggggtag ctaagggctg agcaacctgt cctacagcac aagccaaacc   34680
agccaagggt tttcctgtgc tgttcacaga ggcagggcca gctggagctg gaggaggttg   34740
tgctgggact cttctccctg tgctgagaat ggagtgattt ctgggtgctg ttcctgtggc   34800
ttgcactgag cagctcaagg gagatcggtg ctcctcatgc agtgccaaaa ctcgtgtttg   34860
atgcagaaag atggatgtgc acctccctcc tgctaatgca gccgtgagct tatgaaggca   34920
atgagccctc agtgcagcag gagctgtagt gcactcctgt aggtgctagg gaaaatctct   34980
ggttcccagg gatgcattca taaggacaat atatcttgag gctgtgccaa atctttctga   35040
aatattcatg catgttccct taatttatag aaacaaacac agcagaataa ttattccaat   35100
gcctcccctc gaaggaaacc catatttcca tgtagaaatg taacctatat acacacagcc   35160
atgctgcatc cttcagaaca tgccagtgct catctcccat ggcaaaatac tacaggtatt   35220
ctcactatgt tggacctgtg aaaggaacca tggtaagaaa ctcaggttaa aggtatggct   35280
gcaaaactac tcataccaaa acagcagagc tccagacctc ctcttaggaa agagccactt   35340
ggagagggat ggtgtgaagg ctggaggtga gagacagagc ctgtcccagt tttcctgtct   35400
ctattttctg aaatgtctgc aggaggaaag gacaactgta ctttcaggca tagctggtgc   35460
cctcacgtaa ataagttccc cgaacttctg tgtcatttgt tcttaagatg ctttggcaga   35520
acactttgag tcaattcgct taactgtgac taggtctgta aataagtgct ccctgctgat   35580
aaggttcaag tgacattttt agtggtattt gacagcattt accttgcttt caagtcttct   35640
accaagctct tctatactta agcagtgaaa ccgccaagaa acccttcctt ttatcaagct   35700
agtgctaaat accattaact tcataggtta gatacggtgc tgccagcttc acctggcagt   35760
ggttggtcag ttctgctggt gacaaagcct ccctggcctg tgcttttacc tagaggtgaa   35820
tatccaagaa tgcagaactg catggaaagc agagctgcag gcacgatggt gctgagcctt   35880
agctgcttcc tgctgggaga tgtggatgca gagacgaatg aaggacctgt cccttactcc   35940
cctcagcgtt ctgtgctatt tagggttcta ccagagtcct taagaggttt ttttttttt   36000 ttggtccaaa agtctgtttg tttggttttg accactgaga gcatgtgaca cttgtctcaa   36060
gctattaacc aagtgtccag ccaaaatcaa ttgcctggga gacgcagacc attacctgga   36120
ggtcaggacc tcaataaata ttaccagcct cattgtgccg ctgacagatt cagctggctg   36180
ctctgtgttc cagtccaaca gttcggacgc cacgtttgta tatatttgca ggcagcctcg   36240
gggggaccat ctcaggagca gagcaccggc agccgcctgc agagccgggc agtacctcac   36300
catggccatg gcaggcgtct tcgtgctgtt ctctttcgtg ctttgtggct tcctcccagg   36360
tgagtaactc ccagagtgct gcagaagctt tgtgcctgcc agtcctggct ctccttagca   36420
gaacatggtg gtgaccatca gagagagact cccctacaaa gtgcctgcaa aggctgcctc   36480
agtacatcag tattaaacgg attactgttg tgctgggtgt ctgttgggtt ctgtgctccc   36540
aacacatttc ttacgctctc agctctgtta cactgcttgc atttgctgca cagttgcata   36600
gaatggataa atgcttgaaa caaggccata acgaggtggt cagacctcca ggaactagtt   36660
agggaaatat tgtcatggcc caagcaagct ctgtgcagga acctggcagc tttcctgcaa   36720
tgcttttgct gctaatggag aaacaagaga tgcaaacaag ccaggatctg atgttctcct   36780
tctgtattta catctcatga aattacaaag tcaaagacaa gcgtggttta tttcttacac   36840
tcagcttctt taaaatgtat atccctgaca acagatgctg tgtatgtttg cttatcctgt   36900
atgtgactat ttgcatttgc atttatctct attgactcag gtttcttttc agatatgtga   36960
tagatgtttt ctagggacaa aacggatgtg tgaatagata aggaaggaaa agatattcat   37020
```

```
ttttcaatta ataaatctac ctatctctta actttttttt tttttttaaga acagagctat   37080 tcaagaactc gtttcatcag ccagcaataa gaagctaaat tatgtttatc agcattaaac   37140
aaaaatcata tatagtttgc ttagttcaag aatcgaatcg gtggaaatca ctcagtttgg   37200
ttctctgtgc tggagttttg cacacacatt tcagctagct gtggtctcac tgatcagact   37260
gcctttgttt cccattttg tccccttttt ttccccagat gctgcctttg gggctgaggt   37320
gagtaagaga gttcttcttg tccacttttc tcttttctct tttctctctc tctcttttt   37380 tcccccccgtc ttaattagta tcactataat cagatcccag agtgtaaaat gttaaattat   37440
gcagttctga gctctacatc tatgctgcat gtaagtaatg tagcagtgat ataaaactgt   37500
tagatgaatt aatttctgac caactctgaa ctggtctaag ctttaagttg atcatatgtt   37560
ctactaaata atacagtggt ttgggttgga agggtccttt aagatcatct acttccaacc   37620
cctctgctat aggcagggac aactcccact agacaagatt gctcaaagct ccatccatat   37680
gatcagctgt agactgatgg ctgtagacta tagcattaaa aactacccca aagcagccta   37740
ctgaaagaag aaagtactgt gaggtgctac agcttccaaa tcccatgttg ttagacctgt   37800
tcttttgaat aaacgtgttt gtacgttgag aatgaatgag taacaatggc agaacactgg   37860
aggggccaac tctcaggctt tgcaaaatgg tgcctgggg gcatgataga tccctgctgg   37920
tttatcacat ggggagctgc atggctataa ccccattgcc cagttctctc ccactgcatg   37980
gagagaaggc tggatctggt cgctgccctg ctgaaaatgg cagatgtaac tacaaaatgt   38040
cactttgtcc tgttactgtg tgtttctttg tcaggtggac tgcagtaggt ttcccaacgc   38100
tacagacaag gaaggcaaag atgtattggt ttgcaacaag gacctccgcc ccatctgtgg   38160
taccgatgga gtcacttaca ccaacgattg cttgctgtgt gcctacagca tgtgtgtact   38220
gcagagagag ctcatactgc aagcaagcag ctgtgcttag ggctcctgac agcacccctt   38280
tccaacaaac agtgatctgt cacatgtcac ttatgtcaac tctttcaggg aaagcttgag   38340
tatcactgcg tgacactcgg ttgcctagac atcactttgg ttactgtgtc ttttttgttg   38400
atgtaattta ttcaggtttt tctcctccat ctcggggatg aggcagatga cagcccctag   38460
ggcatatttc atcccagcaa aaaaggagca aaaggatgga gaggtgctcc agtctgaatg   38520
gtccaaaaca gtcctaaaga tttcagagtc tttagatccc tgccagccac tcagtatggc   38580
actaccctct ccaatacaaa tatatatata tacaaagatg acttagccag actcagcctc   38640
attgcattag gtacatattc ccaataacga gaagctgagc ttcctaatac ctgttttccc   38700
tcttcagaga atttggaacc aatatcagca aagagcacga tggagaatgc aaggaaactg   38760
ttcctgtaag tgaaaccaag ttcatccttt gtgcagccaa aactgctat tgacttgccc   38820 aataaataat gtaaatgctg actaagaggc catgtgagat gtcagaatct tgtattgatc   38880
atcttcaggt gaagtttcat cacaataaca caaaaaaaga ctttatttcc tgctgaggtg   38940
gcatttttag agacccaacg cacgcgctcc gctggtctac gtggtccctg taagccctca   39000
ccagcgcttt gctgtgtgct ccttccacag atgaactgca gtagttatgc caacacgaca   39060
agcgaggacg gaaaagtgat ggtcctctgc aacagggcct tcaaccccgt ctgtggtact   39120
gatggagtca cctacgacaa tgagtgtctg ctgtgtgccc acaaagtgta agtaccgagc   39180
tgtgctccct tggcaggaat gggtcctgcg ctcctggcag ccactctttg agcactggga   39240
tttccaatga ggcttttctct gtatggctct tggactccgt ccctcctctc cctgataacc   39300
tcatgctgtt ttcctttgtg attagaaaga gaactgtggc tttgatcttg agagagaagc   39360
```

```
agagagctgg gtggggactt aagagaagca ctctgttctg tgttaactaa gttaaaaggg    39420
tctgtgtggc acacactgcc ttgcagagga cagcagtgaa cctctgctgc acctatattg    39480
taaaacaacc tagctcctag gccatgacag cctgtcacct ctcctccttt gcatcatgca    39540
atactgcaac actgtggcac atagtaccac ctcccataag gactgatatg ttgaaccagt    39600
gtgtcagaga ccagtagcat ctctgtcttc aggatcatca ggtagcattc tatatacagg    39660
gtgttgccca ggactccgag tcccatgaag tatggcaggg gttttggaac tggatgacct    39720
tcgaggtcac ttccaaccca agccattcta ttattctgtg aaagccaggg aggtgggggt    39780
gcttgcaggg ctggtatctt gagcagtgtg ggcacaaact aggctgggca tctgcagccc    39840
atcagcactg cggggatgtg gagttcagca cagcaggatg caggcacagc tccctaacat    39900 ggatttttt cctttcagag agcagggggc cagcgttgac aagaggcatg atggtggatg     39960
taggaaggaa cttgctgctg tgagtgtgag tagcacaatg aaggagcagg ttctggtccc    40020
actgatgtca agggaaacat ggccagcatc tttagtagcc tcaggagcat cagttgtgct    40080
tcagcacaga gaagatttta ctttctacac acgtaataca cattatccac agtaatgtca    40140
ggaagggaag aggatgactg cacaggcagg atcagtaaa agaccataag cagaaataac    40200
ccatgagggc agaactgaga ataagaactg agactagatc caggggg tca gaccaatggg    40260 ccatcaaacc catgatggtt tgatgcagag tccactcttt cagcattcat aagaattgag    40320 tagggggag taagggtggg gtgagtacgt acggatcttc ccaaacaccc ttccaaccta     40380
cagctatgca cctcagccag gtgtgatttc tgtgtagttc acaagcctca gtggatttct    40440
ctcccatggg attctccagc ctctttctgg acctgtatac acggtagttg ggttggtttt    40500
ttttttctgt ctctcttttt ttccccccac tacaatgtcc ctcagcaaac atagtcctca    40560
tctctcaaac aaacaaatct cattctctaa gtacccagat aagagctgat ttttgcttta    40620
agcctgtggg ggagatgctg gactattata aaggtatcag tgctgcctct tctccagaca    40680
ccaatgtttt ttccattta aa tttcctgaac aggtcaggaa cacggtgcaa catgattgta    40740
agcacagcac gttcatggag cgagctgctg ctgcagctca gaaatgcagc agtcagattg    40800
tgatatgcat ctcttacaca ggaaattatg ctctattttt atattattaa atctagcata    40860
cgagaaagga catccagttt atatcagatc gtgcaaggaa gttaattatt tttagtttga    40920
tcattatcat cggcactgca gctgtagcta gggaggggtt gaagctcttc agctatcgac    40980
tccttcatat cctccacgtt acaattgtgt ttttgcaggt tgactgcagc gagtacccta    41040
agcctgactg cacggcagaa gacagacctc tctgtggctc cgacaacaaa acatatgcaa    41100
acaagtgcaa cttctgcaat gcagtcgtgt acgtacagcc ctgattgcat tcacgttgtc    41160
ggctgcctcc tacaggcacc agcttgcaca gttcctgctt cgttgctga ttgctgacca     41220 ggatctgggg gcagaaaaga acaccgggca tcacgccagc cattcatttg atttttcacc    41280
agagcttgtc tggtttgtta ggatggatgt tttgaacgcc attaaccta agggaagttt     41340 tccttgctgc gaagaaaatc agatttggtg tttcattata gttttcagaa ggggttaaac    41400
gatttcactc atctcctaat aatcaggtag ctgaggagat gctgagtctg ccagttcttg    41460
ggctctgggc aggatcccat ctcctgcctt tctaggaca gagctcagca ggcagggctc      41520
tgtggctctg tgtctaaccc acttcttcct ctcctcgctt tcagggaaag caacgggact    41580
ctcactttaa gccatttttgg aaaatgctga atatcagagc tgagagaatt caccacagga   41640
tccccactgg cgaatcccag cgagaggtct cacctcggtt catctcgcac tctggggagc    41700
tcagctcact cccgatttc tttctcaata aactaaatca gcaacactcc tttgtcttgt     41760
```

```
ttaatgctct gcctcatgca atgttttctt ctgatttgtt ggacggtgat accagactca   41820
atatgttcca tgctcgtggc tctggggtat aacaagaaca acatcttgct cccatccctg   41880
tcataaaagg cagaaaatta aatacagatg cataaacctc ggctgtgtga ctttgcgcat   41940
aaatgacagt cagcctccat tagtgttcag acccttttag acagctgaaa tactgctacg   42000
aactgctgat gctggctgag ctccccatgg tacgtgtggt gcactttccc tgcgcagcat   42060
tagcagtgaa agcagctcag ggtgcggtgg tggccaaacc cagggccgat cccacggcct   42120
cctgtacctg gtcatacccc cgggcacagc tgctagtgag gtgcgtgctt ttcagacacg   42180
tcatataagt gtgccctgcc tacatgtctg ggtcctccaa atgacgttgc aaggtttatc   42240
tcatcttgga attgtccctt actgaccacc aagtgttttg agatgaatgc cctcctaggt   42300
ctggttctgc tcttgcctgc tggtcttttc tcatagtagt ccttgccagc ccaagtatct   42360
gagcagtgtt ttgcaatcca aggacaaagt acccctctgc ctttgagagt gtgacctctg   42420
tcattggcac attgtccgtg aaatatattt tgcttttgtc ctttgttggt gtattgaact   42480
gatgttttct tgatccacat gagagaaact ttaataaaaa ttataaaaaa taatgcctcc   42540
cttaagcatt tctttttccct gatggaatga ggccattcaa aagaaggatg ctttggcggt   42600
aaaacagagg atttatgttg agatgggcag atgaatcaag cagtgatttc cagtttggat   42660
tgaacttttc tgggatccag gctgtgggcc tcatgtcatt ctgtcatcat caggctatca   42720
gtctgctgct gcaaatcctc cccacaacgc taatggcttt tagggaaaat cgcaattgtt   42780
agttctttgc taatgcccat aaaacttctt ccatcacttg tccagctcca ggactccctt   42840
cagccccagg tttccctctt gctctctctc ccagttcagt ttttctggat ttgctatgat   42900
ttgatgatgc attattgaca ggacaagggg aaatggtttc aaaccagagg agaggagatt   42960
tagactggac ataagcaaga catttttttac aatggtggtg aggcactgac agaggttgcc   43020
cagagaggtg gtggtgcccc atccatggag acagccaagg tcaggagggg ctctgagcac   43080
tgatggagct gtgggtgccc ctgttcattg caggggggttg gaccagatgg ccttttaaaga   43140
tcccttccaa ctcaaatgct tcaatgattc tgtgattcta ttgggttgaa gcatgccaac   43200
taagactttc cactctggaa aacattcaat tcagttcaac aacatttttcc agcaacagtg   43260
agaaagcact gcatataggt aagcactgat aacatgcaca tggaggaaat cctgcagcat   43320
tctctcttca ggtttgtaca gttgcccttt tgcccacagg aattttccat ggtccttcag   43380
caggcacctg tcacacactt cactggaaat aatgaagccg agggcgtact tcacatattt   43440
aaacctgcaa ttgctgttga taaagaagca ttctttgtgg ctcacttgtg taagtgccat   43500
caagatttac aaccctgaca ccagagctgg aacgctggtt atttcaaagt agggggtggc   43560
taaaccaaac gtgaatgcac acagccacgc acacacagat caggtggcca tccaagggca   43620
gaagggccgc attccatgag cacgatgcac ttctgcccctt tgctgctgcc caggtgagtg   43680
gctgtgctcc tgctccgtgc ttcgtcgagt gctggctgta aaaacacaac aaacatcctc   43740
agactggaaa gagctgtgtt ctacaaggac ttatttactc ctagagggat ggtgttgaaa   43800
agacttgaca tcaaagacta tcacttatgg ggtaatattt tagcaacaga actgagtggg   43860
taagaacaac tgtgggaaca gctccgcgct cggtgctagt ttatgcataa tgaaagcagt   43920
gacacgtacg tggtaccacg acatccacca ttgaacctcc gaaacgctgc agaatcacaa   43980
attcttttac tgaatggaag cgagcgtttc ccgcagtcat cctgaactga gatgcaattg   44040
gaggggctga gcggctgcag cagcgttagg ggagtttcac ctcgctgagc cctcccgtta   44100
```

```
tttcagtgct gttgtggagc tgcacgcagg agctgccgcc agtccgtgcc agctctgcgg   44160
ccctgcttcc ccggcacctt gcttatctct gagcacctgt ccttgctcat cctgtgaatc   44220
acggagaatt gctttctctt cctcccttc atttcgcgcg tccttctcca cccgggctgt    44280
aaccctcctg agaaaaaacg tagtacggaa tcgatgttgt aaacactcag cgtggcacaa   44340
cgttttgcct gaaatccctt ttgtctgaga gtcacacact gaattgcaag ttgtttattc   44400
aggacatgca ctcacggatt taacactaa cgaaggagat gaattgcatt tgtgtcacac    44460
ttcctattcc cttctttact ccagacccca ctgcactgaa ggtaagggac agatctttca   44520 ggttttttt tttttttctc catcatttct ttcctcaaag cagtttccgt ataaatcatt    44580
actaatcgca ttgtgatcga gcgtttgaaa gccctgagtc atcccacagc ctgagcaata   44640
tttgctacag atattaccga gtgaaatggc cattttcatc tgatggtttc aaaaaaaaaa   44700
aaaagataat aataataata ataataataa ataatagcg cagcattcag ttggtgtcca    44760
agttattgtc acggttactg cagcagcact gaggatgttt acatgggatt tacatcactg   44820
gaggctgaaa gggcactgca ggcgtgtacc gcgctattcg ctgccccatc cttaagctct   44880
tctttgacat ctgctgatgg tcggtgctgg gggaagcccg gggctgtggg ggtctcctgg   44940
catctgccct gctgatagct gtgctgctga gggtatttct gtgagcacaa ggctgcatcg   45000
atccacaggg cgactgcagt gcctgcgccg taccccgcaa tttctgctct cgggagcgca   45060
tcccacactg cgggtctgat ggcgtaacat atgccagcga gtgtttattc cgcaatgcat   45120
ttctgggtgt atgaaaataa atctcttcgc tcactgagtg gtgaacttca actgtcttat   45180
caacctcagg gactgcctgg agatggaagg tggttgtgtt tggcgctctc ctcttctctt   45240
gctagcaagg gcagcacttt tttttttaaa ctgggaggat ttaccaggga ctccttttctt  45300 tcaggtaaaa agaagtcaca tttagcagag atcttcatct ccacgttggg taatttgctg   45360
aagagctcgc ttccagcaaa tacagtctat ttcctacagc ctatttgttc ttcttttaaa    45420
ttaagtcttt atcgtgcctt tgaatgttag taataagagg aagtagctgg aatagctttc   45480
cgaatgttct gttttggtta agttcctctg tgatgtatcc ttaagcagag ggagggatgc   45540
acagcagaag cgcagaggtt caatctctga ggccctgagc tctttctctc cagaactcat   45600
tgagttctca ccttgctgtg ccctgcgcag cgctcacatc acagcccacc gggctccagc   45660
tcagacagga ggaccctctc tggctgtgtt ccttacaggg gatgctgccc aaagcctcgt   45720
cctgaacttt gagtgctcct gataaagcct gaagctatgc tcaataaaaa aaaaaaccct   45780
tcagcatttt ggtcttgctt tcatactacg tatcatgctg ttgtttttt tcttaagat     45840 gctgtgtgat tgcatcactg caacagtcct ggggtgtggg tcttaatggg aaaattacag   45900
ggagaaagaa cgggttgtct gatttatgaa gaaatcaacc cctccaaaag gccatgagct   45960
tctgctttct tccagatttc caaaagaaag ccactgctgg ggatgagatc cagtgcagtg   46020
ttcagggcat cctgtgcaga cattgactcc ttaggagctg aaaataaagt agtggtgggt   46080
acccgtaggt gtgggaagcc tttctgcagc cacctggtct gcctcccaaa gcagaggatg   46140
ggatgttttc ccctccgggc agcaccaaca gaggggtggc agcagggtga ggaagatgat   46200
tggcccctct gctctgctct tgtggggacc acatgcagta ttgcatccag gcctggggcc   46260
ccagcatgag aaagacgtgg aactgttgga gtgggtccat aggaggccat gaagacaatc   46320
acagggctgg agcacctctc ttatgaagaa aggctgaggg agctgggctt gttcagcatc   46380
aagaagggaa agctgagagg acacctcatt ggagtcttcc agtacttgaa gggagcttgc   46440
aagcaggaag gggaacaaac ttctacatgg tctgacagag atagaacaag ggggagtggc   46500
```

```
tttaagctaa aagagggaag atttgggtga gatgttggga agaaatactt tactcagagg   46560
ttggtgtgac actggcactg ctgcccagag ctgtgggtgc cccatccctg tacatgagct   46620
gaaggccaga ttggatgggg ctctgtgcag cctgatctgg tggggggcag ccagcccatg   46680
gcaggggttg gggtagatgg gttgtatggc ccttttcaac ccaaaccatt caatgattct   46740
atgattctca gataagcctg cctgcccaca tctgagctca cggtgctcgc tggggtgggg   46800
gtatggtaca ctaaatgatg ctcagaggac tgcacgcagg acctgccgca gacgtttatc   46860
acctcaccca ccacttagct gctgcttgta gttaattacg tcagctgtca cttgtagaga   46920
atcctttgag atccttgggc ctccggaaat cttggctgat gaaaggaagg gctcagagtc   46980
atagcgttaa tttattattc attaacacca aagtgtcggc tgtacgggca gtgggctcac   47040
agtcaaatag ttaatgatct taagtgacaa tgtgtcactt tgcagacagc agagagaaca   47100
gctctcctaa gggagacagc atcttttcca ttctgcagcc attcagtgcc aagctcctct   47160
ttgggacgaa agtgaagatg aggaaggcaa tgaggatgag gaggggcctc aaggaacctg   47220
gctggcttgg agacaagtga tgatcccagc tgctctcagg gtcccagcgg tcttcaaagg   47280
gcatcttgca ggggctgtgt cctctgaaca gcaaaaccca ggtcatagag gggaaagtgt   47340
gagcagagat gggacaaatc tcccatcctg ccacggagct gcactgctaa gggggtgatg   47400
gggagcagca tgggacccca gcgttccccc catccctgca ccaggcccag ctctgcggga   47460
tggcgaggag gacaaggctc tgtcacaagc atcgctggca attattattt tgttgttgct   47520
gctcaataaa atcctgacac agtacaacac aatatcctct catcattact aatctaactc   47580
tccctccagg aaatttcagg caggaaacgt tgtctgcctg ccgaggtgct ttatggcact   47640
gttctttagt ggtacctcag cacttcgtgt cattatctgg tgtcagtgaa tttaggaaat   47700
gccattcaat taccccgcaa actgattaac gcattgcgtg cagttatttt gttctgctct   47760
attttatatc agttcctctg ttttatgtat ttctctactt gttgctggcc agaacacacc   47820
tcgggccagt ctagaccttg ctgttgatgc agcttttccc cagggcttca tcagcacaaa   47880
tggtttgtca acgtggggaa aaataaaatt atgctttaaa ataaaaccac ctggagatgc   47940
tgttctgggg tctggctgtg tcacagctat tgcagcgatg gagctgaggg attgggatgt   48000
gctgggccgg atcctcagcg ctttgctata agccaaataa ttccagacac ccttcttccc   48060
tcagatatca tctgtgctta agcagcagga gatatgcagg cagcgatcag atagctgagc   48120
tgcaaggaga aatatcacaa gagcgcggct tagagcaggg gctttgctcg ctctaaattg   48180
aattcccatc ctcataggag atccagtcct gcccccgtgt gcatcgctcc ggtaacagca   48240
atgtgttttg ctccatcttg cagagggtcc agaagctggg gaaaggaaat gtgtcgtgcg   48300
ttcgtccctg cagcagctcg gcccataaaa ttaatgaaaa tctttttttag gtcatggtag   48360
attacagatt tctttgagat agagaatctc aagagcagag gagaagattc tcagaaaata   48420
gcagtgatat gagatggcat aacgctgagt tggaaactgg ggaggatttc cagggttact   48480
ggaaatttac ttaagcacga gagaatgcat cgtgtgactg ccagtgcttc cccactcaca   48540
tggctataac cttcttgcat acaattacca tcttggaact tgaaatagct gaaagagttt   48600
tatttgatct tttcaatgga tcttacatct gcagaaaaaa aaaaaaaagg ctagaaataa   48660
tcctgcactc aaactcactt tactgaacca ccatcatgaa actccagcaa cacacaggga   48720
tttgggcagg cgtgttcatc ttcctcttcc catttgcaac atgtgtatgg catttcctga   48780
agctcactcc tccaaatgca ttgagacagt tgttttttcat tcttcctaat gcctgcatcc   48840
```

```
acccatctgc tgatcggcaa ttatttctat cccattccct tctgtttctt attaatcaag    48900
ctctttatgc aatcccacgt aacactttgc ccagctgccc tgccctaacc actaccaatt    48960
atctcatcct gttttataga ccctgtagca agactctggc cttgctcctc ttcctctccc    49020
tgatagagct tttggtgcag ggctggctgg ctcctcaggt gttcagagga tcagaggtct    49080
cccagaagga tcttgttaat caaggacagg tgctggctat atgggaggat ggcaccgtat    49140
cctaaagctc tacaagaagg agacggagct cagcctggga ggacagagag aagcagcagc    49200
acaggtttca ggatccaggg atggcagacc tgggtgtggg ctcataggat tgaagaaggg    49260
ataggctgtg ctcctgtagc ctcactgcag aagcagcact gctatctccc cagcgaagct    49320
gtgtgtgccc catccctgga ggtgctcagg accaggtggg atggggccct gggcagtctg    49380
agccggaggg agcagccggc ccacagcagg ggttggaatg gggtgggttt taagttcccc    49440
tccaaccaaa gccatttctt gatctctgtt ggtggctggt gcaagttctg aggaaacctc    49500
attttcagct caggcgttct tgtccctggg gaaaaatcaa tattaatgct tcagtgatta    49560
ctgctcgcct tccaaatgtg cttctgatca gttcaagaaa tctgacagtc acgtcgctca    49620
ggatgctaag aatacaacag aaacagcttt gaaaggaacc cttcaactct tgatatttgt    49680
gaatgagctc caaagaacat tactcattta ttttcagga aaatgatttc attgacatga    49740
acaggccaaa gcctacaagc tctgttttgt gactgcagct ccttacactt tcagctgcat    49800
tttcatgatt tatgtgccca tgatgagact tgaacacctc ccaggataat gggaaaagca    49860
gttctgattt cccatttaaa acgtaggctg cctttaagcc atgtgtgtgg ctcaggctcc    49920
ttctgaagca caaggtgtt ccaccctcg ctccttttc attacaactt tcaatcaaaa    49980
atgtgtttta tgagatattt gttttgccat gtatctgtga cggagttgaa ccccttagtg    50040
aaacctctgt tcttcactta gctgagaggt atttcttagg gaatgtgatg ccctaaattt    50100
attgtggtgt aatagaaggg gggatgtgtg gactcacctt ctgtttgttg tggctgcagt    50160
ggttttatgc actacctgag tattaagcaa gcccttttca tctgcacgga acacctcctg    50220
cttgccagtg ggatgaaaca acaacaacaa agatttaagg tttgctattc tcaatgtttc    50280
ttaatcgggt tcacattgat tgccaacaga tgaataattc ctccttctcc atggatgtac    50340
ctcttaaact tgtgaagtct taggtaacgc ttttctgctg tgatgactgt ttcagtcccc    50400
tcagtgagaa atcaggcgca ccagtaagac acaaaggaga ccgtggagat gttcattgtg    50460
ccctcagcat ctccaaaagg cactgctgcc tgccgagccc cagacttcgc tcctgtaaaa    50520
gcaaagcatg tccaattctg ctgtgccata agagtcctgt ggagcccaga cacggcgtag    50580
cgtgtgtaac atagcgtgca cgagctcaaa cgctttcaac aaatcagctt ttttgctttg    50640
ccaacttcca tatgtaattt cacaacatct agtattgaga cagtgctgtt gtttgggcag    50700
cataaatcac tcattgtaca gcagggcgcc tctcttaaca agttgggtgt agttcatgtt    50760
tttgtctaat tcctctgcgc atctctctaa caaacaacta ttctttaggg ctcgactcaa    50820
taatcaatac attttttca gtttacagag caaataatta cttgacctga tgacttcaca    50880
aggttaggga gatgggtgta taaagtctgc agtgtgaagg cagagcaaca tctctgcaga    50940
ccttgagagc aacaggtctg caagtaacag gctgcacagc cacctctgcc atggaggcaa    51000
tgagagctgc tgccctcctt ggattggtgc ttctcagctc cttcctggt aagttgtttt    51060
tgttacattc tctgcttata tctctactcc tactgaacta aatgtggttc aggatgcctt    51120
tagaatccta aaagagagct cagcctgccg gagaagtgat ggtttggtaa aacatgagct    51180
ctcttctaat gatctttatc cttgtgcaaa tatttacgta actctagcag gatgcctctg    51240
```

```
tctgacataa actcattatc ctcagtaagt ctcatagcac tcgagagaga aaatgtatac   51300
cctatttctt ccttagtgag tcaaagttta tattttcacc caaaatggct attttttta    51360
atcataggat atagcttgct tataggaact ggataaaata tttaggaaac aagtaattct   51420
cagtgataaa aagaagtat gtgatgactc tgtagggaaa ttgataattc cagaggaatt    51480
gtaaccaagg acgccgtaac attctgtatt ttataacctc tgttttttcc agatattgtt   51540
tctggtcatc aacgggtgag tagcagatct gcatcattta gttgtggttt ctatgaatag   51600
atgaataatt catactcaca ccatatccta cgggagccta gagggagaaa aaaaaaaag   51660
aaagaaaat aacaagggaa ggagaaaaag ggccccagg aattatgtga cattttctcc     51720
ccagcaaata agaaaacatc tttgtcagag aaagataacg taccacgttg gtgataagag   51780
ttggcaatta ataatgcaga gtgggagccg gcgtggcaca gcgtgccagc agaaaatctg   51840
cacagctttt ccctaactgc ctccatatct cccctgcctg attccctgag acccatcag    51900
tcagtcgtgt gtctgccatg ccaaaagcct cagtagtgac actgtgctca ggcatactgt   51960
aaggaacgct gtaatttgct cccacttctt caccgtggag gagtgacaga gaataaaatg   52020
accgcctgca gcacggctat gcgtggaaaa cacaagcaga cccttccgtg ccctgcagag   52080
ctgtcccact tgtgctcttc ccaggcctcc tgcggtgagt accggctgtt aggcagcagg   52140
aacctcgcct gttccaggat cttccagccc gtctgtggca ccaataacat cacctacccc   52200
aatgagtgct cgctctgcag agaaatcctg tgagtagcga tcgcccgatt acccatcgtg   52260
atggctcagg tggcagacag aagccttttg aattgtgact aatcacgggt ggattcgatt   52320
tttttttccc ctgtttctgt cttcccagag tgcaggctgt gtttcttcct tgtcaaaact   52380
cctgagtcta attaattagt ggggctgggc gtggagaggc ttgatgagtg aggtgactgc   52440
atggcaccac caggttaacc cttccctcc ttctctccta gccggagtgg gacggttgac    52500
aagaagcacg atgggaggtg tgtgaaggta tggttccagc tcagccactg tgtggagcga   52560
tggcagaatc ccttcccagc actgattgta catttagaat ggacagctcc aaacccattg   52620
gaaatgtaac agaaaggaag aatttcaggt ctttttatata tatatatata tatatatata   52680
tgtatgtatt aatttcattt tgaacagtgc aaatctgttt caacggtgag ttttgagatg   52740
ttatcttgtg tagcacagct gacttaaaaa cagaatcctc tcatttcaat aatccttgg    52800
tgttgttgaa atagttccct ttagacttag acagaagtct gttgaaatta agaagttccc   52860
caaggaagtc tggattttga ctaaatcata attttgtaac agggaaaaag aaaaaaaaaa   52920
aggattccat cagaacatct accctgaggt ttgtttatca atacacggag ctgccacgaa   52980
gtggagaagt gtctctattt ttagattaga gagataatgt aaagaaacac tccggctgtg   53040
caattgaaca taatgctaca attttcactt cagtacactc agagtaatgg caggaacacc   53100
gaggtgagca tcagctccat tttcaagtgg agcagacatt tcacagcagc agttgctgcc   53160
atgtagggca tgttaggcac agatcctatg tggtggcatt tggggtggaa agccctaaga   53220
tgacaccaac aaaacccatt ctgtgaaccc atttcctcca ggattctgct gggctcatgt   53280
cctcaaaggc aggacttcac ctgcctgtgc tcccttgccc gcactgtgct gggttggaag   53340
ctcacatctc catacagccc cactcaccgt gagtctgggg gtgggagaca cctctcacac   53400
catgcaccat tacacagggc tgacggaagt gttgttctgt ggctgtttca ggttgattgc   53460
actggctaca tgagaacaac tgatgggctt ggaacagcct gcatccagca gtacagcccg   53520
ctctatgcca ccaacgggct cgtctacagc aacaagtgca ccttctgctc ggcagtggcg   53580
```

```
tgagtggtgg gtcacaccct gggtgctggg gtctgggtgg tggtgtttgc agcatattga    53640
ggcttctgga gtggctgtgc tgtgctcatt cattctcaac ttgctttctt ccccaaggaa    53700
tggagaggac atagatctgc tcgctgttgg aaaagagccc gaggtaaagc tcgaaagtct    53760
gcgctatgaa ctgttgttat aatatattat acagcacaaa ttcagtgagt cagaactacg    53820
caatagcaat gtcttcactg tgctggtgta tttgtcctgg aaaaagggtt tgaggaaaat    53880
gactcaagta tgccagggtc agaggacgat gaacaaaact cctggctcct gtgtcagtat    53940
cacctgcaca gccctgaca ggggttgatg ctcagagcat tgttcagatg gtggctgtgc     54000
cagaggtgct caccgctcct ggtgagcgtg ggctcatgc agcaccagct gtcattactt     54060
gggtgggtgg acttcatagt gtgctgttgg agacacactg cttcctggca gcccctctct    54120
gctggctgct gaaccagagc agagcaggta gcgggccgcc agccggggag cactgctttg    54180
gctgtgtcgc tgcttctgag ggtatttagt agatttttcc ctctgacttc tccttttgtg    54240
ctctgctggg caagagcatt agaatttgca gagttgctag aacaacagga gcctgcatct    54300
gaaaaaatgt ttttttttgct ttgccatgac ataaatgtaa agcgcccatg taggaaaata   54360
caccaaacaa aggcttctca atacgttctt gctccattac ctacagattg actgcagtga    54420
attcaagagc actgatgcct actgcactga agagtacatg cccctttgcg gctctgacgg    54480
cgtaacgtat gggaacaaat gccacttctg cattgcagtt ttgtaagtac agtgctcccc    54540
atgcagccat gaaaccactg ctgtgccgga gtatgaaggc agaagctgcc aggaagcctt    54600
tgtgctcccg ttatccccttt ggtaaatccg tccccatccc caacctgatc ccagctctac   54660
ctctgctgtg ccttccccaa gcactgcaga tcttgaacac aggtgagtct tctccctccc    54720
tcaccattaa attcagattc tcatttgcgg gctcatagcg ctcctgatcc atccctgcga    54780
gagtaatttg agtggtaact gtagaaggag tatccaaaat tacagggttt gtcccagatc    54840
tctctaacat gacaaaacgt gtaacctggg gaatcaggag acgggtgaag gtgcaactgg    54900
gacagcatgg agcattggct tgcccatgca aagtcagcag tggcaccatc agggctataa    54960
aaccaccttc catgtcagtg attttggcct cctcctttct ctgcaggaag agtcatggat    55020
ctctgtctct gcagcaccgt ggagaatgct gaatgctgga tcgtaacctt taccctcatc    55080
catctttcac ttccaaagcc tgcaattcca acacgctctt ccccgctccc tgctgtacat    55140
tgctttctgc cttgacccgc cagtaaatca cagacagcaa ctctcttcgc catgggctgg    55200
tgtgttattt atttatttat ttatttattg ttgttattat ttttttccagg gcagaggtaa   55260 aagtcttcag gctttcaggc acttatctgt caggcaggag aagttttgaa ataaaccaca    55320
ataaaggcca aagtgcaaca cccatcacac aaaagccata agccctcacg aaagtgcgtc    55380
accccattcc aaaccatcag aagaggaaat gttgctataa aacacatgct gctctcccca    55440
gttctgtgtc ttacagcaca taaatggatt tgctttaaga gtcaggatgt ggctttgtag    55500
aagcacggag ccctggagga agcagtcctt ttgggagcct tggtatggag aaagatggc     55560 tttgatacac ctgagcaagg ggcaagtctg gcggcacgtt acaaggaggc ttatggcaaa    55620
gggaggagac tatctcacag ggaagaaaat taggaactgt tgcttccttg aagggtgtgt    55680
cccttgagag tgtggtgatc agcagaaaat tgcagccagc tgggcaaggc tgtaatgagc    55740
ctaatgagga ccagaggaga aaccagattg ggctcaggct tcttggaaaa gagatctgaa    55800
aagctgcact gggagcgttt gaggcagagg aaagagaaag gactcttcag gaaaaggttt    55860
gggagtcttc atgcctagaa aagaaaggac agaaggagtg cttggtagct ccaaggtcgt    55920
ttctgtctgc agtgaaaggt gatgtgtgga tgatgcgtgt gagcgttcac agtgatgtgc    55980
```

```
catctctttg ggcgagtcaa ggaatgagta tgcaaacaac aggtgaaaag tcccaagtgc    56040
ctccactcat gccaccttcc ccttcctttc tccacctccc atcctctcat tacgtaggaa    56100
gacattcagc tgttcaggct gatattgagg acaaaatctg tgacttccaa gcttttctct    56160 ggctttatttt cctgaaatag gctgtatctt gacctagaaa tcttatgggt gcttcctgcc   56220
agaagatggg aagctgtcct ttaatagcgt gtcagggcag tgctccgtcc taggaagaca    56280
gatggaactt tgaaatgttt attctattag cacaggcagt ataaagcaca gtgtgcctct    56340
gtgcctgctg gtgagaaaag gcaagctgca gagccgtgag ggtgctccct gctaatctgc    56400
ctagaaggga aaagagtaga caagaaatag catatgctac tactgaatgt gagcagaaga    56460
cctttagtga aggacacagc tcagctgtaa tgtcctgttg gccaggaggt ttgttgagtt    56520
atcgcagagc ggtagagttc tggtcagagc aggaaggtgc cttcaacagc aagatcccat    56580
ggtaggcctc ttctgcagtg tgctggcaca agcctggtac ctgctcagga gcaaaaaaag    56640
gctttggaaa agctcaaaga agggctgatg tcttacaggg aaagggaggg caaaaggcaa    56700
gtgcagagca tatggctgta cagacaaaaa cccttcagaa aatggaaaag gttttttatca   56760 agtaagccca gaagttggcc cagtgcaggt aaacacttgg ctaggtaaca gtgaggctct    56820
gcccagccat acccattcct ctgtaaggca aatcccaggt gccttttgtct tgtctggtcc    56880 tgttctgttc ctattttttct gagaaaatcag acagaacttc cccacctaca gcatcaagca   56940
gctactttat aggtgaagaa gtgcaaagag aagcaataag gataatcacc acttggctaa    57000
tttagtctct tcctctcagc ccacaaagga ctggtccctg tggtacattt tctaaggctt    57060
ttcccagtca gctgtgctgt agcaaatgaa atgtttggct agataaagag ctgaggtatt    57120
agtgctgggg cggcgagcag tgtctggagc aagaaaaggc aaacgaggga ttctgcgagt    57180
ggcagaacta agcctgattt tgaatggcgt tgtggctggc ggacttgtaa attatatgag    57240
aggctgtgct gtgagctcac cctaatagac atctgagaac tcacctgtca atcgcggttc    57300
ctctgctgtg tgggttttat ggtgtctagt gagctgcaag ctctaatgct ttcccaggtg    57360
cagggcagtt gtggcattgc tctcctacag aaactctcac ttgctggctg aggatgttta    57420
ggaagtcctt ggttgctaga aaaaatatat tgaagtgctt ttttttgtttg tttgtttttcc   57480 attcttgtgt gaaattttgt tggaatcaca gaatcataga ggttgaaaga gaaactctgg    57540
aaattatcaa gttcaacccc ttgctaaagc aggcttcata cagtaggttg cagttacaac    57600
atttgctggg gaaatgaata tgaagatctg tctataaaga gtgttcccat agcacttgtt    57660 tcttaggaa agcatgctga aattctaaag gctgtgccta tctgaagaga tactttgcaa    57720
gtggtgcaac taaatgctgc tcttggtgga gagatggctg gagatggatc gatggttggg    57780
tgatcttcgt ggtcttttcc aactttaatg attctatgat tctatactct ttacacagaa    57840
tcagctggga atagagtgag agtctcctga ttccccacca aattcctttg attgatgctt    57900
ggtgtggaag cagagctctg ggacacgttg gtgagtgtga aaactggaaa acattgacag    57960
ctatagttta aatagttcag ggaggagagg cagccatcct atgtgggact ctgcacacgg    58020
ctatgagagc atcagtgcgc ttctccaccc caacccaaca aatttagagc catcctccaa    58080
aatagccagg gaacaacgca taattggttt cacagacaac acattctcat gctgtgattt    58140
atttcgtaat gtctggtgag tgtcatcacg ccgtgctcaa agcctgggagc tggcattcag    58200 cgaggaccca gagaatgaaa attaccagct tccccgatga atcaccactt tgaaaattca    58260
cccttgtgag aatcctgtga ctattcagaa aaaaaaaaaa aaagaagaa gaagaagaag    58320
```

```
aagatattac aggcccaagt ctatcagtca tgtaattagc cctttctagg tttgatgtgg   58380
acagggcggc attcctaaag caccataaac acggccggga ccaataatgg ctctagaatc   58440
gaagcggaga agttctcaca attaaggtga ggaatgaggc cagcagcgga taggtacata   58500
aatacacgga ggcagggccg tgagcacgct gtgggcttgt ggctgagaca cacctccca   58560 aaccggtcgc ttgccgggga ctaaaagagc agcatgaagg caacaggcac ctcggtgctc   58620
ctcagcctgc tgctgctgct gtcgttcttc tcgggtaagt tatatttctg tagcctagaa   58680
agaaacttta tgacgagagc aacttcagag agccttgatc aacgatgac aggcttgaag    58740 agaaagctga gcaagtagaa aatatctgcg ggactcgctt gcttgtgtca catctttcca   58800
ttcctcgtgt gcctccgcag tgaataacac tgtggaggtg tcactgggag acagaatgag   58860
caaattgtaa gcagctcgtt cagcagaggc accaaagcag agcgtaatta tgagttttgg   58920
tggaaatgtt tgctggagag ctttgctgaa ccagttagag aagaaactca tacctcaggg   58980
tcatcagctc ctgttctgat gctaagcact tgggggttgg tgttctcctc agagatgtgg   59040
cagcgtaatt agatgaaagt ttcagcttcc aaatacgttg cagaggaggg ctcgaaaatt   59100
aaattcagat gtcctcgagg aacccgaaca agagggcaa attgaaaggg tccagcgttt     59160
atttatcttg aggtttacac gtctctctgt tggtctgggg aggctggctg atggtttggg   59220
ggtgtgtagg gcacaccggg gtgctcaaat gctcgcgtgc ggccgatgcg aatgtggaag   59280
cgttgcggtg gccattactg aagactgcag accaaggatt atttatactt gttttctgt   59340 gaataatttg aataaagaat tcgcttgaga aaatcgcagg ctgtgcatgg agagaagagg   59400
tgaattactt tgtacacatc attaattatg aaatattcat ctgtctttaa ttgagtctta   59460 attgggctg ggttccgtca gagtgctaaa gcttcttcc aaggccaggc agaatagcag     59520
caaactctgt gatctcaaat aagataaaca gatgccaaga gacgttctca caaagtcttg   59580
tgtagctgca tgtaatattt ataaaaatta tctaatgagc tgttttgtaa ataatatgca   59640
gatagcccta acggcggctt ccctgtccag cctagctgag gatgtgacag atacagcagt   59700
ggcaaggatc aaacactgaa aggcatcgca gcaggcagaa gctgggtggg gtgatggatg   59760
gtcccgctga gcgtgatgct gcaatgctcc cagcctgcac cctaaccaaa gggatgcccc   59820
attgcaatgc gccccagccc ctgcagcgct gtgtgcagcc cactccctgt ccccgacacc   59880
acaggatcca tcccgtggct gtgacctggc cccatgcaaa gtttgcaggc aggaaatagc   59940
aaagaggatg gactgattgt ctccaggccc agagcctgtg cctgcagcag gtattttgc    60000 tctgctgctg tctggcactg cctgttctgc cccagatcac gccaggctat ccctttgtat   60060
ctcatccgga tgaggctgtt ctgggagcct cggctgtgct gtactgcaga cggctctgat   60120
gctgactgcg gggtctcctc catctcccct gtgtgctttt gttaccgtac tggccagttt   60180
tgtaattcag aggtgcaaga gcctaaaagc cataagactc aatgaagctt taaaatctct   60240
gctgagagag gctcagctct tacatagctc cccgcttccc cggcggtggc tgcctgccag   60300
ggagatgggt ttatgtgtct gtggtgcagt tagcagctga atgactgatt acatggtatt   60360
ttagtaacat ttttcaaata gcaaaatact gaaaagcaat tccgataatg tatttcctac   60420
ccctcctcca ccacacagaa cggcagagga gggaaaacct ggtgtgtgct gtgctgcagt   60480
ttgcaaaggg atttgtgact tcggttcagt cctctcagaa aataatgcta atgtggataa   60540 aatcttttt tttgttgcaa ttctaggtgt agcagctcaa gacattgaag aggttagtgc    60600 agctcttct gctttctgaa tctgcatttt ctcctggctc tggaagaatg cttttctaac    60660
agatcttggt gcattggtgc atgctgaact gctttgggtt ttgctgggat caggtgggtc   60720
```

```
ctgccaaggt gccccaatgc ttcggagtgc tcacacagta cagggggtgtt agctatggcc    60780
acagtagcaa acaagttggg gatgatttag ctggtttagc acatgctccc catggtctga    60840
tccagcacag ggctgtctgc agtatcgctt ctgtctgctt tgctcctcca cgaaacaaat    60900
gtgatatcag gagtgatata ctcctttaaa ccatatccat aactgggggct tgtccaaaag    60960
cctgttcact tcatagaatc attaaggttg gaaagaccac tatggtcatc gagtgcaacc    61020
actccatgcc cagatccctg tgtatggcag ccccaggcca cgtggtggtg tgagctgcat    61080
ggtaccgggc actgatatgg ggctgcatca gtgctgatgc tctcctgttg aacccactca    61140
tgttcttgga acaccagagc tgctccctgg tggtgacagc ttccctcctc tgccacaggg    61200
cagaaattcc cccatttcag ccagttctga caggcctttg tttttcaagt aagcaggccg    61260
tgcctcgttg ctgcttttgg cctctgggtg ggaagaagat cacattagag atcttctttc    61320
ctgtttggaa agcgaaaccc gacggtttat tgctgttatt attttgatt tcttttgcag    61380
atctgcaaag agttcttaaa caggagcgtg ttctgcacca gggagtccaa ccctcactgc    61440
ggcacggatg gcgtgacgta cggcaacaag tgtgccttct gcaaggccgt gctgtaagtg    61500
ggggcggtgg gatacggacc cacacaggga tggtccactt ccaaccccgc gctgctgctc    61560
ccctcacaca gagcaatccc tggccataga atcatagaac tagagaatgg ttaaggttgg    61620
aaaagaccaa taagtgcatc tagttcaaat ggcagctcct caccgccacg cttgggaata    61680
tttcagctta atgttgattc atttctaggc ttagtgtgat gctcatagcc gtacagagat    61740
ggcacagagc ctgggaggcc attgtacctg cctgtacctt ctgcgtgggc taaattgatg    61800
cacatttttcc tctgtgtgcc acaggctgaa gctctccctg tccacacctc tggatgctga    61860
agtgtgtgga ggaacgcagg cttatgcatg ccaaattatt agaggaaagt catagactcg    61920
tagaatcata gattcgtttg agtcgaatgg gaccttttgaa ggtcatctgg tccagcatcc    61980
ctgcaacgag cagggaaagt gctgaaatga aagtctgaat ggacttagtg gaaaagtaca    62040
caaaatctca gaggaagggc tgcagtttct cctctcctgt ctcctctaaa ggagctgtaa    62100
taggagccaa cacctctgga ctgaaggcct gcaaaaattg atttatcctt atcaatcctg    62160
cactctggag gctgccttat cctaagggaa attagagaag agggaaagat ggcttgatgc    62220
tccctgtgag gcaccagagt gaggcaaatg atcgtgctcg gagggacaag ctccctgtcc    62280
cagccgctgt gtctgtgctg gatgccatac actgctttgt ttccataccg ctccttttac    62340
aggaggagtg gagggaagat acgattgaag cacatgggga agtgctgagc ctgagcacca    62400
agcactgatc ttcgtcggtc acaggtgcag gagcctgggc acggcagcag ctgtcctcat    62460
ctctgccata tctgctcaat aaagtaaagc tcagcacacc tccttgactg gattccttt    62520
tccataacac ccggataagc cttccatgca gccgtgctag cagctaaaat gtttgccgca    62580
ctgtgctgtt acatcttaga atcacagaat caggcaccat gctgcctgag caggagcaat    62640
gattcccaca gctcttccat gccatgccat gccatgccat gccatgccat gccatgccat    62700
gccatgccat gccatgccat gccatgccat gccatgccat cccatcccat cccatcccat    62760
cccatcccac tgacaaatgg acacatggcc acccagcttg actgtccat gggtgggtga    62820
cagcatgcaa cgttgcctct cagcagcctc cccatatgtg tccctctcgc tgaggtgtga    62880
gcatgaaggt ggcagagagc tatgagtggt gtggctgtgg atgcctcatc tgcttgggaa    62940
gccagaagca aacaggctga ggctgaggag tgttgctgca tgtaagcctg caccgggaag    63000
gtggcagggg aagctggctt taggcagaaa cacaaaggct ttgctttcct tgtgtgtcct    63060
```

```
aagagaggac tttgcctcaa agactgtcaa ctcgccagca tcaggttgca gttgcacaca  63120
aacttgattt ctttctttag ttttcacact gctgctctct ctctccttga tgctggctgg  63180 aaaatcctt c tttgcgccag cgagggaaaa taaagcctat agtctctccc cattcgctgt  63240
acaaaatata cacagggaaa tgcttgtggc atccctcgt taaaacgttg gcagcacatc  63300
aatgggactc tactcactta atgttgaaca cttaagtttc aaagggagct ttagatttta  63360
tcgtgaggtc agccaactca ttttgcaaac acctctatgc tgagcatctc agctcctgga  63420
tggtgtttgg acagagctga gtgtttgcct gtggtgccac gctgcaggct ttgaagtgaa  63480
ttgggacatt atattttgta gccaaggaga gttgcagttt gctttgttcc aattcagatg  63540
tttctttagt aaacacaaca gctagacctc cagaacatgg ataagcttga ggggaggaaa  63600
aagcacctcc tgcacgagga cagctgatca caaaggaccc cagtgggcag tgggagaacc  63660
ttcatcatcc tctctaccgc ctggatcagg atgagccctg catacccttt ccaactggag  63720
ttaccctgtg agccaacttg tggctctgga gtagtgctgt atctcaatac agtttctcag  63780
atgggaagag gcatttcaat gagagggggg atatgggaca tttctatgcc tgagatggct  63840
ctcggagact ccaaaagcct cacggcgtat ccccatgcct aatcctttt aatctggagg  63900 ctgaaataac aaggacagat cacaagagaa cagaagcggc gagacttctc tgctttataa  63960
tcagcctgca ttttgctctt tcagtgcaaa cagcaaatag aaccgcctct gtacccctcc  64020
agacccaacc accatcccca gcaacactgt ggcaggctgg agaagggtgg ctctgcccct  64080
ccttgcctca actggttgtg tcagcacgac cataaccaga gctctccttg gccccagctg  64140
ggcttatcca tgtaaacctc tcagtgcccc aggagctggc tggtggtcct gtccatttca  64200 cttcctcca gcaggtgttc cctttaacaa gcatccaagt gcctggagca ggagcaggca  64260
ctgcagaaga tgagctcagg caaggacatg gcatgtgggg atccatgctg ttgtgcaatg  64320
cagatgacgt tagatacgtg caaagcagat ctcagcaatc acccaacgac tcataactgc  64380
aatcatggaa cgcaattgca tctggaagta aaaagcaca gtgataccag gaagctcttg  64440
ttaatggcac agccattttg gagcaatttg cccaggtggg gagagccctc acagcgcctt  64500
cagtcacagg gagtggtgtg agtgcccca tggctgctcc cagcccccag ccctgggtga  64560
tgggggtcac ttggctgtaa ccctctgaac acagggacag tgagacagcc ctctggcctg  64620
gctgagctct tggctacgtc cagctgcagt cctgggcaca tactgaacca gaaagcaagc  64680
attcagctgg tattttcct ttaatttcct tcctccacat tttaagttgt gggattttt  64740 tttttttttt ttgacagctt tgagagatga gtgagtcacg aagcactcga gatctctatt  64800
agataacaga gcatctctgc agctcttcct ggggagggag ttccttggac caagggccaa  64860
ggctgggtga gaattgtccc agcatcacag tggctgctcc atcacctgac acagcccctc  64920
tgcagtgaaa caagggaagc attacatctt tgcacggctg ctttcactga acaaaaagcg  64980
ctgcttcaca gctgagcacc atgatgaagg ggaaggagca tctccatgat gaaggggaag  65040
gagcatctcc acatctccat cacgagctct gctctgctgg tgatgcggct gacaccatgg  65100
tgtgccctga ctcctggccc atttaactgc tgtgcaccag tgcctcctcc ccagcatagc  65160
cctgtgtccc tgccacaact cattgcaatc ctttgtccta cttcttccct tgacattcac  65220
agctcttgat aaggctttt gagccactcc tggctgatgt gggctggtgg ttcctgctgc  65280
agggttccca ccacccagct gggcagcatt cggttgttgt tccagttccc aggggattgg  65340
gacagattgg aagggtcttt gggactgtgg aagagtatct cctgaagtca gggcagactg  65400
ctcagcgctt tgtcccatcc agacttgaaa acatccaagg gtggagaaca cacagactcc  65460
```

```
ctgggctgcc agtcccagag tttgactgtc atcacgttga agacttttg  ccttgtctcc    65520 atttgcaacc tctttccttt cagctgcccc atctctcagc catgcaccac tggggagccc    65580
agctctgtct ggtcaggaac agagcccta cagagccaca gcatcctcct gaagtgtcca     65640
tctcaccact cagcctcagc aagtgctcca gccctcaact cccatttcc  attatctttc    65700 tatcactgga tatgggaggg aaggcagagc tgtggggcca agagaaacga ttgctcagga    65760
ggcagttggg agaactttat tgcaaagcac tgaagagata taaagtgaca tttgcaggaa    65820
aaagtagaag ggtatctgtg tgtgttggtt cctttaagga ttagagagca gctgagcttt    65880
gggatgagag ggctcccaga tgctgtgaat cagctaacag atccctccac cccgtcattg    65940
gtggtgaagt taaatagggg cccaggggaa acatcagggt tgttttctt  tttacggact    66000 ccagagcaag gagaaggtga gggggttgtg ctttggaatg ggagtgaaag agtttgttgg    66060
tgttttcctc tccccagaat aagtagtgtg gtgtaggagc gtctcatagg agtagctgcg    66120
ttaattgtgg ctggtgttag catcctataa tgttgctcca gaaatgctgg agcaggctta    66180
taatgatgtg tatgtattac cataatacat gaagggagaa tggggggggg ggggtagat     66240 ttaagatgta tgcccttaga aaggcgggtg tcacttaaag aagtacttgc tttatagctc    66300
cagtgataga attcattgag atactctgaa cctatgggc  atgaagtgac cagatcttca    66360
gtttggtcag ctctgggggt ttctggggg  agcggggata gagcctcaat ccaggtctga    66420
aagacaaggc tgagatgtgc tgggcctggg gtgctgccct gagcaacgtg gggctggccc    66480
tagagagcag cattagtgcc tgcagcaggg ctggcccttg tgcccagtgt gtggggtaag    66540
gtggggaacg taggtgctgc ataatgtggt gcttctgatc taaaactgct ctgttaattg    66600
ggagtgacca gagatggccc tatggctttc ttcccaaaga gctctgtgtc cttctctgca    66660
gggtaatctg tgataaaaac atcgcctatg ctctgccctg cagatgcagg ggttttgtc     66720 atcctccttc tcgagacata ctctaatcct tacgcaagca gggagctcca agcttttggt    66780
gataacctct caaggaggag ctggaagggc agctctgccg agcagtgact gcgctgcacg    66840
gggcgcatcc tgcaggaggc ggtggtgtaa gcgggactcc gctcgttccc ggctatgggg    66900 ctcccctgc  tgaccgccgg gcggtggcca ggagacctcg gggccgctgc tgcccctcgg    66960
tggtgctttt cggacagct  ttcaggatgg ggcagcccag ctgctctcgc ggggaattaa    67020
gcggctcggt gcagggcggc acggcgctga gctgcccag  caaagcgccg ctcgtcccgc    67080
ggcaccttcg gtagatgctc tctgcttggc agctccttgg tcgttctctt ggccggtggc    67140
caccccagca tcgctcgggg ctcggtgcca tccccccag  ggcctgcgga ggtgccggtg    67200
cccgtcccgg gggtggcgga cgggcggtgc agtaccgatg ctgggcgctg ggtgctgccg    67260
cagaccgagc ggcgctgcgc ggctccgggg cgctcctgga gtgcgagctg agcaacctgg    67320
tagaaaaata agtgttgtcc cgtgataaac gtcatcgtgc tgagctctca gactctgcca    67380
gaggcctgaa tgaagctgcg tcaggggaga atcaggttgg ggctaaggaa aggtcctgcc    67440
ccagagggcg gtgggtatag aagggtgcc  cagggcagtg ggtgcagtgc tgggctccca    67500
gagctggagg agcgtctgga cagtgctcag gtttggatgt tgggtggttt tctgaaggga    67560
cggattctgg gctcgtttat cctgagggtc ccttccaact tgggttgttc tattcaatga    67620
atattgttta tgttcattct attctatgat cttgttcagg ctctcactgc tgcctccaag    67680
ggttcagctc cccagagct  ggcagggctt cagccacttg cttacagtgc tcatttcatg    67740
cctggcccat ggcttctgcc tgagccttgt gggagatcag ctgctgccag aaacccagcc    67800
```

```
ctcagcactc cacttgccca gcttgctgcc ttagtagtct aacttggcag tggtctgaca  67860
tgacttgagg ttgtttttta tttccaaggt gccactgact tttttccttc catagtttct  67920
ggaagcattt ccttcctact tgactgagtc gtgctctgtg gatctgtaat tatccaccct  67980
ggctatgtgt cctttacggg attttatatg ttaacctccc aagatcattt tgctgctctc  68040
atcttagtgg ctgctgtgag ctccaccagc accacactgg atgagctgca ggctgaggcc  68100
gggcacctct cctgactctg ctcttctctg accccagagc tgtgcagttg ggatcctaac  68160
accatgcaga tgctccagga cctgcaccga gccccagcac tggcactcat ctcttctttc  68220
cacccctctg agagcaacaa gtggctctgc aatggcaatg taagtgaaac cgggcgggta  68280
tcttagagca cctggaagct tgcatgcctg caggtcgact ctagaggatc cccgggtacc  68340
gagctcgaat tcgccctata gtgagtcgta ttacaattca ctggccgtcg ttttacaacg  68400
tcgtgactgg gaaaaccctg gcgttaccca acttaatcgc cttgcagcac atccccCttt  68460
cgccagctgg cgtaatagcg aagaggcccg caccgatcgc ccttcccaac agttgcgcag  68520
cctgaatggc gaatggcgcc tgatgcggta ttttctcctt acgcatctgt gcggtatttc  68580
acaccgcata tggtgcactc tcagtacaat ctgctctgat gccgcatagt taagccagcc  68640
ccgacacccg ccaacacccg ctgacgcgaa ccccttgcgg ccgcatcgaa tataacttcg  68700
tataatgtat gctatacgaa gttattagcg atgagctcgg acttccattg ttcattccac  68760
ggacaaaaac agagaaagga acgacagagc cgcaaaaagc tcgctttcag cacctgtcgt  68820
ttcctttctt ttcagagggt attttaaata aaaacattaa gttatgacga agaagaacgg  68880
aaacgcctta aaccggaaaa ttttcataaa tagcgaaaac ccgcgaggtc gccgccccgt  68940
aacctgtcgg atcaccggaa aggacccgta aagtgataat gattatcatc tacatatcac  69000
aacgtgcgtg gaggccatca aaccacgtca aataatcaat tatgacgcag gtatcgtatt  69060
aattgatctg catcaactta acgtaaaaac aacttcagac aatacaaatc agcgacactg  69120
aatacggggc aacctcatgt ccgagctcgc gagctcgtcg acagcgacac acttgcatcg  69180
gatgcagccc ggttaacgtg ccggcacggc ctgggtaacc aggtattttg tccacataac  69240
cgtgcgcaaa atgttgtgga taagcaggac acagcagcaa tccacagcag gcatacaacc  69300
gcacaccgag gttactccgt tctacaggtt acgacgacat gtcaatactt gcccttgaca  69360
ggcattgatg gaatcgtagt ctcacgctga tagtctgatc gacaatacaa gtgggaccgt  69420
ggtcccagac cgataatcag accgacaaca cgagtgggat cgtggtccca gactaataat  69480
cagaccgacg atacgagtgg gaccgtggtc ccagactaat aatcagaccg acgatacgag  69540
tgggaccgtg gttccagact aataatcaga ccgacgatac gagtgggacc gtggtcccag  69600
actaataatc agaccgacga tacgagtggg accatggtcc cagactaata atcagaccga  69660
cgatacgagt gggaccgtgg tcccagtctg attatcagac cgacgatacg agtgggaccg  69720
tggtcccaga ctaataatca gaccgacgat acgagtggga ccgtggtccc agactaataa  69780
tcagaccgac gatacgagtg gaccgtggt cccagtctga ttatcagacc gacgatacaa  69840
gtggaacagt gggcccagag agaatattca ggccagttat gctttctggc ctgtaacaaa  69900
ggacattaag taaagacaga taaacgtaga ctaaacgtg tcgcatcag ggtgctggct   69960
tttcaagttc cttaagaatg gcctcaattt tctctataca ctcagttgga acacgagacc  70020
tgtccaggtt aagcaccatt ttatcgccct tatacaatac tgtcgctcca ggagcaaact  70080
gatgtcgtga gcttaaacta gttccttgatg cagatgacgt tttaagcaca gaagttaaaa  70140
gagtgataac ttcttcagct tcaaatatca ccccagcttt tttctgctca tgaaggttag  70200
```

```
atgcctgctg cttaagtaat tcctctttat ctgtaaaggc ttttttgaagt gcatcacctg   70260 accgggcaga tagttcaccg gggtgagaaa aaagagcaac aactgattta ggcaatttgg   70320
cggtgttgat acagcgggta ataatcttac gtgaaatatt ttccgcatca gccagcgcag   70380
aaatatttcc agcaaattca ttctgcaatc ggcttgcata acgctgacca cgttcataag   70440
cacttgttgg gcgataatcg ttacccaatc tggataatgc agccatctgc tcatcatcca   70500
gctcgccaac cagaacacga taatcacttt cggtaagtgc agcagcttta cgacggcgac   70560
tcccatcggc aatttctatg acaccagata ctcttcgacc gaacgccggt gtctgttgac   70620
cagtcagtag aaaagaaggg atgagatcat ccagtgcgtc ctcagtaagc agctcctggt   70680
cacgttcatt acctgaccat acccgagagg tcttctcaac actatcaccc cggagcactt   70740
caagagtaaa cttcacatcc cgaccacata caggcaaagt aatggcatta ccgcgagcca   70800
ttactcctac gcgcgcaatt aacgaatcca ccatcggggc agctggtgtc gataacgaag   70860
tatcttcaac cggttgagta ttgagcgtat gttttggaat aacaggcgca cgcttcatta   70920
tctaatctcc cagcgtggtt taatcagacg atcgaaaatt tcattgcaga caggttccca   70980
aatagaaaga gcatttctcc aggcaccagt tgaagagcgt tgatcaatgg cctgttcaaa   71040
aacagttctc atccggatct gacctttacc aacttcatcc gtttcacgta caacatttttt  71100 tagaaccatg cttccccagg catcccgaat ttgctcctcc atccacgggg actgagagcc   71160
attactattg ctgtatttgg taagcaaaat acgtacatca ggctcgaacc ctttaagatc   71220
aacgttcttg agcagatcac gaagcatatc gaaaaactgc agtgcggagg tgtagtcaaa   71280
caactcagca ggcgtgggaa caatcagcac atcagcagca catacgacat taatcgtgcc   71340
gatacccagg ttaggcgcgc tgtcaataac tatgacatca tagtcatgag caacagtttc   71400
aatggccagt cggagcatca ggtgtggatc ggtgggcagt ttaccttcat caaatttgcc   71460
cattaactca gtttcaatac ggtgcagagc cagacaggaa ggaataatgt caagccccgg   71520
ccagcaagtg ggctttattg cataagtgac atcgtccttt tccccaagat agaaaggcag   71580
gagagtgtct tctgcatgaa tatgaagatc tggtacccat ccgtgataca ttgaggctgt   71640
tccctggggg tcgttacctt ccacgagcaa acacgtagc ccctttcagag ccagatcctg   71700 agcaagatga acagaaactg aggttttgta acgccacct ttatgggcag caaccccgat   71760
caccggtgga aatacgtctt cagcacgtcg caatcgcgta ccaaacacat cacgcatatg   71820
attaatttgt tcaattgtat aaccaacacg ttgctcaacc cgtcctcgaa tttccatatc   71880
cgggtgcggt agtcgccctg cttttctcggc atctctgata gcctgagaag aaacccccaac  71940 taaatccgct gcttcaccta ttctccagcg ccgggttatt ttcctcgctt ccgggctgtc   72000
atcattaaac tgtgcaatgg cgatagcctt cgtcatttca tgaccagcgt ttatgcactg   72060
gttaagtgtt tccatgagtt tcattctgaa catcctttaa tcattgcttt gcgttttttt   72120
attaaatctt gcaatttact gcaaagcaac aacaaaatcg caaagtcatc aaaaaaccgc   72180
aaagttgttt aaaataagag caacactaca aaaggagata agaagagcac ataccctcagt  72240 cacttattat cactagcgct cgccgcagcc gtgtaaccga gcatagcgag cgaactggcg   72300
aggaagcaaa gaagaactgt tctgtcagat agctcttacg ctcagcgcaa gaagaaatat   72360
ccaccgtggg aaaaactcca ggtagaggta cacacgcgga tagccaattc agagtaataa   72420
actgtgataa tcaaccctca tcaatgatga cgaactaacc cccgatatca ggtcacatga   72480
cgaagggaaa gagaaggaaa tcaactgtga caaactgccc tcaaatttgg cttccttaaa   72540
```

```
aattacagtt caaaaagtat gagaaaatcc atgcaggctg aaggaaacag caaaactgtg    72600
acaaattacc ctcagtaggt cagaacaaat gtgacgaacc accctcaaat ctgtgacaga    72660
taaccctcag actatcctgt cgtcatggaa gtgatatcgc ggaaggaaaa tacgatatga    72720
gtcgtctggc ggcctttctt tttctcaatg tatgagaggc gcattggagt tctgctgttg    72780
atctcattaa cacagacctg caggaagcgg cggcggaagt caggcatacg ctggtaactt    72840
tgaggcagct ggtaacgctc tatgatccag tcgattttca gagagacgat gcctgagcca    72900
tccggcttac gatactgaca cagggattcg tataaacgca tggcatacgg attggtgatt    72960
tcttttgttt cactaagccg aaactgcgta accggttct gtaacccgat aaagaaggga    73020
atgagatatg ggttgatatg tacactgtaa agccctctgg atggactgtg cgcacgtttg    73080
ataaaccaag gaaaagattc atagccttt tcatcgccgg catcctcttc agggcgataa    73140
aaaaccactt ccttccccgc gaaactcttc aatgcctgcc gtatatcctt actggcttcc    73200
gcagaggtca atccgaatat ttcagcatat ttagcaacat ggatctcgca gataccgtca    73260
tgttcctgta gggtgccatc agattttctg atctggtcaa cgaacagata cagcatacgt    73320
ttttgatccc gggagagact atatgccgcc tcagtgaggt cgtttgactg gacgattcgc    73380
gggctatttt tacgtttctt gtgattgata accgctgttt ccgccatgac agatccatgt    73440
gaagtgtgac aagtttttag attgtcacac taaataaaaa agagtcaata agcagggata    73500
actttgtgaa aaaacagctt cttctgaggg caatttgtca cagggttaag ggcaatttgt    73560
cacagacagg actgtcattt gagggtgatt tgtcacactg aaaggggaat tgtcacaac    73620 accttctcta gaaccagcat ggataaaggc ctacaaggcg ctctaaaaaa gaagatctaa    73680
aaactataaa aaaaataatt ataaaaatat ccccgtggat aagtggataa ccccaaggga    73740
agttttttca ggcatcgtgt gtaagcagaa tatataagtg ctgttccctg gtgcttcctc    73800
gctcactcga gggcttcgcc ctgtcgctcg actgcggcga gcactactgg ctgtaaaagg    73860
acagaccaca tcatggttct gtgttcatta ggttgttctg tccattgctg acataatccg    73920
ctccacttca acgtaacacc gcacgaagat ttctattgtt cctgaaggca tattcaaatc    73980
gttttcgtta ccgcttgcag gcatcatgac agaacactac ttcctataaa cgctacacag    74040
gctcctgaga ttaataatgc ggatctctac gataatggga gattttcccg actgtttcgt    74100
tcgcttctca gtggataaca gccagcttct ctgtttaaca gacaaaaaca gcatatccac    74160
tcagttccac atttccatat aaaggccaag gcatttattc tcaggataat tgtttcagca    74220
tcgcaaccgc atcagactcc ggcatcgcaa actgcacccg gtgccgggca gccacatcca    74280
gcgcaaaaac cttcgtgtag acttccgttg aactgatgga cttatgtccc atcaggcttt    74340
gcagaacttt cagcggtata ccggcataca gcatgtgcat cgcataggaa tggcggaacg    74400
tatgtggtgt gaccggaaca gagaacgtca caccgtcagc agcagcggcg gcaaccgcct    74460
ccccaatcca ggtcctgacc gttctgtccg tcacttccca gatccgcgct ttctctgtcc    74520
ttcctgtgcg acggttacgc cgctccatga gcttatcgcg aataaatacc tgtgacggaa    74580
gatcacttcg cagaataaat aaatcctggt gtccctgttg ataccgggaa gccctgggcc    74640 aactttggc gaaatgaga cgttgatcgg cacgtaagag gttccaactt tcaccataat    74700
gaaataagat cactaccggg cgtatttttt gagttatcga gattttcagg agctaaggaa    74760
gctaaaatgg agaaaaaat cactggatat accaccgttg atatatccca atggcatcgt    74820
aaagaacatt ttgaggcatt tcagtcagtt gctcaatgta cctataacca gaccgttcag    74880
ctggatatta cggcctttttt aaagaccgta aagaaaaata agcacaagtt ttatccggcc    74940
```

-continued

```
tttattcaca ttcttgcccg cctgatgaat gctcatccgg aatttacatc tggaattacg    75000
tatggcaatg aaagacggtg agctggtgat atgggatagt gttcaccctt gttacaccgt    75060
tttccatgag caaactgaaa cgttttcatc gctctggagt gaataccacg acgatttccg    75120
gcagtttcta cacatatatt cgcaagatgt ggcgtgttac ggtgaaaacc tggcctattt    75180
ccctaaaggg tttattgaga atatgttttt cgtctcagcc aatccctggg tgagtttcac    75240
cagttttgat ttaaacgtgg ccaatatgga caacttcttc gcccccgttt tcaccatggg    75300
caaatattat acgcaaggcg acaaggtgct gatgccgctg gcgattcagg ttcatcatgc    75360
cgtttgtgat ggcttccatg tcggcagaat gcttaatgaa ttacaacagt actgcgatga    75420
gtggcagggc ggggcgtaat ttttttaagg cagttattgg tgcccttaaa cgcctggttg    75480
ctacgcctga ataagtgata ataagcggat gaatggcaga aattcgatga taagctgtca    75540
aacatgagaa ttggtcgacg gcccggacgg ccgcaagggg ttcgcgttgg ccgattcatt    75600
aatgcagctg gcacgacagg tttcccgact ggaaagcggg cagtgagcgc aacgcaatta    75660
atgtgagtta gctcactcat taggcacccc aggctttaca ctttatgctt ccggctcgta    75720
tgttgtgtgg aattgtgagc ggataacaat ttcacacagg aaacagctat gaccatgatt    75780
acgccaagct atttaggtga cactatagaa tactc                              75815
```

```
<210> SEQ ID NO 37
<211> LENGTH: 26
<212> TYPE: DNA
<213> ORGANISM: chicken

<400> SEQUENCE: 37
cgggcagtac ctcaccatgg acatgt                                              26

<210> SEQ ID NO 38
<211> LENGTH: 21
<212> TYPE: DNA
<213> ORGANISM: chicken

<400> SEQUENCE: 38
attcgcttaa ctgtgactag g                                                   21

<210> SEQ ID NO 39
<211> LENGTH: 20
<212> TYPE: DNA
<213> ORGANISM: chicken

<400> SEQUENCE: 39
cgaggaactt gaagcctgtc                                                     20

<210> SEQ ID NO 40
<211> LENGTH: 20
<212> TYPE: DNA
<213> ORGANISM: chicken

<400> SEQUENCE: 40
ggcctgcact ctccatcata                                                     20

<210> SEQ ID NO 41
<211> LENGTH: 1680
<212> TYPE: DNA
<213> ORGANISM: chicken
<220> FEATURE:
<221> NAME/KEY: misc_feature
<222> LOCATION: (823)..(1203)
```

<223> OTHER INFORMATION: n is a, c, g, or t

<400> SEQUENCE: 41

```
gatttcactc atctcctaat aatcaggtag ctgaggagat gctgagtctg ccagttcttg      60
ggctctgggc aggatcccat ctcctgcctt ctctaggaca gagctcagca ggcagggctc     120
tgtggctctg tgtctaaccc acttcttcct ctcctcgctt tcagggaaag caacgggact     180
ctcactttaa gccattttgg aaaatgctga atatcagagc tgagagaatt ccgcccctct     240
ccctccccc ccctaacgt tactggccga agccgcttgg aataaggccg gtgtgcgttt     300
gtctatatgt tattttccac catattgccg tcttttggca atgtgagggc ccggaaacct     360
ggccctgtct tcttgacgag cattcctagg ggtctttccc ctctcgccaa aggaatgcaa     420
ggtctgttga atgtcgtgaa ggaagcagtt cctctggaag cttcttgaag acaaacaacg     480
tctgtagcga ccctttgcag gcagcggaac cccccacctg gcgacaggtg cctctgcggc     540
caaaagccac gtgtataaga tacacctgca aggcggcac aacccagtg ccacgttgtg     600
agttggatag ttgtggaaag agtcaaatgg ctctcctcaa gcgtattcaa caaggggctg     660
aaggatgccc agaaggtacc ccattgtatg ggatctgatc tggggcctcg gtgcacatgc     720
tttacgtgtg tttagtcgag gttaaaaaac gtctaggccc cccgaaccac ggggacgtgg     780
ttttcctttg aaaaacacga tgataagctt gccacaacca tgnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnacggtgg cggcgccatc tgtcttcatc ttcccgccat ctgatgagca gttgaaatct    1260
ggaactgcct ctgttgtgtg cctgctgaat aacttctatc ccagagaggc caaagtacag    1320
tggaaggtgg ataacgccct ccaatcgggt aactcccagg agagtgtcac agagcaggac    1380
agcaaggaca gcacctacag cctcagcagc accctgacgc tgagcaaagc agactacgag    1440
aaacacaaag tctacgcctg cgaagtcacc catcagggcc tgagctcgcc cgtcacaaag    1500
agcttcaaca ggggagagtg ttagggatcc actagtccag tgtggtggaa ttcaccacag    1560
gatccccact ggcgaatccc agcgagaggt ctcacctcgg ttcatctcgc actctgggga    1620
gctcagctca ctcccgattt tctttctcaa taaactaaat cagcaacact cctttgtctt    1680
```

<210> SEQ ID NO 42
<211> LENGTH: 2340
<212> TYPE: DNA
<213> ORGANISM: chicken
<220> FEATURE:
<221> NAME/KEY: misc_feature
<222> LOCATION: (823)..(1224)
<223> OTHER INFORMATION: n is a, c, g, or t

<400> SEQUENCE: 42

```
gatttcactc atctcctaat aatcaggtag ctgaggagat gctgagtctg ccagttcttg      60
ggctctgggc aggatcccat ctcctgcctt ctctaggaca gagctcagca ggcagggctc     120
tgtggctctg tgtctaaccc acttcttcct ctcctcgctt tcagggaaag caacgggact     180
ctcactttaa gccattttgg aaaatgctga atatcagagc tgagagaatt ccgcccctct     240
```

```
ccctccccccc cccctaacgt tactggccga agccgcttgg aataaggccg gtgtgcgttt    300
gtctatatgt tattttccac catattgccg tcttttggca atgtgagggc ccggaaacct    360
ggccctgtct tcttgacgag cattcctagg ggtctttccc ctctcgccaa aggaatgcaa    420
ggtctgttga atgtcgtgaa ggaagcagtt cctctggaag cttcttgaag acaaacaacg    480
tctgtagcga ccctttgcag gcagcggaac cccccacctg cgacaggtg cctctgcggc    540
caaaagccac gtgtataaga tacacctgca aaggcggcac aaccccagtg ccacgttgtg    600
agttggatag ttgtgaaag agtcaaatgg ctctcctcaa gcgtattcaa caaggggctg    660
aaggatgccc agaaggtacc ccattgtatg ggatctgatc tggggcctcg gtgcacatgc    720
tttacgtgtg tttagtcgag gttaaaaaac gtctaggccc cccgaaccac ggggacgtgg    780
ttttcctttg aaaaacacga tgataagctt gccacaacca tgnnnnnnnn nnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnntcagct agcaccaagg gcccatcggt cttccccctg   1260
gcaccctcct ccaagagcac ctctgggggc acagcggccc tgggctgcct ggtcaaggac   1320
tacttccccg aaccggtgac ggtgtcgtgg aactcaggcg ccctgaccag cggcgtgcac   1380
accttccccgg ccgtcctaca gtcctcagga ctctactccc tcagcagcgt ggtgaccgtg   1440
ccctccagca gcttgggcac ccagacctac atctgcaacg tgaatcacaa gcccagcaac   1500
accaaggtgg acaagagagt tgagcccaaa tcttgtgaca aaactcacac atgcccaccg   1560
tgcccagcac ctgaactcct ggggggaccg tcagtcttcc tcttcccccc aaaacccaag   1620
gacaccctca tgatctcccg gacccctgag gtcacatgcg tggtggtgga cgtgagccac   1680
gaagaccctg aggtcaagtt caactggtac gtggacggcg tggaggtgca taatgccaag   1740
acaaagccgc gggaggagca gtacaacagc acgtaccgtg tggtcagcgt cctcaccgtc   1800
ctgcaccagg actggctgaa tggcaaggag tacaagtgca aggtctccaa caaagccctc   1860
ccagccccca tcgagaaaac catctccaaa gccaaagggc agccccgaga accacaggtg   1920
tacaccctgc cccatcccg ggatgagctg accaagaacc aggtcagcct gacctgcctg   1980
gtcaaaggct tctatcccag cgacatcgcc gtggagtggg agagcaatgg gcagccggag   2040
aacaactaca agaccacgcc tcccgtgctg gactccgacg gctccttctt cctctacagc   2100
aagctcaccg tggacaagag caggtggcag caggggaacg tcttctcatg ctccgtgatg   2160
catgaggctc tgcacaacca ctacacgcag aagagcctct ccctgtctcc gggtaaatag   2220
ggatccacta gtccagtgtg gtggaattca ccacaggatc cccactggcg aatcccagcg   2280
agaggtctca cctcggttca tctcgcactc tggggagctc agctcactcc cgattttctt   2340
```

<210> SEQ ID NO 43
<211> LENGTH: 11
<212> TYPE: PRT
<213> ORGANISM: SV40

<400> SEQUENCE: 43

Cys Gly Gly Pro Lys Lys Lys Arg Lys Val Gly
1               5                   10

<210> SEQ ID NO 44
<211> LENGTH: 77872
<212> TYPE: DNA
<213> ORGANISM: chicken

<400> SEQUENCE: 44

| | | | | | |
|---|---|---|---|---|---|
| attcaccaca | ggatccccac | tggcgaatcc | cagcgagagg | tctcacctcg | gttcatctcg | 60 |
| cactctgggg | agctcagctc | actcccgatt | ttctttctca | ataaactaaa | tcagcaacac | 120 |
| tcctttgtct | tgtttaatgc | tctgcctcat | gcaatgtttt | cttctgattt | gttggacggt | 180 |
| gataccagac | tcaatatgtt | ccatgctcgt | ggctctgggg | tataacaaga | acaacatctt | 240 |
| gctcccatcc | ctgtcataaa | aggcagaaaa | ttaaatacag | atgcataaac | ctcggctgtg | 300 |
| tgactttgcg | cataaatgac | agtcagcctc | cattagtgtt | cagacccttt | tagacagctg | 360 |
| aaatactgct | acgaactgct | gatgctggct | gagctcccca | tggtacgtgt | ggtgcacttt | 420 |
| ccctgcgcag | cattagcagt | gaaagcagct | cagggtgcgg | tggtggccaa | acccagggcc | 480 |
| gatcccacgg | cctcctgtac | ctggtcatac | ccacgggcac | agctgctagt | gaggtgcgtg | 540 |
| cttttcagac | acgtcatata | agtgtgccct | gcctacatgt | ctgggtcctc | caaatgacgt | 600 |
| tgcaaggttt | atctcatctt | ggaattgtcc | cttactgacc | accaagtgtt | ttgagatgaa | 660 |
| tgccctccta | ggtctggttc | tgctcttgcc | tgctggtctt | ttctcatagt | agtccttgcc | 720 |
| agcccaagta | tctgagcagt | gttttgcaat | ccaaggacaa | agtacccctc | tgcctttgag | 780 |
| agtgtgacct | ctgtcattgg | cacattgtcc | gtgaaatata | ttttgctttt | gtcctttgtt | 840 |
| ggtgtattga | actgatgttt | tcttgatcca | catgagagaa | actttaataa | aaattataaa | 900 |
| aaataatgcc | tcccttaagc | atttcttttc | cctgatggaa | tgaggccatt | caaaagaagg | 960 |
| atgctttggc | ggtaaaacag | aggatttatg | ttgagatggg | cagatgaatc | aagcagtgat | 1020 |
| ttccagtttg | gattgaactt | ttctgggatc | caggctgtgg | gcctcatgtc | attctgtcat | 1080 |
| catcaggcta | tcagtctgct | gctgcaaatc | ctccccacaa | cgctaatggc | ttttagggaa | 1140 |
| aatcgcaatt | gttagttctt | tgctaatgcc | cataaaactt | cttccatcac | ttgtccagct | 1200 |
| ccaggactcc | cttcagcccc | aggtttccct | cttgctctct | ctcccagttc | agttttctg | 1260 |
| gatttgctat | gatttgatga | tgcattattg | acaggacaag | gggaaatggt | ttcaaaccag | 1320 |
| aggagaggag | atttagactg | gacataagca | agacattttt | tacaatgtg | gtgaggcact | 1380 |
| gacagaggtt | gcccagagag | gtggtggtgc | cccatccatg | gagacagcca | aggtcaggag | 1440 |
| gggctctgag | cactgatgga | gctgtgggtg | ccctgttca | ttgcagggg | ttggaccaga | 1500 |
| tggcctttaa | agatcccttc | caactcaaat | gcttcaatga | ttctgtgatt | ctattgggtt | 1560 |
| gaagcatgcc | aactaagact | ttccactctg | gaaaacattc | aattcagttc | aacaacattt | 1620 |
| tccagcaaca | gtgagaaagc | actgcatata | ggtaagcact | gataacatgc | acatggagga | 1680 |
| aatcctgcag | cattctctct | tcaggtttgt | acagttgccc | ttttgcccac | aggaattttc | 1740 |
| catggtcctt | cagcaggcac | ctgtcacaca | cttcactgga | ataatgaag | ccgagggcgt | 1800 |
| acttcacata | tttaaacctg | caattgctgt | tgataaagaa | gcattctttg | tggctcactt | 1860 |
| gtgtaagtgc | catcaagatt | tacaaccctg | acaccagagc | tggaacgctg | ttatttcaa | 1920 |
| agtaggggt | ggctaaacca | aacgtgaatg | cacacagcca | cgcacacaca | gatcaggtgg | 1980 |
| ccatccaagg | gcagaagggc | cgcattccat | gagcacgatg | cacttctgcc | ctttgctgct | 2040 |

```
gcccaggtga gtggctgtgc tcctgctccg tgcttcgtcg agtgctggct gtaaaaacac    2100
aacaaacatc ctcagactgg aaagagctgt gttctacaag gacttattta ctcctagagg    2160
gatggtgttg aaaagacttg acatcaaaga ctatcactta tggggtaata ttttagcaac    2220
agaactgagt gggtaagaac aactgtggga acagctccgc gctcggtgct agtttatgca    2280
taatgaaagc agtgacacgt acgtggtacc acgacatcca ccattgaacc tccgaaacgc    2340
tgcagaatca caaattcttt tactgaatgg aagcgagcgt ttcccgcagt catcctgaac    2400
tgagatgcaa ttggaggggc tgagcggctg cagcagcgtt aggggagttt cacctcgctg    2460
agccctcccg ttatttcagt gctgttgtgg agctgcacgc aggagctgcc gccagtccgt    2520
gccagctctg cggccctgct tccccggcac cttgcttatc tctgagcacc tgtccttgct    2580
catcctgtga atcacggaga attgctttct cttcctccct ttcatttcgc gcgtccttct    2640
ccacccgggc tgtaaccctc ctgagaaaaa acgtagtacg gaatcgatgt tgtaaacact    2700
cagcgtggca caacgttttg cctgaaatcc cttttgtctg agagtcacac actgaattgc    2760
aagttgttta ttcaggacat gcactcacgg attttaacac taacgaagga gatgaattgc    2820
atttgtgtca cacttcctat tcccttcttt actccagacc ccactgcact gaaggtaagg    2880
gacagatctt tcaggttttt tttttttttt ctccatcatt tctttcctca aagcagtttc    2940
cgtataaatc attactaatc gcattgtgat cgagcgtttg aaagccctga gtcatcccac    3000
agcctgagca atatttgcta cagatattac cgagtgaaat ggccattttc atctgatggt    3060
ttcaaaaaaa aaaaaaagat aataataata ataataataa taaataaata gcgcagcatt    3120
cagttggtgt ccaagttatt gtcacggtta ctgcagcagc actgaggatg tttacatggg    3180
atttacatca ctggaggctg aaagggcact gcaggcgtgt accgcgctat tcgctgcccc    3240
atccttaagc tcttctttga catctgctga tggtcggtgc tgggggaagc ccggggctgt    3300
gggggtctcc tggcatctgc cctgctgata gctgtgctgc tgagggtatt tctgtgagca    3360
caaggctgca tcgatccaca gggcgactgc agtgcctgcg ccgtaccccg caatttctgc    3420
tctcgggagc gcatcccaca ctgcgggtct gatggcgtaa catatgccag cgagtgttta    3480
ttccgcaatg catttctggg tgtatgaaaa taaatctctt cgctcactga gtggtgaact    3540
tcaactgtct tatcaacctc agggactgcc tggagatgga aggtggttgt gtttggcgct    3600
ctcctcttct cttgctagca agggcagcac ttttttttt aaactgggag gatttaccag    3660
ggactccttt ctttcaggta aaaagaagtc acatttagca gagatcttca tctccacgtt    3720
gggtaatttg ctgaagagct cgcttccagc aaatacagtc tatttcctac agcctatttg    3780
ttcttctttt aaattaagtc tttatcgtgc ctttgaatgt tagtaataag aggaagtagc    3840
tggaatagct ttccgaatgt tctgtttttgg ttaagttcct ctgtgatgta tccttaagca    3900
gagggaggga tgcacagcag aagcgcagag gttcaatctc tgaggccctg agctctttct    3960
ctccagaact cattgagttc tcaccttgct gtgccctgcg cagcgctcac atcacagccc    4020
accgggctcc agctcagaca ggaggaccct ctctggctgt gttccttaca ggggatgctg    4080
cccaaagcct cgtcctgaac tttgagtgct cctgataaag cctgaagcta tgctcaataa    4140
aaaaaaaaaa ccttcagcat tttggtcttg cttcatact acgtatcatg ctgttgtttt    4200
tttttcttaa gatgctgtgt gattgcatca ctgcaacagt cctggggtgt gggtcttaat    4260
gggaaaatta cagggagaaa gaacgggttg tctgatttat gaagaaatca acccctccaa    4320
aaggccatga gcttctgctt tcttccagat ttccaaagga aagccactgc tggggatgag    4380
atccagtgca gtgttcaggg catcctgtgc agacattgac tccttaggag ctgaaaataa    4440
```

```
agtagtggtg ggtacccgta ggtgtgggaa gcctttctgc agccacctgg tctgcctccc    4500
aaagcagagg atgggatgtt ttcccctccg ggcagcacca acagaggggt ggcagcaggg    4560
tgaggaagat gattggcccc tctgctctgc tcttgtgggg accacatgca gtattgcatc    4620
caggcctggg gccccagcat gagaaagacg tggaactgtt ggagtgggtc cataggaggc    4680
catgaagaca atcacaggge tggagcacct ctcttatgaa gaaaggctga gggagctggg    4740
cttgttcagc atcaagaagg gaaagctgag aggacacctc attggagtct tccagtactt    4800
gaagggagct tgcaagcagg aaggggaaca aacttctaca tggtctgaca gagatagaac    4860 aaggggagt ggctttaagc taaaagaggg aagatttggg tgagatgttg ggaagaaata     4920
ctttactcag aggttggtgt gacactggca ctgctgccca gagctgtggg tgccccatcc    4980
ctgtacatga gctgaaggcc agattggatg gggctctgtg cagcctgatc tggtggggggg   5040 cagccagccc atggcagggg ttggggtaga tgggttgtat ggccctttc aacccaaacc     5100 attcaatgat tctatgattc tcagataagc ctgcctgccc acatctgagc tcacggtgct    5160
cgctgggggt ggggtatggt acactaaatg atgctcagag gactgcacgc aggacctgcc    5220
gcagacgttt atcacctcac ccaccactta gctgctgctt gtagttaatt acgtcagctg    5280
tcacttgtag agaatccttt gagatccttg ggcctccgga atcttggct gatgaaagga     5340 agggctcaga gtcatagcgt taatttatta ttcattaaca ccaaagtgtc ggctgtacgg    5400
gcagtgggct cacagtcaaa tagttaatga tcttaagtga caatgtgtca ctttgcagac    5460
agcagagaga acagctctcc taagggagac agcatctttc caattctgca gccattcagt    5520
gccaagctcc tctttgggac gaaagtgaag atgaggaagg caatgaggat gaggaggggc    5580
ctcaaggaac ctggctggct tggagacaag tgatgatccc agctgctctc agggtcccag    5640
cggtcttcaa agggcatctt gcaggggctg tgtcctctga acagcaaaac ccaggtcata    5700
gaggggaaag tgtgagcaga gatgggacaa atctcccatc ctgccacgga gctgcactgc    5760 taaggggtg atggggagca gcatgggacc ccagcgttcc ccccatccct gcaccaggcc     5820
cagctctgcg ggatggcgag gaggacaagg ctctgtcaca agcatcgctg gcaattatta    5880
ttttgttgtt gctgctcaat aaaatcctga cacagtacaa cacaatatcc tctcatcatt    5940
actaatctaa ctctccctcc aggaaatttc aggcaggaaa cgttgtctgc ctgccgaggt    6000
gctttatggc actgttcttt agtggtacct cagcacttcg tgtcattatc tggtgtcagt    6060
gaatttagga aatgccattc aattaccccg caaactgatt aacgcattgc gtgcagttat    6120
tttgttctgc tctattttat atcagttcct ctgttttatg tatttctcta cttgttgctg    6180
gccagaacac acctcgggcc agtctagacc ttgctgttga tgcagctttt ccccagggct    6240
tcatcagcac aaatggtttg tcaacgtggg gaaaaataaa attatgcttt aaaataaaac    6300
cacctggaga tgctgttctg gggtctggct gtgtcacagc tattgcagcg atggagctga    6360
gggattggga tgtgctgggc cggatcctca gcgctttgct ataagccaaa taattccaga    6420
cacccttctt ccctcagata tcatctgtgc ttaagcagca ggagatatgc aggcagcgat    6480
cagatagctg agctgcaagg agaaatatca caagagcgcg gcttagagca ggggctttgc    6540
tcgctctaaa ttgaattccc atcctctag gagatccagt cctgcccccg tgtgcatcgc    6600
tccggtaaca gcaatgtgtt ttgctccatc ttgcagaggg tccagaagct ggggaaagga    6660
aatgtgtcgt gcgttcgtcc ctgcagcagc tcggcccata aaattaatga aaatcttttt    6720
taggtcatgg tagattacag atttctttga gatagagaat ctcaagagca gaggagaaga    6780
```

```
ttctcagaaa atagcagtga tatgagatgg cataacgctg agttggaaac tggggaggat    6840
ttccagggtt actggaaatt tacttaagca cgagagaatg catcgtgtga ctgccagtgc    6900
ttccccactc acatggctat aaccttcttg catacaatta ccatcttgga acttgaaata    6960
gctgaaagag ttttatttga tcttttcaat ggatcttaca tctgcagaaa aaaaaaaaaa    7020
aggctagaaa taatcctgca ctcaaactca ctttactgaa ccaccatcat gaaactccag    7080
caacacacag ggatttgggc aggcgtgttc atcttcctct tcccatttgc aacatgtgta    7140
tggcatttcc tgaagctcac tcctccaaat gcattgagac agttgttttt cattcttcct    7200
aatgcctgca tccacccatc tgctgatcgg caattatttc tatcccattc ccttctgttt    7260
cttattaatc aagctcttta tgcaatccca cgtaacactt tgcccagctg ccctgcccta    7320
accactacca attatctcat cctgttttat agaccctgta gcaagactct ggccttgctc    7380
ctcttcctct ccctgataga gcttttggtg cagggctggc tggctcctca ggtgttcaga    7440
ggatcagagg tctcccagaa ggatcttgtt aatcaaggac aggtgctggc tatatgggag    7500
gatggcaccg tatcctaaag ctctacaaga aggagacgga gctcagcctg gaggacaga    7560 gagaagcagc agcacaggtt tcaggatcca gggatggcag acctgggtgt gggctcatag    7620
gattgaagaa gggataggct gtgctcctgt agcctcactg cagaagcagc actgctatct    7680
ccccagcgaa gctgtgtgtg ccccatccct ggaggtgctc aggaccaggt gggatgggc    7740 cctgggcagt ctgagccgga gggagcagcc ggcccacagc aggggttgga atgggtggg    7800 ttttaagttc ccctccaacc aaagccattt cttgatctct gttggtggct ggtgcaagtt    7860
ctgaggaaac ctcattttca gctcaggcgt tcttgtccct ggggaaaaat caatattaat    7920
gcttcagtga ttactgctcg ccttccaaat gtgcttctga tcagttcaag aaatctgaca    7980
gtcacgtcgc tcaggatgct aagaatacaa cagaaacagc tttgaaagga acccttcaac    8040
tcttgatatt tgtgaatgag ctccaaagaa cattactcat ttattttca ggaaaatgat    8100 ttcattgaca tgaacaggcc aaagcctaca agctctgttt tgtgactgca gctccttaca    8160
ctttcagctg cattttcatg atttatgtgc ccatgatgag acttgaacac ctcccaggat    8220
aatgggaaaa gcagttctga tttcccattt aaaacgtagg ctgcctttaa gccatgtgtg    8280
tggctcaggc tccttctgaa gcacaaaggt gttccacccc tcgctccttt ttcattacaa    8340
ctttcaatca aaatgtgtt ttatgagata tttgttttgc catgtatctg tgacggagtt    8400 gaaccccta gtgaaacctc tgttcttcac ttagctgaga ggtatttctt agggaatgtg    8460
atgccctaaa tttattgtgg tgtaatagaa gggggatgt gtggactcac cttctgtttg    8520
ttgtggctgc agtggttta tgcactacct gagtattaag caagccctt tcatctgcac    8580 ggaacacctc ctgcttgcca gtgggatgaa acaacaacaa caaagattta aggtttgcta    8640
ttctcaatgt ttcttaatcg ggttcacatt gattgccaac agatgaataa ttcctccttc    8700
tccatggatg tacctcttaa acttgtgaag tcttaggtaa cgcttttctg ctgtgatgac    8760
tgtttcagtc ccctcagtga gaaatcaggc gcaccagtaa gacacaaagg agaccgtgga    8820
gatgttcatt gtgccctcag catctccaaa aggcactgct gcctgccgag ccccagactt    8880
cgctcctgta aaagcaaagc atgtccaatt ctgctgtgcc ataagagtcc tgtggagccc    8940
agacacggcg tagcgtgtgt aacatagcgt gcacgagctc aaacgctttc aacaaatcag    9000 ctttttttgct ttgccaactt ccatatgtaa tttcacaaca tctagtattg agacagtgct    9060
gttgtttggg cagcataaat cactcattgt acagcagggc gcctctctta acaagttggg    9120
tgtagttcat gttttttgtct aattcctctg cgcatctctc taacaaacaa ctattcttta    9180
```

```
gggctcgact caataatcaa tacattttt tcagtttaca gagcaaataa ttacttgacc    9240
tgatgacttc acaaggttag ggagatgggt gtataaagtc tgcagtgtga aggcagagca    9300
acatctctgc agaccttgag agcaacaggt ctgcaagtaa caggctgcac agccacctct    9360
gccatggagg caatgagagc tgctgccctc cttggattgg tgcttctcag ctccttcct     9420 ggtaagttgt ttttgttaca ttctctgctt atatctctac tcctactgaa ctaaatgtgg    9480
ttcaggatgc ctttagaatc ctaaaagaga gctcagcctg ccggagaagt gatggtttgg    9540
taaaacatga gctctcttct aatgatcttt atccttgtgc aaatatttac gtaactctag    9600
caggatgcct ctgtctgaca taaactcatt atcctcagta agtctcatag cactcgagag    9660
agaaaatgta taccctattt cttccttagt gagtcaaagt ttatattttc acccaaaatg    9720 gctattttt ttaatcatag gatatagctt gcttatagga actggataaa atatttagga    9780
aacaagtaat tctcagtgat aaaaagaag tatgtgatga ctctgtaggg aaattgataa     9840
ttccagagga attgtaacca aggacgccgt aacattctgt attttataac ctctgttttt    9900
tccagatatt gtttctggtc atcaacgggt gagtagcaga tctgcatcat ttagttgtgg    9960
tttctatgaa tagatgaata attcatactc acaccatatc ctacgggagc ctagagggag   10020
aaaaaaaaaa aagaaaagaa aataacaagg gaaggagaaa aagggccccc aggaattatg   10080 tgacatttt cccccagcaa ataagaaaac atctttgtca gagaaagata acgtaccacg    10140
ttggtgataa gagttggcaa ttaataatgc agagtgggag ccggcgtggc acagcgtgcc   10200
agcagaaaat ctgcacagct tttccctaac tgcctccata tctcccctgc ctgattccct   10260
gaggacccat cagtcagtcg tgtgtctgcc atgccaaaag cctcagtagt gacactgtgc   10320
tcaggcatac tgtaaggaac gctgtaattt gctcccactt cttcaccgtg gaggagtgac   10380
agagaataaa atgaccgcct gcagcacggc tatgcgtgga aaacacaagc agacccttcc   10440
gtgccctgca gagctgtccc acttgtgctc ttcccaggcc tcctgcggtg agtaccggct   10500
gttaggcagc aggaacctcg cctgttccag gatcttccag cccgtctgtg gcaccaataa   10560
catcacctac cccaatgagt gctcgctctg cagagaaatc ctgtgagtag cgatcgcccg   10620 attcccatc gtgatggctc aggtggcaga cagaagcctt ttgaattgtg actaatcacg    10680
ggtggattcg attttttttc cccctgtttc tgtcttccca gagtgcaggc tgtgtttctt   10740
ccttgtcaaa actcctgagt ctaattaatt agtggggctg ggcgtggaga ggcttgatga   10800
gtgaggtgac tgcatggcac caccaggtta accttcccc tccttctctc ctagccggag    10860
tgggacggtt gacaagaagc acgatgggag gtgtgtgaag gtatggttcc agctcagcca   10920
ctgtgtggag cgatgcaga atcccttccc agcactgatt gtacatttag aatgacagc     10980 tccaaaccca ttggaaatgt aacagaaagg aagaatttca ggtcttttat atatatatat   11040
atatatatat atatgtatgt attaatttca ttttgaacag tgcaaatctg tttcaacggt   11100
gagttttgag atgttatctt gtgtagcaca gctgacttaa aaacagaatc ctctcatttc   11160
aataatcctt tggtgttgtt gaaatagttc cctttagact tagacagaag tctgttgaaa   11220
ttaagaagtt ccccaaggaa gtctggattt tgactaaatc ataattttgt aacagggaaa   11280
aagaaaaaaa aaaaggattc catcagaaca tctaccctga ggtttgttta tcaatacacg   11340
gagctgccac gaagtggaga agtgtctcta tttttagatt agagagataa tgtaaagaaa   11400
cactccggct gtgcaattga acataatgct acaattttca cttcagtaca ctcagagtaa   11460
tggcaggaac accgaggtga gcatcagctc cattttcaag tggagcagac atttcacagc   11520
```

```
agcagttgct gccatgtagg gcatgttagg cacagatcct atgtggtggc atttggggtg   11580
gaaagcccta agatgacacc aacaaaaccc attctgtgaa cccatttcct ccaggattct   11640
gctgggctca tgtcctcaaa ggcaggactt cacctgcctg tgctcccttg cccgcactgt   11700
gctgggttgg aagctcacat ctccatacag ccccactcac cgtgagtctg ggggtgggag   11760
acacctctca caccatgcac cattacacag ggctgacgga agtgttgttc tgtggctgtt   11820
tcaggttgat tgcactggct acatgagaac aactgatggg cttggaacag cctgcatcca   11880
gcagtacagc ccgctctatg ccaccaacgg gctcgtctac agcaacaagt gcaccttctg   11940
ctcggcagtg gcgtgagtgg tgggtcacac cctgggtgct ggggtctggg tggtggtgtt   12000
tgcagcatat tgaggcttct ggagtggctg tgctgtgctc attcattctc aacttgcttt   12060
cttccccaag gaatggagag gacatagatc tgctcgctgt tggaaaagag cccgaggtaa   12120
agctcgaaag tctgcgctat gaactgttgt tataatatat tatacagcac aaattcagtg   12180
agtcagaact acgcaatagc aatgtcttca ctgtgctggt gtatttgtcc tggaaaaagg   12240
gtttgaggaa aatgactcaa gtatgccagg gtcagaggac gatgaacaaa actcctggct   12300
cctgtgtcag tatcacctgc acagccctg acaggggttg atgctcagag cattgttcag   12360
atggtggctg tgccagaggt gctcaccgct cctggtgagc gtgggctca tgcagcacca   12420 gctgtcatta cttgggtggg tggacttcat agtgtgctgt tggagacaca ctgcttcctg   12480
gcagcccctc tctgctggct gctgaaccag agcagagcag gtagcgggcc gccagccggg   12540
gagcactgct ttggctgtgt cgctgcttct gagggtattt agtagatttt tccctctgac   12600
ttctcctttt gtgctctgct gggcaagagc attagaattt gcagagttgc tagaacaaca   12660
ggagcctgca tctgaaaaaa tgttttttt gctttgccat gacataaatg taaagcgccc   12720
atgtaggaaa ataccaaa caaaggcttc tcaatacgtt cttgctccat tacctacaga   12780
ttgactgcag tgaattcaag agcactgatg cctactgcac tgaagagtac atgccccttt   12840
gcggctctga cggcgtaacg tatgggaaca aatgccactt ctgcattgca gttttgtaag   12900
tacagtgctc cccatgcagc catgaaacca ctgctgtgcc ggagtatgaa ggcagaagct   12960
gccaggaagc ctttgtgctc ccgttatccc cttggtaaat ccgtccccat ccccaacctg   13020
atcccagctc tacctctgct gtgccttccc caagcactgc agatcttgaa cacaggtgag   13080
tcttctccct ccctcaccat taaattcaga ttctcatttg cgggctcata gcgctcctga   13140
tccatccctg cgagagtaat ttgagtggta actgtagaag gagtatccaa aattacaggg   13200
tttgtcccag atctctctaa catgacaaaa cgtgtaacct ggggaatcag gagacgggtg   13260
aaggtgcaac tgggacagca tggagcattg gcttgcccat gcaaagtcag cagtggcacc   13320
atcagggcta taaaaccacc ttccatgtca gtgattttgg cctcctcctt tctctgcagg   13380
aagagtcatg gatctctgtc tctgcagcac cgtggagaat gctgaatgct ggatcgtaac   13440 ctttacccctc atccatcttt cacttccaaa gcctgcaatt ccaacacgct cttccccgct   13500
ccctgctgta cattgctttc tgccttgacc cgccagtaaa tcacagacag caactctctt   13560
cgccatgggc tggtgtgtta tttatttatt tatttattta ttgttgttat tatttttttcc   13620 agggcagagg taaagtctt caggctttca ggcacttatc tgtcaggcag gagaagtttt   13680
gaaataaacc acaataaagg ccaaagtgca acacccatca cacaaaagcc ataagccctc   13740
acgaaagtgc gtcacccccat tccaaccat cagaagagga aatgttgcta taaaacacat   13800
gctgctctcc ccagttctgt gtcttacagc acataaatgg atttgcttta agagtcagga   13860
tgtggctttg tagaagcacg gagccctgga ggaagcagtc cttttgggag ccttggtatg   13920
```

```
gaggaaagat ggctttgata cacctgagca aggggcaagt ctggcggcac gttacaagga    13980
ggcttatggc aaagggagga gactatctca cagggaagaa aattaggaac tgttgcttcc    14040 ttgaaggtg tgtcccttga gagtgtggtg atcagcagaa aattgcagcc agctgggcaa    14100
ggctgtaatg agcctaatga ggaccagagg agaaaccaga ttgggctcag gcttcttgga    14160
aaagagatct gaaaagctgc actgggagcg tttgaggcag aggaaagaga aaggactctt    14220
caggaaaagg tttgggagtc ttcatgccta gaaaagaaag gacagaagga gtgcttggta    14280
gctccaaggt cgtttctgtc tgcagtgaaa ggtgatgtgt ggatgatgcg tgtgagcgtt    14340
cacagtgatg tgccatctct ttgggcgagt caaggaatga gtatgcaaac aacaggtgaa    14400
aagtcccaag tgcctccact catgccacct tccccttcct ttctccacct cccatcctct    14460
cattacgtag gaagacattc agctgttcag gctgatattg aggacaaaat ctgtgacttc    14520
caagcttttc tctggcttta tttcctgaaa taggctgtat cttgacctag aaatcttatg    14580
ggtgcttcct gccagaagat gggaagctgt cctttaatag cgtgtcaggg cagtgctccg    14640
tcctaggaag acagatggaa ctttgaaatg tttattctat tagcacaggc agtataaagc    14700
acagtgtgcc tctgtgcctg ctggtgagaa aaggcaagct gcagagccgt gagggtgctc    14760
cctgctaatc tgcctagaag ggaaaagagt agacaagaaa tagcatatgc tactactgaa    14820
tgtgagcaga agacctttag tgaaggacac agctcagctg taatgtcctg ttggccagga    14880
ggtttgttga gttatcgcag agcggtagag ttctggtcag agcaggaagg tgccttcaac    14940
agcaagatcc catggtaggc ctcttctgca gtgtgctggc acaagcctgg tacctgctca    15000
ggagcaaaaa aaggctttgg aaaagctcaa agaagggctg atgtcttaca gggaaaggga    15060
gggcaaaagg caagtgcaga gcatatggct gtacagacaa aaacccttca gaaaatggaa    15120
aaggttttta tcaagtaagc ccagaagttg gcccagtgca ggtaaacact tggctaggta    15180
acagtgaggc tctgcccagc catacccatt cctctgtaag gcaaatccca ggtgcctttg    15240
tcttgtctgg tcctgttctg ttcctatttt tctgagaaat cagacagaac ttccccacct    15300
acagcatcaa gcagctactt tataggtgaa gaagtgcaaa gagaagcaat aaggataatc    15360
accacttggc taatttagtc tcttcctctc agcccacaaa ggactggtcc ctgtggtaca    15420
ttttctaagc cttttcccag tcagctgtgc tgtagcaaat gaaatgtttg gctagataaa    15480
gagctgaggt attagtgctg gggcggcgag cagtgtctgg agcaagaaaa ggcaaacgag    15540
ggattctgcg agtggcagaa ctaagcctga ttttgaatgg cgttgtggct ggcggacttg    15600
taaattatat gagaggctgt gctgtgagct caccctaata gacatctgag aactcacctg    15660
tcaatcgcgg ttcctctgct gtgtgggttt tatggtgtct agtgagctgc aagctctaat    15720
gctttcccag gtgcagggca gttgtggcat tgctctccta cagaaactct cacttgctgg    15780
ctgaggatgt ttaggaagtc cttggttgct agaaaaaata tattgaagtg ctttttttgt    15840
ttgtttgttt tccattcttg tgtgaaattt tgttggaatc acagaatcat agaggttgaa    15900
agagaaactc tggaaattat caagttcaac cccttgctaa agcaggcttc atacagtagg    15960
ttgcagttac aacatttgct ggggaaatga atatgaagat ctgtctataa agagtgttcc    16020
catagcactt gtttctttag gaaagcatgc tgaaattcta aaggctgtgc ctatctgaag    16080
agatactttg caagtggtgc aactaaatgc tgctcttggt ggagagatgg ctggagatgg    16140
atcgatggtt gggtgatctt cgtggtcttt tccaacttta atgattctat gattctatac    16200
tctttacaca gaatcagctg ggaatagagt gagagtctcc tgattcccca ccaaattcct    16260
```

```
ttgattgatg cttggtgtgg aagcagagct ctgggacacg ttggtgagtg tgaaaactgg    16320
aaaacattga cagctatagt ttaaatagtt cagggaggag aggcagccat cctatgtggg    16380
actctgcaca cggctatgag agcatcagtg cgcttctcca ccccaaccca acaaatttag    16440
agccatcctc caaaatagcc agggaacaac gcataattgg tttcacagac aacacattct    16500
catgctgtga tttatttcgt aatgtctggt gagtgtcatc acgccgtgct caaagcctgg    16560
agctggcatt cagcgaggac ccagagaatg aaaattacca gcttccccga tgaatcacca    16620
ctttgaaaat tcaccttgt gagaatcctg tgactattca gaaaaaaaaa aaaaaaagaa     16680
gaagaagaag aagaagatat tacagcccca agtctatcag tcatgtaatt agcccttct    16740 aggtttgatg tggacagggc ggcattccta aagcaccata acacggccg ggaccaataa     16800 tggctctaga atcgaagcgg agaagttctc acaattaagg tgaggaatga ggccagcagc    16860
ggataggtac ataaatacac ggaggcaggg ccgtgagcac gctgtgggct tgtggctgag    16920 acaaccctc ccaaaccggt cgcttgccgg ggactaaaag agcagcatga aggcaacagg     16980
cacctcggtg ctcctcagcc tgctgctgct gctgtcgttc ttctcgggta agttatattt    17040
ctgtagccta gaaagaaact ttatgacgag agcaacttca gagagccttg atcaacggat    17100
gacaggcttg aagagaaagc tgagcaagta gaaaatatct gcgggactcg cttgcttgtg    17160
tcacatcttt ccattcctcg tgtgcctccg cagtgaataa cactgtggag gtgtcactgg    17220
gagacagaat gagcaaattg taagcagctc gttcagcaga ggcaccaaag cagagcgtaa    17280
ttatgagttt tggtggaaat gtttgctgga gagctttgct gaaccagtta gagaagaaac    17340
tcatacctca gggtcatcag ctcctgttct gatgctaagc acttggggt tggtgttctc     17400 ctcagagatg tggcagcgta attagatgaa agtttcagct tccaaatacg ttgcagagga    17460
gggctcgaaa attaaattca gatgtcctcg aggaacccga acaaagaggg caaattgaaa    17520
gggtccagcg tttatttatc ttgaggttta cacgtctctc tgttggtctg gggaggctgg    17580
ctgatggttt gggggtgtgt agggcacacc ggggtgctca aatgctcgcg tgcggccgat    17640
gcgaatgtgg aagcgttgcg gtggccatta ctgaagactg cagaccaagg attatttata    17700 cttgttttc tgtgaataat ttgaataaag aattcgcttg agaaaatcgc aggctgtgca     17760
tggagagaag aggtgaatta cttgtacac atcattaatt atgaaatatt catctgtctt     17820
taattgagtc ttaattgggg ctgggttccg tcagagtgct aaagcttctt tccaaggcca    17880
ggcagaatag cagcaaactc tgtgatctca aataagataa acagatgcca agagacgttc    17940
tcacaaagtc ttgtgtagct gcatgtaata tttataaaaa ttatctaatg agctgttttg    18000
taaataatat gcagatagcc ctaacggcgg cttccctgtc cagcctagct gaggatgtga    18060
cagatacagc agtggcaagg atcaaacact gaaaggcatc gcagcaggca gaagctgggt    18120
ggggtgatgg atggtcccgc tgagcgtgat gctgcaatgc tcccagcctg caccctaacc    18180
aaagggatgc cccattgcaa tgcgccccag cccctgcagc gctgtgtgca gcccactccc    18240
tgtccccgac accacaggat ccatcccgtg gctgtgacct ggcccatgc aaagtttgca     18300 ggcaggaaat agcaaagagg atggactgat tgtctccagg cccagagcct gtgcctgcag    18360
caggtatttt tgctctgctg ctgtctggca ctgcctgttc tgccccagat cacgccaggc    18420
tatccctttg tatctcatcc ggatgaggct gttctgggag cctcggctgt gctgtactgc    18480
agacggctct gatgctgact gcggggtctc ctccatctcc cctgtgtgct tttgttaccg    18540
tactggccaa ttttgtaatt cagaggtgca agagcctaaa agccataaga ctcaatgaag    18600 cttttaaaatc tctgctgaga gaggctcagc tcttacatag ctccccgctt cccggcggt    18660
```

```
ggctgcctgc caggagatg ggtttatgtg tctgtggtgc agttagcagc tgaatgactg    18720
attacatggt atttagtaa cattttcaa atagcaaaat actgaaaagc aattccgata     18780
atgtatttcc tacccctcct ccaccacaca gaacggcaga ggagggaaaa cctggtgtgt   18840
gctgtgctgc agttttgcaaa gggatttgtg acttcggttc agtcctctca gaaaataatg  18900
ctaatgtgga taaaatcttt tttttgttg caattctagg tgtagcagct caagacattg    18960
aagaggttag tgcagctctt tctgctttct gaatctgcat tttctcctgg ctctggaaga   19020
atgcttttct aacagatctt ggtgcattgg tgcatgctga actgctttgg gttttgctgg   19080
gatcaggtgg gtcctgccaa ggtgccccaa tgcttcggag tgctcacaca gtacaggggt   19140
gttagctatg ccacagtag caaacaagtt ggggatgatt tagctggttt agcacatgct    19200
ccccatggtc tgatccagca cagggctgtc tgcagtatcg cttctgtctg ctttgctcct   19260
ccacgaaaca aatgtgatat caggagtgat atactccttt aaaccatatc cataactggg   19320
gcttgtccaa aagcctgttc acttcataga atcattaagg ttggaaagac cactatggtc   19380
atcgagtgca accactccat gcccagatcc ctgtgtatgg cagccccagg ccacgtggtg   19440
gtgtgagctg catggtaccg ggcactgata tgggctgca tcagtgctga tgctctcctg    19500
ttgaacccac tcatgttctt ggaacaccag agctgctccc tggtggtgac agcttccctc   19560
ctctgccaca gggcagaaat tccccattt cagccagttc tgacaggcct ttgtttttca    19620
agtaagcagg ccgtgcctcg ttgctgcttt tggcctctgg gtgggaagaa gatcacatta   19680
gagatcttct ttcctgtttg gaaagcgaaa cccgacggtt tattgctgtt attatttttg   19740
atttcttttg cagatctgca aagagttctt aaacaggagc gtgttctgca ccagggagtc   19800
caaccctcac tgcggcacgg atggcgtgac gtacggcaac aagtgtgcct tctgcaaggc   19860
cgtgctgtaa gtggggcgg tgggatacgg acccacacag ggatggtcca cttccaaccc    19920
cgcgctgctg ctcccctcac acagagcaat ccctggccat agaatcatag aactagaaa    19980 tggttaaggt tggaaaagac caataagtgc atctagttca aatggcagct cctcaccgcc   20040
acgcttggga atatttcagc ttaatgttga ttcatttcta ggcttagtgt gatgctcata   20100
gccgtacaga gatggcacag agcctgggag gccattgtac ctgcctgtac cttctgcgtg   20160
ggctaaattg atgcacattt tcctctgtgt gccacaggct gaagctctcc ctgtccacac   20220
ctctggatgc tgaagtgtgt ggaggaacgc aggcttatgc atgccaaatt attagaggaa   20280
agtcatagac tcgtagaatc atagattcgt ttgagtcgaa tgggaccttt gaaggtcatc   20340
tggtccagca tccctgcaac gagcagggaa agtgctgaaa tgaaagtctg aatggactta   20400
gtggaaaagt acacaaaatc tcagaggaag ggctgcagtt tctcctctcc tgtctcctct   20460
aaaggagctg taataggagc caacacctct ggactgaagg cctgcaaaaa ttgatttatc   20520
cttatcaatc ctgcactctg gaggctgcct tatcctaagg gaaattagag aagagggaaa   20580
gatggcttga tgctccctgt gaggcaccag agtgaggcaa atgatcgtgc tcggagggac   20640
aagctccctg tcccagccgc tgtgtctgtg ctggatgcca tacactgctt tgtttccata   20700
ccgctccttt tacaggagga gtggagggaa gatacgattg aagcacatgg ggaagtgctg   20760
agcctgagca ccaagcactg atcttcgtcg gtcacaggtg caggagcctg gcacggcag    20820 cagctgtcct catctctgcc atatctgctc aataaagtaa agctcagcac acctccttga   20880
ctggattcct ttttccataa cacccggata agccttccat gcagccgtgc tagcagctaa   20940
aatgtttgcc gcactgtgct gttacatctt agaatcacag aatcaggcac catgctgcct   21000
```

```
gagcaggagc aatgattccc acagctcttc catgccatgc catgccatgc catgccatgc    21060
catgccatgc catgccatgc catgccatgc catgccatgc catgccatgc catcccatcc    21120
catcccatcc catcccatcc cactgacaaa tggacacatg gccacccagc ttgactgtcc    21180
catgggtggg tgacagcatg caacgttgcc tctcagcagc ctccccatat gtgtccctct    21240
cgctgaggtg tgagcatgaa ggtggcagag agctatgagt ggtgtggctg tggatgcctc    21300
atctgcttgg gaagccagaa gcaaacaggc tgaggctgag gagtgttgct gcatgtaagc    21360
ctgcaccggg aaggtggcag gggaagctgg ctttaggcag aaacacaaag gctttgcttt    21420
ccttgtgtgt cctaagagag gactttgcct caaagactgt caactcgcca gcatcaggtt    21480
gcagttgcac acaaacttga tttctttctt tagttttcac actgctgctc tctctctcct    21540
tgatgctggc tggaaaatcc ttctttgcgc cagcgaggga aaataaagcc tatagtctct    21600
ccccattcgc tgtacaaaat atacacaggg aaatgcttgt ggcatcccct cgttaaaacg    21660
ttggcagcac atcaatggga ctctactcac ttaatgttga acacttaagt ttcaaaggga    21720
gctttagatt ttatcgtgag gtcagccaac tcattttgca aacacctcta tgctgagcat    21780
ctcagctcct ggatggtgtt tggacagagc tgagtgtttg cctgtggtgc cacgctgcag    21840
gctttgaagt gaattgggac attatatttt gtagccaagg agagttgcag tttgctttgt    21900
tccaattcag atgtttcttt agtaaacaca acagctagac ctccagaaca tggataagct    21960
tgaggggagg aaaaagcacc tcctgcacga ggacagctga tcacaaagga ccccagtggg    22020
cagtgggaga accttcatca tcctctctac cgcctggatc aggatgagcc ctgcataccc    22080
tttccaactg gagttaccct gtgagccaac ttgtggctct ggagtagtgc tgtatctcaa    22140
tacagtttct cagatgggaa gaggcatttc aatgagaggg gggatatggg acatttctat    22200
gcctgagatg gctctcggag actccaaaag cctcacggcg tatccccatg cctaatcctt    22260
tttaatctgg aggctgaaat aacaaggaca gatcacaaga gaacagaagc ggcgagactt    22320
ctctgcttta taatcagcct gcattttgct ctttcagtgc aaacagcaaa tagaaccgcc    22380 tctgtaccccc tccagaccca accaccatcc ccagcaacac tgtggcaggc tggagaaggg    22440
tggctctgcc cctccttgcc tcaactggtt gtgtcagcac gaccataacc agagctctcc    22500
ttggccccag ctgggcttat ccatgtaaac ctctcagtgc cccaggagct ggctggtggt    22560
cctgtccatt tcactttcct ccagcaggtg ttcccttttaa caagcatcca agtgcctgga    22620
gcaggagcag gcactgcaga agatgagctc aggcaaggac atggcatgtg gggatccatg    22680
ctgttgtgca atgcagatga cgttagatac gtgcaaagca gatctcagca atcacccaac    22740
gactcataac tgcaatcatg gaacgcaatt gcatctggaa gtataaaagc acagtgatac    22800
caggaagctc ttgttaatgg cacagccatt ttggagcaat ttgcccaggt ggggagagcc    22860 ctcacacgcgc cttcagtcac agggagtggt gtgagtgccc ccatggctgc tcccagcccc    22920
cagccctggg tgatgggggt cacttggctg taaccctctg aacacaggga cagtgagaca    22980
gccctctggc ctggctgagc tcttggctac gtccagctgc agtcctgggc acatactgaa    23040
ccagaaagca agcattcagc tggtattttt ccttta attt ccttcctcca cattttaagt    23100
tgtgggattt tttttttttt tttttgacag ctttgagaga tgagtgagtc acgaagcact    23160
cgagatctct attagataac agagcatctc tgcagctctt cctggggagg gagttccttg    23220
gaccaagggc caaggctggg tgagaattgt cccagcatca cagtggctgc tccatcacct    23280
gacacagccc ctctgcagtg aaacaaggga agcattacat ctttgcacgg ctgctttcac    23340
tgaacaaaaa gcgctgcttc acagctgagc accatgatga aggggaagga gcatctccat    23400
```

```
gatgaagggg aaggagcatc tccacatctc catcacgagc tctgctctgc tggtgatgcg    23460
gctgacacca tggtgtgccc tgactcctgg cccatttaac tgctgtgcac cagtgcctcc    23520
tccccagcat agccctgtgt ccctgccaca actcattgca atcctttgtc ctacttcttc    23580
ccttgacatt cacagctctt gataaggctt tttgagccac tcctggctga tgtgggctgg    23640
tggttcctgc tgcagggttc ccaccaccca gctgggcagc attcggttgt tgttccagtt    23700
cccaggggat tgggacagat tggaagggtc tttgggactg tggaagagta tctcctgaag    23760
tcagggcaga ctgctcagcg ctttgtccca tccagacttg aaaacatcca agggtggaga    23820
acacacagac tccctgggct gccagtccca gagtttgact gtcatcacgt tgaagacttt    23880
ttgccttgtc tccatttgca acctctttcc tttcagctgc cccatctctc agccatgcac    23940
cactggggag cccagctctg tctggtcagg aacagagccc ttacagagcc acagcatcct    24000
cctgaagtgt ccatctcacc actcagcctc agcaagtgct ccagccctca actcccattt    24060
tccattatct ttctatcact ggatatggga gggaaggcag agctgtgggg ccaagagaaa    24120
cgattgctca ggaggcagtt gggagaactt tattgcaaag cactgaagag atataaagtg    24180
acatttgcag gaaaaagtag aagggtatct gtgtgtgttg gttcctttaa ggattagaga    24240
gcagctgagc tttgggatga gagggctccc agatgctgtg aatcagctaa cagatccctc    24300
caccccgtca ttggtggtga agttaaatag gggcccaggg gaaacatcag ggttgttttt    24360 cttttttacgg actccagagc aaggagaagg tgaggggtt gtgctttgga atgggagtga    24420
aagagtttgt tggtgttttc ctctccccag aataagtagt gtggtgtagg agcgtctcat    24480
aggagtagct gcgttaattg tggctggtgt tagcatccta taatgttgct ccagaaatgc    24540
tggagcaggc ttataatgat gtgtatgtat taccataata catgaaggga gaatgggggg    24600 gggggggta gatttaagat gtatgcccct agaaaggcgg gtgtcactta aagaagtact    24660
tgctttatag ctccagtgat agaattcatt gagatactct gaacctatgg ggcatgaagt    24720
gaccagatct tcagtttggt cagctctggg ggtttctggg gggagcgggg atagagcctc    24780
aatccaggtc tgaaagacaa ggctgagatg tgctgggcct ggggtgctgc cctgagcaac    24840
gtggggctgg ccctagagag cagcattagt gcctgcagca gggctggccc ttgtgcccag    24900
tgtgtggggt aaggtgggga acgtaggtgc tgcataatgt ggtgcttctg atctaaaact    24960
gctctgttaa ttgggagtga ccagagatgg ccctatggct ttcttcccaa agagctctgt    25020
gtccttctct gcagggtaat ctgtgataaa aacatcgcct atgctctgcc ctgcagatgc    25080
aggggttttt gtcatcctcc ttctcgagac atactctaat ccttacgcaa gcagggagct    25140
ccaagctttt ggtgataacc tctcaaggag gagctggaag ggcagctctg ccgagcagtg    25200
actgcgctgc acgggcgca tcctgcagga ggcggtggtg taagcgggac tccgctcgtt    25260
cccggctatg ggctccccc tgctgaccgc cgggcgtgg ccaggagacc tcggggccgc    25320
tgctgcccct cggtggtgct tttcgggaca gctttcagga tggggcagcc cagctgctct    25380
cgcggggaat taagcggctc ggtgcagggc ggcacggcgc tgagctgccc cagcaaagcg    25440
ccgctcgtcc cgcggcacct tcggtagatg ctctctgctt ggcagctcct tggtcgttct    25500
cttggccggt ggccacccca gcatcgctcg gggctcggtg ccatcccccc cagggcctgc    25560
ggaggtgccg gtgcccgtcc cggggtggc ggacgggcgg tgcagtaccg atgctgggcg    25620
ctgggtgctg ccgcagaccg agcggcgctg cgcggctccg gggcgctcct ggagtgcgag    25680
ctgagcaacc tggtagaaaa ataagtgttg tcccgtgata aacgtcatcg tgctgagctc    25740
```

```
tcagactctg ccagaggcct gaatgaagct gcgtcagggg agaatcaggt tggggctaag   25800
gaaaggtcct gccccagagg gcggtgggta tagaaggggt gcccagggca gtgggtgcag   25860
tgctgggctc ccagagctgg aggagcgtct ggacagtgct caggtttgga tgttgggtgg   25920
ttttctgaag ggacggattc tgggctcgtt tatcctgagg gtcccttcca acttgggttg   25980
ttctattcaa tgaatattgt ttatgttcat tctattctat gatcttgttc aggctctcac   26040
tgctgcctcc aagggttcag ctcccccaga gctggcaggg cttcagccac ttgcttacag   26100
tgctcatttc atgcctggcc catggcttct gcctgagcct tgtgggagat cagctgctgc   26160
cagaacccca gccctcagca ctccacttgc ccagcttgct gccttagtag tctaacttgg   26220
cagtggtctg acatgacttg aggttgtttt ttatttccaa ggtgccactg actttttttcc   26280 ttccatagtt tctggaagca tttccttcct acttgactga gtcgtgctct gtggatctgt   26340
aattatccac cttggctatg tgtcctttac gggattttat atgttaacct cccaagatca   26400
ttttgctgct ctcatcttag tggctgctgt gagctccacc agcaccacac tggatgagct   26460
gcaggctgag gccgggcacc tctcctgact ctgctcttct ctgacccag agctgtgcag   26520 ttgggatcct aacaccatgc agatgctcca ggacctgcac cgagcccag cactggcact   26580 catctcttct ttccacccct ctgagagcaa caagtggctc tgcaatggca atgtaagtga   26640
aaccgggcgg gtatcttaga gcacctggaa gcttgcatgc ctgcaggtcg actctagagg   26700
atccccgggt accgagctcg aattccaggt accgtcgacg atgtaggtca cggtctcgaa   26760
gccgcggtgc gggtgccagg gcgtgccctt gggctccccg ggcgcgtact ccacctcacc   26820
catctggtcc atcatgatga acgggtcgag gtggcggtag ttgatcccgg cgaacgcgcg   26880
gcgcaccggg aagccctcgc cctcgaaacc gctgggcgcg gtggtcacgg tgagcacggg   26940
acgtgcgacg gcgtcggcgg gtgcggatac gcggggcagc gtcagcgggt tctcgacggt   27000
cacggcgggc atgtcgacag ccaagccgaa ttcgccctat agtgagtcgt attacaattc   27060
actggccgtc gttttacaac gtcgtgactg ggaaaaccct ggcgttaccc aacttaatcg   27120
ccttgcagca catccccctt tcgccagctg gcgtaatagc gaagaggccc gcaccgatcg   27180
cccttcccaa cagttgcgca gcctgaatgg cgaatggcgc ctgatgcggt attttctcct   27240
tacgcatctg tgcggtattt cacaccgcat atggtgcact ctcagtacaa tctgctctga   27300
tgccgcatag ttaagccagc cccgacaccc gccaacaccc gctgacgcga accccttgcg   27360
gccgcatcga atataacttc gtataatgta tgctatacga agttattagc gatgagctcg   27420
gacttccatt gttcattcca cggacaaaaa cagagaaagg aaacgacaga ggccaaaaag   27480
ctcgctttca gcacctgtcg tttcctttct tttcagaggg tatttttaaat aaaaacatta   27540 agttatgacg aagaagaacg gaaacgcctt aaaccggaaa attttcataa atagcgaaaa   27600
cccgcgaggt cgccgccccg taacctgtcg gatcaccgga aaggacccgt aaagtgataa   27660
tgattatcat ctacatatca aacgtgcgt ggaggccatc aaaccacgtc aaataatcaa   27720
ttatgacgca ggtatcgtat taattgatct gcatcaactt aacgtaaaaa caacttcaga   27780
caatacaaat cagcgacact gaatacgggg caacctcatg tccgagctcg cgagctcgtc   27840
gacagcgaca cacttgcatc ggatgcagcc cggttaacgt gccggcacgg cctgggtaac   27900
caggtatttt gtccacataa ccgtgcgcaa aatgttgtgg ataagcagga cacagcagca   27960
atccacagca ggcatacaac cgcacaccga ggttactccg ttctacaggt tacgacgaca   28020
tgtcaatact tgcccttgac aggcattgat ggaatcgtag tctcacgctg atagtctgat   28080
cgacaataca agtgggaccg tggtcccaga ccgataatca gaccgacaac acgagtggga   28140
```

```
tcgtggtccc agactaataa tcagaccgac gatacgagtg ggaccgtggt cccagactaa    28200
taatcagacc gacgatacga gtgggaccgt ggttccagac taataatcag accgacgata    28260
cgagtgggac cgtggtccca gactaataat cagaccgacg atacgagtgg gaccatggtc    28320
ccagactaat aatcagaccg acgatacgag tgggaccgtg gtcccagtct gattatcaga    28380
ccgacgatac gagtgggacc gtggtcccag actaataatc agaccgacga tacgagtggg    28440
accgtggtcc cagactaata tcagaccga cgatacgagt gggaccgtgg tcccagtctg    28500
attatcagac cgacgataca gtggaacag tgggcccaga gagaatattc aggccagtta    28560
tgctttctgg cctgtaacaa aggacattaa gtaaagacag ataaacgtag actaaaacgt    28620
ggtcgcatca gggtgctggc ttttcaagtt ccttaagaat ggcctcaatt ttctctatac    28680
actcagttgg aacacgagac ctgtccaggt taagcaccat tttatcgccc ttatacaata    28740
ctgtcgctcc aggagcaaac tgatgtcgtg agcttaaact agttcttgat gcagatgacg    28800
ttttaagcac agaagttaaa agagtgataa cttcttcagc ttcaaatatc accccagctt    28860
ttttctgctc atgaaggtta gatgcctgct gcttaagtaa ttcctcttta tctgtaaagg    28920 cttttttgaag tgcatcacct gaccgggcag atagttcacc ggggtgagaa aaaagagcaa    28980
caactgattt aggcaatttg gcggtgttga tacagcgggt aataatctta cgtgaaatat    29040
tttccgcatc agccagcgca gaaatatttc cagcaaattc attctgcaat cggcttgcat    29100
aacgctgacc acgttcataa gcacttgttg ggcgataatc gttacccaat ctggataatg    29160
cagccatctg ctcatcatcc agctcgccaa ccagaacacg ataatcactt tcggtaagtg    29220
cagcagcttt acgacggcga ctcccatcgg caatttctat gacaccagat actcttcgac    29280
cgaacgccgg tgtctgttga ccagtcagta gaaaagaagg gatgagatca tccagtcgct    29340
cctcagtaag cagctcctgg tcacgttcat tacctgacca tacccgagag gtcttctcaa    29400
cactatcacc ccggagcact tcaagagtaa acttcacatc ccgaccacat acaggcaaag    29460
taatggcatt accgcgagcc attactccta cgcgcgcaat taacgaatcc accatcgggg    29520
cagctggtgt cgataacgaa gtatcttcaa ccggttgagt attgagcgta tgttttggaa    29580
taacaggcgc acgcttcatt atctaatctc ccagcgtggt ttaatcagac gatcgaaaat    29640
ttcattgcag acaggttccc aaatagaaag agcatttctc caggcaccag ttgaagagcg    29700
ttgatcaatg gcctgttcaa aaacagttct catccggatc tgacctttac caacttcatc    29760
cgtttcacgt acaacatttt ttagaaccat gcttccccag gcatcccgaa tttgctcctc    29820
catccacggg gactgagagc cattactatt gctgtatttg gtaagcaaaa tacgtacatc    29880
aggctcgaac cctttaagat caacgttctt gagcagatca cgaagcatat cgaaaaactg    29940
cagtgcggag gtgtagtcaa acaactcagc aggcgtggga acaatcagca catcagcagc    30000
acatacgaca ttaatcgtgc cgatacccag gttaggcgcg ctgtcaataa ctatgacatc    30060
atagtcatga gcaacagttt caatggccag tcggagcatc aggtgtggat cggtgggcag    30120
tttaccttca tcaaatttgc ccattaactc agtttcaata cggtgcagag ccagacagga    30180
aggaataatg tcaagccccg gccagcaagt gggctttatt gcataagtga catcgtcctt    30240
ttccccaaga tagaaaggca ggagagtgtc ttctgcatga atatgaagat ctggtaccca    30300
tccgtgatac attgaggctg ttccctgggg gtcgttacct tccacgagca aaacacgtag    30360
ccccttcaga gccagatcct gagcaagatg aacagaaact gaggttttgt aaacgccacc    30420
tttatgggca gcaaccccga tcaccggtgg aaatacgtct tcagcacgtc gcaatcgcgt    30480
```

```
accaaacaca tcacgcatat gattaatttg ttcaattgta taaccaacac gttgctcaac   30540
ccgtcctcga atttccatat ccgggtgcgg tagtcgccct gctttctcgg catctctgat   30600
agcctgagaa gaaaccccaa ctaaatccgc tgcttcacct attctccagc gccgggttat   30660
tttcctcgct tccgggctgt catcattaaa ctgtgcaatg gcgatagcct tcgtcatttc   30720
atgaccagcg tttatgcact ggttaagtgt ttccatgagt ttcattctga acatccttta   30780
atcattgctt tgcgtttttt tattaaatct tgcaatttac tgcaaagcaa caacaaaatc   30840
gcaaagtcat caaaaaaccg caaagttgtt taaataagga gcaacactac aaaaggagat   30900
aagaagagca catacctcag tcacttatta tcactagcgc tcgccgcagc cgtgtaaccg   30960
agcatagcga gcgaactggc gaggaagcaa agaagaactg ttctgtcaga tagctcttac   31020
gctcagcgca agaagaaata tccaccgtgg gaaaaactcc aggtagaggt acacacgcgg   31080
atagccaatt cagagtaata aactgtgata tcaaccctc atcaatgatg acgaactaac   31140
ccccgatatc aggtcacatg acgaaggaa agagaaggaa atcaactgtg acaaactgcc   31200
ctcaaatttg gcttccttaa aaattacagt tcaaaaagta tgagaaaatc catgcaggct   31260
gaaggaaaca gcaaaactgt gacaaattac cctcagtagg tcagaacaaa tgtgacgaac   31320 cacccctcaaa tctgtgacag ataaccctca gactatcctg tcgtcatgga agtgatatcg   31380
cggaaggaaa atacgatatg agtcgtctgg cggccttttct ttttctcaat gtatgagagg   31440
cgcattggag ttctgctgtt gatctcatta acacagacct gcaggaagcg gcggcggaag   31500
tcaggcatac gctggtaact ttgaggcagc tggtaacgct ctatgatcca gtcgattttc   31560
agagagacga tgcctgagcc atccggctta cgatactgac acagggattc gtataaacgc   31620
atggcatacg gattggtgat ttcttttgtt tcactaagcc gaaactgcgt aaaccggttc   31680
tgtaacccga taagaaggg aatgagatat gggttgatat gtacactgta aagccctctg   31740
gatggactgt gcgcacgttt gataaaccaa ggaaaagatt catagccttt ttcatcgccg   31800
gcatcctctt cagggcgata aaaaaccact tccttccccg cgaaactctt caatgcctgc   31860
cgtatatcct tactggcttc cgcagaggtc aatccgaata tttcagcata tttagcaaca   31920
tggatctcgc agataccgtc atgttcctgt agggtgccat cagattttct gatctggtca   31980
acgaacagat acagcatacg ttttttgatcc cgggagagac tatatgccgc ctcagtgagg   32040
tcgtttgact ggacgattcg cgggctattt ttacgtttct tgtgattgat aaccgctgtt   32100
tccgccatga cagatccatg tgaagtgtga caagttttta gattgtcaca ctaaataaaa   32160
aagagtcaat aagcagggat aactttgtga aaaaacagct tcttctgagg gcaatttgtc   32220
acagggttaa gggcaatttg tcacagacag gactgtcatt tgagggtgat ttgtcacact   32280
gaaagggcaa tttgtcacaa caccttctct agaaccagca tggataaagg cctacaaggc   32340
gctctaaaaa agaagatcta aaaactataa aaaaataat tataaaaata tccccgtgga   32400
taagtggata accccaaggg aagttttttc aggcatcgtg tgtaagcaga atatataagt   32460
gctgttccct ggtgcttcct cgctcactcg agggcttcgc cctgtcgctc gactgcggcg   32520
agcactactg gctgtaaaag gacagaccac atcatggttc tgtgttcatt aggttgttct   32580
gtccattgct gacataatcc gctccacttc aacgtaacac cgcacgaaga tttctattgt   32640
tcctgaaggc atattcaaat cgttttcgtt accgcttgca ggcatcatga cagaacacta   32700
cttcctataa acgctacaca ggctcctgag attaataatg cggatctcta cgataatggg   32760
agattttccc gactgtttcg ttcgcttctc agtggataac agccagcttc tctgtttaac   32820
agacaaaaac agcatatcca ctcagttcca catttccata taaaggccaa ggcatttatt   32880
```

```
ctcaggataa ttgtttcagc atcgcaaccg catcagactc cggcatcgca aactgcaccc    32940
ggtgccgggc agccacatcc agcgcaaaaa ccttcgtgta gacttccgtt gaactgatgg    33000
acttatgtcc catcaggctt tgcagaactt tcagcggtat accggcatac agcatgtgca    33060
tcgcatagga atggcggaac gtatgtggtg tgaccggaac agagaacgtc acaccgtcag    33120
cagcagcggc ggcaaccgcc tccccaatcc aggtcctgac cgttctgtcc gtcacttccc    33180
agatccgcgc tttctctgtc cttcctgtgc gacggttacg ccgctccatg agcttatcgc    33240
gaataaatac ctgtgacgga agatcacttc gcagaataaa taatcctgg tgtccctgtt    33300
gataccggga agccctgggc caacttttgg cgaaaatgag acgttgatcg gcacgtaaga    33360
ggttccaact ttcaccataa tgaaataaga tcactaccgg gcgtattttt tgagttatcg    33420
agattttcag gagctaagga agctaaaatg gagaaaaaaa tcactggata taccaccgtt    33480
gatatatccc aatggcatcg taagaacat tttgaggcat ttcagtcagt tgctcaatgt    33540
acctataacc agaccgttca gctggatatt acggcctttt taaagaccgt aaagaaaaat    33600
aagcacaagt tttatccggc ctttattcac attcttgccc gcctgatgaa tgctcatccg    33660
gaatttacat ctggaattac gtatggcaat gaaagacggt gagctggtga tatgggatag    33720
tgttcaccct tgttacaccg ttttccatga gcaaactgaa acgttttcat cgctctggag    33780
tgaataccac gacgatttcc ggcagttct acacatatat tcgcaagatg tggcgtgtta    33840
cggtgaaaac ctggcctatt tccctaaagg gtttattgag aatatgtttt tcgtctcagc    33900
caatccctgg gtgagtttca ccagttttga tttaaacgtg gccaatatgg acaacttctt    33960
cgcccccgtt ttcaccatgg gcaaatatta tacgcaaggc gacaaggtgc tgatgccgct    34020
ggcgattcag gttcatcatg ccgtttgtga tggcttccat gtcggcagaa tgcttaatga    34080
attacaacag tactgcgatg agtggcaggg cggggcgtaa ttttttttaag cagttattg    34140
gtgcccttaa acgcctggtt gctacgcctg aataagtgat aataagcgga tgaatggcag    34200
aaattcgatg ataagctgtc aaacatgaga attggtcgac ggcccgggcg gccgcaaggg    34260
gttcgcgttg gccgattcat taatgcagct ggcacgacag gtttcccgac tggaaagcgg    34320
gcagtgagcg caacgcaatt aatgtgagtt agctcactca ttaggcaccc caggctttac    34380
actttatgct tccggctcgt atgttgtgtg gaattgtgag cggataacaa tttcacacag    34440
gaaacagcta tgaccatgat tacgccaagc tatttaggtg acactataga atactcaagc    34500
tttgtgcttt ctgcctgaat aaaagaaacc tgaactctgt tcacccagtc cctgtcaggc    34560
aattactgac agagcaccta tggtctgtgt ttggccagaa cataggctaa ggaagatacc    34620
tcctgtttat aaagcacgcc tttggcatct ggcaagtaat tagtgatggc gcatgagagc    34680
tctgactagg gcagggtgtg ggacaggctg gctctaattg tgccctgttt atcttgttga    34740
tgcacacggc tggtttcttt cacccacagc tgtctctcta gacaacatac ctttatggag    34800
aggaacgtgt cttttccaat cttgggtttt cattcagaat tggagtgaac tggtctccat    34860
cagatagcat tggctgcggt gatttattct tttacacttc ctagttaagc aggataactc    34920
tctggctctg ctgtgtctag gcaatttaaa tgatttataa agcatagctg ttttaaggaa    34980
atcttttttt aaacatttga cttgccaatg tgtggtccta aaggcagaag gactgttcca    35040
gagtgtcagg cagagaccta ccctggattt cgttgttcag ctacccattc agtgtggctt    35100
ttggcaagga attctctgga cctgacttcc ctacctgcag agctgggata agctatcaaa    35160
ccatctcctc cacacactgt gagggtggga aaaaaaccca aacccttaaa agtgctgtat    35220
```

```
aaaggcgcct taaggctcag tatagcatgt gtgctgctga tgccccagac ctgtttgcgg   35280
gtcctgaagg tcataggaga actgctcaga agagacagaa atgcttaaga aggttttact   35340
acaaaagtct tgtgatgtta acacataata tcacattgtg cagaaggtac aaatgccccc   35400
tcctatccct gcacacctgg aagctcaagg tatggaaggg tttgttgtct gcagcctctt   35460
cgctgccctc tgcttttaa gatcctgggt agtgtgctca gtgtgtgccc tcagcagttt   35520
gggaaacgga catcttcatg caaaattaag caaggaagtg ttgcttttat actcagagta   35580
gaatctaagt tcttcaggca ggctcttgtg tgccgcctct attagaaata aaactccccc   35640
ggatcagaag atgaatgtgc tcagctaaga acacagattt atttgcttta caatgcgtgc   35700
tatggtttaa gaaaaacaca tcaggcaaac aatttatggt ttgccactga gttgtgcctg   35760
aaggaaacac aactgttaga gatgtaattg attgggcggt gacgctgtgt ggattcatgg   35820
gagatgcatc ttggtcagca tgtctgtgtg aaaccacatt tctggtgctg ctgcaggacg   35880
agtgccggga gttccgggat ctgttcaaga atggaagct tcctgcacg agggagaatg   35940 atcccgtccg ggattcctcg gggaagcagc acagcaataa gtgcatcatg tgtgcggaga   36000
agttgtgagt agaggaagcc aatgtttgtt atcgagagtg gcaatgggc cggggtgggc   36060 tcctacagca atgttctcct cactttctca tccttctctt tcagcaaaag ggagaatgag   36120
cagaaggcga cctcaaccag agggaaacaa aaggtgaggt aaagtattg ggttcatata   36180 caagtctata ggattcttac ccaatattac cacacttgat ttctttgtca ctctggggat   36240
ccatgtggct tttcctgctt gtatctcgtt gatgctcttt catgccctga gagaatagtt   36300
tgtctgaacg ctgcagtcta tcccactgac cgcagtgaca tgggagcaaa ccccatcgca   36360
ataagaagct gagcagaact gccctgacat ctggcacaag gcaagaagg cactgctgct   36420 gagagcgcta atgaggttga aaagaaaatc tgggtgagaa gctttaaatg tgagctctga   36480
gatgctcaaa agttcattat gtcgtgggag gagagttcag ccctgtgctg tccctggggt   36540
ggctcggttt cagctttccc tgattggaaa cctcactctc atgatgcagc tgctgtgccc   36600
ttgtgcaccg atacttctct ggtgagagca attcagcaag gggaaggaaa agaagcact   36660 aagtaaatct tgccatttct gtcttgcgag gaactggtac ggtcccctta agcctcattc   36720
ttggggataa tcctgtttca gtgcttttcc taatgacagt ggcacaaaaa aaatggaagc   36780
gttaatgaaa cttgctgatg gcaaagctgg gagggaggat cagcagatca ctcaggacta   36840
attggatagc actgaggcct ggagtaatag aaacaagata aaatgtaata acagagagtg   36900
caagatcaca caggcagtga ttaacgagaa ttcctgctca tcaattagaa atgacaaagg   36960
ataagaaagc tctgcattta ttagtgggtc acggatgcgg caggcctgag aaggaggcaa   37020
atgcacatct cagcaaggtc tgtgcagcag aggtcgggct ggcagcaaat ctccagaaat   37080
actgctttga agagagggg tttgagagac gctgttaggg agaagcagct ctgccacagc   37140
aggtctgggg ttcacctggg gttttggctca ttgcctccct gtgtccctcc tccacgctgc   37200
cagtgctgca ctgggaaggt gtgggtaaga agcaatggct aagggatctg gttatacacc   37260
tcctgtatct gctatttggg attggctact gcagggcctc aggtccctga cttaaaagtg   37320
gggacttcga agcatgtttg cattgtgctg tcgtgcctta gatgttgctg ctgggtcctc   37380
aaagtcctgt tggttgtggg gtgggggga cttcttgctt cctatgtgaa gttttctgag   37440
ctgcaacttc agcaacagct gtaagagtgc attaagggca gtgggagaag tgggagggac   37500
cccattacct catcgggtat cgctggcatg ctttggatag ccccacgtgg agcgtgacaa   37560
ttagagcacg gcagagagct cccaacacgt gccatgcagg cagaggcacc cgccgctctt   37620
```

```
ctgactcact ctgtttgtag ccatgaggct gtgccacgtg ccctcttctc tctctcacac   37680
ctgggctctc ctggggcgcg tttgggaagc ctctggagga tcggagggat gtggcagggt   37740
gccctgactg ctgctccttc cgcaggatga ctgcagtgag taccgctccc agtttgaggc   37800
tggcggacgc ctgtcctgca cgcgggagaa cgaccccgtc aggattcct ctggcaagca    37860
gcacaccaac aagtgcctca tgtgtgccga aagctgtga gtacagttcc tgcaacagc     37920
aaagagggaa acctcacatt gcgaaactgc agcttctgcc tgtgtggctg cgcctggggg   37980
agtcccgagt cccagcggcc ccccaggagc tgctcctgct gtagggctgt ggctactgcc   38040
cctcttccca cctcccccct aaccctcag ggagcagagg agaagcaggg ttgatagaga    38100
gcagcccttt ccttgggca gctcccaagg aaagtttccc acgcgtgtac tttgccttcc    38160
agatgctctc tctactccca tagagcatat gcagaagcag ccctgatatg aaagcagcca   38220
cctggagccg ggatgtagca tacagtggga atggtgagga aagggagaa gcttaggggg    38280
tgggaattag gtgcagggcc accagggatg gggaggctgg tgcctaatga catgatgctg   38340
gcttgcaggg cagccccagg tcctggcagc gttcgcactg ccatagtgct cctttctttc   38400
tcctctccct ttttccagc aaaaagaag ctcaaagagg aggtcagtct ggtggaactg     38460
cccagcgcaa caagcagtcc actgcagagt gtgcaaacca ggtgagactg agctcagagc   38520
ctcaccaggc ttgggaaaag gggttggtgg atctggggac cccgatggtc aagggctgcc   38580
tgtggtcctg tgtgtttgggg tgcaggagcc tgctggtgat ggcagagagg caggttgcat  38640
tgcaagccct gctagttcat gggatgggtt tgtgtatgag cgtgcatagt gggcagttct   38700
ggactcctct atggggcacg catcagagct atttcttcag aaagagcccc atggttccta   38760
gggtccaggg ggatgagagg gaaggacagg agctgcttta atctcactgc tttactgctt   38820
ggttgtcaaa cacgatcctg ccccttttcc agaagagctg cagtggctca gggttacagc   38880
ggggtgtaaa tgagagacgg ccgttctcca caaacagagg gtgagtacag cagcactggg   38940
atcccagcct ggccccacaa gtcctggggt cttgacactg agaagaaaca cataaaatag   39000
ggcatataca accctttctc cttttccaaag acattcttgc ttcccctgca cacgaagcac   39060
tggtgactgc tacactcaaa atccctcccc agccttgccc cctgaatcct gcctcctggc   39120
aggcacacac ttgtcctgct gcctggtcca gcgcatcctc atctgctgac ctgaggcagt   39180
gctgtgtgtg caccatgtgc tgtctgggca ctgagcgact cctctgggtt tttagggctg   39240
ccaggctctg gcagggtgca gatgctgtgt tatctaagcc ttgaggaact ctcttagtct   39300
tcctgttttt gttggtgagg cccattcatc tgcccccagt cagcactgcc agcagacaaa   39360
cagtgcacag ctctccatgg cagcaatggc tgtagcatat gtaggggcca ggtttctggg   39420
atcatctctg tgacggacat ctcttgctga ccgcccataa ggactcaaaa gtcccgttgc   39480
agggagtgcc tccatcccat ggcaagccaa gtgccctgtt gaaaaaacaa ggtgcagaat   39540
aatggcaatg gaccttagtg cagtttaatt ccaccctggg gtgatgatgt ggctgagtgg   39600
gtctgcatac ccttggctgt gccatgagct ctgtgctttc tctccctgcc agcccacaag   39660
gagacttggc tcaggactgc agcccggcac ctggccgcca gggacagagc ggaggcacca   39720
acacctacca gccggtatgc ccagctcatg tgggtcaggc acagcctttc ccagcagctg   39780
ccccagtttc cattgtcaac ctaaagcctc acaatggac ctgtatcctt ggaggggttt    39840
aaatgggtgg tagagtccgt accctgatgc tgtcccctgg cctcaaagag gagtgaggct   39900
gcacacgtcc aaacgggagt cactgaagcc agtgctgctg ctggtgttgg ctcactgtag   39960
```

```
aagtatgtca ggtatgagag agcatcctcc aggaggtgat ggtggtgtcc cttcctgcat   40020
gctgagatgt tgggttgaag actgtggcca gagcagggtc ctggggctga gcggggata    40080 aggacaaggc tgataagagg aggggagagg gagtagtggg ggaggacacg gtgagcaata   40140
gataacgact gtttgtggaa tcatgtggga gggagaagag ggtgtatgct ctctccatct   40200
ccacaaaaag aaaatttgtt attttcaacc aagctaaagc agaaattatg aaactaatag   40260
gagaaaataa gttactataa aaaggatgac taacctgtgg atcttgctgt cacggggtgt   40320
tgccaagagc tacagtgatt aaaaaaaatg acttgccact tatagtccat acagcaattt   40380
aggtaacatt ttggaaggga taggaaatgc ctttctgtgg ggctggaggg acctgagtgc   40440
agactgcctt aactctctct gaagtctctg tcactgactg cccttagaaa aatgatatta   40500
gaatagaaaa accagggagg cggttcaggt atggcagttt taatgcattc cagaggaagc   40560
attaggcata ataatgccag tctgcttcag ggcttagtgg tatttcctgg tagctccggt   40620
gaaggagtgg atgctgatca gcctgactga cgagggggtga ttcagagagc agatctgtgt  40680
ctctcctcgc tgcagggcca cccgtgggct ctgtcccagg gagatgctgt cctgaaggag   40740
aggtggcagt cactgtgagg actgtggggg actgttggtg tggcggcggt tgcacacgcg   40800
tgggtcacac cgtgggcagt ggtgtctggt gtgtgggaag gcatctggca gggaactgca   40860
aaggtcagcg ctgtctgtct ttgtgtcatc gttaattacc caggtgaggg aggaagcagc   40920
acattaatga aattagcaag tgatgtttaa acagagggtg ttactgcagc aacctgtgcc   40980
actgaacccc ctgcattgcc cagctgggaa accttttcttc tccatggtgc tttcaaccccc  41040 atagtgctgc tgaccccagc aaagcaatga gccattgctt agtgctgaat ggggttttt   41100 ttctccaagt gggacaggag gtgagatgtc cttcctgcag ctcttctcca attgcaccat   41160
ttgcagtcat tgcaacattt tttataggac ctggagaagg ggatgggaac agagaattca   41220
ctccttttgt ctctgcatct tttttttttt ggcctttggt gcagaggtgg gcagtgaggc   41280
tgaggaagag aggggggctgt aggatctctg acctctgctg tctgaaactt gccatgattc   41340
tgcaggcacc tgtgccagaa tgctcatggg ctgataatct aatcatgagg agtcttgttc   41400
ctcctgctcc gagctctttc tagctgtgcc acgtctgctt tgtaggaaat tcgatgccta   41460
gatgctcctg ctgttatgct ggagaataaa acgagagggc acgcttaatt agtcagagct   41520
tttcatacat gtttgcatct cttccattccg tgggtgtcaa gttgtgctgt gtgtcgggct   41580
gcccttgggc agctggactc aattgtcaag gttttccctt tgtttctgcc aagtggcttg   41640
cagaagcaac aggtgtgaaa gctctgataa aggacaaagg acaggtagca gaagtttatt   41700
gtattctcgt ggatttgcag ggagaagtaa aagtgccctg gactgagatg tcagggtgga   41760
tcagatgagt gtatccatgc ctggcaatgg ggtcagggca gctttgtccc cacatcgtgg   41820
ctggttggcc caataggagg cgttacctct ttgctgaagg tgtgatggag ctcagggcaa   41880
cgcctggttt gtgagtgctt tgagcggtgc gcaggaggggt cttgcaagag aaccagcacc   41940
aaatgtgatt tctttctctc ttcagctgga ctgtgatcga attctgcacg gggtaaaggg   42000
tggaaggatt ttctgcagcg aatcctcaca acccgtctgt ggcactgatg ggaaaacata   42060
cagaaatgaa tgtgacttgt gttcagctgc catgtgagta ggcggagaga tttcagtaat   42120
acagggccat ccaccattcc cgagtgtctt ttgcagcaca gtgtttgttt tgatataccaa   42180 tgactcacta tcaagtgtgt ccttggtgcc tcgctgttaa gcaaacatag atcaaatgtc   42240
tgagattaat atgatgacag ctaattaaga tacacaactt tccagagtcc cttattccct   42300
ttctgctcaa tcataggatt gtttggggag taataaatgc catcaaattg gaagtagcat   42360
```

```
caaaggttta aggagcccac agaggaccac cgtgacgatg tcagggagct gtggcactgg    42420
aagtgaataa gcaatgtctt gttctccctt tgcaggagag catcagttta catcacggta    42480
aactaccgag gtgaatgccg aaagactgtc cctgaaatgg taagtgcctc cctgctgtgg    42540
catcccattt cttgttctgg gtgtgtgctg agacccagc ctggatcccg tatctgtggt     42600
gggatcatca gagccctgtt agcagggtgc ttgtggttca catgcgtaaa tacacttcag    42660
gcttggattt aaggcatttt gaggcataat ctccacgttt tttccaggct gtgtggtagg    42720
ggagtgacat gtctgggaaa acatgtggct ttcctcctgg gattttggtg aggccaagaa    42780
aagattgcaa tcgcacaaac cataagggcc taatttccca aatgatatcc aggcagttgg    42840
ttgggaagga aatatattcc ctaagtggta tccttttggg aaaggtcttg aatcttgtgt    42900
gattgccttg tagtagatga gtcaaagatt tgttagtggt gctttgtctt cccgctcgtg    42960
gcagctcagc ggcattcaga gctttggttt ggagccaggg tgtcccagtt tgtgtgtctt    43020
gagtgtatgg gactgacctt agtgttggca tggactgttg gaaagctgag tattcatttc    43080
cccagggaaa caccgacatc tatccccatt ccaaacttgg aatgaatcaa aatatcaaat    43140
cagccaaatg gagaagttgt gcaagttttt tttgcaatga gagagatggc ttctgaatat    43200
gaatttgctg acagtttgta ggtaaaacag tattgcccgt tgaaaagctt tagagcaaaa    43260
ttaccatcat agggctttta ctctcctctg cttattgaca ggatgcccac ccatccccac    43320
aacattagaa atgaggcatc cccattcctc ttcctctctt ctgtgaagta ccagagtgct    43380
ctcaacgctg tttaaagctg aagaaaaaat gcagagaaag agttttgctt gtgatcgtgc    43440
tggaggtctt tgtgtctcgc ccttggtgc gatggagcca ttgctggttt gtgtatgctg     43500
ggagtggagg cactatgcat acctgctggt ggctgtgcta atgatgctgg agacagacaa    43560
ggttgggtgt accacggcaa ctgaaaacca gagaggactc cctcagagtt gtgcctggct    43620
gggattcctc accattttgt gttttaccaa gacgttttac cagctctcca gtctttgcag    43680
ttagaggaat atgccataca ctaaaagtca gacaatttgt agctattcca aggagagctg    43740
gaagcaatta aagggaaagt gataaggttt ttccactggg gaaaatcccc cacaaaaaac    43800 accctccaa acaaagactt attatttcgt tcttatgta tattgtgtca cctgaagaat       43860
cagattggaa atttatggaa gcccatttcc ttagcaaacc ccttgtgtcc atcaaagact    43920 tcccttttt ttctcagttg gaagcttatg aacaatgtac tgaccagtgt tatttatgc       43980 ctctgaaatt catgctaaca ttcagcttaa tgcatcctttc tgaaggccca ggcactcgct   44040
gtgtgaagga gatcacagtg cctttggcgt cagaaatgat ttcaggctgt tgcaatacgc    44100
agcacgaaga tgcaaaggcc caaagacttg agccttggaa aaagatagga gattgctgcc    44160
cgaaaatgta gtttgtcctt gagttgtgtt ttgaaattag ccacggtaat gctgtgttgc    44220
ctgccaaaat gtgtgtccaa gctcagagcc tgcagccatt cctgctagca aagcccctcc    44280
tggatttcca gcagtttgtg gcagtccttc cctagcagtg gctggattgc catcagggag    44340
ggatggctgt aggaagggac aggagaaatg tggttggaga gagatctgac attaaagggt    44400
gcatccggac agcctgcact gatgtggtgg aaaaccttcc tgcagagaga gccctggggc    44460
tggctggcag ctgggcccct gctgcctgtg tgagctctgt gccacaacca gcctcctctg    44520
atcctgttct gctttactgc agatgaatgt agctgagtct agggtttaga tttctatgtt    44580
tatttttaac aaggcagctg gcctctgcgt cctccatgct gtgacataca gctgtattaa    44640
tggtgggtct ttccagaatg tttcactttc aatgctgtat tttttttat tttgcagttt     44700
```

-continued

```
ctcttttttgt tcagatgctt tttcacacat ctcccatgtg acagatacca gtctgtccat    44760
gttagttgac aggtcaggca aaaaaaaaaa agggatatcc agtttctcct ttttaatctg    44820
ttttctaaag aacaaagaac tcccagcttt ctaatgggca aggccatttt cttacagtgc    44880 tcttttttgtc ataccttttct taagaatgta gtagaaggga aaagaaacaa acaaaaaacc   44940
caggaccttt tccagcttga tattggtttt ggaaagcaca cagatccagg ctgaaatctg    45000
tttgttttct gagtctggca gtgacccatc cactgcccca tcccacctgg ttcctgtggc    45060
cactgagctg cccaaagggg ctgtcatgta gcccctaatg ctctgccagc gtaacagcag    45120
tggatgtact tgtggatcca cttatatttt gctctttctt tccagaaata atggagttca    45180
gactgccagc aaataccagg gatcagctgt gaccaaaggt acagtggtgc ggtgatttgc    45240
tccctcttgg acaacttgtc cgcatttcac aagggtttgg gtgtcagacc ttgcctgggc    45300
aggctgctgg gtatgtctgg ggcaagggc tctgcaacac accttccct attgccacag     45360 cacaagaatg aggcgtgtgt cttttgcaga agtagcaagg tgatgggaag cccctgccaa    45420
gggggctgag cccttgggg tgtgcaaact tcatgaggac ctcctcatct ctcagggtg     45480 ggccttgccc gttccttttc cctcagatat ccctgcagag ggggaaggat gctggcagag   45540
cagagtactg cagtccctcc tcacaaggag gtggaggtgg cccaaagcaa cctggctttg   45600 agcttttcctt gtggttcttc tgtgtccctt gccttttgga gccatagtaa taaacccgtc   45660 tgcccccctgt ttctctagga caagtaaagg aagatctgat gtcaggcacc agggaagctg   45720
ctgagttccc cagtgctgtt ggatccacct tcatctcctt ctgcagccaa cgggcctgtc   45780
cttgctcagg tggagggtga agggctgtgg ggacccagtg gtggcttccc acgttggccc   45840
cacgcatgtt gttgtagtcg ctgctcggct cgggctctgc cgcctcgctg tgtcttagca    45900
tgtttctaca ataaagataa ctccacagcg tcctgtcgct tttcttcact gagcctcacg   45960
ggagggacgt gtgagtccc gctccggctg ctcgccacgc gtcccttgag ctctaaagca    46020
ccaaacccaa gcggagatgt cagacgcaga gaagaagaac gtggtctggg ttctgttagc   46080
agggaccagc agttgggttc tctgactcgc tgtgtagggc tttgggtgta tctctttgtc    46140
tcccttcagc ccttttctct tgcctgtaaa aacggacatt aaaggatgct tacctacctc    46200
agagggttgt ttggagattt taattggttt acgttagaga gcccacgggt ggaattctgt   46260
tcctatgtgc caatgctggt gtgcaggagg tttaactgtt gcagtcatgg cctcttccag   46320
ccaacacccg atgggccgta tgtatttcct gttctttcgt ttatggctgt tacttaaagc    46380
aaatatgttc ttatttgtat aaactttatt gcaggacatt tccagaagac cttgagtgaa   46440
cgtacagtgt ttgagtccac tttagctgtg acctgatctg caaatacact ctgctgtaga   46500
taaggctgga gtaactttca gattttggca gggtttcgct caatgccaat taatttggct    46560
ccctccacag atattgattt ttttttttct tttcaattaa gttatcgaga tcttttttc    46620 ttaatgcagc taatgaaaat cgattttac tctcataaag tacttccgca tgtgtcacat    46680
tgatctgtct atggcttgat tatcggcagg ctttgacatg aggttaatat tttgtgtgct   46740
ggtttttttt caccgtgtgc aaacactgtg gtttagaaat atgttaccgc tgcttatttc    46800
tacgtggaaa atcccacggc gtggttatgc atggcagaag tcaccagttt gatccaattt   46860
agctgtttct agggatgcaa gattcctctg cctttgagcg ggtgaatcct cgggtgttat    46920
ttatacattc tgagaaggat gaacagaaga cggtaaaaac gtttgctaat gatgtctgct   46980
ggctgattcc ggctaaaatc gtgtgcaggg acctcgacgt gatttttata aaggcagctc   47040
acaatttgag gcttaaagta agttcttgca aatgaaaatg ggcgcacttg agcgcgctat    47100
```

```
tataacttgt agtgatttca agcacttaga ttttgaaata atcgcccata aaaacctgca    47160
ttaattgtgc tccaaaacca atgagctgat gaggagggtg ccctggtagc ctcttttgct    47220
ggatttgagc accttctgaa tttctcctgc caccagcaga aattagccac agaaatcata    47280
gctgctataa gggtttatta atcagattac gaaactgcta agaaggcaca caacagtgac    47340
ttgctgaagc tgcctgtgct gctgttagcg agcctcccgt aggtagcaat gctaactcct    47400
tccttttagc agtttaccca ctgcttcctt ccatcactcc ttccttttgt agggcctact    47460
tttgcagttt gatccagtgg cttgcaggca atatctgtcc ccagcggtgc tctatgcagc    47520
tgacctccag gtagggctcc atgtgagcga tgcaatgtgt tatttccatg gggttcctaa    47580
gaaggaggaa gcaaaaagct caggaggtgc tccaaatata ttatcctgtc tctgttttg    47640 ctctttgtgg tgcccttta cactgtaaag agaccatagg agtcctctat gaacctggaa    47700
aggtaccagc actatgggag gtcttcagtt tgctgtaaat tatgctttat tagaggtatt    47760
tcttctgcca agacccactg accccatgcg gctcacagtg ttttctaagg ctttgcagga    47820
ctggtgttac gaattggcac cctccaggcc tctcacaaat ctcctgcttc tcacagcgtt    47880
tcttcaagtt ctcccaagca cagctgagtt ttgagctcaa ctgctccctg caggggcctt    47940
gagcctcctg ccttttgca taaaggtgt caggtactta tgcaatcctt agaggcatgc    48000
aaatgctgct ctggttatat actgaggact gttgattctg gcagaaccct ttgcagacct    48060
tgtactccct tgctatttcc caatccctgc agcctagcag ctctgcctaa caactgccat    48120
agccaacaca gcagcaggct gtgcatggtg caaggtgatg tggaaaggga tgattgtatg    48180
aaagcgtgat gctgtggtac tgcctctgca ggagactcgc actatttgtg taagaggacc    48240
ttatttgtct gctgcagagc tgtttcaagg ctgtccatac accccgtga tgctgagccc    48300 ctccaagcaa tgcactggga aaaggaggct gggggagac cttattgctc tcctccaata    48360
tttgaaaggt gcttacagcg agagcagggt tggtctcttc tcactggtga caggatgagg    48420
ggaaatggcc tcaagttgca ccagggtatg tttagattgg atatcaggaa acacttattt    48480
actaaaaggt tgttaagcac tggaatcagc tccccaggga ggtggttgag tcaccatccc    48540
tggatgtgtt taaaaactgt ttggatatgg tgctcaggga catgatttag cggagggttg    48600
ttagttaggg tagtgtggtt aggttgtggt tcactcgatg gtctttaagg tcttttccaa    48660
cctgagcaat tctatgatat ggatccctgg ggctttcagt cttatctccc tggattatca    48720
caggttcagc tctatggccc atttgattta taccgggtc tgatgaacag gttttttctct    48780 tggctcttca gggatcctat ttagcacttt ttggtacatt cccctgccct acaagtctcc    48840
ctgatacaca gagctcttat ccaagacttg ggaccttccc tactccagcc ctctgcagga    48900
ggtttcttgc taaccagtcc tccaaccagg actgcagtac acgacaaaga gctggaagag    48960
gtctgcaata cttccccagc atgaaggtat gagcactcct tttgagtagg ttactgaaag    49020
tagtaagatg tcaatacaac caactgcaag atacaaaacc gcatgaaaat tcagtttact    49080
ttgatgctga agggctgaaa agaaatgctg tggtgttagc acagatgcac tgctggcaaa    49140
gtgaaaatga gcaaagagga tgagatggat ggacagctga tggaaaaact cttcctaatt    49200
gctccacaga gcagcttgct cgcctgcagg gctgcagcat ggagctgctt gtgcataatg    49260
cagacacccc aagaccagtg ctgtttgtct tagccaagac acagttgcag ctgcagcaat    49320
tttttctaga tgtcagttcc ttccctatgt tgctgacagg tgtttgctgt tctgtccctt    49380
taatctgtat cctacagcaa acattccttg aatttaataa cttagctgga agacaattgc    49440
```

```
tgtgatcttg atagaacatg ctgagccaat ctattttaac tgcagattta gtttgcaaat    49500
actgtctcct tgccgataag attcaggtgt catctttgtg gacattggca ggaattttct    49560
tgaccgtgac aggttttaca gagtctggca attaagctgt caagacacat tttcctctgc    49620
caggaagcat taattgatga tagtcttggc tgcaataggc acagagagat ggatattgta    49680
atcagaatga atagaggtcc ttgtagttga gagctacgtt ggtccaaagt tttgtagtcg    49740
ttgacgtttg gtgatactga gataaggaac aaggcacaga atattagagc taaatatcag    49800
gcacagcatg agaataaaga cctctctagc tggaactgtt ggtatctggg gagattttaa    49860
cttcctggat gcatactgca aagtactaat attagtagag ctactggatg cgagagcaaa    49920
tagttttcca ttaagtaatc ccaaaaatca tgttgttgtt ggtttgcttt tcaagtgcga    49980
ggggtgttgg agatgtattt ccctcagaaa ataaacctga tatgattcaa cctgagctct    50040
ctctgtttaa atcacactga aaatagatct gcaaatgggg attttgatta ccgagtacag    50100
aatatgaaag attaaaactt gggaaagtta gggttctgat tgagaaaact tttgtttttg    50160
tggccgaccc ttgcagctta caaaaatctg cctaaataaa ggagaaaacc acatttagaa    50220
cccatccaag ctatgctact tcagtactgg gcaaaacttc aggagacgtt tgaagaaaac    50280
tgaagacgtg aagtataaag gaatgattga tgtgcacagt aaactttctt ggaaggtaat    50340
cacgcatggg ctaatatcaa tctttacaaa gttggctgac ttcctagata aggaagtac    50400
agtagatcta gtctacccag gcagcaaaaa tgtttgacct gttgccctgt ggggtggtgt    50460
cacctgggct tggggagggg ggtcaggatg aggttacagg ggatgtggaa gcatactgtg    50520
gaggagcagg tggggcaccc acaggagtta gcagtgagca gacagaaagg tggatctgag    50580
gaccgaactt cgtattttg ttccttgcat taatacacaa aaagcagaca cacacacaga    50640
gcagattgct gctggttttt gttttctttt ttaaacagca gaagagcagg attttttccca    50700
cagagaatgg ggtgaccttc taggctgtga ttgcctgggc tcaagctgag atgaaacgca    50760
gtgatgagga gcacaaaacc gtgctctgag gttaaataat gagggcttcg gctatcagtt    50820
cagagctcag taaaaactgc agaggaggag gaagacctaa ttgcatgtag ccagccacag    50880
ggcaaatgag agctgcagcg tgctggggca gatccgggag cagaggggcc gtggcacgct    50940
ccctgttcac tggctcccct ggagccacac aaaaggcccc ttcctggcaa ttgtgcccac    51000
atcaatcatt agctagaaac ccagagctgg gtaaatacgt tttggcttcc cgtcttgatg    51060
acagattggg tgttacatca caaggtggga ccacttgata tgacaacacg ctatatattc    51120
ccgctgctac ctctgcccctt cctcccccac tctgagagca agcgggctgt gtgtgcaccg    51180
aggtgctctg ccatgaggac tgccaggcag tttgtacagg tggctctggc cctctgctgc    51240
tttgcaggtg agtgtttcct gctataccc gtaggtgact atagctagac cagagactag    51300
gctatctgtg agagtatctg ggtattgtaa tgtgttagag agccttgttc catgaaggaa    51360
tgctctttct gacagtgtag caaaacacca gactgcaaga tccaggtttc agcaaacctc    51420
atacagacga ctgttttcgt cgtggtttat aggagcaaat tgctgaggga gcagtgctag    51480
tgcagggcag gagcttgcac gtgcaagcac tgagtataac ggcaaagcaa agctatgtga    51540
aatggctcct gtgtccatgt aagcaataca acactgcat cttgtatcat ctataaattt    51600
tctgtgctgt tcctggcagc tgagaagttt gttgtgggaa gaacagtgct agtggtcaac    51660
agccacctga aacgtgcatg tctgagctcc tgcaagtcaa atacagagtc ttgcagaaga    51720
gtttaaactc agtgcaggct tgaaaatacc tacatttctt ccctgggca tcttaggaac    51780
tggctaacac atgtggcctc ctactgaaag tgcagtgaaa cttcatttaa taacctctga    51840
```

```
ttcattttat ggacgtacat cactggcata atgtaaaatt gcattttcct aaacccaata    51900
agccaatcaa caacggtatc taaatgtaac tgtttcatcg aaagatttgc atatgtcatc    51960
tctgcatatt aataatatgt atttattttc tgtctctact tttcttttag atattgcctt    52020
tggaattgag gtgagttaca gatttttttt cccatttatt cttttctatt ccaggcttct    52080
ggtcaaataa gagcagtata taattacctg atgagcaagt ggattaatct aatgaaagcc    52140
tggttgctca aataatactt gccagtgcat gattgaatga tattgccaag tcacgaaaaa    52200
gtaaaacaca ccccgtttat actattttcc attcatgcaa taaatgaag aaaggaagaa     52260 ttgtacgatc ctattatgtt aacttttgga tataactgcg ttagtccaag tcaaggggtg    52320
gtagttacct cctcgagagg aaagctgtct taagatgata agctccaaag catcaaagac    52380
agtgattctg gtatctttt ctatacagta agacacacac tacagtgttc ctgcctatac     52440
ccatatcaaa gcgaggaaag cagcagggtc tgtgcagtgc atttgtctgc aggttcttcc    52500
cacgcagtta tgagattcct gcaaatcacc agagactgca gcgtgattgg aaacgatcag    52560
attttgagtt gagcggctgt ggagcatggc caggctccca attaccagct gccttcgtta    52620
ggcgctgtct cacccacagc tctccttcct ccatgtcatg cttccccag tccccgcag      52680 gaaagcgtga tcagaagaag attcccacct cctgactgcc tgagcagatt ccaaatgata    52740
cctcaggtgt ttgtcccggc tggagctgtg ggtggcagga ggtttccata ctgtcttttg    52800
ttgtggaaac tgaccccagg gctgatgttg tgctgcttcc ataggttaat tgcagcctgt    52860
atgccagcgg catcggcaag gatgggacga gttgggtagc ctgcccgagg aacttgaagc    52920
ctgtctgtgg cacagatggc tccacataca gcaatgagtg cgggatctgc ctctacaaca    52980
ggtgagctta tgtggaagcc caggggagct gcagggcagg agactcgagg tgagggcggc    53040
agctctgtcc ccaaaatatg gtctgtgtgg aggagtatgt gagttagtac caggatgctg    53100
acctccagcc tggggtggt ggctgctctc tgccatctct gacacagatc tgcgttcttc     53160
cagggagcac ggggcaaacg tggagaagga atatgatgga gagtgcaggc caaagcacgt    53220
tacggtaagt ccaacagtaa gatgaagtct tgctctgttg gtgcccataa agacttattt    53280
ttatttcata gaatcattga acagcttagg ttggaaggga ccttaaagat cattgggctc    53340 taaccccct ggcctggccg ggctgccttc aaccaaatca gtttgcccag tcaaatgggc     53400
cttgggcacc tccagggatg gggcacctgc tctgctcagc ctgttactta tttacttgtt    53460
tttttcccat tcctgctatc cttacagatt gattgctctc cgtacctcca agttgtaaga    53520
gatggtaaca ccatggtagc ctgcccaagg attctgaaac cagtctgtgg ctcagatagc    53580
ttcacttatg acaacgaatg tgggatttgc gcctacaacg cgtaagtctt ttctgtggag    53640
catccttctg ggtaattaga gatggctaag tcccttggaa acgcttacat aaaacacttt    53700
ctaagccttt cttagggtag atgtttctgt gggactcttt gaagctggct acttgtgatt    53760
ctccagccag ctgcagattt cttccccatc ctctgtctgt gctcatgaag ggaatcacaa    53820
aaaagacaga ggacaaccca cagcagaggc atgaatagat caaagtgttg ctcagtgctg    53880
tgtgatatgg aaataccatg cattttctgc tcacaagtgg ttgctaccac ctgtgggctg    53940
catccagacc actcagcagt tccttacgtg aagggtggga ccttgctttc ttgccccagt    54000
atctaaggct tttcacgagg ctctctaact aaaacagctc tttctttcag agaacatcac    54060
accaacattt ccaaactgca cgatgggaga tgcaagctgg agatcggctc ggtaagtgta    54120
acagaaataa aaatccatct cctagggctg ttaacggaga gaatcccatt gatttcccta    54180
```

```
agaaaatgta tgaccgggct gatcggggt cccggtccac gctctgcttc ctgcctggtg   54240
agggtggctt ctgaaacaaa gcggtaaagg aagaggcccc agattttcct tgcattgtgc   54300
tgtgcagatt ggcaggtttc tctctggagg cgacaagcat ttccaccctt tgtaacaagc   54360
attcaaaatt ctagtgctgg tagcttggtt agatatagtg agattcataa gagcaccaag   54420
catacatatt tatagggtat agcttattgt atatttatac tggggtaaga gtccagtgcc   54480
tcaggaagaa aagcttatat atttcagcac aaaaattctg ggatgcaggg agtccgttct   54540
ccaacgacg gattcctcct ttatcacttc aactcccgtg cttaactgca gggaatctga    54600
attattaagc aatcacagca ctggggaagg aaggagaaaa accaacacaa accaaaacaa   54660
tgttaatcag atttccagct gttggaaaat atttcccact taattcaagg ctgttgtgtc   54720
gatgagaaga gggctgaaaa ggctgttttc agttcctctg cctgaaggtt tcattctcta   54780
agagaggtcc ctttttcttgt ctcctagaga atgagggtag tgttctgaaa gcctatttct   54840
gatagacagt ttagttaagt gtagcagggc tttgtcctgt cacaaaaact aggaagccgg   54900
gaatacagga tgaaaaggtg ttacattgac ttctcccgtg tagcacaggc tccgggaggg   54960
cttattctcc ttattttggc aggttgactg cagtaagtac ccatccacag tctctaagga   55020
tggcaggact ttggtagcct gcccaaggat cctgagcccg gtttgcggca ccgatggttt   55080
cacctatgac aacgaatgcg ggatctgcgc ccacaatgcg taagtgctgc tcatctccca   55140
ctcctccaaa gtagccagca atgctttgcc gtgctgggag ccttccttct acgttgctgc   55200
ttatgcctgt ttcttcaagc ctcttagaaa ctgcattttt tttgttgttg ttcttactga   55260
gttttcttct gatgccttct ttgtgatcac gaggggaaat ctgcaagact cagaacacag   55320
ctccttggat tagtctgtgg gctgggcagt gactgagcag agaaaggaat agttcagaat   55380
cttgctttaa ataacacgag aagacgtgat gagcttgtta acgagcagag taatgtagct   55440
atatcaatac aatcgtgcag agaggctgaa gccctacttt gttaggtacc tgctttaggc   55500
tacgtctggt tcattctgca tgcaagtgtt taaaccaaga gttaaagcat ctccttactc   55560
actttgtctc cctcttttcag agagcagagg acccatgtca gcaagaagca tgatggaaaa   55620
tgcaggcagg agattcctga agtgagtata caacgtaagg tgtatttctc cccttgcctc   55680
tgcccactga gctatttgct gaggccacgt ctactctgaa agtgagctgg cttgaagcct   55740
ggctctctgc acgtgtcctt tgggatgtgc caacgtgtat ccaacacaca aacagtgtgg   55800
aagttgggca gggggaactt aggtctttta aggatgatca ctaaatgcat tgccagcaaa   55860
gtccttttgt gccagtgaag tcctattatg tttgccttct tttgtttcat tctatagtgc   55920
agagagaaaa ggagatgata tatctttgtt ggttttttt ttgtttgttt gttttgcttt    55980
tctgccatat ctagcaaact gtttcagtag ttgtgaccc ctttggatca caagtgaagc     56040
tcagtggcat ttgggattga ctgagctgtc tgccctggtg atttggcatc tcacagatta   56100
cacagcgcca tgtagctcct cctgggcatg agagagtttc tgcagagctg actcaggctg   56160
gctttgagag aactgaagtg tagcaccagc gttgtttcag catcccagcg taaaagacat   56220
ggattgcagc aggaggcaat gctagggttt gtctttgaga gcaagggctt tttcagggct   56280
gacgctccta cttttttgcag attgactgtg atcaataccc aacaagaaaa accactggtg   56340
gcaaactcct ggtgcgctgc ccaaggattc tgctcccagt ctgtggcaca gacggattta   56400
cttatgacaa cgagtgtggc atttgtgccc ataatgcgta agtactgcaa acaggacttc    56460
cttttgtagc gactagccac gttagtactg cagatggctt cccctccacc cttcatcttc   56520
ttctttcttt ctttttttttt gatagcagta tgtctatatg tctcctgttc ttccttcaac   56580
```

```
ctcctgaagc tctgtcgcct cggtttcctt tcctgatgtg ctcctcaggg agctgtggga    56640
gagccagcta acagctgagt gtcctatgag ggctgtggca tttgtgcaga ggaaaaagag    56700
aatgggtctg ctacaagtag acctgagaag cctgtaactt cttaggatca tgatccctaa    56760
tggcagcctt tcccttcag acaacatggg actgaggtta agaagagcca cgatggaaga     56820
tgcaaggagc ggagcacccc ggtaagtggg gatggatgtc agatgagcgc cagctcctgt    56880
acgtgccttg tggctgcaga ggttgctaac cagggtctgt ccattcaggc agcagagaag    56940
gggaatgggc caggatttag gtaacaaaat gtcccaatac tgcaggtctc tggagggaaa    57000
catcagaggc agcccagaac agcacagcct gtttagcac agtaggagag gaagagcaga      57060
agctgtgtta gatgcctgtg tagtcattca gtgctaggat ttccattgca gcagacaggt    57120 taaaaatct ctgtaccgtg gtcagccaag aaaaggctgc ttgcaggaat gcacgcagaa      57180
atagctctat aaacatgcac ggtaacaata tgtgctgata atatctcagc acatttattc    57240
tgcttatgca gagcagctct aaaacactga aaataacttt gtgcatctca agggattgct    57300
gtatcttttc tgtagtaaag acacactgtt atggtgctgt cttgctata atttgctctt      57360 ggactgtgtg gggaaatatg ggtaataaga gctactacac aggggaaggt atgcaaaacg    57420
attgtgaagt gtcagaagct tagccagtgt agactgactt ccagtgccat cagtagatac    57480
ttgcttattt atcctcaaat attggaactg tttttaagta ctgtgaggat ttctgcagca    57540
gcagctgatg agctgatgga acagtttctt cttgccgttt tgaaaacgtg gaaacaaaat    57600
ctaaggctta gctaagtcag gcatgaccta atgtcaaact ggacataaca tcaaactcct    57660
tatatcaaat tcctttgaat aatgcttgtt ttgaaacttg gacatacgct gcataaggaa    57720
gatgatcttt ctggtctgct attcctttgc gttccctttg ttagtgagca atatcaaacc    57780
caaccacaat tagttcattt ataatgggag actaaactga aatcaacccct gattttcct     57840 atggctcgag gcagtctgtc ccccagctcc cagcacctga ctcagcatcc ttactgtttt    57900
ctccccagct tgactgcacc caatacctga gcaatacccca aaacggtgaa gccattaccg    57960
cctgccccct catcctgcag gaggtctgtg gcactgacgg cgtcacctac agcaacgact    58020
gttctctgtg tgcccacaac atgtaagccc tgcaggtcac ccactcgtgt gtcaccgcag    58080
ctgcttgttg agctttgtca actctgtttt ctctctcttc cagtgaattg ggaaccagcg    58140
ttgccaaaaa gcacgatggg aggtgcagag aggaggttcc tgaggtaagc gataaagaaa    58200
acaagagctt gaggtggtgc ttattgccta acaagtacaa cgctggctgg ttttggtgat    58260
gctgggtcat gccctcctgc tgccatcctt cctgcaggta aacatcaacc ctggcagcag    58320
ggatgctgtg cattttctgc atgtagtcag ggaaagaaag agaagaggac gggtgaggaa    58380
tgagttatga tgcaggtagc ataaatgatt taaggcgtta cgaagaaatc tctttcccac    58440
agcagtctat catacctgcc gtgggagtgt agctgtctgt tctggcaata tgggaagggg    58500
acacagagca cccgcaggta cctggtgcct tctggatacc tgtgctgtgc aaaaggatgt    58560
tgtgcaaaga tcagaaaact acctgcattt tgaatgcttt tacctaatgt accagaggat    58620
tcaaacacct ctctcttcct attgtaaatg cgatataatg taatgtatac caacaatgaa    58680
tcttgtaaaa ataccagata aactatattt ggccagctct aaactattta cgctcactgg    58740
ggaatagaaa aacaaagcca tctcattatc ttgtgtttga aagagtcaac gtcgtgagtc    58800
agatatttca tttctatgca aacagactat gaaatgtcat tgctttgttt cctgcgtatg    58860
ctctgtgctc agaccaagtc agatgcataa atcagtgagg aagagctcac actggagaaa    58920
```

```
ctgggatagc tgaaactcaa ggccagttct tcaaatggca taaatcattt tgaactgctg   58980
ttggtccttc tgtccgattg caacacacag aaccagcccc tcgcaacaaa aggcatgtca   59040
gcacatctcc tcagttcttg tgggccgtga cacactcctt ggccacactg agcttctctt   59100
gcaggaattg cataaatcac gccagtttga tttgcagatt atttatgagc tgcgttttgc   59160
agcgtcccag caagtggttc agcaagctct aagggcatcg tgataaatgc agggctgaat   59220
gagtgatacg cgccttcaag cttttgattca gtcttctcca gtataaggct gtgacagaaa   59280
attgatagtt ttcaatgaag aatgagtcaa tgcataacca taatccatcc tgtggcagat   59340
cttgaaaggc agaggcgtaa ggaaggggggt tgtgtctgag cacccttaca cagagcattt   59400
gctgcctttg tttcctagct tgactgcagc aagtacaaaa cctccacgct gaaggatggc   59460
agacaggtgg tggcctgcac catgatctac gatcccgtct gtgctaccaa tggtgtcacc   59520
tatgccagcg aatgcacgct gtgcgctcac aacctgtaag tactcattca tctccagggg   59580
gacccaccgt ggctgtgact ggacacatct ttgagtgctg aataacatgc aagggctctg   59640
tctaaaatct cgtgctgcat gggtcctgtc tgcctatccc cgtttccctg gttgccatgg   59700
ttggtgtttg agatgggcat ttagcaaggc ccactgcccc cagtgaccca gaaaaagggt   59760
tcactgcctg ggaaagcatt attccaaaag acacatccct agtccttaag ggcatgttct   59820
tgctaatgct tctcaggcaa tgcttagcta atttatctga aattgtcctg tgtaccacat   59880
gggaacgagg ttgtgctctt gtactacggt tgtaaatggg aagggtttct gctaatatcc   59940
atctctcctt cctccaggga gcagcggacc aatcttggca agagaaagaa tggaagatgt   60000
gaagaggata taacaaaggt gagtgtgaaa ggatgggcac aaagagttac agtcgtaggg   60060
gaccgtcctc tgctccacat caaaaactgg gggagcggtg tgcagccctg gcgaggtcgc   60120
ttgggaatgt catactggtt atagaatagc tgccatccat cccatgggaa tggacatggc   60180
agtgaacagg aacagtgtga ggtcacatcc ctcaccagga ggaactgagc tgattactgc   60240 cgtaatttc cagtttcact ctttgtgctg ggggaatact gtttgctccc aggcagagac   60300
tcacatcttc cttgtgtgtg caggaacatt gccgtgagtt ccagaaagtc tctcccatct   60360
gcaccatgga atacgtaccc cactgtggct ctgatggcgt aacatacagc aacagatgtt   60420
tcttctgcaa cgcatatgtg taagtatagg agtgaaaccc ttcctgtaac tgctacaaac   60480
gcagagttga ttttataagg agttctttac taacactttta tgggtgtgtg ctagacattt   60540
cggatgcacc gtgacgtgca aggaggtgct ttttgctttt ttaagaaaaa atgcaaagca   60600
cccacatctg cccatgtgta tgtggcttcc tgttttattt agtttcaaag acattttgct   60660
aattttcacc agcatagttt gtcccacaag ctcatcaggg tatggggaaa gtacttcacc   60720 aaaactacctg gagcgtttca agtgtgtgaa acctgtcatc tttcctttaa ttttcataat   60780
gaaaggaagt ggttggcctt ctgagactgt tctttatctt ctgccaacat tatcaacatt   60840
tgggctggta aggagaggaa caaggctgca gcacaaattc tattgtgttt aatccttcct   60900
tctcttttca ttaggcagag caataggact ctcaacctcg tgagtatggc agcgtgttaa   60960
ctctgcactg gagtccatcg tgggaaacaa tctgccttgc acatgagtct tcgtgggcca   61020
atattcccca acggttttcc ttcagcttgt cttgtctccc aagctctcaa aacacctttt   61080
tggtgaataa actcacttgg caacgtttat ctgtcttacc ttagtgtcac gtttcatccc   61140
tattcccctt tctcctcctc cgtgtggtac acagtggtgc acactggttc ttctgttgat   61200
gttctgctct gacagccaat gtgggtaaag ttcttcctgc catgtgtctg tgttgttttc   61260
acttcaaaaa gggccctggg ctcccctttgg agctctcagg catttcctta atcatcacag   61320
```

-continued

```
tcacgctggc aggattagtc tctcctaaac cttagaatga cctgaacgtg tgctccctct    61380
ttgtagtcag tgcagggaga cgtttgcctc aagatcaggg tccatctcac ccacagggca    61440
attcccaaga tgaggtggat ggtttactct cacaaaaagt tttcttacgt tttgctagaa    61500
aggagagctc actgcctacc tgtgaattcc cctagtcctg gttctgctgc caccgctgcc    61560
tgtgcagcct gtcccatgga gggggcagca actgctgtca caaggtgat cccaccctgt     61620
ctccactgaa atgacctcag tgccacgtgt tgtataggat ataaagtacg ggaggggaat    61680
gcccggctcc cttcagggtt gcagggcaga agtgtctgtg tatagagtgt gtgtcttaat    61740
ctattaatgc aacagaacaa cttcagtcct ggtgttttgt gggctggaat tgcccatgtg    61800
gtagggacag gcctgctaaa tcactgcaat cgcctatgtt ctgaaggtat ttgggaaaga    61860
aagggatttg ggggattgcc tgtgattggc tttaattgaa tggcaaatca caggaaagca    61920
gttctgctca acagttggtt gtttcagcca attcttgcag ccaaagagcc gggtgcccag    61980
cgatataata gttgtcactt gtgtctgtat ggatgacagg gaggtagggt gacctgagga    62040
ccaccctcca gcttctgcca gcgtaggtac agtcaccacc tccagctcca cacgagtccc    62100
atcgtggttt accaaagaaa cacaattatt tggaccagtt tggaaagtca cccggtgtat    62160
tgtgaggcta gattaatagg ctgaaggcaa atgttcccaa cttggagata ctgttggtat    62220
tgtatcaggg aacagggcca tagcacctcc atgctattag attccggctg gcatgtactt    62280
ttcaagatga tttgtaacta acaatggctt attgtgcttg tcttaagtct gtgtcctaat    62340
gtaaatgttc ctttggtttta tataaccttc ttgccgtttg ctcttcaggt gttcttgcag    62400
aacactggct gctttaatct agtttaactg ttgcttgatt attcttaggg ataagatctg    62460
aataaacttt ttgtggcttt ggcagacttt agcttgggct tagctcccac attagctttt    62520
gcagcctttt ctgtgaagct atcaagatcc tactcagtga cattagctgg gtgcaggtgt    62580
accaaatcct gctctgtgga acacattgtc tgatgatacc gaaggcaaac gtgaactcaa    62640
agaggcacag agttaagaag aagtctgtgc aattcagagg aaaagccaaa gtggccatta    62700
gacacacttt ccatgcagta tttgccagta ggtttcatat aaaactacaa aatggaataa    62760
accactacaa atgggaaaaa cctgatactg gaatttaaat attcacccag gctcaagggg    62820
tgtttcatgg agtaacatca ctctataaaa gtagggcagc caattattca cagacaaagc    62880
tttttttttt ttctgtgctg cagtgctgtt tttcggctga tccagggtta cttattgtgg    62940
gtctgagagc tgaatgattt ctccttgtgt catgttggtg aaggagatat ggccaggggg    63000
agatgagcat gttcgagagg aaacgttgca ttttggtggc ttgggagaaa ggtagaacga    63060
tatcaggtct acagtgtcac taagggatct gaaggatggt tttacagaac agttgacttg    63120
gctgggtgca ggcttggctg taaatggatg gaaggatgga cagatgggtg gacagagatt    63180
tctgtgcagg agatcatctc ctgagctcgg tgcttgacag actgcagatc catcccataa    63240
ccttctccag catgagagcg cggggagctt tggtactgtt cagtctgctg cttgttgctt    63300
cctgggtgca cagtggtgat tttcttactc acacagggca aaaacctgag cagcttcaaa    63360
gtgaacaggt tgctctcata ggccattcag ttgtcaagat gaggttttg gtttcttgtt    63420
ttgtaaggtg ggaagaagca ctgaaggatc ggttgcgagg gcaggggttt agcactgttc    63480
agagaagtct tatttttaact cctctcatga acaaaaagag atgcaggtgc agattctggc    63540
aaggatgcag tgaaggagaa agccctgaat ttctgtatata tgtgcaatgt tgggcaccta    63600
acattccctg ctgaagcaca gcagctccag ctccatgcag tactcacagc tggtgcagcc    63660
```

```
ctcggctcca gggtctgagc agtgctggga ctcatgaggt tccatgtctt tcacactgat    63720
aatggtccaa tttctggaat gggtgcccat ccttggaggt ccccaaggcc aggctggctg    63780
cgtctccgag cagcccgatc tggtggtgag tagccagccc atggcaggag ttagagcctg    63840
atggtcttta aggtcccttc caacctaagc catcctacga ttctaggaat catgacttgt    63900
gagtgtgtat tgcagaggca atattttaaa gttataaatg ttttctcccc ttccttgttt    63960
gtcaaagtta tcttgatcgc cttatcaatg cttttggagt ctccagtcat ttttcttaca    64020
acaaaaagag gaggaagaat gaagagaatc atttaatttc ttgattgaat agtaggattc    64080
agaaagctgt acgtaatgcc gtctctttgt atcgagctgt aaggtttctc atcatttatc    64140
agcgtggtac atatcagcac ttttccatct gatgtggaaa aaaaaatcct tatcatctac    64200
agtctctgta cctaaacatc gctcagactc tttaccaaaa aagctatagg ttttaaaact    64260
acatctgctg ataatttgcc ttgttttagc tcttcttcca tatgctgcgt ttgtgagagg    64320
tgcgtggatg ggcctaaact ctcagttgct gagcttgatg ggtgcttaag aatgaagcac    64380
tcactgctga aactgttttc atttcacagg aatgttttag tggcattgtt tttataacta    64440
catattcctc agataaatga aatccagaaa taattatgca aactcactgc atccgttgca    64500
caggtcttta tctgctagca aaggaaataa tttggggatg gcaaaaacat tccttcagac    64560
atctatattt aaaggaatat aatcctggta cccacccact tcatccctca ttatgttcac    64620
actcagagat actcattctc ttgttgttat catttgatag cgttttcttt ggttctttgc    64680
cacgctctgg gctatggctg cacgctctgc actgatcagc aagtagatgc gagggaagca    64740
gcagtgagag gggctgccct cagctggcac ccagccgctc agcctaggag gggaccttgc    64800
cttccacca gctgaggtgc agccctacaa gcttacacgt gctgcgagca ggtgagcaaa    64860
gggagtcctc atggtgtgtt tcttgctgcc cggaagcaaa actttacttt cattcattcc    64920
ccttgaagaa tgaggaatgt ttggaaacgg actgctttac gttcaatttc tctcttccct    64980
ttaaggctca gccaggggcc attgctgagg acggcatcgg ggcccctgg accaaatctg    65040
tggcacagat ggtttcactt acatcagtgg atgtgggatc tgcgcctgta atgtgtcctt    65100
ctgaaggaag gaacgtgcct tccaagtgcc agccccacag cccccagccc ctccctgtgc    65160
tgctccaatt catctcctct tcctccttct ccctttgctg tttgtgctcg ggtagaaatc    65220
atgaagattt agaagagaaa acaaaataac tggagtggaa acccaggtga tgcagttcat    65280
tcagctgtca taggttttgtc attgctatag gtctgtatca gagatgctaa caccactttg    65340
ctgtcggtgc ttaactcggg tgaactctcc ttcactcgca tcatttgcgg gccttattta    65400
catcccagc atccatcacc ctctgggaaa atgggcacac tggatctcta atggaagact    65460
ttccctcttt cagagcctgt gggatgtgca gtgacaagaa acgtggaggg gctgagcagc    65520
agcactgccc ccaggagca ggagcggatg ccatcggtgg cagcatccca aatgatgtca    65580
gcggatgctg agcaggcagc ggacgaacag acagaagcga tgcgtacacc ttctgttgac    65640
atggcatttg gcagcgattt aacactcgct tcctagtcct gctattctcc acaggctgca    65700
ttcaaatgaa cgaagggaag ggaggcaaaa agatgcaaaa tccgagacaa gcagcagaaa    65760
tatttcttcg ctacggaagc gtgcgcaaac aaccttctcc aacagcacca gaagagcaca    65820
gcgtaacctt tttcaagacc agaaaaggaa attcacaaag cctctgtgga taccagcgcg    65880
ttcagctctc ctgatagcag atttcttgtc aggttgcaaa tggggtatgg tgccaggagg    65940
tgcagggacc atatgatcat atacagcaca gcagtcattg tgcatgtatt aatatatatt    66000
gagtagcagt gttactttgc caaagcaata gttcagagat gagtcctgct gcatacctct    66060
```

```
atcttaaaac taacttataa atagtaaaac cttctcagtt cagccacgtg ctcctctctg    66120
tcagcaccaa tggtgcttcg cctgcaccca gctgcaagga atcagcccgt gatctcatta    66180
acactcagct ctgcaggata aattagattg ttccactctc ttttgttgtt aattacgacg    66240
gaacaattgt tcagtgctga tggtcctaat tgtcagctac agaaaacgtc tccatgcagt    66300
tccttctgct ccagcaaact gtccaggcta tagcaccgtg atgcatgcta cctctcactc    66360
catccttctt ctctttccca ccagggagag ctgtgtgttt tcactctcag ccgctctgaa    66420
caataccaaa ctgctacgca ctgcctccct cggaaagaga atccccttgt tgcttttta    66480
tttacaggat ccttcttaaa aagcagacca tcattcactg caaacccaga gcttcctgcc    66540
tctccttcca caaccgaaaa cagccggctt catttgtctt ttttaaatgc tgttttccag    66600
gtgaattttg ccagcgtgt tggctgagat ccaggagcac gtgtcagctt tctgctctca    66660
ttgctcctgt tctgcattgc ctcttttctgg ggcttccaag agggggggag actttgcacg    66720
gggatgagat aatgccccctt ttcttagggt ggctgctggg cagcagagtg gctctgggtc    66780
actgtggcac caatgggagg caccagtggg ggtgtgtttt gtgcagggag gaagcattca    66840
cagaatgggg ctgatcctga agcttgcagt ccaaggcttt gtctgtgtac ccagtgaaat    66900
ccttcctctg ttacataaag cccagatagg actcagaaat gtagtcattc cagccccct    66960
cttcctcaga tctggagcag cacttgtttg cagccagtcc tccccaaaat gcacagacct    67020
cgccgagtgg agggagatgt aaacagcgaa ggttaattac ctccttgtca aaaacacttt    67080
gtggtccata gatgtttctg tcaatcttac aaaacagaac cgagggcagc gagcactgaa    67140
ggcgtgttcc catgctgagt taatgagact tggcagctcg ctgtgcagag atgatccctg    67200
tgcttcatgg gaggctgtaa cctgtctccc catcgccttc acaccgcagt gctgtcctgg    67260
acacctcacc ctccataagc tgtaggatgc agctgcccag ggatcaagag acttttccta    67320
aggctcttag gactcatctt tgccgctcag tagcgtgcag caattactca tcccaactat    67380
actgaatggg tttctgccag ctctgcttgt ttgtcaataa gcatttttc attttgcctc    67440
taagtttctc tcagcagcac cgctttgggt gacttcagtg gccgcctgga acccgagggg    67500
cacagccacc acctccctgt tgctgctgct ccggggactc acgtgctgct ggatgggggg    67560
aagcatgaag ttcctcaccc agacacctgg gttgcaatgg ttgcagtgtg ctcttcttgg    67620
tatgcagatt gtttctagcc attacttgta gaaatgtgct gtggaagccc tttgtatctc    67680
tttctgtggc ccttcagcaa aagctgtggg aaagctctga ggctgctttc ttgggtcgtg    67740
gaggaattgt atgttccttc tttaacaaaa attatcctta ggagagagca ctgtgcaagc    67800
attgtgcaca taaacaatt caggttgaaa gggctctctg gaggtttcca gcctgactac    67860
tgctcgaagc aaggccaggt tcaaagatgg ctcaggatgc tgtgtgcctt cctgattatc    67920
tgtgccacca atggaggaga ttcacagcca ctctgcttcc cgtgccactc atggagagga    67980
atattccctt atattcagat agaatgtcat cctttagctc agccttccct ataaccccat    68040
gagggagctg cagatcccca tactctcctc ttctctgggg tgaaggccgt gtcctccagc    68100
cccccttccc accctgtgcc ctgagcagcc cgctggcctc tgctggatgt gtgcccatat    68160
gtcaatgcct gtccttgcag tccagcctgg aacatttaat tcatcaccag ggtaatgtgg    68220
aactgtgtca tcttcccctg cagggtacaa agttctgcac ggggtccttt cggttcagga    68280
aaaccttcgc tggtgctacc tgaatcaagc tctatttaat aagttcataa gcacatggat    68340
gtgttttcct agagatacgt tttaatggta tcagtgattt ttatttgctt tgttgcttac    68400
```

```
ttcaaacagt gcctttgggc aggaggtgag ggacgggtct gccgttggct ctgcagtgat    68460
ttctccaggc gtgtggctca ggtcagatag tggtcactct gtggccagaa gaaggacaaa    68520
gatggaaatt gcagattgag tcatgttaag caggcatctt ggagtgattt gaggcagttt    68580
catgaaagag ctacgaccac ttattgttgt tttccccttt tacaacagaa gttttcatca    68640
aaataacgtg gcaaagccca ggaatgtttg ggaaaagtgt agttaaatgt tttgtaattc    68700
atttgtcgga gtgttaccag ctaagaaaaa agtcctacct ttggtatggt agtcctgcag    68760
agaatacgac atcaatatta gtttggaaaa aaacaccacc accaccagaa actgtaatgg    68820
aaaatgtaaa ccaagaaatt ccttgggtaa gagagaaagg atgtcgtata ctggccaagt    68880
cctgcccagc tgtcagcctg ctgaccctct gcagctcagg accatgaaac gtggcactgt    68940
aagacgtgtc cctgcctttg cttgctcaca gatctctgcc ctcgtgctga ctcctgcaca    69000
caagagcatt tccctgtagc caaacagcga ttagccataa gctgcacctg actttgagga    69060
ttaagagttt gcaattaagt ggattgcagc aggagatcag tggcagggtt gcagatgaaa    69120
tcctttctag gggtagctaa gggctgagca acctgtccta cagcacaagc caaaccagcc    69180
aagggttttc ctgtgctgtt cacagaggca gggccagctg gagctggagg aggttgtgct    69240
gggactcttc tccctgtgct gagaatggag tgatttctgg gtgctgttcc tgtggcttgc    69300
actgagcagc tcaagggaga tcggtgctcc tcatgcagtg ccaaaactcg tgtttgatgc    69360
agaaagatgg atgtgcacct ccctcctgct aatgcagccg tgagcttatg aaggcaatga    69420
gccctcagtg cagcaggagc tgtagtgcac tcctgtaggt gctagggaaa atctctggtt    69480
cccagggatg cattcataag gacaatatat cttgaggctg tgccaaatct ttctgaaata    69540
ttcatgcatg ttcccttaat ttatagaaac aaacacagca gaataattat tccaatgcct    69600
cccctcgaag gaaacccata tttccatgta gaaatgtaac ctatatacac acagccatgc    69660
tgcatccttc agaacatgcc agtgctcatc tcccatggca aaatactaca ggtattctca    69720
ctatgttgga cctgtgaaag gaaccatggt aagaaactca ggttaaaggt atggctgcaa    69780
aactactcat accaaaacag cagagctcca gacctcctct taggaaagag ccacttggag    69840
agggatggtg tgaaggctgg aggtgagaga cagagcctgt cccagttttc ctgtctctat    69900
tttctgaaat gtctgcagga ggaaaggaca actgtacttt caggcatagc tggtgccctc    69960
acgtaaataa gttccccgaa cttctgtgtc atttgttctt aagatgcttt ggcagaacac    70020
tttgagtcaa ttcgcttaac tgtgactagg tctgtaaata agtgctccct gctgataagg    70080
ttcaagtgac attttagtg gtatttgaca gcatttacct tgctttcaag tcttctacca    70140
agctcttcta tacttaagca gtgaaaccgc caagaaaccc ttccttttat caagctagtg    70200
ctaaatacca ttaacttcat aggttagata cggtgctgcc agcttcacct ggcagtggtt    70260
ggtcagttct gctggtgaca aagcctccct ggcctgtgct tttacctaga ggtgaatatc    70320
caagaatgca gaactgcatg gaaagcagag ctgcaggcac gatggtgctg agccttagct    70380
gcttcctgct gggagatgtg gatgcagaga cgaatgaagg acctgtccct tactcccctc    70440
agcgttctgt gctatttagg gttctaccag agtcctaagg aggttttttt ttttttttgg    70500
tccaaaagtc tgtttgtttg gttttgacca ctgagagcat gtgacacttg tctcaagcta    70560
ttaaccaagt gtccagccaa aatcaattgc ctggagacg cagaccatta cctggaggtc    70620
aggacctcaa taaatattac cagcctcatt gtgccgctga cagattcagc tggctgctct    70680
gtgttccagt ccaacagttc ggacgccacg tttgtatata tttgcaggca gcctcggggg    70740
gaccatctca ggagcagagc accggcagcc gcctgcagag ccgggcagta cctcaccatg    70800
```

```
gccatggcag gcgtcttcgt gctgttctct ttcgtgcttt gtggcttcct cccaggtgag   70860
taactcccag agtgctgcag aagctttgtg cctgccagtc ctggctctcc ttagcagaac   70920
atggtggtga ccatcagaga gagactcccc tacaaagtgc ctgcaaaggc tgcctcagta   70980
catcagtatt aaacggatta ctgttgtgct gggtgtctgt tgggttctgt gctcccaaca   71040
catttcttac gctctcagct ctgttacact gcttgcattt gctgcacagt tgcatagaat   71100
ggataaatgc ttgaaacaag gccataacga ggtggtcaga cctccaggaa ctagttaggg   71160
aaatattgtc atggcccaag caagctctgt gcaggaacct ggcagctttc ctgcaatgct   71220
tttgctgcta atggagaaac aagagatgca aacaagccag gatctgatgt tctccttctg   71280
tatttacatc tcatgaaatt acaaagtcaa agacaagcgt ggtttatttc ttacactcag   71340
cttctttaaa atgtatatcc ctgacaacag atgctgtgta tgtttgctta tcctgtatgt   71400
gactatttgc atttgcattt atctctattg actcaggttt cttttcagat atgtgataga   71460
tgttttctag ggacaaaacg gatgtgtgaa tagataagga aggaaaagat attcattttt   71520
caattaataa atctacctat ctcttaactt tttttttttt ttaagaacag agctattcaa   71580
gaactcgttt catcagccag caataagaag ctaaattatg tttatcagca ttaaacaaaa   71640
atcatatata gtttgcttag ttcaagaatc gaatcggtgg aaatcactca gtttggttct   71700
ctgtgctgga gttttgcaca cacatttcag ctagctgtgg tctcactgat cagactgcct   71760
ttgtttccca ttttttgtccc ctttttttcc ccagatgctg cctttgggc tgaggtgagt   71820 aagagagttc ttcttgtcca cttttctctt ttctcttttc tctctctctc ttttttttccc   71880 cccgtcttaa ttagtatcac tataatcaga tcccagagtg taaaatgtta aattatgcag   71940
ttctgagctc tacatctatg ctgcatgtaa gtaatgtagc agtgatataa aactgttaga   72000
tgaattaatt tctgaccaac tctgaactgg tctaagcttt aagttgatca tatgttctac   72060
taaataatac agtggtttgg gttggaaggg tcctttaaga tcatctactt ccaacccctc   72120
tgctataggc agggacaact cccactagac aagattgctc aaagctccat ccatatgatc   72180
agctgtagac tgatggctgt agactatagc attaaaaact acccccaaagc agcctactga   72240 aagaagaaag tactgtgagg tgctacagct tccaaatccc atgttgttag acctgttctt   72300
ttgaataaac gtgtttgtac gttgagaatg aatgagtaac aatggcagaa cactggaggg   72360
gccaactctc aggctttgca aaatggtgcc tgggggggcat gatagatccc tgctggttta   72420
tcacatgggg agctgcatgg ctataacccc attgcccagt tctctcccac tgcatggaga   72480
gaaggctgga tctggtcgct gccctgctga aaatggcaga tgtaactaca aaatgtcact   72540
ttgtcctgtt actgtgtgtt tctttgtcag gtggactgca gtaggtttcc caacgctaca   72600
gacaaggaag gcaaagatgt attggtttgc aacaaggacc tccgccccat ctgtggtacc   72660
gatggagtca cttacaccaa cgattgcttg ctgtgtgcct acagcatgtg tgtactgcag   72720
agagagctca tactgcaagc aagcagctgt gcttagggct cctgacagca cccctttcca   72780
acaaacagtg atctgtcaca tgtcacttat gtcaactctt tcagggaaag cttgagtatc   72840
actgcgtgac actcggttgc ctagacatca ctttggttac tgtgtctttt ttgttgatgt   72900
aatttattca ggttttttctc ctccatctcg gggatgaggc agatgacagc ccctagggca   72960
tatttcatcc cagcaaaaaa ggagcaaaag gatggagagg tgctccagtc tgaatggtcc   73020
aaaacagtcc taaagatttc agagtctttta gatccctgcc agccactcag tatggcacta   73080
ccctctccaa tacaaaatata tatatataca aagatgactt agccagactc agcctcattg   73140
```

```
cattaggtac atattcccaa taacgagaag ctgagcttcc taatacctgt tttccctctt    73200
cagagaattt ggaaccaata tcagcaaaga gcacgatgga gaatgcaagg aaactgttcc    73260
tgtaagtgaa accaagttca tcctttgtgc agccaaaact gcttattgac ttgcccaata    73320
aataatgtaa atgctgacta agaggccatg tgagatgtca gaatcttgta ttgatcatct    73380
tcaggtgaag tttcatcaca ataacacaaa aaaagacttt atttcctgct gaggtggcat    73440
tttaggagac ccaacgcacg cgctccgctg gtctacgtgg tccctgtaag ccctcaccag    73500
cgctttgctg tgtgctcctt ccacagatga actgcagtag ttatgccaac acgacaagcg    73560
aggacggaaa agtgatggtc ctctgcaaca gggccttcaa ccccgtctgt ggtactgatg    73620
gagtcaccta cgacaatgag tgtctgctgt gtgcccacaa agtgtaagta ccgagctgtg    73680
ctcccttggc aggaatgggt cctgcgctcc tggcagccac tctttgagca ctgggatttc    73740
caatgaggct ttttctgtat ggctcttgga ctccgtccct cctctccctg ataacctcat    73800
gctgttttcc tttgtgatta gaaagagaac tgtggctttg atcttgagag agaagcagag    73860
agctgggtgg ggacttaaga gaagcactct gttctgtgtt aactaagtta aaagggtctg    73920
tgtggcacac actgccttgc agaggacagc agtgaacctc tgctgcacct atattgtaaa    73980
acaacctagc tcctaggcca tgacagcctg tcacctctcc tcctttgcat catgcaatac    74040
tgcaacactg tggcacatag taccacctcc cataaggact gatatgttga accagtgtgt    74100
cagagaccag tagcatctct gtcttcagga tcatcaggta gcattctata tacagggtgt    74160
tgcccaggac tccgagtccc atgaagtatg gcagggtttt tggaactgga tgaccttcga    74220
ggtcacttcc aacccaagcc attctattat tctgtgaaag ccagggaggt gggggtgctt    74280
gcagggctgg tatcttgagc agtgtgggca caaactaggc tgggcatctg cagcccatca    74340
gcactgcggg gatgtggagt tcagcacagc aggatgcagg cacagctccc taacatggat    74400
ttttttcctt tcagagagca gggggccagc gttgacaaga ggcatgatgg tggatgtagg    74460
aaggaacttg ctgctgtgag tgtgagtagc acaatgaagg agcaggttct ggtcccactg    74520
atgtcaaggg aaacatggcc agcatctta gtagcctcag gagcatcagt tgtgcttcag    74580
cacagagaag attttacttt ctacacacgt aatacacatt atccacagta atgtcaggaa    74640
gggaagagga tgactgcaca ggcagggatc agtaaaagac cataagcaga aataacccat    74700
gagggcagaa ctgagaataa gaactgagac tagatccagg gggtcagacc aatgggccat    74760
caaacccatg atggtttgat gcagagtcca ctctttcagc attcataaga attgagtagg    74820
ggggagtaag ggtgggg tga gtacgtacgg atcttcccaa acacccttcc aacctacagc    74880
tatgcacctc agccaggtgt gatttctgtg tagttcacaa gcctcagtgg atttctctcc    74940
catgggattc tccagcctct ttctggacct gtatacacgg tagttgggtt ggttttttt    75000
ttctgtctct ctttttttcc ccccactaca atgtccctca gcaaacatag tcctcatctc    75060
tcaaacaaac aaatctcatt ctctaagtac ccagataaga gctgattttt gctttaagcc    75120
tgtgggggag atgctggact attataaagg tatcagtgct gcctcttctc cagacaccaa    75180
tgttttttcc atttaatttc ctgaacaggt caggaacacg gtgcaacatg attgtaagca    75240
cagcacgttc atggagcgag ctgctgctgc agctcagaaa tgcagcagtc agattgtgat    75300
atgcatctct tacacaggaa attatgctct attttttatat tattaaatct agcatacgag    75360
aaaggacatc cagtttatat cagatcgtgc aaggaagtta attatttta gtttgatcat    75420
tatcatcggc actgcagctg tagctaggga ggggttgaag ctcttcagct atcgactcct    75480
tcatatcctc cacgttacaa ttgtgttttt gcaggttgac tgcagcgagt accctaagcc    75540
```

```
tgactgcacg gcagaagaca gacctctctg tggctccgac aacaaaacat atggcaacaa    75600
gtgcaacttc tgcaatgcag tcgtgtacgt acagccctga ttgcattcac gttgtcggct    75660
gcctcctaca ggcaccagct tgcacagttc ctgctttcgt tgctgattgc tgaccaggat    75720
ctggggcag aaaagaacac cgggcatcac gccagccatt catttgattt ttcaccagag    75780
cttgtctggt tgttaggat ggatgttttg aacgccatta accttaaggg aagttttcct    75840
tgctgcgaag aaaatcagat ttggtgtttc attatagttt tcagaagggg ttaaacgatt    75900
tcactcatct cctaataatc aggtagctga ggagatgctg agtctgccag ttcttgggct    75960
ctgggcagga tcccatctcc tgccttctct aggacagagc tcagcaggca gggctctgtg    76020
gctctgtgtc taacccactt cttcctctcc tcgctttcag ggaaagcaac gggactctca    76080
ctttaagcca ttttggaaaa tgctgaatat cagagctgag agaattccgc ccctctccct    76140
cccccccccc taacgttact ggccgaagcc gcttggaata aggccggtgt gcgtttgtct    76200
atatgttatt ttccaccata ttgccgtctt ttggcaatgt gagggcccgg aaacctggcc    76260
ctgtcttctt gacgagcatt cctagggtc ttttcccctct cgccaaagga atgcaaggtc    76320
tgttgaatgt cgtgaaggaa gcagttcctc tggaagcttc ttgaagacaa acaacgtctg    76380
tagcgaccct ttgcaggcag cggaaccccc cacctggcga caggtgcctc tgcggccaaa    76440
agccacgtgt ataagataca cctgcaaagg cggcacaacc ccagtgccac gttgtgagtt    76500
ggatagttgt ggaaagagtc aaatggctct cctcaagcgt attcaacaag gggctgaagg    76560
atgcccagaa ggtaccccat tgtatgggat ctgatctggg gcctcggtgc acatgcttta    76620
catgtgttta gtcgaggtta aaaaaacgtc taggcccccc gaaccacggg gacgtggttt    76680
tcctttgaaa aacacgatga taagcttgcc acaaccatgg gtgtactgct cacacagagg    76740
acgctgctca gtctggtcct tgcactcctg tttccaagca tggcgagcat ggcaatgcac    76800
gtggcccagc ctgctgtggt actggccagc agccgaggca tcgccagctt tgtgtgtgag    76860
tatgcatctc caggcaaagc cactgaggtc cgggtgacag tgcttcggca ggctgacagc    76920
caggtgactg aagtctgtgc ggcaacctac atgatgggga atgagttgac cttcctagat    76980
gattccatct gcacgggcac ctccagtgga aatcaagtga acctcactat ccaaggactg    77040
agggccatgg acacgggact ctacatctgc aaggtggagc tcatgtaccc accgccatac    77100
tacctgggca taggcaacgg aacccagatt tatgtaattg atccagatac cgtgcccaga    77160
ttctgatcag gagcccaaat cttctgacaa aactcacaca tccccaccgt ccccagcacc    77220
tgaactcctg ggtggatcgt cagtcttcct cttccccccca aaacccaagg acaccctcat    77280
gatctcccgg acccctgagg tcacatgcgt ggtggtggac gtgagccacg aagaccctga    77340
ggtcaagttc aactggtacg tggacggcgt ggaggtgcat aatgccaaga caaagccgcg    77400
ggaggagcag tacaacagca cgtaccgggt ggtcagcgtc ctcaccgtcc tgcaccagga    77460
ctggctgaat ggcaaggagt acaagtgcaa ggtctccaac aaagcccctcc cagcccccat    77520
cgagaaaacc atctccaaag ccaaagggca gccccgagaa ccacaggtgt acaccctgcc    77580
cccatcccgg gatgagctga ccaagaacca ggtcagcctg acctgcctgg tcaaaggctt    77640
ctatcccagc gacatcgccg tggagtggga gagcaatggg cagccggaga caactacaa     77700
gaccacgcct cccgtgctgg actccgacgg ctccttcttc ctctacagca agctcaccgt    77760
ggacaagagc aggtggcagc aggggaacgt cttctcatgc tccgtgatgc atgaggctct    77820
gcacaaccac tacacgcaga gagagcctctc cctgtctccg ggtaaatgag ga            77872
```

<210> SEQ ID NO 45
<211> LENGTH: 780
<212> TYPE: DNA
<213> ORGANISM: SV40

<400> SEQUENCE: 45

| | | | | | |
|---|---|---|---|---|---|
| cccagagctg | tgcagttggg | atcctaacac | catgcagatg | ctccaggacc | tgcaccgagc | 60 |
| cccagcactg | gcactcatct | cttctttcca | cccctctgag | agcaacaagt | ggctctgcaa | 120 |
| tggcaatgta | agtgaaaccg | gcgggtatc | ttagagcacc | tggaagcttg | catgcctgca | 180 |
| ggtcgactct | agaggatccc | cgggtaccga | gctcgaattc | caggtaccgt | cgacgatgta | 240 |
| ggtcacggtc | tcgaagccgc | ggtgcgggtg | ccagggcgtg | cccttgggct | ccccgggcgc | 300 |
| gtactccacc | tcacccatct | ggtccatcat | gatgaacggg | tcgaggtggc | ggtagttgat | 360 |
| cccggcgaac | gcgcggcgca | ccgggaagcc | ctcgccctcg | aaaccgctgg | gcgcggtggt | 420 |
| cacggtgagc | acgggacgtg | cgacggcgtc | ggcgggtgcg | gatacgcggg | gcagcgtcag | 480 |
| cggggttctcg | acggtcacgg | cgggcatgtc | gacagccaag | ccgaattcgc | cctatagtga | 540 |
| gtcgtattac | aattcactgg | ccgtcgtttt | acaacgtcgt | gactgggaaa | accctggcgt | 600 |
| tacccaactt | aatcgccttg | cagcacatcc | ccctttcgcc | agctggcgta | atagcgaaga | 660 |
| ggcccgcacc | gatcgccctt | cccaacagtt | gcgcagcctg | aatggcgaat | ggcgcctgat | 720 |
| gcggtatttt | ctccttacgc | atctgtgcgg | tatttcacac | cgcatatggt | gcactctcag | 780 |

<210> SEQ ID NO 46
<211> LENGTH: 1957
<212> TYPE: DNA
<213> ORGANISM: human

<400> SEQUENCE: 46

| | | | | | |
|---|---|---|---|---|---|
| ataatcaggt | agctgaggag | atgctgagtc | tgccagttct | tgggctctgg | gcaggatccc | 60 |
| atctcctgcc | ttctctagga | cagagctcag | caggcagggc | tctgtggctc | tgtgtctaac | 120 |
| ccacttcttc | ctctcctcgc | tttcagggaa | agcaacggga | ctctcacttt | aagccatttt | 180 |
| ggaaaatgct | gaatatcaga | gctgagagaa | ttccgcccct | ctccctcccc | ccccccctaac | 240 |
| gttactggcc | gaagccgctt | ggaataaggc | cggtgtgcgt | ttgtctatat | gttatttcc | 300 |
| accatattgc | cgtcttttgg | caatgtgagg | gcccggaaac | ctggccctgt | cttcttgacg | 360 |
| agcattccta | ggggtctttc | ccctctcgcc | aaaggaatgc | aaggtctgtt | gaatgtcgtg | 420 |
| aaggaagcag | ttcctctgga | agcttcttga | agacaaacaa | cgtctgtagc | gaccctttgc | 480 |
| aggcagcgga | accccccacc | tggcgacagg | tgcctctgcg | gccaaaagcc | acgtgtataa | 540 |
| gatacacctg | caaaggcggc | acaaccccag | tgccacgttg | tgagttggat | agttgtggaa | 600 |
| agagtcaaat | ggctctcctc | aagcgtattc | aacaaggggc | tgaaggatgc | ccagaaggta | 660 |
| ccccattgta | tgggatctga | tctggggcct | cggtgcacat | gctttacatg | tgtttagtcg | 720 |
| aggttaaaaa | aacgtctagg | ccccccgaac | cacggggacg | tggttttcct | ttgaaaaaca | 780 |
| cgatgataag | cttgccacaa | ccatgggtgt | actgctcaca | cagaggacgc | tgctcagtct | 840 |
| ggtccttgca | ctcctgtttc | caagcatggc | gagcatggca | atgcacgtgg | cccagcctgc | 900 |
| tgtggtactg | gccagcagcc | gaggcatcgc | cagctttgtg | tgtgagtatg | catctccagg | 960 |
| caaagccact | gaggtccggg | tgacagtgct | tcggcaggct | gacagccagg | tgactgaagt | 1020 |
| ctgtgcggca | acctacatga | tggggaatga | gttgaccttc | ctagatgatt | ccatctgcac | 1080 |
| gggcacctcc | agtggaaatc | aagtgaacct | cactatccaa | ggactgaggg | ccatggacac | 1140 |

```
gggactctac atctgcaagg tggagctcat gtacccaccg ccatactacc tgggcatagg    1200
caacggaacc cagatttatg taattgatcc agataccgtg cccagattct gatcaggagc    1260
ccaaatcttc tgacaaaact cacacatccc caccgtcccc agcacctgaa ctcctgggtg    1320
gatcgtcagt cttcctcttc cccccaaaac ccaaggacac cctcatgatc tcccggaccc    1380
ctgaggtcac atgcgtggtg gtggacgtga gccacgaaga ccctgaggtc aagttcaact    1440
ggtacgtgga cggcgtggag gtgcataatg ccaagacaaa gccgcgggag gagcagtaca    1500
acagcacgta ccgggtggtc agcgtcctca ccgtcctgca ccaggactgg ctgaatggca    1560
aggagtacaa gtgcaaggtc tccaacaaag ccctcccagc ccccatcgag aaaaccatct    1620
ccaaagccaa agggcagccc cgagaaccac aggtgtacac cctgccccca tcccgggatg    1680
agctgaccaa gaaccaggtc agcctgacct gcctggtcaa aggcttctat cccagcgaca    1740
tcgccgtgga gtgggagagc aatgggcagc cggagaacaa ctacaagacc acgcctcccg    1800
tgctggactc cgacggctcc ttcttcctct acagcaagct caccgtggac aagagcaggt    1860
ggcagcaggg gaacgtcttc tcatgctccg tgatgcatga ggctctgcac aaccactaca    1920
cgcagaagag cctctccctg tctccgggta aatgagg                             1957
```

METHODS AND PROTEIN PRODUCTION USING OVOMUCOID PROMOTERS

RELATED APPLICATION INFORMATION

This application is a continuation of U.S. patent application Ser. No. 11/649,543, filed Jan. 4, 2007, now U.S. Pat. No. 7,507,873, issued Mar. 24, 2009, the disclosure of which is incorporated in its entirety herein by reference, which is a continuation of U.S. patent application Ser. No. 11/047,184, filed Jan. 31, 2005, now U.S. Pat. No. 7,335,761, issued Feb. 26, 2008, which is a continuation-in-part of U.S. patent application Ser. No. 10/856,218, filed May 28, 2004, now U.S. Pat. No. 7,294,507, issued Nov. 13, 2007, which is a continuation-in-part of U.S. patent application Ser. No. 10/496,731, filed May 21, 2004, now U.S. Pat. No. 7,375,258, issued May 20, 2008, which is a 371 of PCT/US02/38413, filed Dec. 2, 2002, and is a continuation-in-part of U.S. patent application Ser. No. 09/998,716 filed Nov. 30, 2001, now U.S. Pat. No. 6,875,588, issued Apr. 5, 2005. The disclosure of each of these three continuation-in-part applications and the PCT application is incorporated in its entirety herein by reference. U.S. patent application Ser. No. 11/047,184, now U.S. Pat. No. 7,335,761, issued Feb. 26, 2008, is also a continuation-in-part of U.S. patent application Ser. No. 10/790,455, now abandoned, filed Mar. 1, 2004, which claims the benefit of U.S. provisional patent application No. 60/476,596, filed Jun. 6, 2003, U.S. provisional patent application No. 60/505,562, filed Sep. 24, 2003 and U.S. provisional patent application No. 60/509,122, filed Oct. 6, 2003. The disclosure of the continuation-in-part application is incorporated by reference herein in its entirety.

GOVERNMENT RIGHTS STATEMENT

This invention was made with government support under a grant from the National Institute of Standards and Technology. Therefore, the U.S. Government may have certain rights in this invention.

FIELD OF THE INVENTION

The present invention relates generally to avian gene expression controlling regions, for example, from the chicken. The invention includes recombinant nucleic acid molecules and expression vectors, transfected cells and transgenic animals that include an avian gene expression controlling region operably linked to a nucleic acid of interest.

BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology for the production of specific proteins such as substances of pharmaceutical interest (Gordon et al., (1987) Biotechnology 5: 1183-1187; Wilmut et al., (1990) Theriogenology 33: 113-123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require maintenance of herds of large species, such as cows, sheep, or goats. Such animals typically have exceedingly long developmental periods and are costly to maintain.

One useful alternative that has shown great promise for heterologous gene expression is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct which is lined with tubular gland cells. These cells secrete the egg-white proteins, including ovalbumin, ovomucoid, ovoinhibitor, conalbumin, ovomucin and lysozyme, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other animal species used for heterologous gene expression. As a result, efforts have been made to create transgenic chickens expressing heterologous proteins in the oviduct.

Chicken oviduct cells, when stimulated by steroid hormones during egg-laying, secrete three principal amino acid sequences, ovalbumin, ovomucoid and lysozyme (Tsai et al., (1978) Biochemistry 17: 5773-5779). The mRNA transcript encoding ovalbumin constitutes about 50% of the total mRNA of these cells. Ovomucoid and lysozyme mRNAs contribute about 6.6% and 3.4% respectively of the total mRNA of the steroid stimulated cells (Hynes et al. (1977) Cell 11:923-932).

Detailed restriction enzyme analysis of fragments of chicken genomic DNA have shown that the ovomucoid-encoding sequence includes seven intronic sequences (Lindenmaier et al. (1979) Nuc. Acid Res. 7:1221-1232; Catterall et al. (1979) Nature 278:323-327; Lai et al. (1979) Cell 18:829-842). Short stretches of the 5' flanking region of the ovomucoid gene have been sequenced (Lai et al. (1979) Cell 18:829-842; Genbank Accession No. J00897), but extending only 579 bases upstream of the recognized transcription start site. The 5' flanking region of the ovomucoid gene has been isolated (Catterall et al. (1979) Nature 278:323-327; Lai et al. (1979) Cell 18: 829-842), but not generally characterized beyond low-resolution restriction site mapping. Scott et al. (1987) Biochemistry 26:6831-6840, identified a CR1-like region within the approximately 10 kb chicken genomic DNA located between the ovoinhibitor-encoding region and the downstream ovomucoid gene. The ovoinhibitor-encoding cDNA and the attached 3'-untranslated region, which extends into the approximately 10 kb ovoinhibitor-ovomucoid region, were also sequenced (Scott et al. (1987) J. Biol. Chem. 262: 5899-5907). There is no evidence that any of the previously identified portions of the ovomucoid gene are capable of regulating gene expression. In particular, there is no indication that any of these known portions are functional to assist in the initiation of transcription of the ovomucoid coding sequence. The chicken ovomucoid gene is highly expressed in the tubular glands of the mature hen oviduct and represents a suitable candidate for an efficient promoter for heterologous protein production in transgenic animals, especially avians, such as chickens.

What is needed are functional ovomucoid gene expression controlling nucleic acid sequences, such as ovomucoid promoters.

SUMMARY OF THE INVENTION

The present invention relates in part to nucleic acids which include an avian ovomucoid gene expression controlling region useful for expression of nucleotide sequences encoding one or more amino acid sequences of interest, such as peptides, polypeptides or proteins.

In one useful embodiment, the ovomucoid gene expression controlling region is effective to facilitate expression of certain nucleotide coding sequences in avian cells, for example, oviduct cells. In one embodiment, the amino acid sequence is heterologous, for example, the amino acid sequence is not the native ovomucoid protein product, and may be a mammalian, for example, a human amino acid sequence.

One aspect of the invention provides for a gene expression controlling region which includes nucleotide sequence found upstream of an ovomucoid coding sequence and/or nucleotide sequence found downstream of an ovomucoid coding sequence. In one aspect of the invention, fragments of an ovomucoid promoter gene which are effective to control gene expression of a nucleic acid sequence of interest are provided. For example, the invention provides for a nucleic acid fragment isolated from a region upstream of a transcription start site of an ovomucoid gene effective to control or regulate gene expression. In another example, the nucleic acid fragment is isolated from a region downstream of a transcription start site of an ovomucoid gene effective to control or regulate gene expression. In another embodiment, the fragment is isolated from a region upstream and downstream of a transcription start site of an ovomucoid gene effective to control gene expression.

In one embodiment of the present invention, the ovomucoid gene expression controlling region is isolated from a chicken. In a specific embodiment, the ovomucoid gene expression controlling region has a nucleotide sequence of OMC 70, which is included in the sequence of SEQ ID NO: 36. In one useful aspect, all or substantially all or a functional fragment of OMC 70 is employed to control the expression of a nucleic acid sequence of interest. The sequence of OMC 70 is included in the sequence of SEQ ID NO: 36 which is a BAC clone. A BAC clone which is believed to contain the nucleotide sequence represented by SEQ ID NO: 36 designated OMC24 has been deposited with the ATCC Patent Depository and has been assigned the deposit number of PTA-6234. The avian nucleotide sequence of PTA-6234 is included in the present application as are all functional fragments of the ovomucoid gene expression controlling sequence or region of PTA-6234. In one particularly useful aspect of the invention, the ovomucoid gene expression controlling region is a fragment or portion of OMC 70 which is effective to control gene expression in a cell, for example, an avian cell (e.g., a chicken cell). In a very useful aspect, fragments of the ovomucoid gene expression controlling region are operably linked or attached to a heterologous coding sequence such as a nucleotide sequence encoding a therapeutic protein.

In certain embodiments, the gene expression controlling region of the invention is at least 60% or at least 75% or at least 85% or at least 90% or at least 95% or at least 99% identical or homologous to an ovomucoid gene expression controlling region disclosed herein (e.g., the ovomucoid gene expression controlling region included in SEQ ID NO: 36) or fragments thereof and can regulate or control expression of a nucleotide sequence in a cell, such as an avian cell (e.g., a chicken cell).

In one embodiment, the avian ovomucoid gene expression controlling region of the present invention is useful for directing tissue-specific expression of an amino acid sequence-encoding nucleic acid. The gene expression controlling regions of the invention may be operably linked to a nucleic acid of interest (i.e., a nucleic acid insert) wherein the nucleic acid insert encodes an amino acid sequence desired to be expressed in a transfected cell. In one embodiment, the nucleic acid insert may be cloned in frame with a nucleotide sequence encoding a signal peptide. Translation may start with the signal peptide and continue through the nucleic acid insert, thereby producing an expressed amino acid sequence having the desired amino acid sequence including a signal sequence.

The nucleic acid of the present invention may include an untranslated 3' region which may include a polyadenylation coding sequence allowing the transcript directed by the ovomucoid gene expression controlling region of the invention to include, in addition to a certain heterologous amino acid sequence (i.e., not the ovomucoid protein that is expressed from the endogenous gene containing the ovomucoid gene expression controlling region), a 3' untranslated region that may include a polyadenylated tail. Any functional polyadenylation signal sequence may be linked to the 3' end of the nucleic acid insert including the SV40 polyadenylation signal sequence, bovine growth hormone adenylation sequence or the like. There are many known useful signal sequences including those disclosed in U.S. Pat. No. 5,856,187, the disclosure of which is incorporated in its entirety herein by reference.

The nucleic acid of the invention may include certain gene expression controlling elements, such as promoters, enhancers, IRES's from a source other than an ovomucoid gene, for example, from a non-avian gene.

The sequence of the expressed nucleic acid insert may be optimized for codon usage by the host cell or host organism. Codon usage can be determined by methods well known in the art. For example, codon usage may be determined for an avian by methods known in the art, for example, by examining nucleotide sequences which encode proteins such as ovalbumin, ovomucoid, ovomucin and ovotransferrin produced by a chicken and comparing the encoded amino acids to the corresponding codons.

Yet another aspect of the invention relates to expression vectors suitable for expressing the nucleic acid coding sequences as disclosed herein. Expression vectors of the present invention may include an avian ovomucoid gene expression controlling region operably linked to a nucleic acid insert encoding a non-ovomucoid amino acid sequence, and optionally, a non-coding sequence such as a polyadenylation signal sequence. The expression vector may also include a bacterial plasmid sequence, a viral nucleic acid sequence, or fragments or variants thereof or other sequences that will allow for maintaining the vector in a suitable host. As contemplated in the present invention, the vector may be a YAC, BAC, HAC, MAC, bacteriophage-derived artificial chromosome (BBPAC), cosmid or P1 derived artificial chromosome (PAC).

The present invention further relates to nucleic acid vectors and transgenes inserted therein that incorporate multiple amino acid sequence-encoding regions, wherein a first amino acid sequence-encoding region is operatively linked to a transcription promoter and a second amino acid sequence-encoding region is operatively linked to an Internal Ribosome Entry Sequence (IRES). For example, the vector may contain coding sequences for two different heterologous proteins (e.g., the heavy and light chains of an immunoglobulin), both sequences under the control of the same promoter. In one useful embodiment, the promoter is an ovomucoid gene expression controlling region as disclosed herein.

Nucleic acid constructs of the invention, when inserted into the genome of a bird and expressed therein, will produce amino acid sequences that may be post-translationally modified, for example, glycosylated or, in certain embodiments, be present as complexes, such as dimmers, (e.g., heterodimers).

Another aspect of the present invention is a method of expressing an amino acid sequence in a eukaryotic cell by transfecting the cell with a recombinant DNA comprising a gene expression controlling region of the invention operably linked to a nucleic acid insert encoding the amino acid sequence and, optionally, a non-coding sequence such as a polyadenylation signal sequence, and culturing the transfected cell in a medium suitable for expression of the amino acid sequence under the control of the gene expression controlling region. In certain embodiments, the amino acid sequence is a therapeutic protein such as a cytokine, growth factor, enzyme, structural protein, an immunoglobulin, or other therapeutic protein including, but not limited to, those disclosed elsewhere herein, or subunit or fragment thereof. In other embodiments, the amino acid sequence is a mammalian, such as a human, amino acid sequence or is substantially similar to a human or mammalian amino acid sequence.

Also within the scope of the present invention are recombinant cells, tissues and animals, for example, avians such as chickens, containing recombinant nucleic acid molecules of the present invention. In certain embodiments, the level of expression of a heterologous protein is greater than 1 μg, 5 μg, 10 μg, 50 μg, 100 μg, 250 μg, 500 μg, 750 μg, 1 mg, 2 mg, 5 mg, 10 mg, 20 mg, 50 mg, 100 mg, 200 mg, 500 mg, 700 mg, 1 gram, 2 grams, 3 grams, 4 grams or 5 grams in an egg produced by the transgenic avian of the invention. In one embodiment, the heterologous protein is present mostly or exclusively in the egg white.

In one embodiment of the invention, the cell is a chicken oviduct cell and the nucleic acid comprises a chicken ovomucoid gene expression controlling region, a nucleic acid insert encoding a heterologous amino acid sequence of interest, which optionally is codon optimized for expression in an avian cell, and a non-coding sequence such as a polyadenylation sequence, for example, an SV40 polyadenylation sequence. In one particularly useful embodiment, the oviduct cell is present in a live avian, such as a chicken.

The present invention includes nucleic acid molecules, for example, DNA, which comprise an artificial chromosome comprising an ovomucoid gene expression controlling region and methods of using the nucleic acid molecules, such as for the production of transgenic avians comprising an artificial chromosome.

In one embodiment, the gene expression controlling region of the present invention is a nucleotide sequence that hybridizes to the nucleotide sequence of SEQ ID NO: 36 or portions thereof such as Fragment A, Fragment B or Fragment C as disclosed in FIG. 14. In another embodiment, the gene expression controlling region of the present invention is a nucleotide sequence that hybridizes to the complement of the nucleotide sequence of SEQ ID NO: 36 or portions thereof such as Fragment A, Fragment B or Fragment C as disclosed in FIG. 14. In one embodiment, the hybridizations are under stringent conditions. High stringency conditions, when used in reference to nucleic acid hybridization, may comprise conditions equivalent to binding or hybridization at 65° C. in a solution consisting of 6×SSPE, 1% SDS, 5×Denhardt's reagent and 100 μg/ml denatured salmon sperm DNA followed by washing in a solution comprising 0.1×SSPE, and 0.1% SDS at 65° C. for about 15 to about 20 minutes. In certain embodiments, the wash conditions may include 50% formamide at 42° C. instead of 65° C. High stringency washes may include 0.1×SSC to 0.2×SSC and 1% SDS at 65° C. for about 15 to about 20 min. (see, Sambrook et al., Molecular Cloning—A Laboratory Manual (2nd ed.) Vol. 1-3, Cold Spring Harbor Laboratory, Cold Spring Harbor Press, N.Y., 1989, the disclosure of which is incorporated herein in its entirety by reference). Exemplary medium stringency conditions are as described above for high stringency except that the washes are carried out at 55° C. or at 37° C. when in the presence of 50% formamide. In a most useful aspect of the invention, a nucleotide sequence that hybridizes to an ovomucoid gene expression controlling region and its complement, such as a nucleotide sequence that hybridizes to the nucleotide sequence of SEQ ID NO: 36 or portions thereof such as Fragment A, Fragment B or Fragment C as disclosed in FIG. 14 and their complement, which serves as a functional gene expression controlling region, is operably linked or attached to a heterologous coding sequence such as a nucleotide sequence encoding a therapeutic protein. In one embodiment of the invention, fragments or portions of the ovomucoid gene expression controlling region as disclosed herein are useful as hybridization probes as is understood in the field of molecular biology.

In one embodiment, the ovomucoid gene expression controlling region is that of SEQ ID NO: 36 or portions thereof such as Fragment A, Fragment B or Fragment C as disclosed in FIG. 14. In another embodiment, the ovomucoid gene expression controlling region comprises a functional portion of SEQ ID NO: 36 or portions thereof such as Fragment A, Fragment B or Fragment C as disclosed in FIG. 14. The ovomucoid gene expression controlling region may also include the complement of SEQ ID NO: 36 or the complement of portions thereof such as the complement of Fragment A, the complement of Fragment B or the complement of Fragment C as disclosed in FIG. 14. In a particularly useful embodiment of the invention, a functional portion of SEQ ID NO: 26 or a functional portion of the avian nucleic acid contained in SEQ ID NO: 36 is operably linked or attached to a heterologous coding sequence such as a nucleotide sequence encoding a therapeutic protein.

In one embodiment, functional portions of the nucleotide sequence of the avian ovomucoid gene expression controlling region contained in SEQ ID NO: 36 are shown in FIG. 14. For example, Fragment A is an approximately 10 kb fragment which spans from about nucleotide 26,416 to about nucleotide 36,390 of FIG. 14 and of SEQ ID NO 36. Fragment B is an approximately 3.9 kb fragment which spans from about nucleotide 32,364 to about nucleotide 36,299 of FIG. 14 and of SEQ ID NO 36. Fragment C is an approximately 1.8 kb fragment which spans from about nucleotide 34,473 to about nucleotide 36,248 of FIG. 14 and of SEQ ID NO 36.

In another example, a potentially useful functional portion of the ovomucoid gene expression controlling region is the portion of SEQ ID NO: 36 which extends from the SbfI site at about nucleotide 14,727 to the EcoRI site at about nucleotide 48,185. Another example of a potentially useful functional portion of the ovomucoid gene expression controlling region is the portion of SEQ ID NO: 36 which extends from the HindIII site at about nucleotide 24,742 to the EcoRI site at about nucleotide 48,185. Another example of a potentially useful functional) portion of the ovomucoid gene expression controlling region is the portion of SEQ ID NO: 36 which extends from the EcoRI site at about nucleotide 27,028 to the EcoRI site at about nucleotide 48,185. Another example of a potentially useful functional portion of the ovomucoid gene expression controlling region is the portion of SEQ ID NO: 36 which extends from the HindIII site at about nucleotide 28,381 to the EcoRI site at about nucleotide 48,185. Another example of a potentially useful functional portion of the ovomucoid gene expression controlling region is the portion of SEQ ID NO: 36 which extends from the EcoRI site at about nucleotide 27,028 to the EcoRI site at about nucleotide 54,424. In addition, a useful ovomucoid gene expression controlling region may extend from about nucleotide 35,861 to about nucleotide 36,252.

Methodologies are well known in the field that are useful to identify gene expression controlling regions within specified nucleic acid sequences (see, for example, Reese, M. G. and Eeckman, F. H. (1995) "Novel Neural Network Algorithms for improved Eukaryotic Promoter Site Recognition" The seventh international Genome sequencing and analysis conference, Hyatt Regency, Hilton Head Island, S.C. Sep. 16-20, 1995 and Reese, M. G., Ph.D. Thesis (2000) UC Berkeley/University Hohenheim). Numerous computer programs are known in the art which can be used to identify gene expression controlling sequences such as promoter sequences within a certain nucleotide sequence. Using such sequence analysis programs, potential gene expression controlling regions can be identified and thereafter tested for gene expression controlling activity by methods known in the field of molecular biology such as those disclosed herein. For example, a 50 nucleotide sequence spanning from nucleotide 36,209 to nucleotide 36,258 was shown to be a potential promoter site with a relatively high degree (match score of 1.0) of certainty using the computer program available at http://www.fruitfly.org/seq_tools/nnppAbst.html.

In one embodiment, the gene expression controlling region comprises a nucleotide sequence that is at least 50% homologous or identical to the ovomucoid gene expression controlling region of the nucleotide sequence of SEQ ID NO: 36 or portions thereof such as Fragment A, Fragment B or Fragment C as disclosed in FIG. 14 or is at least 50% homologous to the complement of the ovomucoid gene expression controlling region of the nucleotide sequence of SEQ ID NO: 36 or portions thereof such as Fragment A, Fragment B or Fragment C as disclosed in FIG. 14. For example, the gene expression controlling region may comprise a nucleotide sequence that is at least 60% homologous or identical to the ovomucoid gene expression controlling region of the nucleotide sequence of SEQ ID NO: 36 or portions thereof such as Fragment A, Fragment B or Fragment C as disclosed in FIG. 14 or is at least 60% homologous to a complement thereof. In another example, the gene expression controlling region comprises a nucleotide sequence that is at least 70% homologous or identical to the ovomucoid gene expression controlling region of the nucleotide sequence of SEQ ID NO: 36 or portions thereof such as Fragment A, Fragment B or Fragment C as disclosed in FIG. 14 or is at least 70% homologous to a complement thereof. In another example, the gene expression controlling region comprises a nucleotide sequence that is at least 75% homologous or identical to the ovomucoid gene expression controlling region of the nucleotide sequence of SEQ ID NO: 36 or portions thereof such as Fragment A, Fragment B or Fragment C as disclosed in FIG. 14 or is at least 75% homologous or identical to a complement thereof. In another example, the gene expression controlling region comprises a nucleotide sequence that is at least 80% homologous or identical to the ovomucoid gene expression controlling region of the nucleotide sequence of SEQ ID NO: 36 or portions thereof such as Fragment A, Fragment B or Fragment C as disclosed in FIG. 14 or is at least 80% homologous or identical to a complement thereof. In another example, the gene expression controlling region comprises a nucleotide sequence that is at least 85% homologous or identical to the ovomucoid gene expression controlling region of the nucleotide sequence of SEQ ID NO: 36 or is at least 85% homologous or identical to a complement thereof. In another example, the gene expression controlling region comprises a nucleotide sequence that is at least 90% homologous or identical to the ovomucoid gene expression controlling region of the nucleotide sequence of SEQ ID NO: 36 or portions thereof such as Fragment A, Fragment B or Fragment C as disclosed in FIG. 14 or is at least 90% homologous or identical to a complement thereof. In another example, the gene expression controlling region comprises a nucleotide sequence that is at least 95% homologous or identical to the ovomucoid gene expression controlling region of the nucleotide sequence of SEQ ID NO: 36 or portions thereof such as Fragment A, Fragment B or Fragment C as disclosed in FIG. 14 or is at least 95% homologous or identical to a complement thereof. In another example, the gene expression controlling region comprises a nucleotide sequence that is at least 99% homologous or identical to the ovomucoid gene expression controlling region of the nucleotide sequence of SEQ ID NO: 36 or portions thereof such as Fragment A, Fragment B or Fragment C as disclosed in FIG. 14 or is at least 99% homologous or identical to a complement thereof.

In one embodiment, nucleic acid molecules of the invention include an attB site. The use of attB is disclosed in, for example, U.S. patent application Ser. No. 10/790,455, filed Mar. 1, 2004, now abandoned, the disclosure of which is incorporated in its entirety herein by reference.

The nucleic acid molecules of the present invention may also include a signal sequence coding region which may be useful for secretion of an amino acid sequence product from a cell. In one embodiment, the signal sequence is cleaved from the amino acid sequence product during the secretion process. For the purposes of the present invention, "signal sequence peptide" refers to amino acid sequences of about 15 to about 25 amino acids in length which are known in the art to be generally located at the amino terminus of proteins and which are capable of facilitating secretion of a peptide or amino acid sequence from a cell.

In one particularly useful embodiment, the nucleic acid molecules of the present invention include an artificial chromosome. Any useful artificial chromosomes are contemplated for use in the present invention. In one embodiment, an artificial chromosome is a DNA molecule which includes a telomere and is capable of self replication in a cell, for example, in an avian cell. In another embodiment, an artificial chromosome includes a telomere and a centromere. Artificial chromosomes include, without limitation, BACs (bacterial artificial chromosomes), YACs (yeast artificial chromosomes), HACs (human artificial chromosomes) MACs (mammalian artificial chromosomes), BBPACs (bacteriophage derived artificial chromosomes) or PACs (P1 derived artificial chromosomes) or combinations thereof. Artificial chromosomes may include a gene expression controlling region as disclosed herein and may be present in cells of a transgenic avian such as a chicken or may be present in cells in culture.

The present invention also relates to compositions and methods for expressing certain peptides and amino acid sequences (e.g., peptides or proteins). The compositions can include a nucleic acid molecule comprising an artificial chromosome and an ovomucoid gene expression controlling region, as disclosed herein, which may be operably linked to a nucleotide sequence encoding an amino acid sequence. The nucleic acid may be inserted into a cell, for example, into a cell of an avian, where the amino acid sequence is expressed. In one embodiment, the nucleic acid molecule is present in cells of a transgenic avian including oviduct cells, for example, tubular gland cells of a transgenic avian. The coding region may encode any useful polynucleotide including pharmaceutical or therapeutic proteins which comprise an amino acid sequence.

The nucleic acid molecules of the present invention may be introduced into a cell, for example, into the cell of an avian, by any useful method. Such methods include, without limitation, microinjecting, transfection, electroporation and lipofection. The nucleic acid molecules may be introduced into a germinal disc or an avian embryo cell such as an early stage avian embryo. In one embodiment, the nucleic acid molecules of the present invention are introduced into an avian embryo cell such as a stage I avian embryo, stage II avian embryo, stage III avian embryo, stage IV avian embryo, stage V avian embryo, stage VI avian embryo, stage VII avian embryo, stage VIII avian embryo, stage IX avian embryo, stage X avian embryo, stage XI avian embryo or stage XII avian embryo.

Certain specific examples of pharmaceutical or therapeutic proteins which are contemplated for production as disclosed herein include, with out limitation, Factor VIII (e.g., Recombinate®, Bioclate®, Kogenate®, Helixate® (Centeon), B-domain deleted Factor VIII (e.g., ReFacto®), Factor VIIa (e.g., NovoSeven®), Factor IX (e.g., Benefix®), anticoagulant; recombinant hirudin (e.g., Revasc®, Refludan®) Alteplase, tPA (e.g., Activase®), Reteplase, tPA, tPA-3 of 5 domains deleted, Ecokinase®, Retavase®, Rapilysin®, insulin (e.g., Humulin®, Novolin®, Insuman®) insulin lispro (e.g., Humalog®), Bio Lysprol, Liprolog®), insulin Aspart, iNovoRapid®, insulin glargine, long-acting insulin analog (e.g., Lantus®), rhGH (e.g., Protropin®, Humatrope®, Nutropin®, BioTropin®, Genotropin®, Norditropin®, Saizen®, Serostim®), glucagons (e.g., Glucagen®), TSH (e.g., Thyrogen®, Gonal F®, Puregon®), follitropin-beta FSH (e.g., Follistim®), EPO (e.g., Epogen®, Procrit®, Neorecormon®), GM-CSF (e.g., Leukine®, Neupogen®), PDGH (e.g., Regranex®), hormones such as cytokines, IFN alpa2a (e.g., Roferon A®), INF-apha (e.g., Infergen®), IFN alpa2b (e.g., Intron A®, Alfatronol®, Virtrong), ribavirin & INF-alpha 2b (e.g., Robetron®) INF-beta 1b, (e.g., Betaferon®), IFN-beta 1a (e.g., Avonex®, Rebif®), IFN-gamma1b (e.g., Actimmune®), IL-2 (e.g., Proleukin®) rIL-11 (e.g., Neumega®), rHBsAg (e.g., Recombivax®), Combination vaccine containing HBsAgn as one component (e.g., Comvax®, Tritarix®, Twinrix®, Primavax®, Procomax®), OspA, a lipoprotein found on the surface of B burgoeri (e.g., Lymerix®), murine MAb directed against t-lymphocyte antigen CD3 (e.g., Orthoclone OKT3®), murine MAb directed against TAG-72, tumor-associated glycoprotein (e.g., OncoScint CR/OV®), FAb fragments derived from chimeric MAb, directed against platelet surface receptor GPII(b)/III(a) (e.g., ReoPro®), murine MAb fragment directed against tumor-associated antigen CA125 (e.g., Indimacis®), murine MAb fragment directed against human carcinoembryonic antigen, CEA (e.g., CEA-scan®), murine MAb fragment directed against human cardiac myosin (e.g., MyoScint®), murine MAb fragment directed against tumor surface antigen PSMA (e.g., ProstaScint®), murine MAb fragments (FAb/FAb2 mix) directed against HMW-MAA (e.g., Tacnemab®), murine MAb fragment (FAb) directed against carcinoma-associated antigen (e.g., Verluma®), MAb fragments (FAb) directed against NCA 90, a surface granulocyte nonspecific cross reacting antigen (e.g., LeukoScan®), chimeric MAb directed against CD20 antigen found on surface of B lymphocytes (e.g., Rituxan®), humanized MAb directed against the alpha chain of the IL2 receptor (e.g., Zenapax®), chimeric MAb directed against the alpha chain of the IL2 receptor (e.g., Simulect®), chimeric MAb directed against TNF-alpha (e.g., Remicade®), humanized MAb directed against an epitope on the surface of respiratory syncytial virus (e.g., Synagis®), humanized MAb directed against HER 2, i.e., human epidermal growth factor receptor 2 (e.g., Herceptin®), human MAb directed against cytokeratin tumor-associated antigen (e.g., Humaspect®), anti-CTLA4, chimeric MAb directed against CD 20 surface antigen of B lymphocytes (e.g., Mabthera®), dornase-alpha DNAse (e.g., Pulmozyme®), beta glucocerebrosidase (e.g., Cerezyme®), TNF-alpha (e.g., Beromun®), IL-2-diptheria toxin fusion protein that targets cells displaying a surface IL-2 receptor (e.g., Ontak®), TNFR-IgG fragment fusion protein (e.g., Enbrel®), Laronidase, Recombinant DNA enzyme, (e.g., Aldurazyme®), Alefacept, Amevive®, Darbepoetin alfa (Colony stimulating factor) (e.g., Aranesp®), Tositumomab and iodine 1 131 tositumomab, murine MAb, Bexxar®, Alemtuzumab, Campath®, Rasburicase, Elitek®), Agalsidase beta, Fabrazyme®, FluMist®, Teriparatide, Parathyroid hormone derivative (e.g., Forteo®), Enfuvirtide Fuzeon®, Adalimumab (IgG1) (e.g., Humira®), Anakinra, Biological modifier (e.g., Kineret®), nesiritide, Human B-type natriuretic peptide (hBNP) (e.g., Natrecor®), Pegfilgrastim, Colony stimulating factor (e.g., Neulasta®), ribavarin and peg Intron A (e.g., Rebetron®), Pegvisomant, PEGylated human growth hormone receptor antagonist, (e.g., Somavert®), recombinant activated protein C (e.g., Xigris®), Omalizumab, Immunoglobulin E (IgE) blocker (e.g., Xolair®) and Ibritumomab tiuxetan (murine MAb) (e.g., Zevalin®).

In one particularly useful embodiment, the amino acid sequence such as a pharmaceutical or therapeutic protein encoded by the nucleotide sequence operably linked to the ovomucoid gene expression controlling region is present in egg white produced by a transgenic avian of the present invention (i.e., an avian comprising a cell which includes a nucleic acid molecule of the present invention)

In one aspect of the invention, the nucleic acid molecule includes a nucleotide sequence encoding a light chain and/or a heavy chain of an antibody or a portion of a light chain and/or a heavy chain of an antibody which is operably linked to the ovomucoid gene expression controlling region. The antibody may be IgG (e.g., IgG1, IgG2, IgG3 or IgG4), IgA (e.g., IgA1 or IgA2), IgD, IgM or IgE. In addition, the light chain of the antibody may be a kappa light chain or a lambda light chain.

The present invention also contemplates the production of useful fusion proteins. For example, an antibody or a portion of an antibody may be produced as a fusion protein with another useful amino acid sequence.

The techniques used to isolate and characterize the nucleic acids and proteins of the present invention are well known to those of skill in the art and standard molecular biology and biochemical manuals may be consulted to select suitable protocols without undue experimentation. See, for example, Sambrook et al. (2001) Molecular Cloning: A Laboratory Manual, 3rd ed., Cold Spring Harbor Press, the content of which is herein incorporated by reference in its entirety.

Any combination of features described herein is included within the scope of the present invention provided that the features included in any such combination are not mutually Definitions Definitions of certain terms used in the present application are set forth below.

As used herein the terms "amino acid sequence" and "protein" refer to a polymer of amino acids of three or more amino acids in a serial array, linked through peptide bonds. The term "amino acid sequence" includes proteins, protein fragments, protein analogues, oligopeptides and the like. The term amino acid sequence as used herein can also refer to a peptide. The term "amino acid sequences" contemplates amino acid sequences as defined above that are encoded by nucleic acids, produced through recombinant technology (isolated from an appropriate source such as a bird), or synthesized. The term "amino acid sequences" further contemplates amino acid sequences as defined above that include chemically modified amino acids or amino acids covalently or noncovalently linked to labeling ligands.

The term "animal" is used herein to include all vertebrate animals, including humans. It also includes an individual animal in all stages of development, including embryonic and fetal stages.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "avian" as used herein refers to any species, subspecies or race of organism of the taxonomic class aves, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and may further comprise any modified or derivatised variant thereof that retains the ability to specifically bind an epitope. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab')$_2$ fragments, disulfide-linked Fvs (sdFv) fragments, e.g., as produced by a Fab expression library, anti-idiotypic (anti-Id) antibodies, intrabodies, synthetic antibodies, and epitope-binding fragments of any of the above.

The term "cytokine" as used herein refers to any secreted amino acid sequence that affects the functions of cells and is a molecule that modulates interactions between cells in the immune, inflammatory or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of an ovomucoid gene expression controlling region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° C. in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

1 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased, for example, by 1 fold, 2 fold, 5 fold, 10 fold, 50 fold, 100 fold, 500 fold, 1000 fold, 10,000 fold, 100,000 fold, or 1,000,000 fold. The other DNA may, for example, be derived from a yeast or bacterial genome, or a cloning vector, such as a plasmid or a viral vector.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "expression vector" as used herein refers to a nucleic acid vector that comprises the ovomucoid gene expression controlling region operably linked to a nucleotide sequence coding at least one amino acid sequence. As used herein, the term "regulatory sequences" includes promoters, enhancers, and other elements that may control gene expression. Standard molecular biology textbooks such as Sambrook et al. eds "Molecular Cloning: A Laboratory Manual" 3rd ed., Cold Spring Harbor Press (2001) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The term "fragment" as used herein can refer to, for example, an at least about 10, 20, 50, 75, 100, 150, 200, 250, 300, 500, 1,000, 2,000, 5,000, 6,000, 8,000, 10,000, 20,000, 30,000, 40,000, 50,000 or 60,000 nucleotide long portion of a nucleic acid (e.g., cDNA) that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to, for example, an at least about 5, 10, 20, 30, 40, 50, 75, 100, 150, 200, 250, 300, 400, 500, 1,000, 2,000, 5,000, 6,000, 8,000 or 10,000 amino acid portion of an amino acid sequence, which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 5%, about 10%, about 20%, about 30%, about 40%, about 50%, about 60%, about 70%, about 80% about 90% about 95% or about 99% of a particular nucleotide or amino acid sequence.

"Functional portion" or "functional fragment" as used herein means a portion or fragment of a whole capable of performing, in whole or in part, a function of the whole. For example, a biologically functional portion of a molecule means a portion of the molecule that performs a biological function of the whole or intact molecule. For example, a functional portion of a gene expression controlling region is a fragment or portion of the specified gene expression controlling region that, in whole or in part, regulates or controls gene expression (e.g., facilitates either in whole or in part) in a biological system (e.g., a promoter). Functional portions may be of any useful size. For example, a functional fragment may range in size from about 20 bases in length to a length equal to the entire length of the specified sequence minus one nucleotide. In another example, a functional fragment may range in size from about 50 bases in length to a length equal to the entire length of the specified sequence minus one nucleotide. In another example, a functional fragment may range in size from about 50 bases in length to about 70 kb in length. In another example, a functional fragment may range in size from about 500 bases in length to about 70 kb in length. In another example, a functional fragment may range in size from about 1 kb in length to about 70 kb in length. In another example, a functional fragment may range in size from about 1 kb in length to about 20 kb in length. In another example, a functional fragment may range in size from about 1 kb in length to about 10 kb in length. Functional portions may include, for example, and without limitation, one or more of a matrix attachment region, a transcription enhancer, a hormone responsive element or a CRI repeat element.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by foreign, heterologous or foreign exogenous genes and are, therefore, not naturally expressed in the cell.

The term "gene expression controlling region" as used herein refers to a nucleotide sequence which regulates, in whole or in part, the expression of a nucleotide sequence, for example, regulates, in whole or in part, the transcription of a nucleotide sequence. Exemplary transcription regulatory sequences include enhancer elements, hormone response elements, steroid response elements, negative regulatory elements, and the like. The "transcription regulatory sequences" may be isolated and incorporated into a nucleic acid vector to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in other regions of nucleic acid sequence. In addition, to "control gene expression," or "controlling gene expression", refers to regulation, in whole or in part, of the expression of a nucleotide sequence, for example, regulation, in whole or in part, of the transcription of a nucleotide sequence.

The term "immunoglobulin amino acid sequence" as used herein refers to an amino acid sequence derived from a constituent amino acid sequence of an immunoglobulin. An "immunoglobulin amino acid sequence" may be, but is not limited to, an immunoglobulin (preferably an antibody) heavy or light chain and may include a variable region, a diversity region, a joining region and/or a constant region or any combination, variant or truncated form thereof. The term "immunoglobulin amino acid sequences" further includes single-chain antibodies comprised of, but not limited to, an immunoglobulin heavy chain variable region, an immunoglobulin light chain variable region and optionally a peptide linker.

The term "isolated nucleic acid" as used herein refers to a nucleic acid that has been substantially removed from other components of the cell containing the nucleic acid or from other components of chemical/synthetic reaction used to generate the nucleic acid. In specific embodiments, the nucleic acid is 50%, 60%, 70%, 80%, 90%, 95%, 99% or 100% pure. The "isolated nucleic acid" does not include nucleic acids that are members of a library, e.g. cDNA or genomic library, unless identified and separated from the other members of the library. The techniques used to isolate and characterize the nucleic acids and proteins of the present invention are well known to those of skill in the art and standard molecular biology and biochemical manuals may be consulted to select suitable protocols without undue experimentation. See, for example, Sambrook et al, 2001, Molecular Cloning: A Laboratory Manual, 3rd ed., Cold Spring Harbor Press; the content of which is herein incorporated by reference in its entirety.

As used herein, the term "locus" or "loci" refers to the site of a gene on a chromosome. Pairs of genes control hereditary traits, each in the same position on a pair of chromosomes. These gene pairs, or alleles, may both be dominant or may both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. Representative examples of the nucleic acids of the present invention include bacterial plasmid vectors including expression, cloning, cosmid and transformation vectors such as, but not limited to, plasmid vectors, animal viral vectors such as, but not limited to, modified adenovirus, influenza virus, polio virus, pox virus, retrovirus, and the like, vectors derived from bacteriophage nucleic acid, e.g., plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "nucleic acid vector" or "vector" as used herein refers to a natural or synthetic single or double stranded plasmid or viral nucleic acid molecule, or any other nucleic acid molecule, such as but not limited to YACs, BACs, bacteriophage-derived artificial chromosome (BBPAC), cosmid or P1 derived artificial chromosome (PAC), that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the pieces together. The nucleic acid molecule can be RNA or DNA.

The terms "operably linked" or "operatively linked" refer to the configuration of the coding and control sequences so as to perform the desired function. Thus, control sequences operably linked to a coding sequence are capable of effecting the expression of the coding sequence and/or regulating in which tissues, at what developmental time points, or in response to which signals a gene is expressed. For example, a coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence. Such intervening sequences include but are not limited to enhancer sequences which are not transcribed or are not bound by polymerase.

The terms "percent sequence identity" or "percent sequence homology" or "percent sequence similarity" as used herein refer to the degree of sequence identity between two nucleic acid sequences or two amino acid sequences as determined using the algorithm of Karlin & Attschul (1990) Proc. Natl. Acad. Sci. 87: 2264-2268, modified as in Karlin & Attschul (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference amino acid sequence. To obtain gapped alignments for comparison purposes, Gapped BLAST is utilized as described in Attschul et al. (1997) Nucl. Acids Res. 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

A "pharmaceutical composition" is a substance that, in whole or in part, makes up a drug. "Therapeutic proteins" or "pharmaceutical proteins" include an amino acid sequence which in whole or in part makes up a drug. In one embodiment, a pharmaceutical composition includes one or more pharmaceutical proteins or therapeutic proteins.

The terms "polynucleotide" and "nucleic acid sequence" are used interchangeably herein and include, but are not limited to, coding sequences (polynucleotide(s) or nucleic acid sequence(s) which are transcribed and translated into amino acid sequence in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "promoter" as used herein refers to the DNA sequence that determines the site of transcription initiation by an RNA polymerase. A "promoter-proximal element" may be a regulatory sequence within about 200 base pairs of the transcription start site. A "magnum-specific" promoter, as used herein, is a promoter that is primarily or exclusively active in the tubular gland cells of the avian magnum. Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter, a heat-inducible promoter, a light-inducible promoter, or a laser inducible promoter. (e.g., Halloran et al. (2000) Development 127: 1953-1960; Gemer et al. (2000) Int. J. Hyperthermia 16: 171-81; Rang and Will, 2000, Nucleic Acids Res. 28: 1120-5; Hagihara et al. (1999) Cell Transplant 8: 4314; Huang et al. (1999) Mol. Med. 5: 129-37; Forster et al. (1999) Nucleic Acids Res. 27: 708-10; Liu et al. (1998) Biotechniques 24: 624-8, 630-2; the contents of which have been incorporated herein by reference in their entireties).

The term "recombinant cell" refers to a cell that has a new combination of nucleic acid segments that are not covalently linked to each other in nature in that particular configuration. A new configuration of nucleic acid segments can be introduced into an organism using a wide array of nucleic acid manipulation techniques available to those skilled in the art. A recombinant cell can be a single eukaryotic cell, such as a mammalian or avian cell (including within a transgenic mammal or avian) or a single prokaryotic cell. The recombinant cell may harbor a vector that is extragenomic. An extragenomic nucleic acid vector does not insert into the cell's genome. A recombinant cell may further harbor a vector or a portion thereof (e.g., the portion containing the regulatory sequences and the coding sequence) that is intragenomic. The term intragenomic defines a nucleic acid construct incorporated within the recombinant cell's genome.

The terms "recombinant nucleic acid" and "recombinant DNA" as used herein refer a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant amino acid sequence" is meant to include an amino acid sequence produced by recombinant DNA techniques such that it is distinct from a naturally occurring amino acid sequence either in its location, purity or structure. Generally, such a recombinant amino acid sequence will be present in a cell in an amount different from that normally observed in nature.

The term "sense strand" as used herein refers to a single stranded DNA molecule from a genomic DNA that may be transcribed into RNA and translated into the natural amino acid sequence product of the gene. The term "antisense strand" as used herein refers to the single strand DNA molecule of a genomic DNA that is complementary with the sense strand of the gene.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell, preferably an avian cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to, e.g., the male germ cells using specific ligands that are recognized by receptors on the cell surface of the germ cell, such as the c-kit ligand or modifications thereof.

Other transfecting agents include but are not limited to lipofectin, lipfectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents.

As used herein, a "transgenic animal" is any non-human animal, such as an avian species, including the chicken, in which one or more of the cells of the animal contain a heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject amino acid sequence, e.g. either agonistic or antagonistic forms, or in which the gene has been disrupted. In certain embodiments, the genome of the animal has been modified such that a heterologous gene expression element is inserted so as to be operably linked to an endogenous coding sequence. The terms "chimeric animal" or "mosaic animal" are used herein to refer to animals in which the recombinant gene is found, or in which the recombinant gene is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human interferon amino acid sequence) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location that differs from that of the natural gene or its insertion results in a knockout). A transgene also includes a regulatory sequence designed to be inserted into the genome such that it regulates the expression of an endogenous coding sequence, e.g., to increase expression and/or to change the timing and or tissue specificity of expression, etc. (e.g., to effect "gene activation").

The terms "unique nucleic acid region" and "unique protein (amino acid sequence) region" as used herein refer to sequences present in a nucleic acid or protein (amino acid sequence) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

This description uses gene nomenclature accepted by the Cucurbit Genetics Cooperative as it appears in the Cucurbit Genetics Cooperative Report 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

Abbreviations

Abbreviations used in the present specification include the following: aa, amino acid(s); bp, base pair(s); cDNA, DNA complementary to RNA; ml, milliliter; min, minute(s); nt, nucleotide(s); SSC, sodium chloride-sodium citrate; µg, microgram(s); µl, microliter(s); µM, micromolar; UTR, untranslated region; DMSO, dimethyl sulfoxide.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 3 shows the PCR primers SEQ ID NOS: 1-25 used to PCR amplify and/or sequence the approximately 10 kb nucleic acid region that is 5' upstream of the chicken ovomucoid transcription start site.

FIG. 4A-4D shows the nucleic acid sequence SEQ ID NO: 26 of the approximately 10 kb nucleic acid region that is 5' upstream of the chicken ovomucoid transcription start site.

FIG. 6A shows the results of transfections of plasmids containing the ovomucoid promoter or CMV promoter linked to a luciferase gene into HD11 cells, a chicken myeloid cell line. FIG. 6B shows the results of transfections of plasmids containing the ovomucoid promoter or CMV promoter linked to a luciferase gene into primary quail tubular gland cells isolated from the magnum portion of the oviduct of a laying quail hen.

FIG. 8A. The ovoinhibitor (OI) and adjacent ovomucoid (OM) regions are shown with transcriptional start sites indicated with bent arrows. The left and right sides of the BAC, relative to an EcoRI site found in the 3' UTR, are shown with their approximate sizes in kilobase pairs (kb). FIG. 8B. The coding region of ovomucoid is shown with exons as white boxes and introns as black boxes. C. The IRES and polynucleotide coding sequence for the light chain and heavy chain of the IgG1 inserted at the EcoR1 site.

FIG. 14 shows the nucleotide sequence of the approximately 70 kb ovomucoid gene expression controlling region which is included in SEQ ID NO: 36. Also indicated in the figure is the approximately 10 kb ovomucoid gene expression controlling region which is designated Fragment A and shown in bold, the approximately 3.9 kb ovomucoid gene expression controlling region which is designated Fragment B and is shown underlined and the approximately 1.8 kb ovomucoid gene expression controlling region which is designated Fragment C and is shown in lower case.

DETAILED DESCRIPTION OF THE INVENTION

Figure 1:
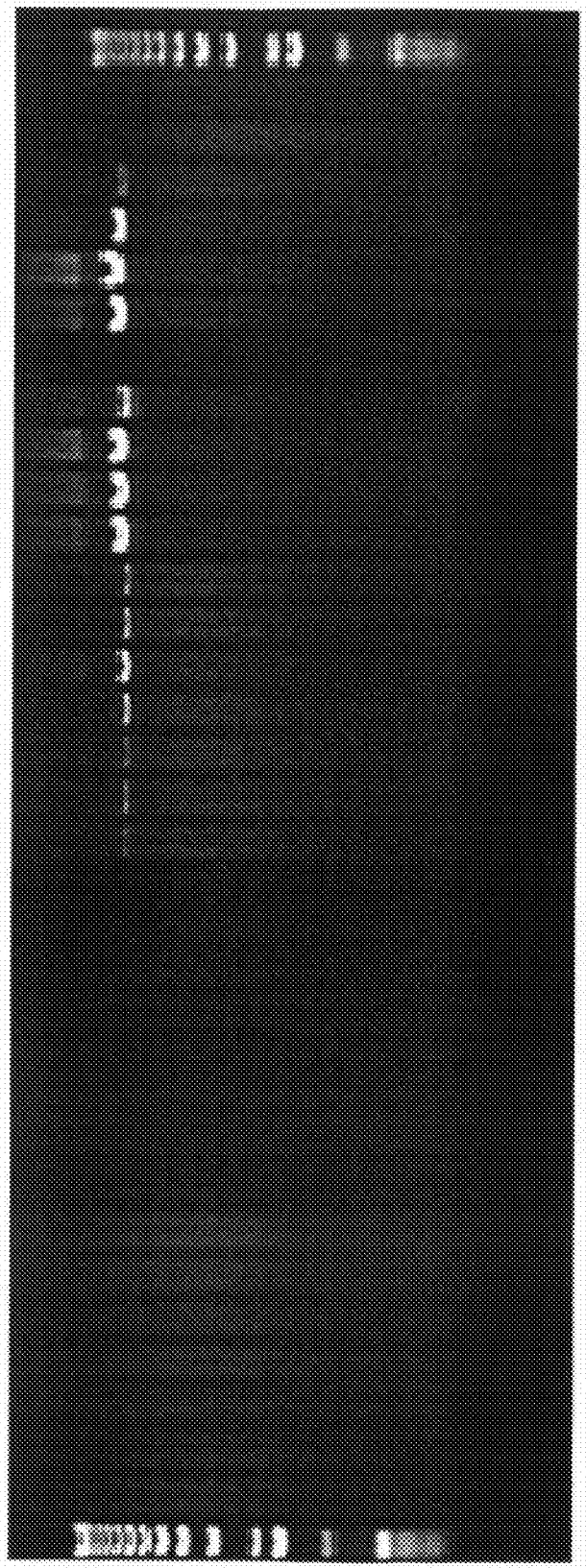
FIG. 1 illustrates an agarose gel analysis of PCR products from PCR amplification of chicken genomic DNA using the primers OVINs2 (SEQ ID NO: 1) and OVMUa2 (SEQ ID NO: 2).

The present invention relates to avian gene expression controlling regions and to methods of their use. In one embodiment, the invention relates to avian (e.g., chicken) ovomucoid promoters and to methods of using such promoters in the production of useful amino acid sequences such as peptides and proteins.

A series of PCR amplifications of template chicken genomic DNA were used to isolate the gene expression controlling region of the chicken ovomucoid locus. For example, the region of the chicken genome lying between the 3' end of the ovoinhibitor gene and the 5' transcription start site of the ovomucoid gene was PCR amplified using the primers OVINs 2,5'-TAGGCAGAGCAATAGGACTCTCAAC-CTCGT-3' (SEQ ID NO: 1) and OVMUa2,5'-AAGCTTCT-GCAGCACTCTGGGAGTTACTCA-3' (SEQ ID NO: 2) as described in detail in Example 1 below and FIG. 1. The approximately 10 kb fragment was blunt-ended and cleaved with the restriction endonuclease Bam HI. The resulting fragments of about 4.7 kb and 5.5 kb were subcloned into the linearized plasmid vector pBluescript KS II (+/−) (Stratagene, La Jolla, Calif.). Each insert was sequenced using the primers SEQ ID NOS: 5 to 25 shown in FIGS. 2 and 3 and as described in Example 3 below. The compiled nucleic acid sequence (SEQ ID NO: 26) of the approximately 10 kb nucleic acid region that is 5' upstream of the chicken ovomucoid transcription start site is shown in FIG. 4.

SEQ ID NO: 26 includes the ovoinhibitor gene 3' untranslated region described by Scott et al. (1987) J. Biol. Chem. 262: 5899-5909, from base positions 1-255 as shown in FIG. 4. A CR1-like element (Scott et al., Biochemistry (1987) 26: 6831-6840; Genbank Accession No: M17966) is located at base positions 2761-3024 as shown in FIG. 4. The region of SEQ ID NO: 26 from base positions 9403-9920, as shown in FIG. 4, has been described in Genbank Accession No: J00897 and in Lai et al., Cell (1979) 18: 829-842 and includes a portion of the 5' untranslated region of the ovomucoid gene.

An avian ovomucoid gene region has been identified in a chicken artificial chromosome library. The library was constructed with HindIII chicken DNA inserts ligated into a BAC vector (see, Crooijmans et al. (2000) Mammalian Genome 11: 360-363, the disclosure of which is incorporated in its entirety by reference). However, the present invention contemplates the employment of any useful artificial chromosome library including, but not limited to, libraries constructed from YACs, HACs, MACs, BBPACs or PACs.

The library was screened by PCR identifying a BAC clone which included a single chicken DNA segment which extends into both the 5' untranslated region of the ovomucoid gene and the 3' ovoinhibitor gene. The nucleotide sequence of the clone, designated OMC24, is shown in SEQ ID NO: 36. The nucleotide region spanning from about nucleotide 68,296 to about nucleotide 75,815 of SEQ ID NO: 36 represents the BAC vector. The ovomucoid region spans from about nucleotide 1 to about nucleotide 68,295 of SEQ ID NO: 36 and is shown in FIG. 14.

The nucleotide sequence of the gene expression controlling region disclosed in SEQ ID NO: 26 is essentially encompassed in SEQ ID NO: 36 from about nucleotide 26,416 to about nucleotide 36,390. Nucleotide sequence alignment between SEQ ID NO: 26 and nucleotides 26,416 to 36,390 of SEQ ID NO: 36 show a 99.0% sequence homology. The chicken genomic DNAs which yielded SEQ ID NO: 26 and SEQ ID NO: 36 were isolated from different strains of White Leghorn chickens (SEQ ID NO: 26-American Strain, SEQ ID NO: 36: Dutch Strain) thus showing the sequence diversity of the ovomucoid gene expression controlling region of the present invention. Other useful fragments or functional portions of SEQ ID NO: 36 can be easily obtained by standard techniques well known in the art.

Fragments or portions of certain DNA sequences which function to control gene expression can be identified by techniques that are well know to practitioners of ordinary skill in the art. For example, promoter analysis by saturation mutagenesis has been described in Biol. Proced. Online (2001) Vol 1, No. 3, pp 64-69, the disclosure of which is incorporated by reference herein in its entirety. Also, for example, fragments or functional portions of the chicken ovomucoid gene region effective to control gene expression, for example, control transcription in a cell, can be identified by techniques disclosed in the Examples of the present specification. For example, functional fragments of SEQ ID NO: 36 can be identified by methods as disclosed in the present specification and by any useful method known in the field of molecular biology.

In one embodiment, the gene expression controlling region comprises a nucleotide or portion of a nucleotide sequence that is at least 50% homologous to the avian nucleic acid contained in SEQ ID NO: 36 or to the complement of the avian nucleic acid contained in SEQ ID NO: 36. For example, the gene expression controlling region may comprise a nucleotide sequence or portion of a nucleotide sequence that is at least 60% homologous to the avian nucleic acid contained in SEQ ID NO: 36 or its complement. In another example, the gene expression controlling region comprises a nucleotide sequence or portion of a nucleotide sequence that is at least 70% homologous to the avian nucleic acid contained in SEQ ID NO: 36 or its complement. In another example, the gene expression controlling region comprises a nucleotide sequence or portion of a nucleotide sequence that is at least 75% homologous to the avian nucleic acid contained in SEQ ID NO: 36 or its complement. In another example, the gene expression controlling region comprises a nucleotide sequence or portion of a nucleotide sequence that is at least 80% homologous to the avian nucleic acid contained in SEQ ID NO: 36 or its complement. In another example, the gene expression controlling region comprises a nucleotide sequence or portion of a nucleotide sequence that is at least 85% homologous to the avian nucleic acid contained in SEQ ID NO: 36 or its complement. In another example, the gene expression controlling region comprises a nucleotide sequence or portion of a nucleotide sequence that is at least 90% homologous to the avian nucleic acid contained in SEQ ID NO: 36 or its complement. In another example, the gene expression controlling region comprises a nucleotide sequence or portion of a nucleotide sequence that is at least 95% homologous to the avian nucleic acid contained in SEQ ID NO: 36 or its complement. In another example, the gene expression controlling region comprises a nucleotide sequence or portion of a nucleotide sequence that is at least 99% homologous to the avian nucleic acid contained in SEQ ID NO: 36 or its complement.

Nucleotide sequences encoding the heavy chain and light chain of an IgG1 monoclonal antibody were inserted into the 3' UTR of the ovomucoid transcript encoding region in two separate ovomucoid BAC clones of SEQ ID NO: 36. The heavy chain and light chain coding sequences each included a signal sequence located at their 5' ends; however, use of a signal sequence may not be required in the present invention. The resulting mRNA transcript produced by the ovomucoid gene expression controlling region for each clone contains two coding sequences; one for the ovomucoid protein and another for the antibody light chain or heavy chain downstream of the ovomucoid coding sequence. To facilitate translation of the downstream heavy chain or light chain coding sequence, an internal ribosome entry site (IRES) was inserted immediately upstream of the heavy chain or light chain coding sequence in each clone.

In another example, a CTLA4-Fc fusion coding sequence comprising a nucleotide coding sequence for the extracellular domains of the CTLA4 (cytotoxic T lymphocyte antigen 4) receptor protein linked to a nucleotide coding sequence for an immunoglobulin constant region (IgG1 Fc) was cloned into an ovomucoid BAC clone of SEQ ID NO: 36. In addition, an attB site was included in the construct. To produce this clone, the IRES-LC portion of the ovomucoid-IRES-antibody light chain clone was deleted and was replaced with an IRES-CTLA4-Fc cassette.

Figure 15:
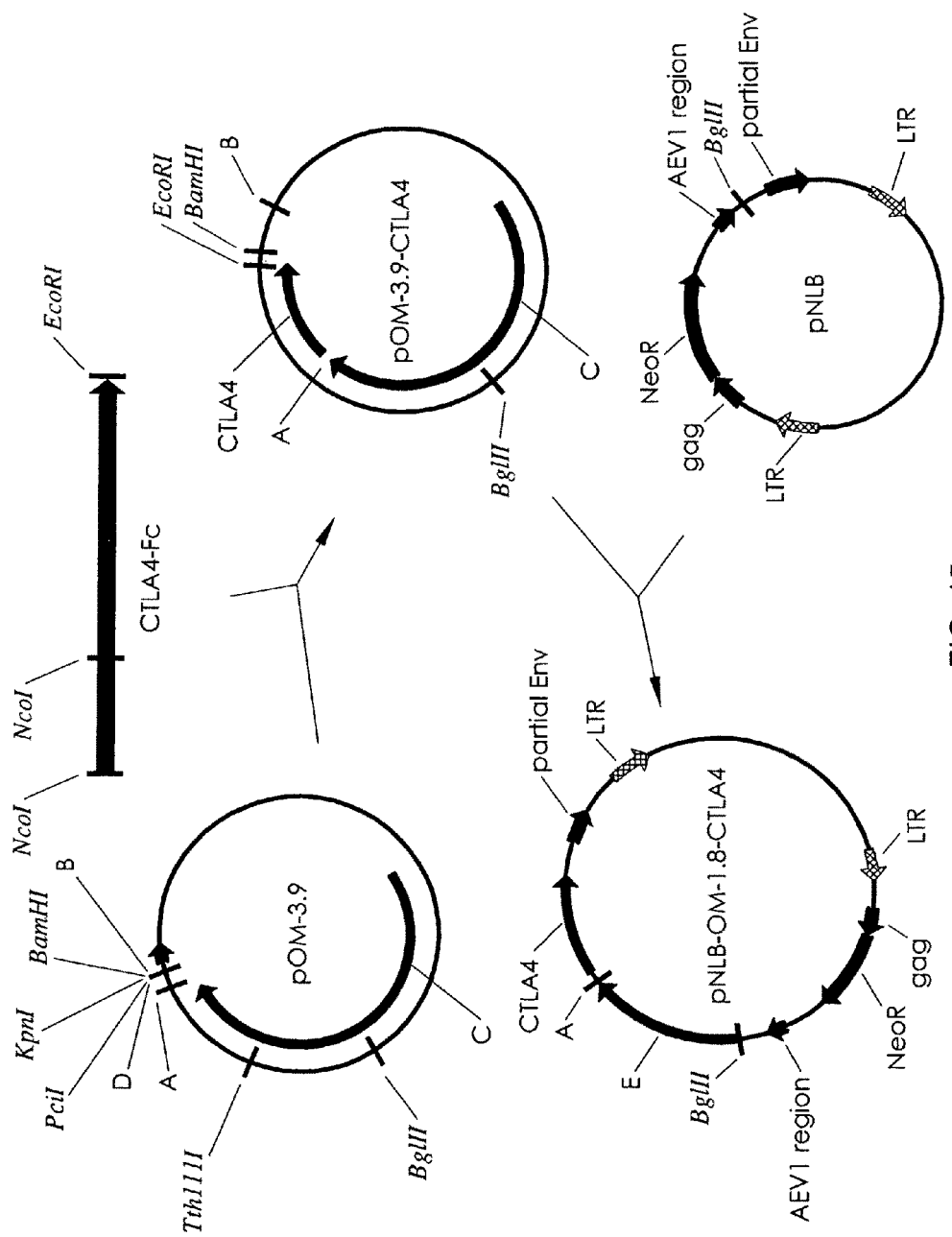
FIG. 15 shows construction of the pOM-3.9-CTLA4 expression vector which includes the approximately 3.9 kb ovomucoid gene expression controlling region (Fragment B of FIG. 14) operably linked to a CTLA4 coding sequence and the construction of pNLB-OM-1.8-CTLA4 which includes the approximately 1.8 kb ovomucoid gene expression controlling region (Fragment C of FIG. 14) operably linked to a CTLA4 coding sequence. In the figure, "A" represents the transcription start site; "B" represents the ovomucoid CDS; "C" represents the approximately 3.9 kb ovomucoid gene expression controlling region; "D" represents the translation start site; and "E" represents the approximately 1.8 kb ovomucoid gene expression controlling region. pNLB is a replication deficient avian leukosis viral vector (ALV). See, for example, U.S. Pat. No. 6,730,822, issued May 4, 2004, the disclosure of which is incorporated in its entirety herein by reference.

The present invention contemplates the introduction of an ovomucoid gene expression controlling region, for example, operably linked to a coding sequence of interest, which is present on a retrovirus vector, such as an ALV vector (e.g., replication deficient ALV vector), into an avian to produce a transgenic avian. One example of an ALV based vector contemplated for use herein is a pNLB vector described in for example, Cosset et al., 1991, J. Virology 65: 3388-3394, the disclosure of which is incorporated in its entirety herein by reference and U.S. patent application Ser. No. 10/463,980, filed Jun. 17, 2003, the disclosure of which is incorporated in its entirety herein by reference. In one example, a CTLA4-Fc fusion coding sequence was operably linked to an approximately 3.9 kb ovomucoid gene expression controlling region (Fragment B of FIG. 14). In yet another example, a CTLA4-Fc fusion coding sequence was operably linked to an approximately 1.8 kb ovomucoid gene expression controlling region (Fragment C of FIG. 14). The Promoter-coding sequence cassette was inserted into a replication deficient avian leucosis virus (ALV) based vector as shown in FIG. 15.

Disclosed above are examples of expression constructs that can be produced in accordance with the present invention. However, these are merely examples and it is contemplated that any nucleic acid sequence encoding a useful amino acid sequence can be operably linked to an avian ovomucoid gene expression controlling region of the present invention so as to be expressed in an avian cell, for example, in cells of a transgenic avian such as a chicken, turkey, duck, goose, quail, pheasant, parrot, finch, ratites including ostrich, emu or cassowary.

The present invention can be used to express, in large yields and at low cost, a wide range of desired proteins including those used as human and animal pharmaceuticals, diagnostics, and livestock feed additives. Proteins such as growth hormones, cytokines, structural proteins and enzymes, including human growth hormone, interferon, lysozyme, and β-casein, are examples of proteins that are desirably expressed in the oviduct and deposited in eggs according to the invention. Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin. Immunoglobulins and genetically engineered antibodies, including immunotoxins that bind to surface antigens on human tumor cells and destroy them, can also be expressed for use as pharmaceuticals or diagnostics. It is contemplated that immunoglobulin amino acid sequences expressed in avian cells following transfection by the methods of the present invention may include monomeric heavy and light chains, single-chain antibodies or multimeric immunoglobulins comprising variable heavy and light chain regions, i.e., antigen-binding domains, or intact heavy and light immunoglobulin chains.

The chicken ovomucoid gene expression controlling region of the present invention may include the nucleotide elements that are positioned 5' upstream of the transcription start site of the native chicken ovomucoid locus and which are necessary for the regulated expression of a downstream amino acid sequence-encoding nucleic acid. It is contemplated that this region may include transcription controlling regions which are regulated by certain hormones including, for example, steroid hormones and the like.

One aspect of the present invention, therefore, provides a novel isolated nucleic acid that comprises the nucleotide sequence SEQ ID NO: 26, shown in FIG. 4, (Genbank Accession No: AF 453747) and derivatives and variants thereof, that is located immediately 5' upstream of the transcription start site of the chicken ovomucoid gene locus.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 26, as shown in FIG. 4, or a variant thereof. SEQ ID NO: 26 was cloned into pBluescript KS II (+/−) vector, as described in Example 2, and named pBS-OVMUP-10. pBS-OVMUP-10 was deposited with American Type Culture Collection (ATCC), 10801 University Blvd., Manassas, Va. 20110, as ATCC No. PTA-4821 on Nov. 26, 2002 under the conditions set forth in the Budapest Treaty.

Another aspect of the invention provides nucleic acids that can hybridize under high, medium or low stringency conditions to an isolated nucleic acid comprising a chicken ovomucoid gene expression controlling region having all, a derivative of, or a portion of the nucleic acid sequence SEQ ID NO: 26 shown in FIG. 4 and direct expression of an amino acid sequence coding sequence in an avian oviduct cell. The nucleotide sequence determined from the isolation of the ovomucoid gene expression controlling region from a chicken (SEQ ID NO: 26) will allow for the generation of probes designed for use in identifying ovomucoid gene expression controlling regions, or homologs thereof in other avian species.

Fragments of a nucleic acid comprising a portion of the subject ovomucoid gene expression controlling region are also within the scope of the invention. As used herein, a fragment of the nucleic acid comprising an active portion of a ovomucoid gene expression controlling region refers to a nucleotide sequence having fewer nucleotides than the nucleotide sequence comprising the entire nucleic acid sequence of the ovomucoid gene expression controlling region.

A fragment of the ovomucoid gene expression controlling region may contain one or more of the following elements: the ovoinhibitor gene 3' untranslated region from bases positions 1-255 as shown in FIG. 4, a CR1-like element located at base positions 2761-3024 as shown in FIG. 4, the region from base positions 9403-9920, as shown in FIG. 4 which includes a portion of the 5' untranslated region of the ovomucoid gene. Alternatively, the fragment may be about 10 or about 20 or about 50 or about 75 or about 100 or about 150 or about 200 or about 250 or about 300 or about 500 or about 1000 or about 2000 or about 4000 or about 5000 or about 6000 or about 7000 or about 8000 or about 9000 or about 10,000 or about 20,000 or about 30,000 or about 40,000 or about 50,000 or about 60,000 nucleotides in length and be capable of directing expression of an operably linked heterologous gene sequence, particularly in an avian cell, for example, in an avian oviduct cell of a transgenic avian or in an avian cell in culture.

In one embodiment of the present invention, the nucleotide sequence of the isolated DNA molecule of the present invention may be used as a probe in nucleic acid hybridization assays for the detection of the ovomucoid gene expression controlling region. The nucleotide sequence of the present invention may be used in any nucleic acid hybridization assay system known in the art, including, but not limited to, Southern blots (Southern, E. M. J. Mol. Biol. 98: 508 (1975)), Northern blots (Thomas et al. (1980) Proc. Natl. Acad. Sci. 77: 5201-05), and Colony blots (Grunstein et al. (1975) Proc. Natl. Acad. Sci. 72: 3961-65), which are hereby incorporated by reference in their entireties. Alternatively, the isolated DNA molecules of the present invention can be used in a gene amplification detection procedure such as a polymerase chain reaction (Erlich et al. (1991) Science 252: 1643-51, which is hereby incorporated by reference in its entirety) or in restriction fragment length polymorphism (RFLP) diagnostic techniques, as described in Watson et al., (2d ed. 1992), Recombinant DNA, Scientific American Books, 519-522, 545-547, which is hereby incorporated by reference.

Nucleic acids constructed in accordance with the present invention can be labeled to provide a signal as a means of detection. For example, radioactive elements such as $^{32}$P, $^{3}$H, and $^{35}$S or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals such as *Promega: Protocol and Applications Guide,* 2nd Edition, 1991 (Promega Corp., Madison, Wis., the disclosure of which is incorporated herein in its entirety) may be consulted to select an appropriate labeling protocol without undue experimentation.

In another embodiment of the present invention, an isolated nucleic acid molecule of the present invention includes a nucleic acid that hybridizes to SEQ ID NO: 26 or the complement thereof, or the insert in pBS-OVMUP-10, under high, moderate or low stringency hybridization conditions.

In another embodiment of the present invention, an avian ovomucoid gene expression controlling region gene or nucleic acid molecule can be an allelic variant of SEQ ID NO: 26 or SEQ ID NO: 36 or a homolog from a different avian, e.g., quail, duck, etc.

The present invention also contemplates the use of anti-sense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized oligonucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

The nucleic acid sequence of a chicken ovomucoid gene expression controlling region nucleic acid molecule of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain ovomucoid gene expression controlling region nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian ovomucoid gene expression controlling region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of libraries to screen, or from which to amplify nucleic acid molecules, include but are not limited to mammalian BAC libraries, genomic DNA libraries, and cDNA libraries. Similarly, sequence databases useful for screening to identify sequences in other species homologous to chicken ovomucoid gene expression controlling region include, but are not limited to, GenBank and the mammalian Gene Index database of The Institute of Genomics Research (TIGR).

Another aspect of the present invention is a recombinant DNA molecule comprising the novel isolated avian ovomucoid gene expression controlling region of the present invention operably linked to a selected amino acid sequence-encoding nucleic acid insert, and which may express the nucleic acid insert when transfected to a suitable host cell, preferably an avian cell. The nucleic acid insert may be placed in frame with a signal peptide sequence, whereby translation initiation from the transcript may start with the signal peptide and continue through the nucleic acid insert, thereby producing an expressed amino acid sequence having the desired amino acid sequence.

It is anticipated that the recombinant DNA may further comprise a polyadenylation signal sequence that will allow the transcript directed by the novel ovomucoid gene expression controlling region to proceed beyond the nucleic acid insert encoding an amino acid sequence and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like, or derivatives thereof. One embodiment of the present invention is a recombinant DNA molecule comprising the isolated avian ovomucoid gene expression controlling region of the present invention, operably linked to a nucleic acid insert encoding an amino acid sequence which may include a polyadenylation signal sequence. In certain embodiments, the recombinant DNA molecule which includes include a polyadenylation signal sequence is an artificial chromosome.

Another aspect of the present invention is to provide nucleic acid sequences of a protein optimized for expression in avian cells, and derivatives and fragments thereof. For example, it is contemplated that when the recombinant DNA is to be delivered to a recipient cell for expression therein, the sequence of the nucleic acid sequence may be modified so that the codons are optimized for the codon usage of the recipient species. When a heterologous nucleic acid is to be delivered to a recipient cell for expression therein, the sequence of the nucleic acid sequence may be modified so that the codons are optimized for the codon usage of the recipient species. For example, if the heterologous nucleic acid is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken. Briefly, the DNA sequence for the target protein may be optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The template and primer oligonucleotides are then amplified, by any means known in the art, including but not limited to PCR with Pfu polymerase (STRATAGENE®, La Jolla Calif.).

In one exemplary embodiment of a heterologous nucleic acid for use by the methods of the present invention, a nucleic acid insert encoding the human interferon $\alpha 2b$ amino acid sequence optimized for codon-usage by the chicken is used. Optimization of the sequence for codon usage is useful in elevating the level of translation in avian eggs.

It is contemplated to be within the scope of the present invention for any nucleic acid encoding an amino acid sequence to be optimized for expression in avian cells. It is further contemplated that the codon usage may be optimized for a particular avian species used as a source of the host cells. In one embodiment of the present invention, the heterologous amino acid sequence is encoded using the codon-usage of a chicken.

In yet another embodiment of the present invention, the recombinant DNA comprises the isolated avian ovomucoid gene expression controlling region operably linked to a nucleic acid encoding a human interferon $\alpha 2b$ and the SV40 polyadenylation sequence.

Proteins produced in accordance with methods of the present invention may be purified by any known conventional technique. In a one embodiment, the protein is purified from chicken eggs, preferably egg whites. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

The invention provides methods for producing multimeric proteins, preferably immunoglobulins, such as antibodies, and antigen binding fragments thereof.

In one embodiment of the present invention, the multimeric protein is an immunoglobulin, wherein the first and second heterologous amino acid sequences are an immunoglobulin heavy and light chain respectively. Illustrative examples of this and other aspects and embodiments of the present invention for the production of heterologous multimeric amino acid sequences in avian cells are fully disclosed in U.S. patent application Ser. No. 09/877,374, filed Jun. 8, 2001, published as US-2002-0108132-A1 on Aug. 8, 2002, and U.S. patent application Ser. No. 10/251,364, filed Sep. 18, 2002, now U.S. Pat. No. 7,312,374, issued Dec. 25, 2007, the disclosures of which are incorporated herein by reference in their entirety. In one embodiment of the present invention, therefore, the multimeric protein is an immunoglobulin wherein the first and second heterologous amino acid sequences are an immunoglobulin heavy and light chain respectively. Accordingly, the invention provides immunoglobulin and other multimeric proteins that have been produced by transgenic avians of the invention.

In the various embodiments of this aspect of the present invention, an immunoglobulin amino acid sequence encoded by the transcriptional unit of at least one expression vector may be an immunoglobulin heavy chain amino acid sequence comprising a variable region or a variant thereof, and may further comprise a D region, a J region, a C region, or a combination thereof. An immunoglobulin amino acid sequence encoded by the transcriptional unit of an expression vector comprising an ovomucoid gene expression controlling region may also be an immunoglobulin light chain amino acid sequence comprising a variable region or a variant thereof, and may further comprise a J region and a C region. It is also contemplated to be within the scope of the present invention for the immunoglobulin regions to be derived from the same animal species, or a mixture of species including, but not only, human, mouse, rat, rabbit and chicken. In certain embodiments, the antibodies are human or humanized.

In other embodiments of the present invention, the immunoglobulin amino acid sequence encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of a heterologous protein capable of forming an antibody suitable for selectively binding an antigen comprising the step of producing a transgenic avian incorporating at least one transgene, wherein the transgene encodes at least one heterologous amino acid sequence selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

In an embodiment of this method of the present invention, the isolated heterologous protein is an antibody capable of selectively binding to an antigen. In one embodiment, the antibody may be generated by combining at least one immunoglobulin heavy chain variable region and at least one immunoglobulin light chain variable region, preferably cross-linked by at least one di-sulfide bridge. The combination of the two variable regions will generate a binding site capable of binding an antigen using methods for antibody reconstitution that are well known in the art.

It is, however, contemplated to be within the scope of the present invention for immunoglobulin heavy and light chains, or variants or derivatives thereof, to be expressed in separate transgenic avians, and therefore isolated from separate media including serum or eggs, each isolate comprising a single species of immunoglobulin amino acid sequence. The method may include combining certain isolated heterologous immunoglobulin amino acid sequences, thereby producing an antibody capable of selectively binding to an antigen. In this embodiment, two individual transgenic avians may be generated wherein one transgenic produces serum or eggs having an immunoglobulin heavy chain variable region, or an amino acid sequence comprising such, expressed therein. A second transgenic avian, having a second transgene, produces serum or eggs having an immunoglobulin light chain variable region, or an amino acid sequence comprising such, expressed therein. The amino acid sequences may be isolated from their respective sera and eggs and combined in vitro to generate a binding site capable of binding an antigen.

The present invention is useful for the production of many biological products such as, pharmaceutical or therapeutic proteins. For example, the present invention can be useful for the production of biological molecules such as hormones including cytokines (i.e., secreted amino acid sequences that affect a function of cells and modulates an interaction between cells in an immune, inflammatory or hematopoietic response), antibodies and other useful pharmaceutical molecules which include amino acid sequences. Cytokines include, but are not limited to, monokines and lymphokines. Examples of cytokines include, but are not limited to, interferon α2b, Interleukin-1 (IL-1), Interleukin-6 (IL-6), Interleukin-8 (IL-8), Tumor Necrosis Factor-α (TNF-α) and Tumor Necrosis Factor β (TNF-β), antibodies such as polyclonal and monoclonal antibodies and fragments thereof, and immunologic binding equivalents thereof. Antibodies may include, but are not limited to polyclonal antibodies, monoclonal antibodies (MAbs), humanized or chimeric antibodies, single chain antibodies, FAb fragments, F(Ab')$_2$ fragments, fragments produced by a FAb expression library, anti-idiotypic (anti-Id) antibodies, and epitope-binding fragments thereof. Also contemplated is the production of antibody fusion proteins, for example, Fc fusion proteins in accordance with the present methods. The methods of the present invention can also be useful for producing immunoglobulin amino acid sequences which are constituent amino acid sequences of an antibody or an amino acid sequence derived therefrom. An "immunological amino acid sequence" may be, but is not limited to, an immunological heavy or light chain and may include a variable region, a diversity region, joining region and a constant region or any combination, variant or truncated form thereof. Immunological amino acid sequences also include single-chain antibodies comprised of, but not limited to, an immunoglobulin heavy chain variable region, an immunoglobulin light chain variable region and optionally a peptide linker.

Examples of certain antibodies that can be produced in methods of the invention may include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primatized anti-CD80 antibody (IDEC Pharm/Mitsubishi); ZEVALIN™ is a radiolabeled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α FAb fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$β_2$ antibody (Cambridge Ab Tech).

Another potentially useful application of the novel isolated ovomucoid gene expression controlling region of the present invention is the possibility of increasing the amount of a heterologous protein present in a bird, (especially the chicken) by gene transfer. In most instances, a heterologous amino acid sequence-encoding nucleic acid insert transferred into the recipient animal host will be operably linked with the ovomucoid gene expression controlling region to allow the cell to initiate and continue production of the genetic product protein. A recombinant DNA molecule of the present invention can be transferred into the extra-chromosomal or genomic DNA of the host.

The recombinant ovomucoid gene expression controlling region of the present invention and amino acid sequence coding sequence, which may include an artificial chromosome and/or a polyadenylation coding sequence, may be introduced into cells by any useful method. The recombinant molecules may be inserted into a cell to which the amino acid sequence-encoding nucleic acid is heterologous (i.e. not normally present). Alternatively, as described more fully below, the recombinant DNA molecule may be introduced into cells which normally contain the amino acid sequence-encoding nucleic acid insert of the recombinant DNA molecule, for example, to correct a deficiency in the expression of an amino acid sequence, or where over-expression of the amino acid sequence is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated ovomucoid gene expression controlling region.

U.S. Pat. No. 4,237,224 to Cohen & Boyer, which is hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an ovomucoid gene expression controlling region expression vector suitable for delivery to a recipient cell for replication or expression of an amino acid sequence-encoding nucleic acid of the vector therein. It is contemplated to be within the scope of the present invention for the expression vector to comprise an isolated avian ovomucoid gene expression controlling region operably linked to a nucleic acid insert encoding an amino acid sequence, and optionally a polyadenylation signal sequence. The expression vector of the present invention may further comprise a bacterial plasmid sequence, a viral nucleic acid sequence, or fragments or variants thereof that may allow for replication of the vector in a suitable host.

The recombinant nucleic acid molecules of the present invention can be delivered to cells using viruses such as vaccinia virus. Methods for making a viral recombinant vector useful for expressing a protein under the control of the ovomucoid promoter are analogous to the methods disclosed in U.S. Pat. Nos. 4,603,112; 4,769,330; 5,174,993; 5,505,941; 5,338,683; 5,494,807; 4,722,848; Paoletti, E. Proc. Natl. Acad. Sci. 93: 11349-11353 (1996); Moss Proc. Natl. Acad. Sci. 93: 11341-11348 (1996); Roizman Proc. Natl. Acad. Sci. 93: 11307-11302 (1996); Frolov et al. Proc. Natl. Acad. Sci. 93: 11371-11377 (1996); Grunhaus et al. Seminars in Virology 3: 237-252 (1993) and U.S. Pat. Nos. 5,591,639; 5,589,466; and 5,580,859 relating to DNA expression vectors, inter alia; the disclosure of each of these patents and publications is incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier, F. W. et. al. (1990) "Use of T7 RNA Polymerase to Direct Expression of Cloned Genes" Gene Expression Technology, vol. 185, which is hereby incorporated by reference in its entirety) and any derivatives thereof, cosmid vectors and, in certain embodiments, artificial chromosomes, such as, but not limited to, YACs, BACs, BBPACs or PACs. Such artificial chromosomes are useful in that a large nucleic acid insert can be propagated and introduced into the avian cell. Recombinant molecules can be introduced into cells via transformation, particularly transduction, conjugation, mobilization, or electroporation. The introduction of recombinant virus to embryonic cells such as blastodermal cells may be accomplished by employing replication defective or replication competent retroviral particles as disclosed in, for example, U.S. Pat. No. 6,730,822, issued May 4, 2004 and U.S. patent application Ser. No. 10/463,980, filed Jun. 17, 2003, the disclosures of which are incorporated in their entirety herein by reference. The DNA sequences are cloned into the vector using standard cloning procedures in the art, as described by Sambrook et al. Molecular Cloning: A Laboratory Manual, $3^{rd}$ ed., Cold Spring Harbor Laboratory, Cold Springs Harbor, N.Y. (2001), which is hereby incorporated by reference in its entirety.

The vectors of the invention comprise one or more nucleotide sequences encoding a heterologous protein desired to be expressed in the transgenic avian, as well as regulatory elements such as promoters, enhancers, Matrix Attachment Regions, IRES's and other translation control elements, transcriptional termination elements, polyadenylation sequences, etc. In particular embodiments, the vector of the invention contains at least two nucleotide sequences coding for heterologous proteins, for example, but not limited to, the heavy and light chains of an immunoglobulin.

The present invention further relates to nucleic acid vectors and transgenes inserted therein, having the avian ovomucoid gene expression controlling region of the invention, that incorporate multiple amino acid sequence-encoding regions, wherein a first amino acid sequence-encoding region is operatively linked to a transcription promoter and a second amino acid sequence-encoding region is operatively linked to an IRES. For example, the vector may contain coding sequences for two different heterologous proteins (e.g., the heavy and light chains of an immunoglobulin).

Such nucleic acid constructs, when inserted into the genome of a bird and expressed therein, will generate individual amino acid sequences that may be post-translationally modified, for example, glycosylated or, in certain embodiments, form complexes, such as heterodimers with each other in the white of the avian egg. Alternatively, the expressed amino acid sequences may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to the ovomucoid gene expression controlling region of the invention are introduced into the avian cell. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

Once the ovomucoid gene expression controlling region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian or avian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection, cytoplasmic injection, pronuclear injection and the like.

Another aspect of the present invention, therefore, is a method of expressing a heterologous amino acid sequence in a eukaryotic cell by transfecting the cell with a recombinant DNA comprising an avian ovomucoid gene expression controlling region operably linked to a nucleic acid insert encoding an amino acid sequence and, optionally, a polyadenylation signal sequence, and culturing the transfected cell in a medium suitable for expression of the heterologous amino acid sequence under the control of the avian ovomucoid gene expression controlling region.

In certain embodiments, the ovomucoid gene expression controlling region directs a level of expression of the heterologous protein in avian eggs that is greater than 5 µg, 10 µg, 50 µg, 100 µg, 250 µg, 500 µg, or 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams per egg. Such levels of expression can be obtained using the expression controlling regions of the invention.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken ovomucoid gene expression controlling region, a nucleic acid insert encoding a human interferon α2d with codons optimized for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal (e.g., a transgenic avian) producing a heterologous protein expressed from a transfected nucleic acid according to the present invention.

One certain aspect of the present invention relates to transgenic animals including avians and methods of producing them. Transgenic animals of the present invention contain a transgene which includes an isolated ovomucoid gene expression controlling region of the present invention and which preferably, though optionally, expresses a heterologous gene in one or more cells in the animal. Transgenic avians can be produced by introduction of nucleic acid molecules disclosed herein into the cells of avians including, but not limited to chicken, turkey, duck, goose, quail, pheasants, parrots, finches, hawks, crows and ratites including ostrich, emu and cassowary. Any useful method for introducing nucleic acid into the cells of an animal may be employed in the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian ovomucoid gene expression controlling region according to the present invention is primarily localized to the white of an egg.

An exemplary approach for the in vivo introduction of an amino acid sequence-encoding nucleic acid operably linked to the subject novel isolated ovomucoid gene expression controlling region into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid comprising a ovomucoid gene expression controlling region, thereby rendering the retrovirus replication defective. Protocols for producing recombinant retroviruses and for infecting cells in vitro or in vivo with such viruses may be found in Current Protocols in Molecular Biology, Ausubel et al. (1989) (eds.) Greene Publishing Associates, Sections 9.10-9.14 and other standard laboratory manuals. Examples of suitable retroviruses include pLJ, pZIP, pWE and pEM which are all well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., Proc. Natl. Acad. Sci. 86: 9079-9083 (1989); Julan et al., J. Gen. Virol. 73: 3251-3255 (1992); and Goud et al., Virology 163: 251-254 (1983)) or coupling cell surface ligands to the viral env proteins (Neda et al., J. Biol. Chem. 266: 14143-14146 (1991)), all of which are incorporated herein by reference in their entireties. Coupling can be in the form of the chemical cross-linking with a protein or other moiety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., BioTechniques 6: 616 (1988); Rosenfeld et al., Science 252: 43 1434 (1991); and Rosenfeld et al., Cell 68: 143-155 (1992)), all of which are incorporated herein by reference in their entireties. Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) may not be integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., Cell 16:683 (1979); Berkner et al., supra; and Graham et al., in Methods in Molecular Biology, E. J. Murray, (1991) Ed. (Humana, Clifton, N.J.) vol. 7. pp. 109-127), all of which are incorporated herein by reference in their entireties. Expression of an inserted gene such as, for example, encoding the human interferon α2b, can be under control of the exogenously added ovomucoid gene expression controlling region sequences.

Yet another viral vector system useful for delivery of, for example, the subject avian ovomucoid gene expression controlling region operably linked to a nucleic acid encoding an amino acid sequence, is the adeno-associated virus (AAV). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993)), all of which are incorporated herein by reference in their entireties.

Most non-viral methods of gene transfer rely on normal mechanisms used by eukaryotic cells for the uptake and intracellular transport of macromolecules. In one embodiment, non-viral gene delivery systems of the present invention rely on endocytic pathways for the uptake of the subject ovomucoid gene expression controlling region and operably linked amino acid sequence-encoding nucleic acid by the targeted cell. Exemplary gene delivery systems of this type include liposomal derived systems, polylysine conjugates, and artificial viral envelopes.

In a representative embodiment, a nucleic acid comprising the novel isolated ovomucoid gene expression controlling region of the present invention can be entrapped in liposomes bearing positive charges on their surface (e.g., lipofectins) and (optionally) which are tagged with antibodies against cell surface antigens of the target tissue (Mizuno et al., NO Shinkei Geka 20:547-551 (1992); PCT publication WO91/06309; Japanese patent application 1047381; and European patent publication EP-A-43075), all of which are incorporated herein by reference in their entireties.

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180), all of which are incorporated herein by reference in their entireties. It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., Science 260: 926 (1993); Wagner et al., Proc. Natl. Acad. Sci. 89:7934 (1992); and Christiano et al., Proc. Natl. Acad. Sci. 90:2122 (1993)), all of which are incorporated herein by reference in their entireties. It is further contemplated that a recombinant DNA molecule comprising the novel isolated ovomucoid gene expression controlling region of the present invention may be delivered to a recipient host cell by other non-viral methods including by gene gun, microinjection, sperm-mediated transfer as described in PCT/US02/30156, filed Sep. 23, 2002 and incorporated herein by reference in its entirety, nuclear transfer, or the like.

Suitable methods for the generation of transgenic avians having heterologous DNA incorporated therein, for example, cytoplasmic injection and pronuclear injection, are described, for example, in U.S. patent application Ser. No. 10/251,364 filed Sep. 18, 2002, now U.S. Pat. No. 7,312,374, issued Dec. 25, 2007, and U.S. patent application Ser. No. 10/679,034, filed Oct. 2, 2003, now U.S. Pat. No. 7,550,650, issued Jun. 23, 2009, the disclosure of both of these patent applications is incorporated herein by reference in its entirety. Other methods for the introduction of nucleic acids of the present invention include those disclosed in U.S. patent application Ser. No. 10/842,606 filed May 10, 2004, now U.S. Pat. No. 7,381,712, issued Sep. 8, 2009, the disclosure of which is incorporated herein by reference in its entirety, and other methods disclosed herein.

In various embodiments of the present invention, the expression of the transgene may be restricted to specific subsets of cells, tissues or developmental stages utilizing, for example, cis-acting sequences acting on the ovomucoid gene expression controlling region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

One embodiment of the present invention, therefore, is a transgenic avian having a heterologous polynucleotide sequence comprising a nucleic acid insert encoding the heterologous amino acid sequence and operably linked to the novel isolated avian ovomucoid gene expression controlling region. In an embodiment of the present invention, the transgenic avian is selected from a chicken, a turkey, a duck, a goose, a quail, a pheasant, a ratite, an ornamental bird or a feral bird. In another embodiment of the present invention, the transgenic avian is a chicken.

In still another embodiment of the transgenic avian of the present invention, the transgenic avian includes an avian ovomucoid gene expression controlling region included in SEQ ID NO: 36 or a functional portion thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In another embodiment of the transgenic avian of the present invention, the nucleic acid insert encoding an amino acid sequence has a codon complement optimized for protein expression in an avian.

In another embodiment of the transgenic avian of the present invention, the transgenic avian produces the heterologous amino acid sequence in the serum or an egg white. In another embodiment of the transgenic avian of the present invention, the transgenic avian produces the heterologous amino acid sequence in an egg white.

In one embodiment, certain pharmaceutical comprising agents that can modulate the regulation of the expression of an amino acid sequence-encoding nucleic acid operably linked to a ovomucoid gene expression controlling region can be administered in dosages and by techniques well known to those skilled in the medical or veterinary arts, taking into consideration such factors as the age, sex, weight, species and condition of the recipient animal, and the route of administration. Standard pharmaceutical texts, such as Remmington's Pharmaceutical Science, 17th edition, 1985 may be consulted to prepare suitable preparations, without undue experimentation. Dosages can generally range from a few hundred milligrams to a few grams.

The present invention is further illustrated by the following examples, which are provided by way of illustration and should not be construed as limiting. The contents of all references, published patents and patents cited throughout the present application are hereby incorporated by reference in their entireties.

EXAMPLE 1

PCR Amplification of Ovomucoid Promoter

Sense primer OVINs-2,5'-TAGGCAGAGCAATAG-GACTCTCAACCTCGT-3' (SEQ ID NO: 1) and the antisense primer, OVMUa2, 5'-AAGCTTCTGCAG-CACTCTGGGAGTTACTCA-3' (SEQ ID NO: 2) were designed according to the sequences of chick ovoinhibitor exon 16 (Genbank Accession No: M16141) and a fragment of the chick ovomucoid promoter region (Genbank Accession No: J00897) respectively. The template DNA for PCR amplification of the ovomucoid promoter region was prepared from White Leghorn chick blood.

A series of different PCR conditions were carried out to optimize synthesis of the approximately 10.0 kb product. In these tests, the template DNA concentrations were 500 ng, 100 ng, 50 ng, or 10 ng. Two sets of primers, OVINs1 (SEQ ID NO: 3) and OVMUa1 (SEQ ID NO: 4), or OVINs2 (SEQ ID NO: 1) and OVMUa2 (SEQ ID NO: 2) shown in FIG. 3, three $Mg^{++}$ concentrations (1.0 mM, 1.5 mM and 2.0 mM) and annealing temperatures from 50° C. to 70° C. were used.

The results of the tests were as shown in FIG. 1. As shown in lanes 1 through 8, test reactions having 500 ng DNA template, the OVINs1 (SEQ ID NO: 3) and OVMUa1 (SEQ ID NO: 4) primers, 60 mM Tris-$SO_4$, pH 9.1, 18 mM $(NH_4)_2SO_4$, 1.0 mM $Mg^{2+}$, and annealing temperatures between 50° C. to 58° C. gave no specific DNA product. Also, as shown in lanes 17 through 24 of FIG. 1, in test reactions having 100 ng DNA template, the OVINs1 and OVMUa1 primers, 60 mM Tris-$SO_4$, pH 9.1, 18 mM $(NH_4)_2SO_4$, 1.0 mM $Mg^{2+}$, and annealing temperatures between 50° C. to 58° C., no specific bands were seen. However, as shown in lanes 9 through 16 of FIG. 1, test reactions having 500 ng DNA template, the OVINs2 (SEQ ID NO: 1) and OVMUa2 (SEQ ID NO: 2) primers, 60 mM Tris-$SO_4$, pH 9.1, 18 mM $(NH_4)_2SO_4$, 2 mM $Mg^{2+}$ and annealing temperatures between 60° C. to 68° C. have the band of the desired length of approximately 10 kb. As shown in lanes 25 through 32, reaction conditions containing 100 ng DNA template, the OVINs2 (SEQ ID NO: 1) and OVMUa2 (SEQ ID NO: 2) primers, 60 mM Tris-$SO_4$, pH 9.1, 18 mM $(NH_4)_2SO_4$, 2 mM $Mg^{2+}$ and annealing temperatures between about 60° C. to about 68° C. gave an increased yield of the desired product.

An approximately 10 kb product was, therefore, detected when the following conditions were used: the optimum DNA template concentration was between about 50 ng to 500 ng; the primers were OVINs2 (SEQ ID NO: 1) and OVMUa2 (SEQ ID NO: 2); the $Mg^{2+}$ concentration was 2 mM; the annealing temperature was at or between about 60° C. to about 68° C. Each 50 μl PCR reaction consisted of 50 ng or 100 ng of template DNA, 0.1 μg each primer, 5 μl buffer B (from Elongase Enzyme Mix kit, Invitrogen Corp., Carlsbad, Calif.), 1 ml of 10 μM dNTP solution, and distilled deionized water. The PCR protocol was one cycle at 94° C. for 30 secs; thirty cycles at 94° C. for 30 secs, 60° C. for 30 secs and 68° C. for 10 mins. One cycle was performed at 68° C. for 10 mins, 35° C. for 30 mins with a final hold at 4° C. The PCR products were examined by 0.65% agarose gel analysis.

EXAMPLE 2

Cloning of PCR Products

The PCR products were purified by standard methods. Briefly, PCI (phenol:chloroform:isoamyl alcohol, 24:25:1) and chloroform extraction were performed once. The DNA was precipitated by adding 3M sodium acetate pH 5.2 to a final concentration of 0.3M together with 2.5 volumes of 100% ethanol. The DNA pellet was dried and dissolved in distilled deionized water and then sequenced on a ABI3700 automatic sequencer (Applied Biosystems, Foster City, Calif.) using the primers OVINs2 (SEQ ID NO: 1) and OVMUa2 (SEQ ID NO: 2) to confirm the identity of each PCR product. After confirmation of the identities, the approximately 10 kb PCR product was treated with T4 polynucleotide kinase to add a phosphate to the 5' end. Mung bean nuclease removed any overhanging adenines from the ends of the PCR products, thereby producing a blunt end. The PCR product was purified by PCI and chloroform extraction and precipitated by standard methods. This approximately 10 kb product was then cleaved with Bam HI to give two fragments, of about 4.7 and about 5.5 kb respectively.

The vector plasmid pBluescript II KS (+/−) was cut by Bam HI and Eco RV and treated with calf intestinal alkaline phosphatase. DNA fragments to be ligated into the vector were analyzed by agarose gel electrophoresis and purified from agarose gel slices using a NucleoTrap Nucleic Acid Purification Kit (BD Biosciences Clontech, Palo Alto, Calif.). Fragments of 4.7 kb and 5.5 kb were inserted into the Bam HI/Eco $R^V$-treated pBluescript to give the constructs pBS-OVMUP4.7 and pBS-OVMUP5.5 respectively.

Positive clones were screened by Xba I/Xho I digestion. Clone pBS-OVMUP4.7, gave fragments of about 4.7 kb and 2.96 kb. Clone pBS-OVMUP5.5 gave fragments of about 5.5 kb and 2.96 kb. Apparent positive clones having the 4.7 kb insert were further confirmed by Xba I/Hind III digestion that gave three fragments of 0.5 kb, 4.2 kb and 2.9 kb. The apparent positive clones with an insert of about 5.5 kb insert were further confirmed by Xba I/Kpn I digestion that gave three fragments of 2 kb, 3.5 kb and 2.96 kb.

A construct, pBS-OVMUP-10, containing the entire approximately 10 kb PCR product cloned into the pBluescript KS II (+/−) vector was made by taking a 4.7 kb Bam HI/Xho I fragment from the pBS-OVMUP4.7 plasmid and inserting it into the Bam HI/Xba I cleaved sites of pBS-OVMUP5.5. The Xho I and Xba I cut ends were blunt-ended by treating the digested fragments with Klenow enzyme and dNTPs at 25° C. for 15 mins before the digestion with Bam HI.

EXAMPLE 3

Sequencing

Figure 2:
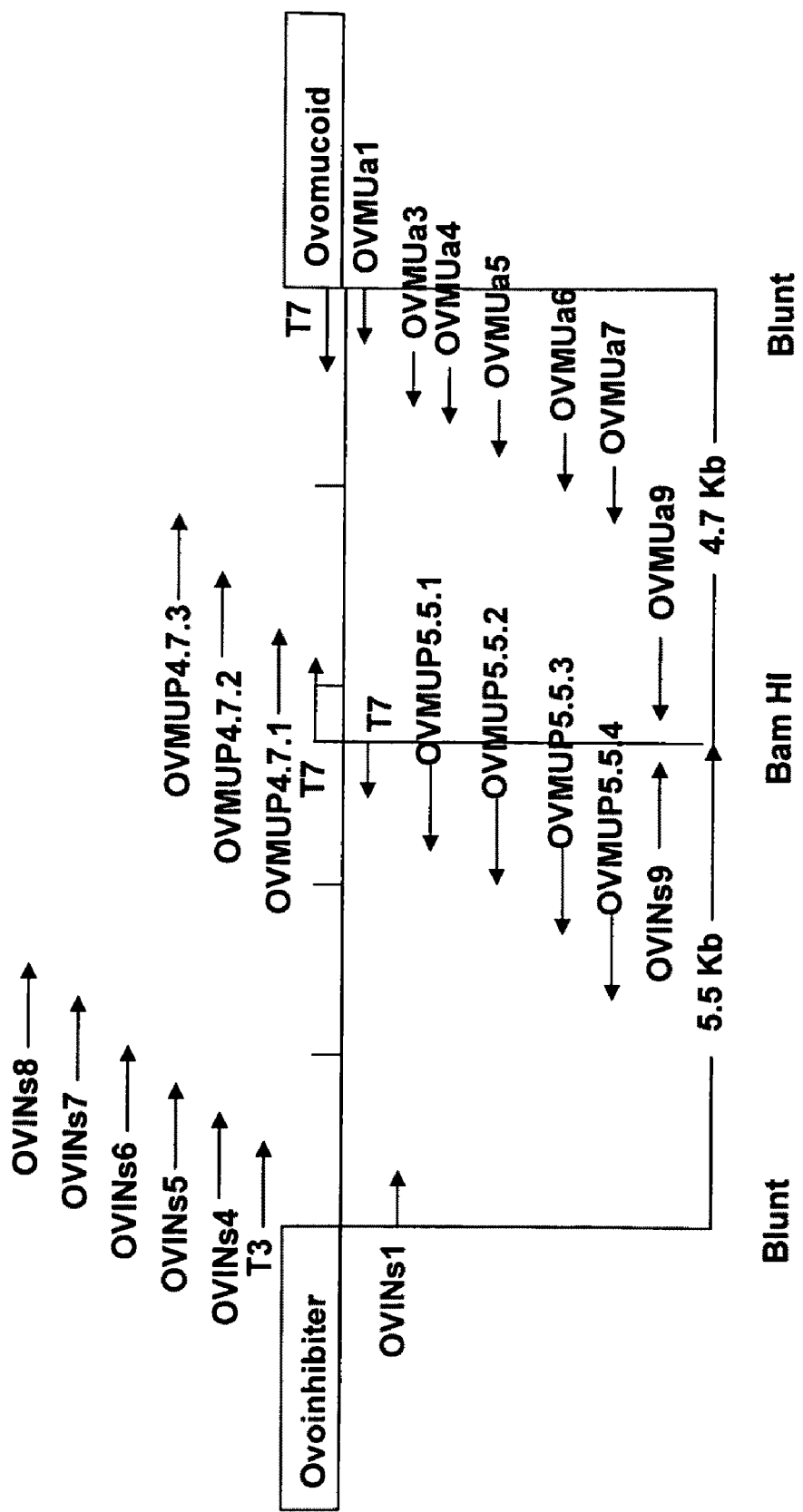
FIG. 2 illustrates the approximately 10 kb nucleic acid region that is 5' upstream of the chicken ovomucoid transcription start site, and the positions and orientations of primers used to sequence this region.

The plasmids pBS-OVMUP4.7 and pBS-OVMUP5.5 were sequenced from both ends of each insert as shown in FIG. 2. The initial primers were T7 and T3 having the nucleic acid sequences 5'-TAATACGACTCACTATAGGG-3' (SEQ ID NO: 5) and 5'-ATTAACCCTCACTAAAGGGA-3' (SEQ ID NO: 6) respectively. Subsequent primers (SEQ ID NOS: 7-25), as shown in FIG. 3, were designed according to the sequence results as they became available. The approximately 10 kb sequence was edited and assembled by the ContigExpress software of the Vector NTI Suite, version 6.0 (InforMax, Inc.). The region of the approximately 10 kb PCR product described in Example 1 above that encompassed the Bam HI junction was sequenced using the primers OVMUa9 (SEQ ID NO 27) and OVINs9 (SEQ ID NO 28) (shown in FIG. 3).

Each sequence chromatogram was visually checked for sequence accuracy and to locate base ambiguities. Regions containing ambiguous bases were re-sequenced with the same primer or, if still ambiguous, with a new primer designed to sequence the complementary strand. Sequencing of the original approximately 10 kb PCR fragment using the primers OVMUa9 (SEQ ID NO 27) and OVINs9 (SEQ ID NO 28) showed that the subcloned inserts of the plasmids pBS-OVMUP4.7 and pBS-OVMUP5.5 included all of the nucleic acid sequence of the parent fragment and no intervening Bam HI-Bam HI fragments were included in the final sequence SEQ ID NO: 26. The sequence (SEQ ID NO: 26) of the region lying between the 3' end of the ovoinhibitor gene and the transcription start site of the ovomucoid-encoding region is shown in FIG. 4.

EXAMPLE 4

Expression in Transfected Cultured Avian Myeloid and Oviduct Cells of Luciferase Regulated by the Approximately 10 kb Ovomucoid Promoter Construction of p10-OM-luc To facilitate insertion of coding sequences behind the ovomucoid promoter and in frame with the second ATG of the ovomucoid coding sequence, the Nco I site which overlaps the second ATG was changed to a Pci I site as depicted below. On the top is the wild type ovomucoid sequence at the start site of translation. On the bottom, the second Nco I site was changed to a Pci I site.

```
Nco I Nco I
  MetAlaMet
CTCACCATGGCCATGGC        (SEQ ID NO: 32)

GAGTGGTACCGGTACCG        (SEQ ID NO: 33)

Nco I Pci I
  MetAspMet
CTCACCATGGACATGGA        (SEQ ID NO: 34)

GAGTGGTACCGGTACCG        (SEQ ID NO: 35)
```

The Pci I site in the Bluescript backbone of pBS-OVMUP-10 was destroyed by cutting with Pci I, filling in the ends with Klenow polymerase and religating, creating pOM-10-alpha. The proximal promoter region was PCR amplified with primers OM-5 (SEQ ID NO.:29) and OM-6 (SEQ ID NO.:30) and template pBS-OVMUP-10. The resulting PCR product (SEQ ID NO.:31) was cut with Not I and Tth111 I and cloned into the 12059 bp Not I-Tth111 fragment of pOM-10-alpha, thereby creating pOM-10-Pci. The 1964 Nco I-S1-treated Kpn I fragment of gWiz-luciferase (Gene Therapy Systems, Inc., San Diego, Calif.) was cloned into the 12824 Pci I-Sma I fragment of pOM-10-Pci, creating p10-OM-luc.

Primer Sequences

```
CGGGCAGTACCTCACCATGGACATGT
(NOTE: sequence of OM5 may not be 100%
complementary to the target ovomucoid sequence)

OM-5
                                         (SEQ ID NO: 29)
5'-GCGCGGCCGCCCGGGACATGTCCATGGTGAGAGTACTGCCC-3'

OM-6
                                         (SEQ ID NO: 30)
5'-GGCCCGGGATTCGCTTAACTGTGACTAGG-3'
```

PCR Product (SEQ ID NO: 31)

```
                         -continued
GCGCGGCCGCCCGGGACATGTCCATGGTGAGAGTACTGCCCGGCTCTGCA

GGCGGCTGCCGGTGCTCTGCTCCTGAGATGGTCCCCCCGAGGCTGCCTGC

AAATATATACAAACGTGGCGTCCGAACTGTTGGACTGGAACACGGAGCAG

CCAGCTGAATCTGTCAGCGGCACAATGAGGCTGGTAATATTTATTGAGGT

CCTGACCTCCAGGTAATGGTCTGCGTCTCCCAGGCAATTGATTTTGGCTG

GACACTTGGTTAATAGCTTGAGACAAGTGTCACATGCTCTCAGTGGTCAA

AACCAAACAAACAGACTTTTGGACCAAAAAAAAAAAAAACCTCTTAAGGA

CTCTGGTAGAACCCTAAATAGCACAGAATGCTGAGGGGAGTAAGGGACAG

GTCCTTCATTTCGTCTCTGCATCCACATCTCCCAGCAGGAAGCAGCTAAG

GCTCAGCACCATCGTGCCTGCAGCTCTGCTTTCCATGCAGTTCTGCATTC

TTGGATATTCACCTCTAGGTAAAAGCACAGGCCAGGGAGGCTTTGTCACC

AGCAGAACTGACCAACCACTGCCAGGTGAAGCTGGCAGCACCGTATCTAA

CCTATGAAGTTAATGGTATTTAGCACTAGCTTGATAAAAGGAAGGGTTTC

TTGGCGGTTTCACTGCTTAAGTATAGAAGAGCTTGGTAGAAGACTTGAAA

GCAAGGTAAATGCTGTCAAATACCACTAAAAATGTCACTTGAACCTTATC

AGCAGGGAGCACTTATTTACAGACCTAGTCACAGTTAAGCGAATTCCCGG

GCC
```

The 1st and 2nd ATGs of the ovomucoid sequence are shown underlined. Note that the ovomucoid coding sequence is in reverse. The underlined, bold A is not in the wildtype sequence but was incorporated into pOM-10-Pci due to a error in the oligo OM-5.

Expression of Luciferase

For expression in avian cells of non-magnum origin, HD11 cells, a chicken myeloid cell line was used. Cells were cultured as described in Beug, H., et al. (Chicken hematopoietic cells transformed by seven strains of defective avian leukemia viruses display three distinct phenotypes of differentiation. (1979) Cell, 18: 375-90, in which these cells were referred to as HBCI cells), herein incorporated by reference in its entirety. Plasmid DNA was transfected into HD11 cells with Lipofectamine 2000 (Invitrogen Corporation, Carlsbad, Calif.) according to the manufacturer's instructions.

48 hours post-transfection, the cells were harvested and pelleted. The supernatant was removed and 20 ml of 10 mM Tris, pH 7.8, 1 mM EDTA (TE) was added. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Results are depicted in FIG. 6A. HD11 cells are permissive for the CMV promoter and is able to weakly activate the ovomucoid promoter. Some expression of the luciferase gene linked to the approximately 10 kb ovomucoid is evident.

For expression in avian oviduct cells, primary tubular gland cells were isolated as follows. The oviduct of a Japanese quail (Coturnix *coturnix japonica*) was removed and the magnum portion minced and enzymatically dissociated with 0.8 mg/ml collagenase (Sigma Chemical Co., St. Louis, Mo.) and 1.0 mg/ml dispase (Roche Molecular Biochemicals, Indianapolis, Ind.) by shaking and titurating for 30 minutes at 37° C. The cell suspension was then filtered through sterile surgical gauze, washed three times with F-12 medium (Life Technologies, Grand Island, N.Y.) by centrifugation at 200× g, and resuspended in OPTIMEM™ (Life Technologies) such that the $OD_{600}$ was approximately 2. 800 µl of the cell suspension was plated in each well of a 6-well dish. For each transfection, 4.0 µl of DMRIE-C liposomes (Life Technologies) and 2.0 µg of plasmid DNA was preincubated for 15 minutes at room temperature in 200 µl of OPTIMEM™, and then added to the oviduct cells. Cells with DNA/liposomes were incubated for about 5 hours at 37° C. in 5% $CO_2$. Next, 2.0 ml of DMEM (Life Technologies), supplemented with 15% fetal bovine serum (FBS) (Atlanta Biologicals, Atlanta, Ga.), 2× penicillin/streptomycin (Life Technologies), 50 ng/ml insulin (Sigma), $10^{-7}$ M α-estradiol (Sigma), and $10^{-6}$ M corticosterone (Sigma) were added to each well, and incubation continued for about 40 hours. Medium was then harvested and centrifuged at 110×g for 5 minutes.

For quantitation, the cells were scraped into the media with a rubber policeman. One milliliter was transferred to an eppendorf tube and the cells pelleted. The supernatant was removed and 20 ml of 10 mM Tris, ph 7.8, 1 mM EDTA (TE) was added. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Figure 6C:
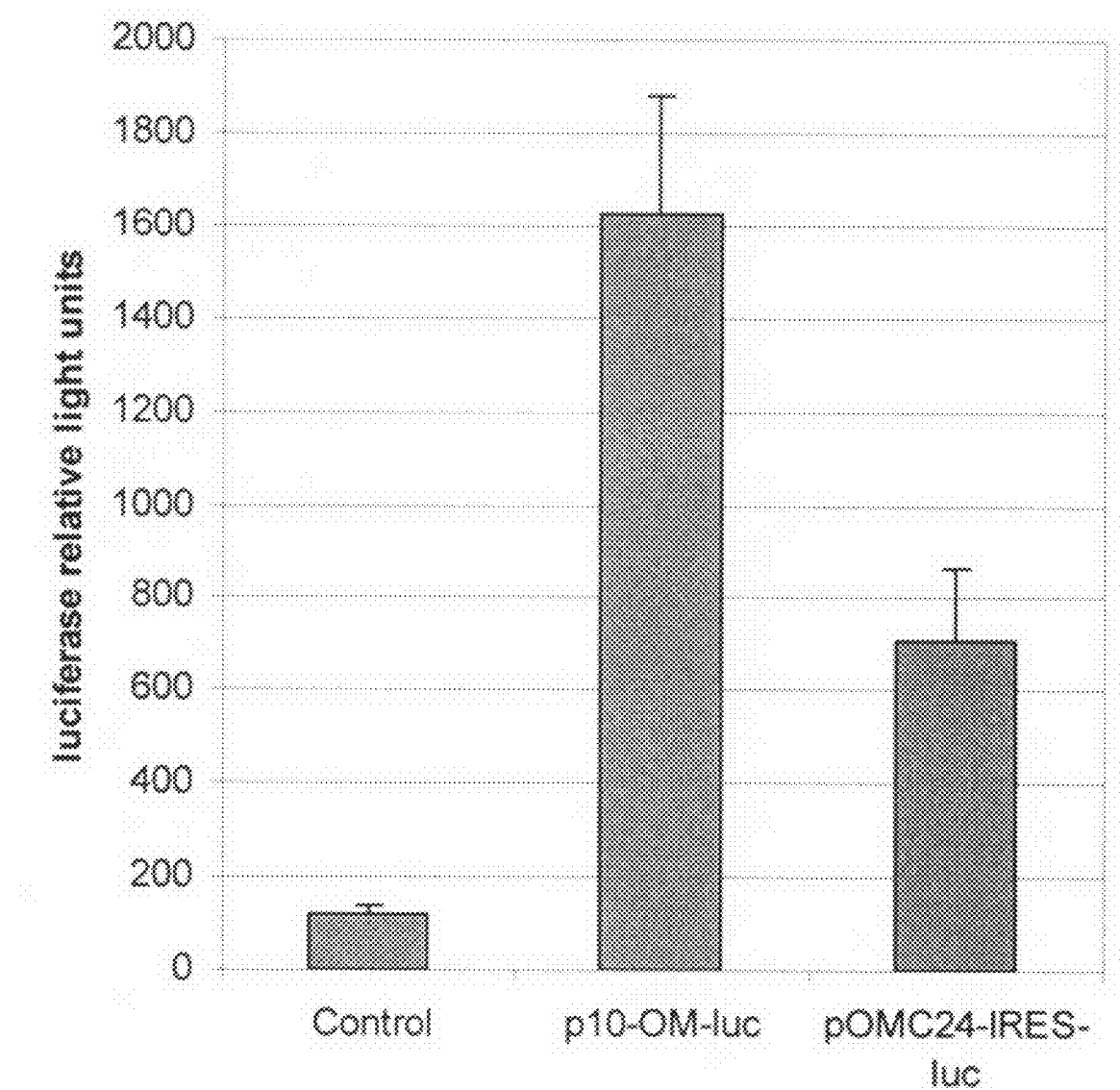
FIG. 6C shows the results of transfection into primary quail tubular gland cells isolated from the magnum of a laying quail hen for the approximately 10 kb ovomucoid promoters and the ovomucoid BAC-IRES construct each comprising an operably linked luciferase coding sequence.

The results are depicted in FIG. 6B. Expression of luciferase is evident from the CMV and approximately 10 kb ovomucoid promoters. The ovomucoid promoter has more activity relative to the CMV promoter in the tubular gland cells (ratio of CMV to ovomucoid is 152) than in the HD11 cells (ratio of CMV to ovomucoid is 2221). FIG. 6C shows the expression of luciferase from a OMC24-IRES-luc vector. This vector is the OMC24-IRES clone described in Example 6 with a luciferase coding sequence inserted 3' to the IRES.

EXAMPLE 5

Figure 5:
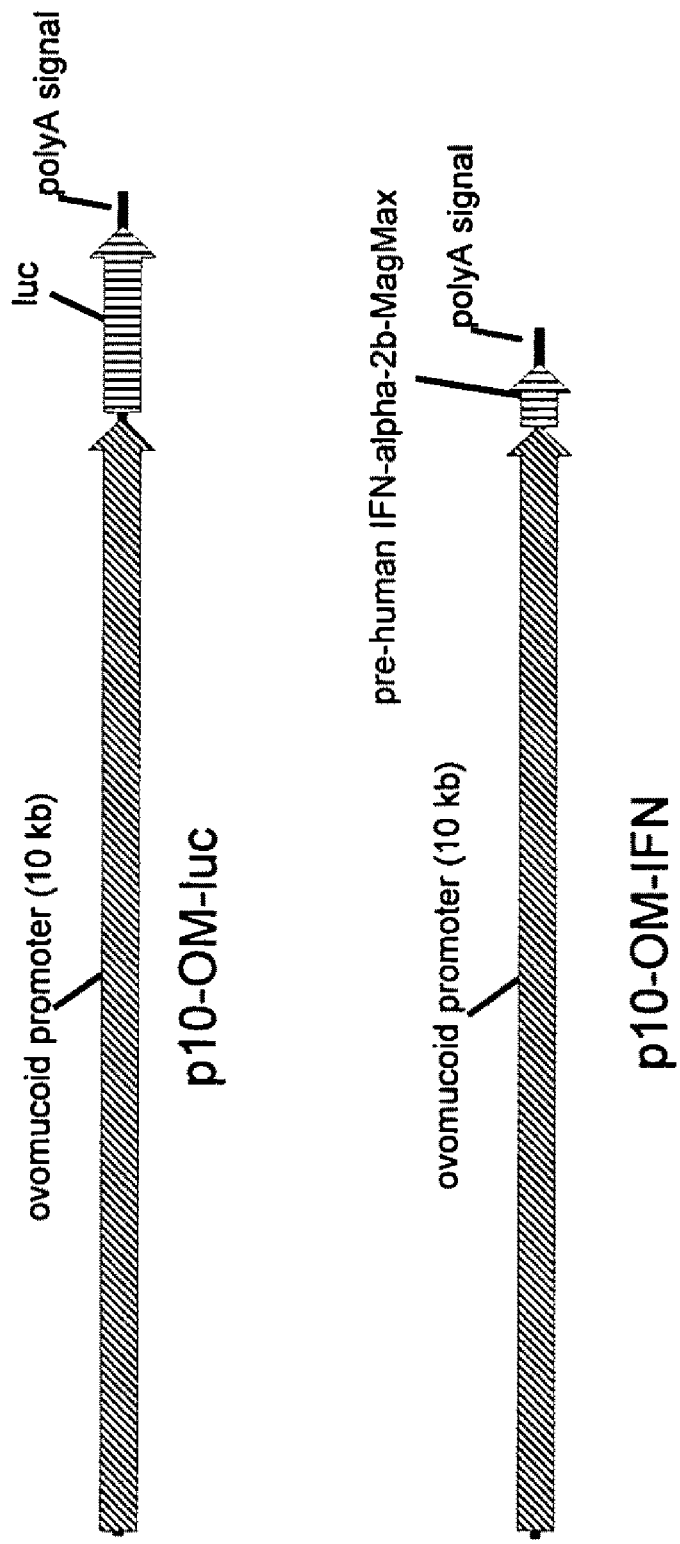
FIG. 5 illustrates the approximately 10 kb ovomucoid promoter linked to the luciferase or human IFNα-2b coding sequences.

Expression in Transfected Cultured Avian Oviduct Cells of Human Interferon α2b Regulated by the Approximately 10 kb Ovomucoid Promoter Construction of p10-OM-IFN The approximately 10 kb ovomucoid promoter fragment of Example 5 was placed in front of a MagMax IFN coding sequence creating p10-OM-IFN as seen in FIG. 5 (MagMag=codon optimized for expression in the magnum of a chicken based on the frequency of codon usage of proteins such as ovalbumin, ovomucoid, lysozyme and ovomucin).

Figure 7:
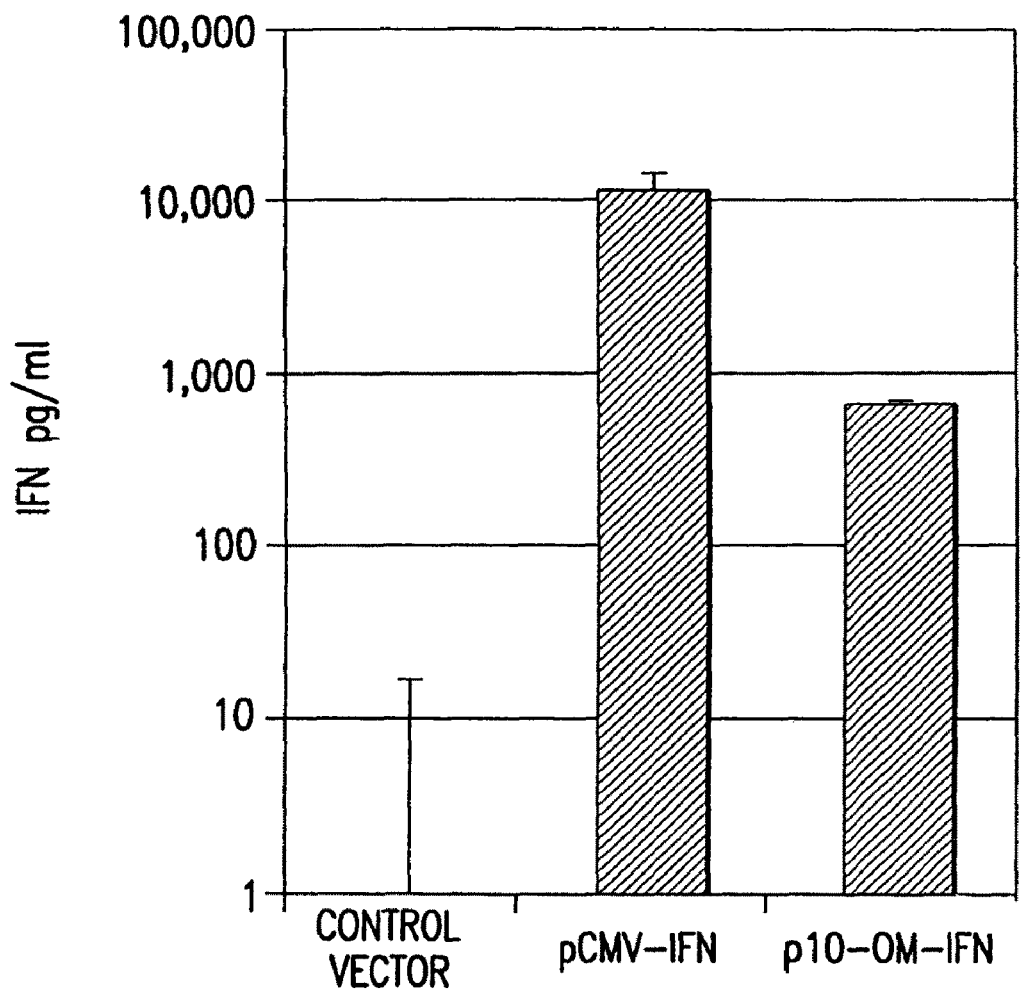
FIG. 7 shows the results of transfections of plasmids containing the ovomucoid promoter or CMV promoter linked to an interferon gene into primary quail tubular gland cells isolated from the magnum portion of the oviduct of a laying quail hen.

Quail primary tubular gland cells were isolated and treated as described in Example 4. 100 ml of supernatants were analyzed by ELISA (PBL Biomedical Laboratories, Flanders, N.J.) for human interferon α2b content. The results are depicted in FIG. 7. Expression of interferon is evident from the CMV and approximately 10 kb ovomucoid promoters.

EXAMPLE 6

Construction of an Ovomucoid Promoter-Bacterial Artificial Chromosome Expression Vector with an Antibody Heavy Chain or Antibody Light Chain Coding Sequence A chicken BAC library constructed with HindIII inserts ligated into pECBAC1 (see, Crooijmans et al., Mammalian Genome 11: 360-363, 2000, the disclosure of which is incorporated herein in its entirety by reference) was screened by PCR with two sets of primers using methods well known in the art. One primer set, OM7 and OM8, was designed to anneal in the 5' untranslated region of the ovomucoid gene. The other primer set, Ovoinhibitor 1 and Ovoinhibitor 2, was designed to anneal in exon 3 and exon 4 of the ovoinhibitor gene.

A BAC clone was identified which yielded the expected size PCR fragment for each primer set. The BAC clone which included an insert encompassing the ovoinhibitor and ovomucoid gene was sequenced by standard techniques and designated OMC24 The sequence for OMC24 is shown in SEQ ID NO: 36.

Primer Sequences

OM7:  (SEQ ID NO: 37)
CGGGCAGTACCTCACCATGGACATGT

OM8:  (SEQ ID NO: 38)
ATTCGCTTAACTGTGACTAGG

OVOINHIBITOR-1:  (SEQ ID NO: 39)
CGAGGAACTTGAAGCCTGTC

OVOINHIBITOR-2:  (SEQ ID NO: 40)
GGCCTGCACTCTCCATCATA

Figure 8:
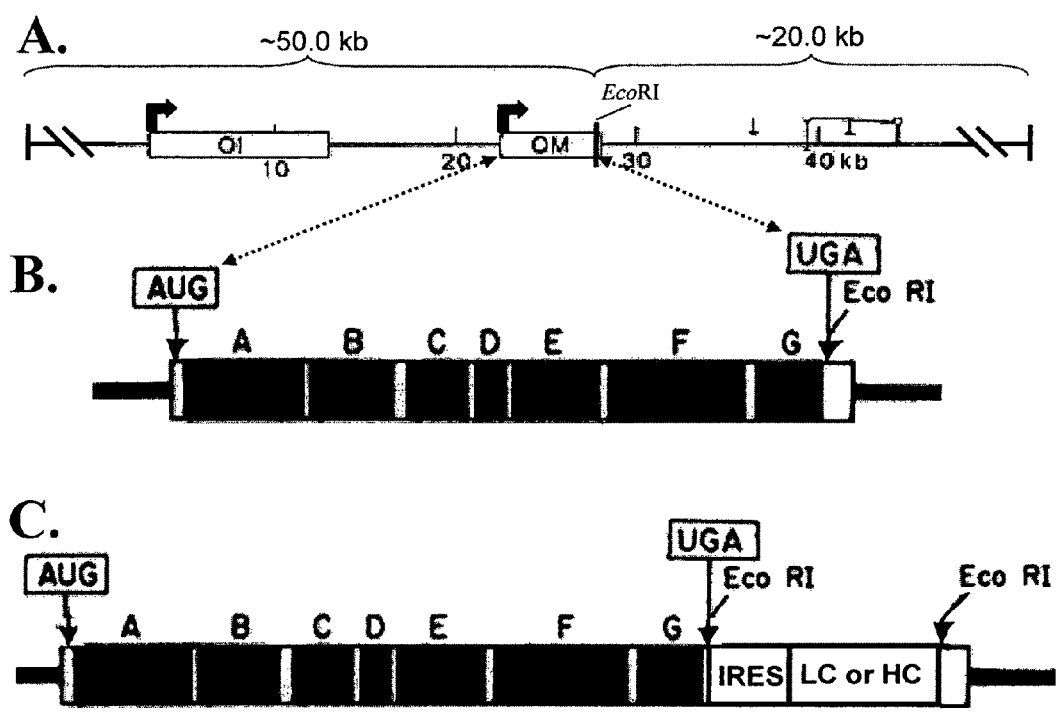
FIG. 8 shows an ovomucoid gene and bacterial artificial chromosome.

Polynucleotide sequences encoding the heavy chain and light chain of an IgG1 (IgG1K) monoclonal antibody were inserted into the 3' UTR of the ovomucoid transcript coding region in two separate OMC24 clones. The heavy chain and light chain coding sequences each included a signal sequence located at their 5' ends. For each clone, the coding sequence of each antibody chain and signal sequence was inserted into the OMC24 vector as an IRES-LC or IRES-HC cassette with the light chain and heavy chain inserts each positioned in the sense orientation SEQ ID NO: 41 shows the IRES-LC cassette inserted in the OMC24 clone. SEQ ID NO: 42 shows the IRES-HC cassette inserted in the OMC24 clone. The IRES sequence is shown in bold. The conserved regions of the IgG1 antibody light chain and heavy chain coding sequence are underlined. The nucleotides for the coding sequences of the variable regions for the IgG1 light chain and heavy chains are represented by N's. The nucleotides encoding the signal sequences in each clone are represented by italicized N's with the start codon indicated as ATG. OMC24 nucleotide sequence flanking the IRES and the antibody coding sequence is also shown for each of the two sequences. These constructs are shown in FIG. 8.

The IRES-antibody light chain and heavy chain cassettes were each inserted into an OMC24 clone at a natural EcoRI site that resides in the 3' UTR of ovomucoid at about position 41,627 of SEQ ID NO: 36. Because there are many EcoRI sites in OMC24, RecA-assisted restriction endonuclease cleavage (RARE) was used to cut only at the desired site. RecA assisted restriction endonuclease cleavage is described in Molecular Biotechnology (2001) Vol 18, pp 233 to 241, the disclosure of which is incorporated herein in its entirety by reference. A portion of the vector from which the cassettes were obtained of about 26 nucleotides in length can be seen 3' of the coding sequence of the light chain and heavy chain in SEQ ID NO: 41 and SEQ ID NO: 42.

OMC24-IRES-LC (SEQ ID NO: 41)
gatttcactc atctcctaat aatcaggtag ctgaggagat

-continued gctgagtctg ccagttcttg ggctctgggc aggatcccat ctcctgcctt ctctaggaca gagctcagca ggcagggctc tgtggctctg tgtctaaccc acttcttcct ctcctcgctt tcagggaaag caacgggact ctcactttaa gccattttgg aaaatgctga atatcagagc tgagagaatt ccgccctct ccctcccccc ccctaacgt tactggccga agccgcttgg aataaggccg gtgtgcgttt gtctatatgt tattttccac catattgccg tcttttggca atgtgagggc ccggaaacct ggccctgtct tcttgacgag cattcctagg ggtctttccc ctctcgccaa aggaatgcaa ggtctgttga atgtcgtgaa ggaagcagtt cctctggaag cttcttgaag acaaacaacg tctgtagcga cccttttgcag gcagcggaac cccccacctg gcgacaggtg cctctgcggc caaaagccac gtgtataaga tacacctgca aaggcggcac aaccccagtg ccacgttgtg agttggatag ttgtggaaag agtcaaatgg ctctcctcaa gcgtattcaa caaggggctg aaggatgccc agaaggtacc ccattgtatg ggatctgatc tggggcctcg gtgcacatgc tttacgtgtg tttagtcgag gttaaaaaac gtctaggccc cccgaaccac ggggacgtgg ttttcctttg aaaaacacga tgataagctt gccacaacca *tgnnnnnnnn nnnnnnnnn*

*nnnnnnnnnn nnnnnnnnnn nnnnnnnnnn nnnnnnnnnn* nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnacggtgg cggcgccatc tgtcttcatc ttcccgccat ctgatgagca gttgaaatct ggaactgcct ctgttgtgtg cctgctgaat aacttctatc ccagagaggc caaagtacag tggaaggtgg ataacgccct ccaatcgggt aactcccagg agagtgtcac agagcaggac agcaaggaca gcacctacag cctcagcagc accctgacgc tgagcaaagc agactacgag aaacacaaag tctacgcctg cgaagtcacc catcagggcc tgagctcgcc cgtcacaaag agcttcaaca ggggagagtg ttagggatcc actagtccag tgtggtggaa ttcaccacag gatccccact ggcgaatccc agcgagaggt ctcacctcgg ttcatctcgc actctgggga gctcagctca ctcccgattt -continued
tctttctcaa taaactaaat cagcaacact cctttgtctt OMC24-IRES-HC (SEQ ID NO: 42)
gatttcactc atctcctaat aatcaggtag ctgaggagat gctgagtctg ccagttcttg ggctctgggc aggatcccat ctcctgcctt ctctaggaca gagctcagca ggcagggctc tgtggctctg tgtctaaccc acttcttcct ctcctcgctt tcagggaaag caacggagct ctcactttaa gccattttgg aaaatgctga atatcagagc tgagagaatt ccgccctct ccctccccc cccctaacgt tactggccga agccgcttgg aataaggccg gtgtgcgttt gtctatatgt tattttccac catattgccg tcttttggca atgtgagggc ccggaaacct ggccctgtct tcttgacgag cattcctagg ggtctttccc ctctcgccaa aggaatgcaa ggtctgttga atgtcgtgaa ggaagcagtt cctctggaag cttcttgaag acaaacaacg tctgtagcga ccctttgcag gcagcggaac cccccacctg gcgacaggtg cctctgcggc caaaagccac gtgtataaga tacacctgca aaggcggcac aaccccagtg ccacgttgtg agttggatag ttgtggaaag agtcaaatgg ctctcctcaa gcgtattcaa caaggggctg aaggatgccc agaaggtacc ccattgtatg ggatctgatc tggggcctcg gtgcacatgc tttacgtgtg tttagtcgag gttaaaaaac gtctaggccc cccgaaccac ggggacgtgg ttttcctttg aaaaacacga tgataagctt gccacaacca tgnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnntcagct agcaccaagg gcccatcggt cttcccctg gcaccctcct ccaagagcac ctctgggggc acagcggccc tgggctgcct ggtcaaggac tacttccccg aaccggtgac ggtgtcgtgg aactcaggcg ccctgaccag cggcgtgcac accttcccgg ccgtcctaca gtcctcagga ctctactccc tcagcagcgt ggtgaccgtg ccctccagca gcttgggcac ccagacctac atctgcaacg tgaatcacaa gcccagcaac accaaggtgg acaagagagt tgagcccaaa tcttgtgaca aaactcacac atgcccaccg -continued
tgcccagcac ctgaactcct ggggggaccg tcagtcttcc tcttcccccc aaaacccaag gacaccctca tgatctcccg gacccctgag gtcacatgcg tggtggtgga cgtgagccac gaagaccctg aggtcaagtt caactggtac gtggacggcg tggaggtgca taatgccaag acaaagccgc gggaggagca gtacaacagc acgtaccgtg tggtcagcgt cctcaccgtc ctgcaccagg actggctgaa tggcaaggag tacaagtgca aggtctccaa caaagccctc ccagccccca tcgagaaaac catctccaaa gccaagggc agccccgaga accacaggtg tacaccctgc cccatcccg ggatgagctg accaagaacc aggtcagcct gacctgcctg gtcaaaggct tctatcccag cgacatcgcc gtggagtggg agagcaatgg gcagccggag aacaactaca agaccacgcc tcccgtgctg gactccgacg gctccttctt cctctacagc aagctcaccg tggacaagag caggtggcag caggggaacg tcttctcatg ctccgtgatg catgaggctc tgcacaacca ctacacgcag aagagcctct ccctgtctcc gggtaaatag ggatccacta gtccagtgtg gtggaattca ccacaggatc cccactggcg aatcccagcg agaggtctca cctcggttca tctcgcactc tggggagctc agctcactcc cgattttctt The resulting mRNA transcript from the ovomucoid promoter for each clone contains two coding sequences; one for the ovomucoid protein and another for the downstream light chain or heavy chain coding sequence. The internal ribosome entry site (IRES) engineered into the vectors is useful to facilitate translation of the downstream heavy chain or light chain coding sequence.

EXAMPLE 7

Production of Transgenic Hens with an Ovomucoid Promoter-Bacterial Artificial Chromosome Expression Vector Transgene 100 µg each of BAC clone OMC24-IRES-LC and OCM24-IRES-HC were linearized by enzymatic restriction digest. The digested DNA was phenol/CHCl$_3$ extracted, ethanol precipitated, suspended in 0.25 M KCl and diluted to a working concentration of approximately 60 µg/ml. The DNA was mixed with SV40 T antigen nuclear localization signal peptide (NLS peptide, amino acid sequence CGGPKKKRKVG (SEQ ID NO: 43) with a peptide DNA molar ratio of 100:1 (Collas and Alestrom, 1996, Mol. Reprod. Develop. 45: 431-438, the disclosure of which is incorporated by reference in its entirety). The DNA samples were allowed to associate with the SV40 T antigen NLS peptide by incubation at room temperature for 15 minutes.

Introduction of the DNA-NLS complex into an avian egg was accomplished essentially as described in U.S. patent application Ser. No. 10/251,364, filed Sep. 18, 2002, now U.S. Pat. No. 7,312,374, issued Dec. 25, 2007, the disclosure of which is incorporated in its entirety herein by reference.

Briefly, the germinal disc of an avian egg was illuminated by an incident light beam and visualized by an oblique macromonitering system. A micropipette injection needle was positioned by micromanipulation such that the tip of the needle was pressed into the vitelline membrane of the avian egg to a depth of about 20 μM. The injection needle was inserted through the membrane into the germinal disc to a point where only the end of the beveled opening of the needle was visible above the membrane, while the remaining of the opening was present inside the germinal disk. The DNA-NLS was then injected into the germinal disc. Approximately 100 nanoliters of DNA were injected into a germinal disc of stage I White Leghorn embryos obtained two hours after oviposition of the previous egg.

Injected embryos were surgically transferred to recipient hens via ovum transfer according to the method of Christmann et al. (PCT Publication WO 02/20752, the disclosure of which is incorporated herein in its entirety by reference) and hard shell eggs were incubated and hatched. See, Olsen and Neher, 1948, J. Exp. Zoo. 109: 355-366, the disclosure of which is incorporated in its entirety herein by reference.

Genomic DNA samples from one-week old chicks were analyzed for the presence of OMC24-IRES-LC or HC by PCR using methods well known in the field of avian transgenics. Briefly, three hundred nanograms of genomic DNA and 1.25 units of Taq DNA polymerase (Promega) were added to a 50 μl reaction mixture of 1× Promega PCR Buffer with 1.5 mM $MgCl_2$, 200 μM of each dNTP, 5 μM primers. The reaction mixtures were heated for 4 minutes at 94° C., and then amplified for 34 cycles each consisting of: 94° C. for 1 min, 60° C. for 1 min and 72° C. for 1 min. A final cycle of 4 minutes at 72° C. was performed. PCR products were detected by visualization on a 0.8% agarose gel stained with ethidium bromide.

EXAMPLE 8

Production of Antibody by Transgenic Hens

Transgenic chicks produced as described in Example 7 were grown to maturity. Eggs were collected from the hens and egg white material was assayed for the IgG1 using sandwich ELISA.

The eggs were cracked and opened and the whole yolk portion was discarded. Both the thick and thin egg white portions were kept. 1 ml of egg white was measured and added to a plastic Stomacher 80 bag. A volume of egg white buffer (5% 1M Tris-HCl pH 9 and 2.4% NaCl) equal to two times the volume of egg white was added to the egg white. The egg white-buffer mixture was paddle homogenized in the Stomacher 80 at normal speed for one minute. The sample was allowed to stand overnight and homogenation was repeated. A 1 ml sample of the mixture was used for testing.

A Costar flat 96-well plate was coated with 100 μl of C Goat-anti-Human kappa at a concentration of 5 μg/ml in PBS. The plate was incubated at 37° C. for two hours and then washed. 200 μl of 5% PBA was added to the wells followed by an incubation at 37° C. for about 60-90 minutes followed by a wash. 100 μl of egg white samples (diluted in 1% PBA:LBP) was added to each well and the plate was incubated at 37° C. for about 60-90 min followed by a wash. 100 μl of a 1:2000 dilution of F'2 Goat anti-Human IgG Fc-AP in 1% PBA was added to the wells and the plate was incubated at 37° C. for 60-90 min followed by a wash.

The transgenic antibody was detected by placing 75 μl of 1 mg/ml PNPP (p-nitrophenyl phosphate) in 5× developing buffer in each well and incubating for about 10-30 mins at room temperature. The detection reaction was stopped using 75 ul of 1N NaOH. The OD405-650 nm was then determined for each sample well. Each OD405-650 nm value was compared to a standard curve to determine the amount of recombinant antibody present in each sample. Approximately 0.3% of hens analyzed expressed antibody in their eggs. Two hens which expressed antibody are Hen 1251 which was found to produce an average of 19 ng of IgG per ml of egg white and Hen 4992 which was found to produce an average of 150 ng of IgG per ml of egg white.

Figure 9:
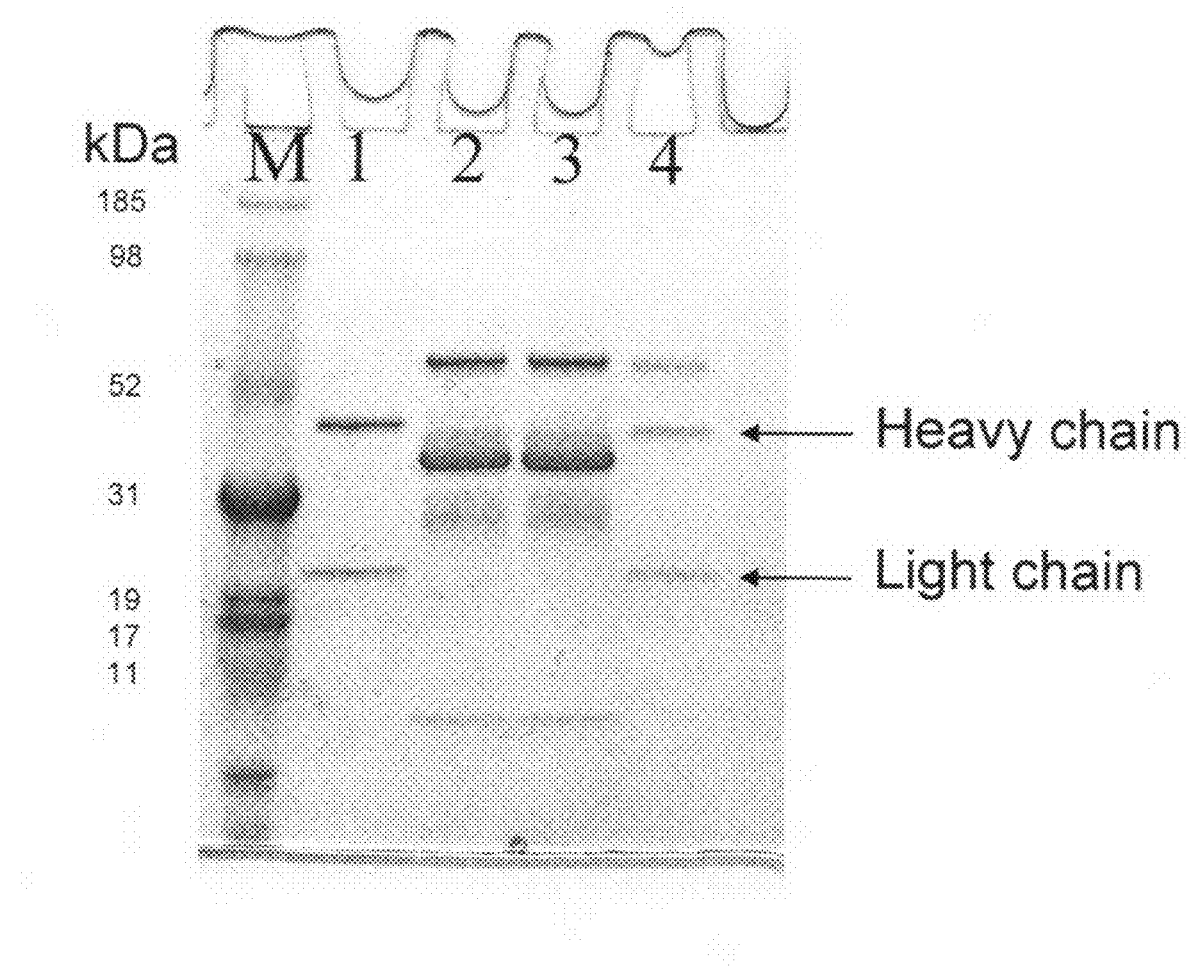
FIG. 9 shows an SDS-PAGE analysis of partially purified hMab derived from a single transgenic hen. (M) Multi-mark standard, lane 1) 1 mg purified hMab (produced by mammalian cells), lane 2) 5 mg pre-column (transgenic avian egg white), lane 3) 5 mg column flow thru from transgenic avian egg white, lane 4) partially purified hMab from transgenic avian egg white.

FIG. 9 shows the results of an SDS-PAGE analysis of the transgenic avian derived hMab compared to the same antibody produced in mammalian cells. The antibody was first purified from egg white proteins by protein A affinity chromatography. The transgenic protein (lane 4) heavy chain and light chain had virtually an identical mobility compared to heavy and light chains of the same antibody produced by standard mammalian cell culture (lane 1). Also shown are pre-chromatography transgenic egg white (lane 2) and affinity chromatography transgenic egg white flow through (lane 3).

EXAMPLE 9

Human Antibody Produced by Transgenic Hens Demonstrates Target Antigen Binding

The human monoclonal antibody produced and identified as described in Examples 7 and 8 was assayed for target antigen binding.

Antibody was captured from the egg white in microplate wells coated with the antibodies target antigen. Antigen-antibody complexes were quantitated using isotype-specific secondary antibody conjugated with alkaline phosphatase. The ability of the transgenic avian produced hMab to bind its target antigen was compared with the binding ability of the same hMab produced in mammalian cells.

Figure 10:
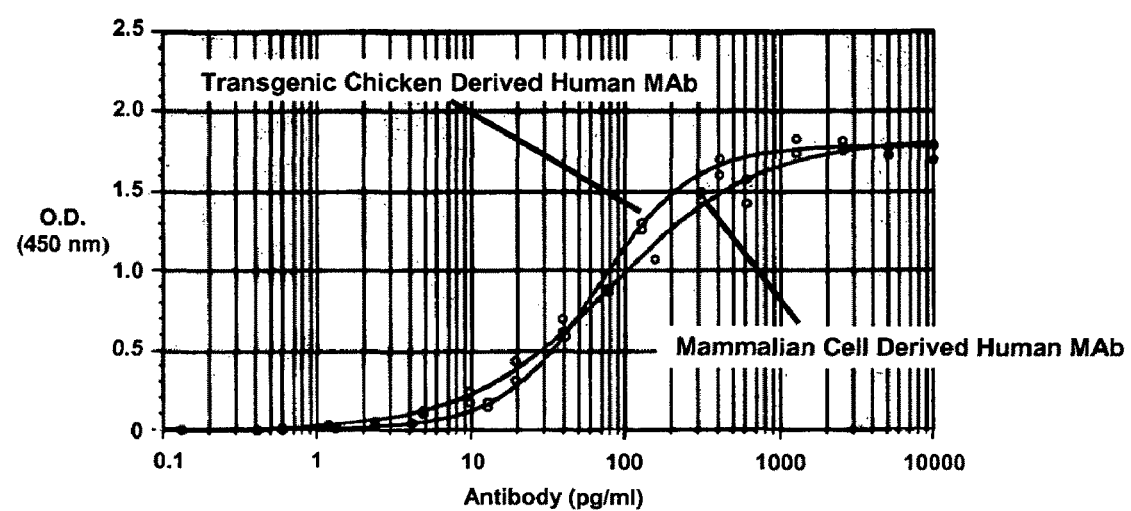
FIG. 10 shows plots of the binding ability of an IgG1 monoclonal antibody produced by a transgenic chicken and the binding ability of the same IgG1 monoclonal antibody produced by mammalian cells.

Plots showing the binding ability of each antibody are shown in FIG. 10. The plots show the level of antigen binding per picogram of antibody tested for both the antibody from transgenic chicken egg white and the antibody from a mammalian cell line. The similarity of the binding curves produced by these two antibodies indicate that the transgenic human antibody has an affinity that is substantially similar to the affinity of the antibody produced by standard methods (i.e., produced in mammalian cells).

A CHO cell line stably transfected with a plasmid that expressed the corresponding cell-surface antigen for the antibody produced by the transgenic avian was used in FACS analysis of the antibody.

Figure 11:
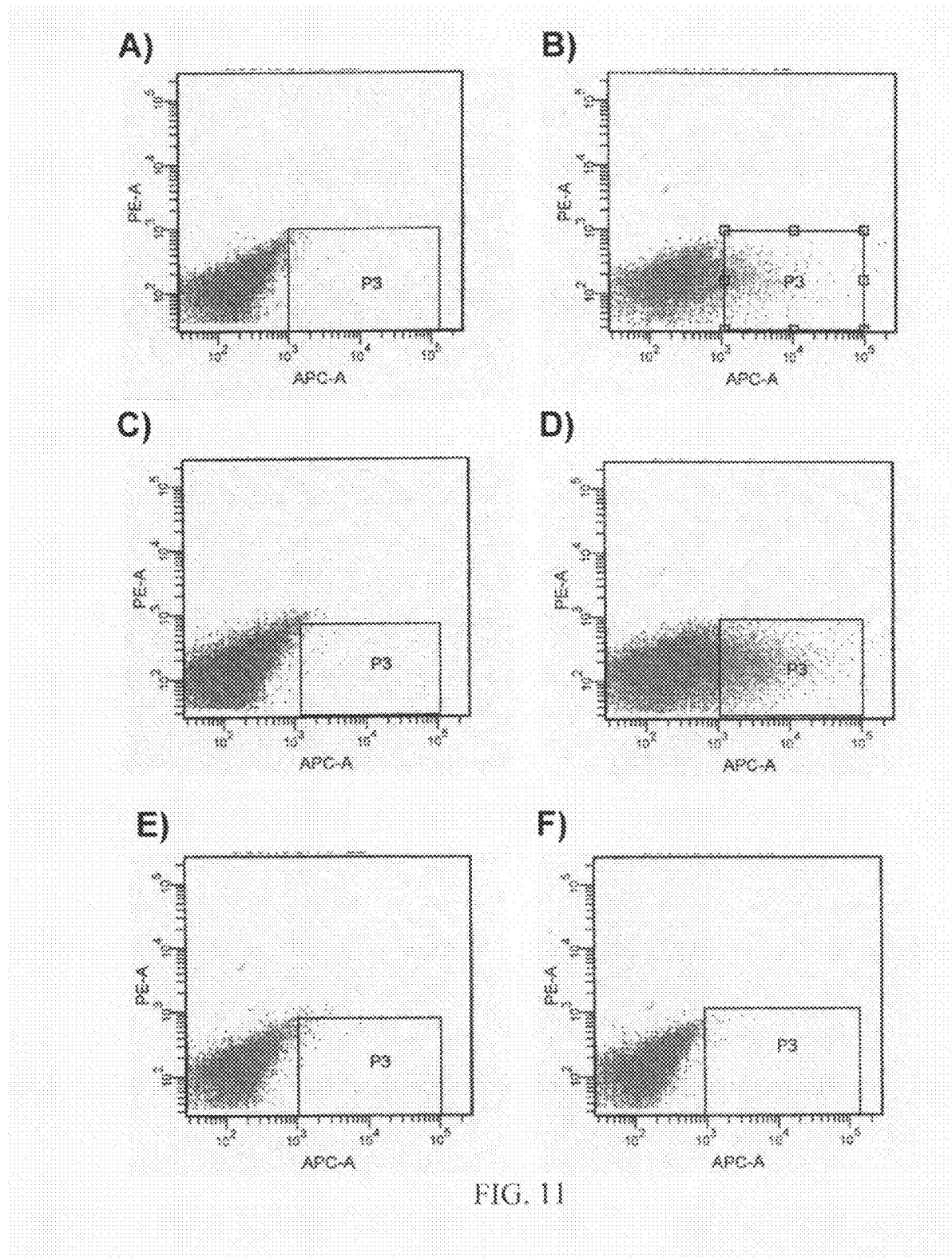
FIG. 11A-11F shows the ability of avian derived hMab to bind target antigen expressed on a cell surface relative to the ability of the mammalian cell derived hMab.

FIG. 11 shows the ability of the transgenic avian derived hMab to bind target antigen expressed on the cell surface of CHO cells relative to the ability of the antibody produced in mammalian cells. CHO cells were transfected with either a luciferase expression plasmid (11A, 11C, and 11E) or an expression plasmid carrying cDNA of the hMab's target antigen (11B, 11D, and 11F). Cells were collected and treated with one of three primary antibodies: 1) the antigen specific hMab produced by mammalian cells (11A and 11B), 2) the antigen specific hMab produced by a transgenic hen (11C and 11D), or 3) human antibody of the same isotype as the antibody produced by the transgenic hen but with different antigen specificity (11E and 11F). An isotype specific antibody conjugated with APC (Allophycocyanin) was used to detect primary antibodies bound to the cells. Cells were sorted by FACS, counted and signal generated by the APC of the secondary antibody was quantitated. Cells that exhibited APC-associated fluorescence are delineated with a box within each graph.

Together the ELISA and FACS data show that a human antibody molecule produced by transgenic hens can bind efficiently to its target antigen.

EXAMPLE 10

Human Antibody Produced by Transgenic Hens Demonstrates Stability

Figure 12:
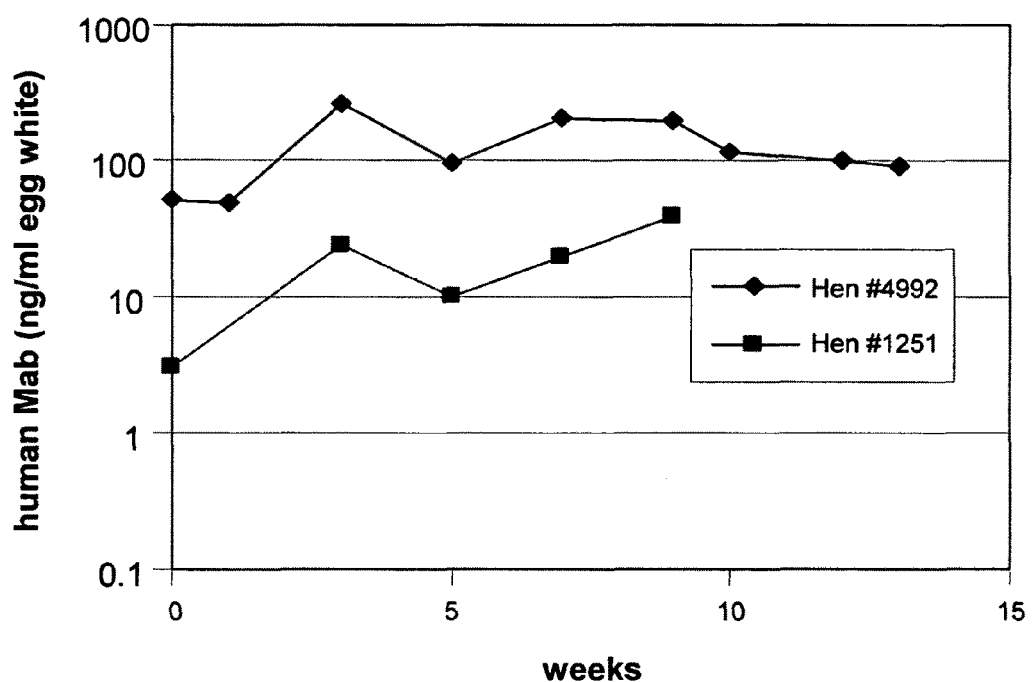
FIG. 12 shows the stability of hMab expression in transgenic hen. Eggs from transgenic hens #4992 and #1251 were collected over several weeks. The amount of hMab in egg white material was quantitated over time via sandwich ELISA for the specific human IgG1 (H+L).

FIG. 12 shows the stability of hMab expression in transgenic hen. Eggs from transgenic hens #4992 and #1251 of Example 8 were collected over several weeks. The amount of hMab in egg white material was quantitated via sandwich ELISA for the specific human IgG1. The results indicate that the antibody produced by an avian and collected in the egg white are stable over a significant period of time.

EXAMPLE 11

Human Antibody Produced by Transgenic Hens Demonstrates Target Cell Killing

The primary mechanism of action of many antibody therapeutics is the cytolysis of target antigen expressing cells via serum complement. This activity may require secondary modifications of the antibody in the form of proper glycosylation of the Fc portion of the antibody. Proper glycosylation has been shown to be essential for the antibody interaction with the C1q molecule of complement and with the Fcγ-family of receptors on effector cells.

The activity of the transgenic IgG1 antibody produced in Example 8 was assessed in antibody-dependent cellular cytotoxicity (ADCC) and complement-dependent cellular cytotoxicity (CDCC) assays using the antigen-expressing CHO cell line described in Example 9 as target cells.

ADCC assay: Surface antigen expressing CHO cells were incubated with purified transgenic MAb at 0.5 µg/ml or no MAb in serum free media. Human PBMCs (peripheral blood mononuclear cells) were added at an effector:target cell ratio of 20:1. The mixture was incubated at 37° C. for 4 hours. Cell lysis was assayed by LDH release and maximal release accomplished by addition of 1% Triton.

CDCC assay: Surface antigen expressing CHO cells were incubated overnight 37° C. with 0.5 µg/ml purified transgenic MAb or no MAb in the presence of 20% normal human serum. Plates were then washed and cell viability was assayed by LDH assay release and maximal release accomplished by addition of 1% Triton.

Activity was calculated for both the ADCC assay and the CDCC assay by methods well known in the art.

Figure 13:
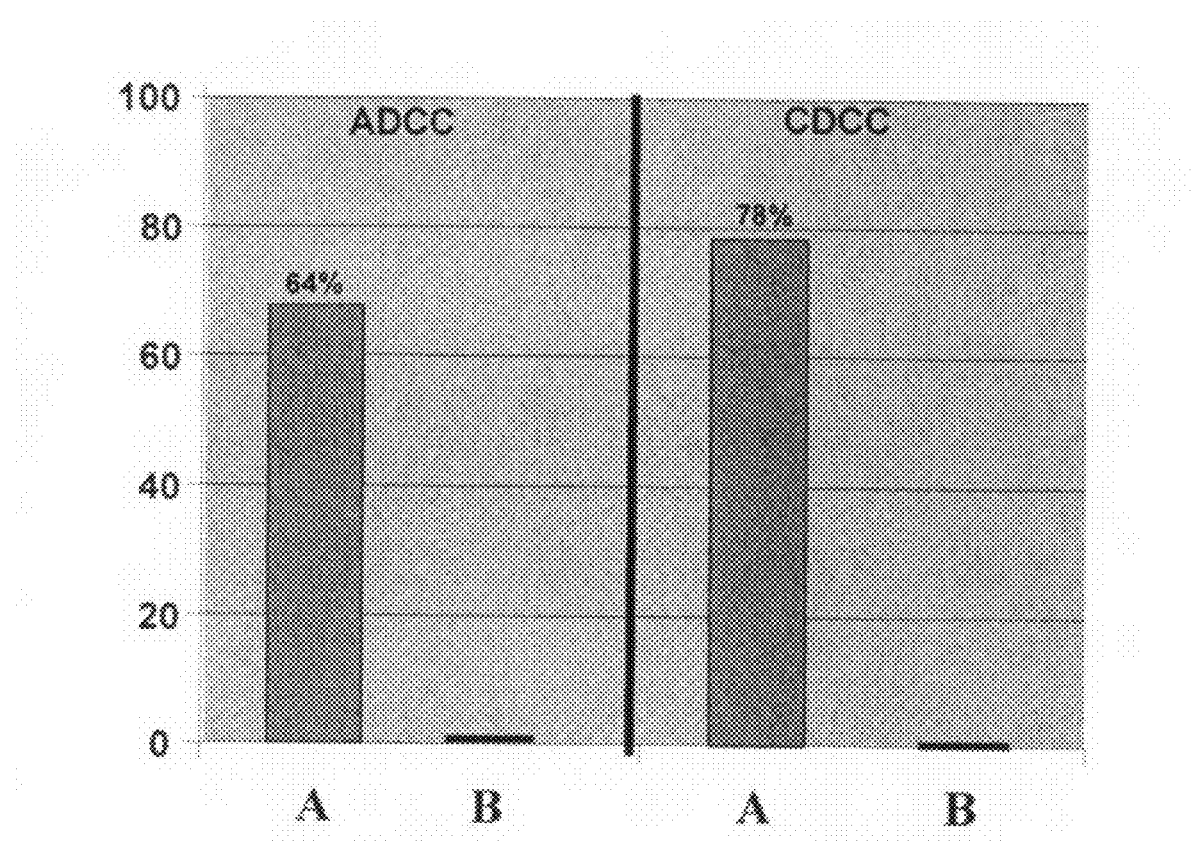
FIG. 13 shows ADCC (antibody dependent cellular cytotoxicity) and CDCC (complement-dependent cellular cytotoxicity) for an IgG1 produced in transgenic avians.

FIG. 13 shows the percent cytotoxicity for incubations with the transgenic antibody (columns A) and incubations with no antibody in serum free medium (columns B). As can be seen in FIG. 13, the transgenic human antibody efficiently mediated both ADCC and CDCC activities indicating that the antibody is appropriately glycosylated during production in avians and is effective in cytolysis of target cells.

EXAMPLE 12

Construction of an Ovomucoid Promoter-Bacterial Artificial Chromosome Expression Vector with a CTLA4-Fc Fusion Coding Sequence and an attB Site An ovomucoid gene expression controlling region-bacterial artificial chromosome expression vector with a CTLA4-Fc fusion coding sequence and attB site was constructed using nucleotide coding sequences for the extracellular domains of the CTLA4 (cytotoxic T lymphocyte antigen 4) receptor protein linked to nucleotide coding sequences for an immunoglobulin constant region (IgG1 Fc). The nucleotide sequence for the vector is shown in SEQ ID NO: 44

To produce this construct, an attB fragment was inserted into an EcoRI site of the OMC24-IRES-LC clone described in Example 6. RecA-assisted restriction endonuclease cleavage (RARE) was used to cut only at the desired EcoRI site in the OMC24-IRES-LC clone. The attB fragment is shown inserted approximately at nucleotide number 26,722 to 27,029 of SEQ ID NO: 44. The attB site is shown in bold below in SEQ ID NO: 45 as it appears in the OMC24-attB-IRES-LC construct.

```
SEQ ID NO: 45
CCCAGAGCTG TGCAGTTGGG ATCCTAACAC CATGCAGATG

CTCCAGGACC TGCACCGAGC CCCAGCACTG GCACTCATCT

CTTCTTTCCA CCCCTCTGAG AGCAACAAGT GGCTCTGCAA

TGGCAATGTA AGTGAAACCG GGCGGGTATC TTAGAGCACC

TGGAAGCTTG CATGCCTGCA GGTCGACTCT AGAGGATCCC

CGGGTACCGA GCTCGAATTC CAGGTACCGT CGACGATGTA

GGTCACGGTC TCGAAGCCGC GGTGCGGGTG CCAGGGCGTG

CCCTTGGGCT CCCCGGGCGC GTACTCCACC TCACCCATCT

GGTCCATCAT GATGAACGGG TCGAGGTGGC GGTAGTTGAT

CCCGGCGAAC GCGCGGCGCA CCGGGAAGCC CTCGCCCTCG

AAACCGCTGG GCGCGGTGGT CACGGTGAGC ACGGGACGTG

CGACGGCGTC GGCGGGTGCG GATACGCGGG GCAGCGTCAG

CGGGTTCTCG ACGGTCACGG CGGGCATGTC GACAGCCAAG

CCGAATTCGC CCTATAGTGA GTCGTATTAC AATTCACTGG

CCGTCGTTTT ACAACGTCGT GACTGGGAAA ACCCTGGCGT

TACCCAACTT AATCGCCTTG CAGCACATCC CCCTTTCGCC

AGCTGGCGTA ATAGCGAAGA GGCCCGCACC GATCGCCCTT

CCCAACAGTT GCGCAGCCTG AATGGCGAAT GGCGCCTGAT

GCGGTATTTT CTCCTTACGC ATCTGTGCGG TATTTCACAC

CGCATATGGT GCACTCTGAG
```

To produce the OMC24-attB-IRES-CTLA4 clone shown in SEQ ID NO: 44, the IRES-LC portion of the OMC24-attB-IRES-LC clone was deleted using RARE and was replaced with an IRES-CTLA4-Fc coding sequence (spanning approximately from nucleotides 76,124 to 77,872 of SEQ ID NO: 44). The portion of the OMC24-attB-IRES-CTLA4-Fc clone comprising the IRES and CTLA4-Fc portions is shown below in SEQ ID NO: 46. The IRES is shown in bold and the CTLA4-Fc coding region is underlined.

SEQ ID NO: 46
ATAATCAGGT AGCTGAGGAG ATGCTGAGTC TGCCAGTTCT

TGGGCTCTGG GCAGGATCCC ATCTCCTGCC TTCTCTAGGA

CAGAGCTCAG CAGGCAGGGC TCTGTGGCTC TGTGTCTAAC

CCACTTCTTC CTCTCCTCGC TTTCAGGGAA AGCAACGGGA

CTCTCACTTT AAGCCATTTT GGAAAATGCT GAATATCAGA

GCTGAGAGAA TTCCGCCCCT CTCCCTCCCC CCCCCCTAAC

GTTACTGGCC GAAGCCGCTT GGAATAAGGC CGGTGTGCGT

TTGTCTATAT GTTATTTTCC ACCATATTGC CGTCTTTTGG

CAATGTGAGG GCCCGGAAAC CTGGCCCTGT CTTCTTGACG

AGCATTCCTA GGGGTCTTTC CCCTCTCGCC AAAGGAATGC

AAGGTCTGTT GAATGTCGTG AAGGAAGCAG TTCCTCTGGA

AGCTTCTTGA AGACAAACAA CGTCTGTAGC GACCCTTTGC

AGGCAGCGGA ACCCCCACC TGGCGACAGG TGCCTCTGCG

GCCAAAAGCC ACGTGTATAA GATACACCTG CAAAGGCGGC

ACAACCCCAG TGCCACGTTG TGAGTTGGAT AGTTGTGGAA

AGAGTCAAAT GGCTCTCCTC AAGCGTATTC AACAAGGGC

TGAAGGATGC CCAGAAGGTA CCCCATTGTA TGGGATCTGA

TCTGGGGCCT CGGTGCACAT GCTTTACATG TGTTTAGTCG

AGGTTAAAAA AACGTCTAGG CCCCCCGAAC CACGGGGACG

TGGTTTTCCT TTGAAAAACA CGATGATAAG CTTGCCACAA

CCATGGGTGT ACTGCTCACA CAGAGGACGC TGCTCAGTCT

GGTCCTTGCA CTCCTGTTTC CAAGCATGGC GAGCATGGCA

ATGCACGTGG CCCAGCCTGC TGTGGTACTG GCCAGCAGCC

GAGGCATCGC CAGCTTTGTG TGTGAGTATG CATCTCCAGG

CAAAGCCACT GAGGTCCGGG TGACAGTGCT TCGGCAGGCT

GACAGCCAGG TGACTGAAGT CTGTGCGGCA ACCTACATGA

TGGGGAATGA GTTGACCTTC CTAGATGATT CCATCTGCAC

GGGCACCTCC AGTGGAAATC AAGTGAACCT CACTATCCAA

GGACTGAGGG CCATGGACAC GGGACTCTAC ATCTGCAAGG

TGGAGCTCAT GTACCCACCG CCATACTACC TGGGCATAGG

CAACGGAACC CAGATTTATG TAATTGATCC AGATACCGTG

CCCAGATTCT GATCAGGAGC CCAAATCTTC TGACAAAACT

CACACATCCC CACCGTCCCC AGCACCTGAA CTCCTGGGTG

GATCGTCAGT CTTCCTCTTC CCCCCAAAAC CCAAGGACAC

CCTCATGATC TCCCGGACCC CTGAGGTCAC ATGCGTGGTG

GTGGACGTGA GCCACGAAGA CCCTGAGGTC AAGTTCAACT

GGTACGTGGA CGGCGTGGAG GTGCATAATG CCAAGACAAA

GCCGCGGGAG GAGCAGTACA ACAGCACGTA CCGGGTGGTC

AGCGTCCTCA CCGTCCTGCA CCAGGACTGG CTGAATGGCA

AGGAGTACAA GTGCAAGGTC TCCAACAAAG CCCTCCCAGC

-continued

CCCCATCGAG AAAACCATCT CCAAAGCCAA AGGGCAGCCC

CGAGAACCAC AGGTGTACAC CCTGCCCCCA TCCCGGGATG

AGCTGACCAA GAACCAGGTC AGCCTGACCT GCCTGGTCAA

AGGCTTCTAT CCCAGCGACA TCGCCGTGGA GTGGGAGAGC

AATGGGCAGC CGGAGAACAA CTACAAGACC ACGCCTCCCG

TGCTGGACTC CGACGGCTCC TTCTTCCTCT ACAGCAAGCT

CACCGTGGAC AAGAGCAGGT GGCAGCAGGG GAACGTCTTC

TCATGCTCCG TGATGCATGA GGCTCTGCAC AACCACTACA

CGCAGAAGAG CCTCTCCCTG TCTCCGGGTA AATGAGGAAT

TCACCACAGG ATCCCCACTG GCGAATCCCA GCGAGAGGTC

TCACCTCGGT TCATCTCGCA CTCTGGGGAG CTCAGCTCAC

EXAMPLE 13

Production of Transgenic Hens with an OMC24-IRES-attB-CTLA4-Fc Fusion Coding Sequence Twenty-five μg of OMC24-attB-IRES-CTLA4-Fc and 2.5 μg of SV40 integrase mRNA was placed in 200 μl of 28 mM Hepes (pH 7.4). The DNA/Hepes was mixed with an equal volume of PEI was diluted 10-fold with water and the mixture was incubated at room temperature for 15 mins. About 5 μl of the mixture was injected into chicken eggs essentially as described in Example 7.

Birds that produce egg white which includes CTLA4-Fc were identified using a procedure essentially as described in Example 8 but tailored specifically for CTLA4-Fc as is understood by a practitioner of ordinary skill in the art. Approximately 20% of the birds analyzed produced eggs positive for CTLA4-Fc.

EXAMPLE 14

Construction of an Ovomucoid Promoter-Bacterial Artificial Chromosome Expression Vector Encoding an Antibody which Binds to CD3

A single vector is constructed to include a cassette comprising an IRES attached to the coding sequence of the light chain of an IgG antibody which binds to CD3 and a cassette comprising an IRES attached to the coding sequence of the heavy chain of an IgG antibody which binds to CD3. The coding sequences for each of the antibody chains are produced by assembling synthetic oligonucleotides to form double stranded DNA segments which encode either the amino acid sequence for the antibody light chain (LC) or heavy chain (HC). Sequences for this particular antibody have been described in, for example, U.S. Pat. No. 6,706,265, the disclosure of which is incorporated in its entirety herein by reference. The IRES-LC cassette and IRES-HC cassette are each inserted into the ovomucoid UTR of a single OMC24 clone described in Example 6.

EXAMPLE 15

Construction of an Ovomucoid Promoter-Human Artificial Chromosome Expression Vector Encoding an Antibody which binds to CD3

A chicken HAC library constructed with genomic chicken DNA restriction digest inserts ligated into a HAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single HAC-chicken DNA clone is identified that includes both the UTR and the ovoinhibitor sequences and is designated HAC-O.

Two vectors are constructed to include a cassette comprising an IRES attached to the coding sequence of either the light chain or the heavy chain of an IgG antibody which binds to CD3. The coding sequences are produced by assembling synthetic oligonucleotides to form two double stranded DNA segments which encode either the amino acid sequence of the antibody light chain (LC) or heavy chain (HC). The IRES-LC cassette and IRES-HC cassette are each inserted into the ovomucoid UTR of a HAC-O clone to produce HAC-O-IRES-LC and HAC-O-IRES-HC.

Transgenic hens which produce egg white which includes IgG antibody that binds to CD3 are produced essentially as described in Example 7.

EXAMPLE 16

Construction of an Ovomucoid Promoter P1 Derived Artificial Chromosome Expression Vector Encoding EPO A chicken PAC library constructed with chicken genomic DNA restriction digest inserts ligated into PAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single PAC-chicken DNA clone is identified that includes both the UTR and the ovoinhibitor sequences and is designated PAC-O.

A vector is constructed which includes a cassette comprising an IRES attached to the coding sequence of human erythropoietin. Sequences for erythropoietin have been described in, for example, U.S. Pat. No. 4,703,008, the disclosure of which is incorporated in its entirety herein by reference. The IRES-EPO cassette is inserted into the ovomucoid UTR of the PAC-O clone.

Transgenic hens which produce egg white which includes EPO are produced essentially as described in Example 7.

EXAMPLE 17

Construction of an Ovomucoid Promoter-Bacterial Artificial Chromosome Expression Vector Encoding Human Gamma-Interferon A vector is constructed which includes a cassette coding sequence of an IRES and human gamma-interferon. Sequences for gamma-interferon have been previously described in, for example, U.S. Pat. No. 4,970,161, the disclosure of which is incorporated in its entirety herein by reference. The interferon coding sequence is inserted into the ovomucoid UTR in an OMC24 clone of Example 6.

Transgenic hens which produce egg white which includes gamma-interferon are produced essentially as described in Example 7.

EXAMPLE 18

Construction of an Ovomucoid Promoter-Yeast Artificial Chromosome Expression Vector Encoding the Fc portion of an Antibody which Binds to CD3

A chicken YAC library constructed with restriction digest inserts ligated into YAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single YAC-chicken DNA clone is identified that includes both the UTR and the ovoinhibitor sequences and is designated YAC-O.

One vector is constructed to include a cassette comprising an IRES attached to the coding sequence of the Lc portion of an IgG antibody which binds to CD3. The coding sequences are produced by assembling synthetic oligonucleotides to form two double stranded DNA segments which encode the Lc portion of an IgG antibody which binds to CD3. The IRES-Lc cassette is inserted into the ovomucoid UTR of a YAC-O clone to produce YAC-O-IRES-Lc.

Transgenic hens which produce egg white which includes the Lc portion of an IgG antibody that binds to CD3 are produced essentially as described in Example 7.

EXAMPLE 19

Construction of an Ovomucoid Promoter-Bacterial Artificial Chromosome Expression Vector Encoding a Monoclonal Antibody that Specifically Recognizes Phosphatidylinositol-3,4-Bisphosphate Two vectors are constructed to include a cassette comprising an IRES attached to the coding sequence of either the light chain or the heavy chain of a monoclonal antibody that specifically recognizes phosphatidylinositol-3,4-bisphosphate. The coding sequences are produced by assembling synthetic oligonucleotides to form two double stranded DNA segments which encode the amino acid sequence of either the antibody light chain (LC) or heavy chain (HC). Sequences for this particular antibody are disclosed in, for example, U.S. Pat. No. 6,709,833, the disclosure of which is incorporated in its entirety herein by reference. The IRES-LC cassette and IRES-HC cassette are each inserted into an OMC24 clone essentially as described in Example 6.

Transgenic hens which produce egg white that includes a monoclonal antibody that specifically recognizes phosphatidylinositol-3,4-bisphosphate are produced essentially as described in Example 7.

EXAMPLE 20

Construction of pNLB-3.9-OM-CTLA4-Fc and CTLA4 Expression Vector

The approximately 3.9 kb ovomucoid gene expression controlling region shown underlined in FIG. 14 (Fragment B)

was cloned into a pBluescript vector using methodologies well know in the art to create the pOM-3.9 vector shown in FIG. 15. In order to facilitate the cloning of a coding sequence to be under the control of the approximately 3.9 kb ovomucoid gene expression controlling region, the first NcoI site that overlaps the start codon of the ovomucoid CDS (and is followed immediately by a second NcoI site) was converted into a PciI site. A NcoI 1155 bp coding sequence fragment for the extracellular domains of the CTLA4 (cytotoxic T lymphocyte antigen 4) receptor protein linked to nucleotide coding sequences for an immunoglobulin constant region (IgG1 Fc) was cloned into the PciI site of the pOM-3.9 vector to produce the pOM-3.9-CTLA4 vector as shown in FIG. 15.

EXAMPLE 21

Construction of pNLB-1.8-OM-CTLA4-Fc Expression Vector

The 2993 bp Bgl II/BamHI fragment of pOM-3.9-CTLA4 (FIG. 15) bearing a 1776 bp fragment of the ovomucoid promoter and the CTLA4-Fc coding region was inserted into the BglII site of the pNLB vector shown in FIG. 15 using standard recombinant DNA methodologies, creating pNLB-OM-1.8-CTLA4.

EXAMPLE 22

Production and Concentration of VSV-G Typed pNLB-1.8-OM-CTLA4-Fc Particles

Sentas and Isoldes are cultured in F10 (Gibco), 5% newborn calf serum (Gibco), 1% chicken serum (Gibco), 50 µg/ml phleomycin (Cayla Laboratories) and 50 µg/ml hygromycin (Sigma). Transduction particles are produced essentially as described in Cosset et al., 1991, J. Virology 65: 3388-3394, herein incorporated by reference, with the following exceptions. Two days after transfection of the retroviral vector pNLB-OM-1,8-CTLA4 (from Example 21, above) into $3 \times 10^5$ Sentas, virus is harvested in fresh media for 6-16 hours and filtered. All of the media is used to transduce $3 \times 10^6$ Isoldes in 3 100 mm plates with polybrene added to a final concentration of 4 µg/ml. The following day the media is replaced with media containing 50 µg/ml phleomycin (Cayla Laboratories), 50 µg/ml hygromycin (Gibco) and 200 µg/ml G4 18 (Gibco).

After 10-12 days, single $G418^R$ colonies are isolated and transferred to 24-well plates. After 7-10 days, the titer from each colony is determined by transduction of Sentas followed by G418 selection. Typically, 2 out of 60 colonies give titers at $1-3 \times 10^5$. Those colonies are expanded and virus concentrated to $2-7 \times 10^7$ as described in Allioli et al., (1994) Dev. Biol. 165:30-7, herein incorporated by reference. The virus particles are stored at −70 degrees C.

EXAMPLE 23

Direct Oviduct Transgenesis (DOT) of pNLB-1.8-OM-CTLA4-Fc Particles and Promoter Assay White Leghorn pullets which are between 10 and 20 weeks old are used in this procedure. One to ten days prior to treatment, the pullets are given daily dosages of diethylstilbestrol (DES, a potent form of estrogen) and progesterone to stimulate proliferation of magnum cells. Typically, doses for a 1 kg hen are 1 mg of DES and 0.8 mg of progesterone, injected intramuscularly in a volume of 0.1 ml of 95% ethanol or sesame oil. Testosterone may be substituted for progesterone.

Additional hormone injections may be given the day of surgery and for several days after. The day before treatment, the pullets are taken off of their diet and 1 mg of DES and 0.8 mg of progesterone per kg of pullet is injected daily for three days.

On the morning of the fourth day, the magnum of the oviduct is accessed by surgical procedures. Pullets are anesthetized with a standard dose of isoflurane. Aliquots of the concentrated pNLB-1.8-OM-CTLA4-Fc particles of Example 22 are thawed on ice. The magnum region of the oviduct is approached through a left lateral abdominal incision. Laparoscopic grasping forceps are used to secure the oviduct during the injection. Typically a volume of 0.5-0.6 ml of particles ($1-5 \times 10^5$ VSV-G typed particles from Example 22) is injected into three locations into the lumen of the magnum using a 1 ml syringe and 22 G needle. The incision is sutured and the birds allowed to wake. The pullets are returned to their cages and given one final injection of DES and progesterone. Particle solutions remaining after injection are retitered on Isoldes and Sentas to confirm the viral titer. Six days later the same pullets are taken off their diet.

One week later the magnum is accessed through the same incision used for the injections. 0.5 ml of phosphate-buffered saline (PBS) is injected into the lumen. The lumen is gently massaged to mix the PBS with the lumen fluid. 0.1 ml PBS samples are removed from the lumen of DOT-treated hens which is assayed with a CTLA4 ELISA kit using a high sensitivity protocol reveals the presence of CTLA4 in the lumen fluid.

EXAMPLE 24

Figure 16:
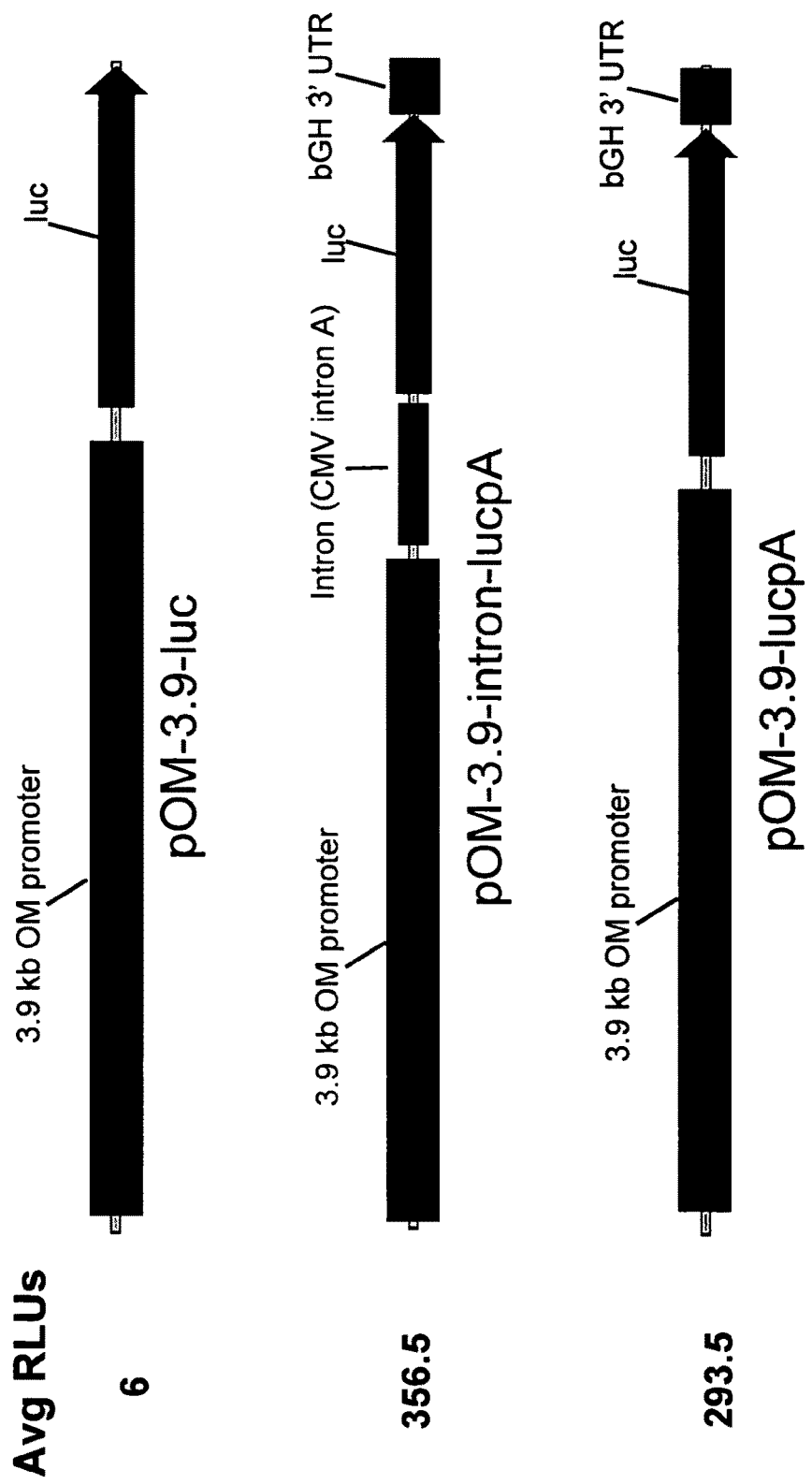
FIG. 16 shows the pOM-3.9-luc construct, the pOM-3.9-intron-lucpA construct and the pOM-3.9-lucpA construct.

Expression in Transfected Cultured Avian Myeloid and Oviduct Cells of Luciferase Regulated by the Approximately 3.9 kb Ovomucoid Promoter pOM-3.9-lucpA was constructed by cloning the 1972 bp NcoI-KpnI fragment of pCMV-luciferase (gWiz™ Expression Vector, Gene Therapy Systems, inc.) into the 7297 bp PciI-KpnI fragment of pOM-3.9. pOM-3.9-luc was constructed by cloning the 1672 bp NcoI-BamHI fragment of pCMV-luciferase (gWiz™ Expression Vector, Gene Therapy Systems, inc.) into the 7295 bp PciI-BamHI fragment of pOM-3.9. pOM-3.9-intron-lucpA was constructed by cloning the 2899 bp SacII (mung bean nuclease treated)-KpnI fragment of pCMV-luciferase (gWiz™ Expression Vector, Gene Therapy Systems, inc.) into the 7297 bp PciI (mung bean nuclease treated)-KpnI fragment of pOM-3.9. These constructs are shown in FIG. 16.

Primary tubular gland cells were isolated as described in Example 4. Transfection was performed for each of the six plasmids indicated in FIG. 17. 4.0 µl of DMRIE-C liposomes (Life Technologies) and 2.0 µg of DNA was preincubated for 15 minutes at room temperature each in a 200 µl aliquot of OPTIMEM™, which was then added to a well containing 800 ul of oviduct cells. Cells with DNA/liposomes were incubated for about 5 hours at 37° C. in 5% $CO_2$. 2.0 ml of DMEM (Life Technologies), supplemented with 15% fetal bovine serum (FBS) (Atlanta Biologicals, Atlanta, Ga.), 2× penicillin/streptomycin (Life Technologies), 50 ng/ml insulin (Sigma), $10^{-7}$ M α-estradiol (Sigma), and $10^{-6}$ M corticosterone (Sigma) were added to each well, and incubation continued for about 40 hours.

For each plasmid to be tested, the cells were scraped into the media with a rubber policeman. One milliliter of the resuspended cells was transferred to an eppendorf tube and the cells pelleted. The supernatant was removed and 20 ml of 10 mM Tris, ph 7.8, 1 mM EDTA (TE) was added to the cell pellet. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Figure 17:
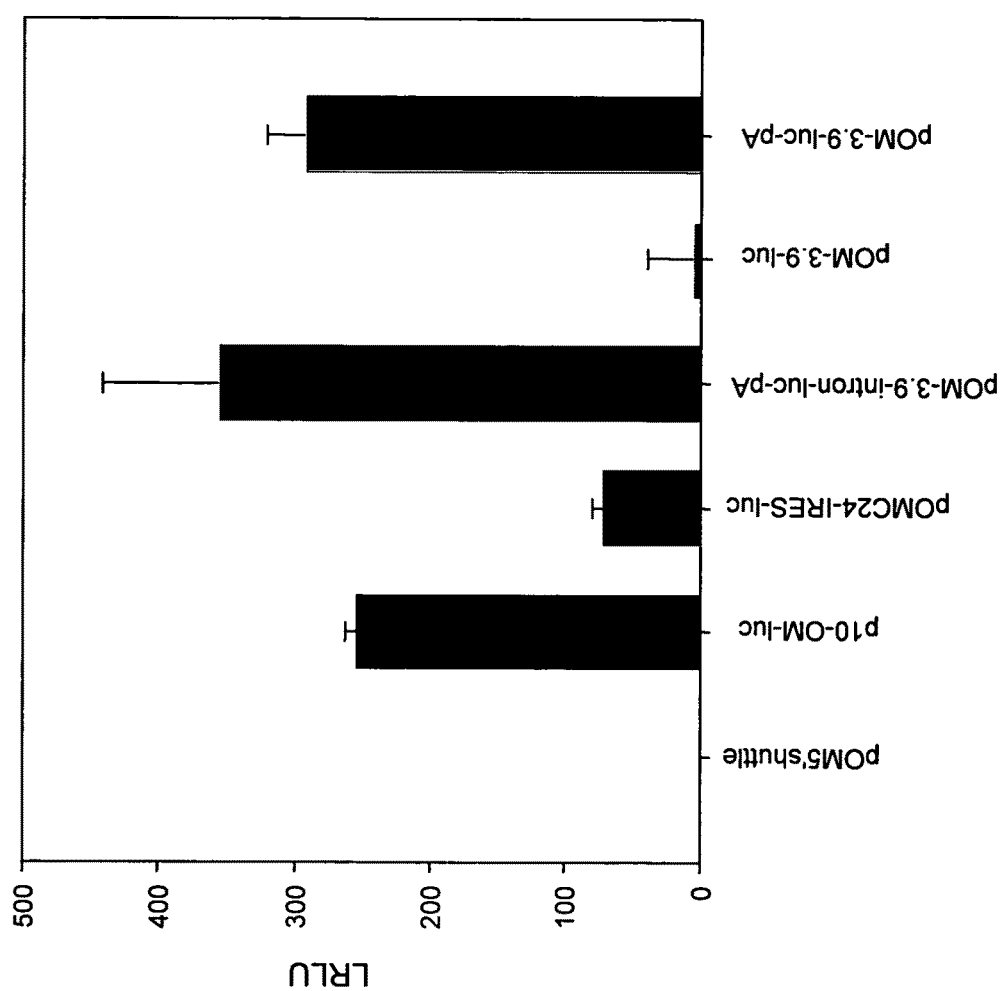
FIG. 17 shows relative measurements in a quail TGC assay for six vectors. LRLU stands for luciferase relative light units.

The results are depicted in FIG. 17. Expression of luciferase is evident from the approximately 3.9 kb OM fragment. The approximately 3.9 kb OM fragment which includes the CMV intron A appears to have more activity relative to the approximately 3.9 kb OM fragment without the CMV intron. Therefore, including an intron in an expression construct may provide for a greater level of expression by an ovomucoid gene expression controlling region, or a functional fragment, relative to the expression level provided by an identical construct without the intron.

All references cited herein are incorporated by reference herein in their entirety and for all purposes to the same extent as if each individual publication, patent or patent application is specifically and individually indicated to be incorporated by reference in its entirety for all purposes.

The citation of any publication is for its disclosure prior to the filing date and should not be construed as an admission that the present invention is not entitled to antedate such publication by virtue of prior invention.

While this invention has been described with respect to various specific examples and embodiments, it is to be understood that the invention is not limited thereto and that it can be variously practiced with the scope of the following claims.

What is claimed is:

1. A method comprising isolating a heterologous protein from an egg laid by a transgenic avian wherein the avian contains in its genome a recombinant nucleic acid comprising a nucleotide sequence that is at least 95% identical to a nucleic acid sequence corresponding to the sequence of about 34,473 to about 36,248 of SEQ ID NO: 36 operably linked to a coding sequence encoding the heterologous protein.

2. The method of claim 1 wherein the nucleotide sequence comprises a sequence at least 99% identical to the sequence of about 34,473 to about 36,248 of SEQ ID NO: 36.

3. The method of claim 1 wherein the nucleotide sequence comprises the sequence of about 34,473 to about 36,248 of SEQ ID NO: 36.

4. The method of claim 1 wherein the nucleic acid comprises an attB site.

5. The method of claim 1 wherein the nucleic acid comprises a signal sequence coding region.

6. The method of claim 1 wherein the nucleic acid comprises an IRES.

7. The method of claim 1 wherein the nucleic acid comprises a vector.

8. The method of claim 7 wherein the vector is selected from the group consisting of a plasmid, a viral vector or an artificial chromosome.

9. The method of claim 1 wherein the nucleic acid comprises an artificial chromosome.

10. The method of claim 1 wherein the transgenic avian is selected from the group consisting of chicken and quail.

11. The method of claim 1 wherein the heterologous protein is a therapeutic protein.

12. The method of claim 1 wherein the heterologous protein is an antibody.

13. The method of claim 1 wherein the heterologous protein is a fusion protein.

14. The method of claim 1 wherein the heterologous protein is selected from the group consisting of erythropoietin (EPO), granulocyte colony-stimulating factor (G-CSF), granulocyte macrophage colony-stimulating factor (GM-CSF), CTLA4-Fc, interferon, interferon alpha, interferon beta FSH, and beta glucocerebrosidase.

15. The method of claim 1 wherein the heterologous protein is selected from the group consisting of MAb directed against t-lymphocyte antigen CD3, MAb directed against TAG-72, tumor-associated glycoprotein, MAb or MAb fragments directed against platelet surface receptor GPII(b) and/or III(a), MAb fragment or MAb directed against tumor-associated antigen CA125, MAb or MAb fragment directed against human CEA (carcinoembryonic antigen), MAb fragment or MAb directed against human cardiac myosin MAb fragment or MAb directed against tumor surface antigen PSMA, MAb fragments or MAb directed against HMW-MAA, MAb fragment or MAb directed against carcinoma-associated antigen, MAb fragments or MAb directed against NCA 90, MAb directed against CD20 antigen found on surface of B lymphocytes, MAb directed against the alpha chain of the IL2 receptor, MAb directed against TNF-alpha, MAb directed against an epitope on the surface of respiratory, syncytial virus, MAb directed against HER 2 (human epidermal growth factor receptor 2), MAb directed against cytokeratin tumor-associated antigen, anti-CTLA4, dornase-alpha DNAse, TNF-alpha, IL-2-diptheria toxin fusion protein that targets cells displaying a surface IL-2 receptor, TNFR-IgG fragment fusion protein, enbrel, laronidase, teriparatide and parathyroid hormone derivatives.

16. A method comprising isolating a heterologous protein from egg white produced by a transgenic avian wherein the genome of the avian contains a recombinant nucleic acid comprising a nucleotide sequence that is at least 95% identical to a nucleic acid sequence corresponding to the sequence of about 34,473 to about 36,248 of SEQ ID NO: 36 operably linked to a heterologous coding sequence and the amino acid sequence encoded by the heterologous coding sequence is produced in an oviduct cell and is isolated from the egg white.

17. The method of claim 16 wherein the nucleotide sequence comprises a sequence at least 99% identical to the sequence of about 34,473 to about 36,248 of SEQ ID NO: 36.

18. The method of claim 16 wherein the nucleotide sequence comprises the sequence of about 34,473 to about 36,248 of SEQ ID NO: 36.

19. The method of claim 16 wherein the oviduct cell is a tubular gland cell.

20. The method of claim 16 wherein the heterologous coding sequence encodes at least one of a light chain and a heavy chain of an antibody.

21. The method of claim 16 wherein the heterologous coding sequence encodes an antibody selected from the group consisting of IgG, IgA, TgD, IgM and IgE.

22. The method of claim 16 wherein the transgenic avian is selected from the group consisting of chicken and quail.

23. A method comprising isolating a heterologous protein from an egg of a transgenic chicken wherein the genome of the transgenic chicken contains a nucleic acid comprising a nucleotide sequence that is at least 95% identical to a nucleic acid sequence corresponding to the sequence of about 34,473 to about 36,248 of SEQ ID NO: 36 operably linked to a heterologous coding sequence, the amino acid sequence encoded by the heterologous coding sequence being produced in an oviduct cell and packaged into the egg laid by the chicken.

24. The method of claim 23 wherein the nucleotide sequence comprises a sequence at least 99% identical to the sequence of about 34,473 to about 36,248 of SEQ ID NO: 36.

25. The method of claim 23 wherein the nucleotide sequence comprises the sequence of about 34,473 to about 36,248 of SEQ ID NO: 36.

26. The method of claim 23 wherein the heterologous protein is a fusion protein.

27. The method of claim 23 wherein the heterologous protein is a therapeutic protein.

28. The method of claim 27 wherein the therapeutic protein is a fusion protein.

29. The method of claim 23 wherein the heterologous protein is selected from the group consisting of erythropoietin (EPO), granulocyte colony-stimulating factor (G-CSF), granulocyte macrophage colony-stimulating factor (GM-CSF), CTLA4-Fc, interferon, interferon alpha, interferon beta, FSH, an antibody and beta glucocerebrosidase.

30. The method of claim 23 wherein the heterologous protein is selected from the group consisting of MAb directed against t-lymphocyte antigen CD3, MAb directed against TAG-72, tumor-associated glycoprotein, MAb or MAb fragments directed against platelet surface receptor GPII(b) and/or III(a), MAb fragment or MAb directed against tumor-associated antigen CA125, MAb or MAb fragment directed against human CEA (carcinoembryonic antigen), MAb fragment or MAb directed against human cardiac myosin, MAb fragment or MAb directed against tumor surface antigen PSMA, MAb fragments or MAb directed against HMW-MAA, MAb fragment or MAb directed against carcinoma-associated antigen, MAb fragments or MAb directed against NCA 90, MAb directed against CD20 antigen found on surface of B lymphocytes, MAb directed against the alpha chain of the IL2 receptor, MAb directed against TNF-alpha, MAb directed against an epitope on the surface of respiratory, syncytial virus, MAb directed against HER 2 (human epidermal growth factor receptor 2), MAb directed against cytokeratin tumor-associated antigen, anti-CTLA4, dornase-alpha DNAse, TNF-alpha, diptheria toxin fusion protein that targets cells displaying a surface IL-2 receptor, TNFR-IgG fragment fusion protein, enbrel, laronidase, teriparatide and parathyroid hormone derivatives.

\* \* \* \* \*